(12) United States Patent
Chang et al.

(10) Patent No.: US 9,034,330 B2
(45) Date of Patent: *May 19, 2015

(54) PREPARATION OF ANTIBODY OR AN ANTIBODY FRAGMENT-TARGETED IMMUNOLIPOSOMES FOR SYSTEMIC ADMINISTRATION OF THERAPEUTIC OR DIAGNOSTIC AGENTS AND USES THEREOF

(75) Inventors: Esther H. Chang, Potomac, MD (US); Kathleen F. Pirollo, Rockville, MD (US)

(73) Assignee: Georgetown University, Washington, DC (US)

( * ) Notice: Subject to any disclaimer, the term of this patent is extended or adjusted under 35 U.S.C. 154(b) by 1345 days.

This patent is subject to a terminal disclaimer.

(21) Appl. No.: 11/798,296

(22) Filed: May 11, 2007

(65) Prior Publication Data

US 2007/0231378 A1 Oct. 4, 2007

Related U.S. Application Data

(63) Continuation-in-part of application No. 10/113,927, filed on Apr. 2, 2002, now Pat. No. 7,780,882, which is a continuation-in-part of application No. 09/914,046, filed as application No. PCT/US00/04392 on Feb. 22, 2000, now Pat. No. 7,479,276.

(60) Provisional application No. 60/121,133, filed on Feb. 22, 1999, provisional application No. 60/280,134, filed on Apr. 2, 2001, provisional application No. 60/800,163, filed on May 15, 2006, provisional application No. 60/844,352, filed on Sep. 14, 2006.

(51) Int. Cl.
| | |
|---|---|
| *A61K 39/395* | (2006.01) |
| *A61K 9/127* | (2006.01) |
| *C12P 21/08* | (2006.01) |
| *A61K 39/00* | (2006.01) |
| *A61K 9/00* | (2006.01) |
| *A61K 41/00* | (2006.01) |
| *A61K 47/48* | (2006.01) |
| *A61K 49/18* | (2006.01) |
| *G01N 33/53* | (2006.01) |

(52) U.S. Cl.
CPC ............... *A61K 9/0019* (2013.01); *A61K 9/127* (2013.01); *A61K 9/1272* (2013.01); *A61K 39/39558* (2013.01); *A61K 41/0038* (2013.01); *A61K 47/48538* (2013.01); *A61K 47/48823* (2013.01); *A61K 49/1812* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 5,688,488 | A | 11/1997 | Low et al. |
| 5,786,214 | A | 7/1998 | Holmberg |
| 5,977,322 | A | 11/1999 | Marks et al. |
| 6,071,533 | A | 6/2000 | Papahadjopoulos et al. |
| 6,099,842 | A | 8/2000 | Pastan et al. |
| 6,200,956 | B1 | 3/2001 | Scherman et al. |
| 6,210,707 | B1 | 4/2001 | Papahadjopoulos et al. |
| 6,693,086 | B1 | 2/2004 | Dow et al. |
| 6,794,128 | B2 | 9/2004 | Marks et al. |
| 7,022,336 | B2 | 4/2006 | Papahadjopoulos et al. |
| 7,741,300 | B2 | 6/2010 | Dow et al. |
| 7,780,882 | B2 * | 8/2010 | Chang et al. ................... 264/4.1 |
| 2001/0008759 | A1 | 7/2001 | Marks et al. |
| 2003/0044407 | A1 | 3/2003 | Chang et al. |
| 2004/0209366 | A1 | 10/2004 | Papahadjopoulos et al. |

FOREIGN PATENT DOCUMENTS

| | | |
|---|---|---|
| EP | 0 451 972 | 10/1991 |
| JP | 09-110722 | 4/1997 |
| JP | 2005306965 A | 11/2005 |
| WO | WO 83/02069 A1 | 6/1983 |
| WO | WO 95/14380 A1 | 6/1995 |
| WO | WO 95/35301 A1 | 12/1995 |
| WO | WO 97/28817 | 8/1997 |
| WO | WO 98/20857 A1 | 5/1998 |
| WO | WO 99/25320 A1 | 5/1999 |
| WO | WO 99/59643 A2 | 11/1999 |
| WO | WO 00/15649 A1 | 3/2000 |
| WO | WO 00/50008 A2 | 8/2000 |
| WO | WO 2005/117876 A1 | 12/2005 |

OTHER PUBLICATIONS

Oncology Times (2004, 26(1): 12).*
Allen, T.M., et al., "A new strategy for attachment of antibodies to sterically stabilized liposomes resulting in efficient targeting to cancer cells," *Biochim. Biophys. Acta 1237*:99-108, Elsevier Science Inc. (1995).
Allen, T.M., et al., "Antibody-Targeted Stealth® Liposomes" in *Stealth Liposomes*, Lasic, D.D. and Martin, F.J., eds., CRC Press Inc., Boca Raton, FL, pp. 233-244 (1995).
Aoki, K., et al., "Liposome-mediated in Vivo Gene Transfer of Antisense K-*ras* Construct Inhibits Pancreatic Tumor Dissemination in the Murine Peritoneal Cavity," *Cancer Res.* 55:3810-3816, American Association for Cancer Research (1995).

(Continued)

*Primary Examiner* — Michael Szperka
*Assistant Examiner* — Marianne DiBrino
(74) *Attorney, Agent, or Firm* — Fanelli Haag PLLC

(57) ABSTRACT

A method of preparing an antibody- or antibody fragment-targeted cationic immunoliposome or polymer complex comprises the steps of (a) preparing an antibody or antibody fragment; (b) mixing said antibody or antibody fragment with a cationic liposome to form a cationic immunoliposome or with a cationic polymer to form a polyplex; and (c) mixing said cationic immunoliposome or said polyplex with a therapeutic or diagnostic agent to form said antibody- or antibody fragment-targeted cationic immunoliposome or polymer complex.

47 Claims, 90 Drawing Sheets

(56) References Cited

OTHER PUBLICATIONS

Bajoria, R., and Contractor, S.F., "Effect of Surface Charge of Small Unilamellar Liposomes on Uptake and Transfer of Carboxyfluorescein across the Perfused Human Term Placenta [Regular Articles]," *Pediatr. Res.* 42:520-527, International Pediatrics Research Foundation, Inc. (1997).

Bajoria, R., et al., "Endocytotic uptake of small unilamellar liposomes by human trophoblast cells in culture," *Hum. Reprod.* 12:1343-1348, European Society for Human Reproduction and Embryology (1997).

Bauer, K. S., et al., "Inhibition of Angiogenesis by Thalidomide Requires Metabolic Activation, Which is Species-dependent," *Biochemical Pharmacology* 55:1827-1834, Elsevier Science Inc. (1998).

Bristow, R.G., et al., "The p53 gene as a modifier of intrinsic radiosensitivity: implications for radiotherapy," *Radiother. Oncol.* 40:197-223, Elsevier Scientific Publishers (1996).

Capitosti, S. M., et al., "Thalidomide analogues demonstrate dual inhibition of both angiogenesis and prostate cancer," *Bioorganic & Medicinal Chemistry* 12: 327-336, Elsevier Science Ltd. (2004).

Chackal-Roy, M., et al., "Stimulation of Human Prostatic Carcinoma Cell Growth by Factors Present in Human Bone Marrow," *J. Clin. Invest.* 84:43-50, The American Socie for Clinical Investigation, Inc. (1989).

Chen, L., et al., "Synergistic activation of p53 by inhibition of *MDM2* expression and DNA damage," *Proc. Natl. Acad. Sci. USA* 95:195-200, National Academy of Sciences (1998).

Cheng, P.-W., "Receptor Ligand-Facilitated Gene Transfer: Enhancement of Liposome-Mediated Gene Transfer and Expression by Transferrin," *Hum. Gene Ther.* 7:275-282, Mary Ann Liebert, Inc. (1996).

Chiarugi, V., et al.,"Cox-2, iNOS and p53 as play-makers of tumor angiogenesis (Review)," *Int. J. Mol. Med.* 2:715-719, D.A. Spandidos (1998).

Clark, P.R. and Hersh, E.M., "Cationic lipid-mediated gene transfer: Current concepts," *Curr. Opin. Mol. Ther.* 1:158-176, Current Drugs Ltd. (Apr. 1999).

Compagnon, B. et al., "Enhanced Gene Delivery and Expression in Human Hepatocellular Carcinoma Cells by Cationic Immunoliposomes," *J Liposome. Res.* 7:127-141, Taylor & Francis (1997).

Cristiano, R.J., and Curiel, D.T., "Strategies to accomplish gene delivery via the receptor-mediated endocytosis pathway," *Cancer Gene Ther.* 3:49-57, Appleton & Lange (1996).

D'Amato, R. J., et al,, "Thalidomide is an inhibitor of angiogenesis," *Proc. Natl. Acad. Sci. USA* 91:4082-4085, National Academy of Sciences (1994).

de Kruif, J., et al., "Biosynthetically lipid-modified human scFv fragments from phage display libraries as targeting molecules for immunoliposomes," *FEBS Letters* 399:232-236, Elsevier Science Ltd. (1996).

Dredge, K., et al., "Novel thalidomide analogues display anti-angiogenic activity independently of immunomodulatory effects," *British Journal of Cancer* 87:1166-1172, Nature Publishing Group (2002).

Dredge, K., et al., "Immunological Effects of Thalidomide and Its Chemical and Functional Analogs," *Critical Reviews in Immunology* 22:425-437, Begell House (2002).

Drummond, D.C., et al., "Optimizing Liposomes for Delivery of Chemotherapeutic Agents to Solid Tumors," *Pharmacol. Rev.* 51:691-743, The American Society for Pharmacology and Experimental Therapeutics (Dec. 1999).

Dubé, D., et al., "Preparation and Tumor Cell Uptake of Poly(*N*-isopropylacrylamide) Folate Conjugates," *Bioconjugate Chem.* 13:685-692, American Chemical Society (May-Jun. 2002).

Elliott, R.L., et al., "Breast Carcinoma and the Role of Iron Metabolism: A Cytochemical, Tissue Culture, and Ultrastructural Study," *Ann. N.Y. Acad. Sci.* 698:159-166, New York Academy of Sciences (1993).

Felgner, P.L., et al., "Improved Cationic Lipid Formulations for In Vivo Gene Therapy," *Ann. N.Y. Acad. Sci.* 772:126-139, New York Academy of Sciences (1995).

Fernandes-Alnemri, T., et al., "CPP32, a Novel Human Apoptotic Protein with Homology to *Caenorhabditis elegans* Cell Death Protein Ced-3 and Mammalian Interleukin-1 β-converting Enzyme," *Journal of Biological Chemistry* 269: 30761-30764, The American Society for Biochemisty and Molecular Biology, Inc. (1994).

Forssen, E. and Willis, M., "Ligand-targeted liposomes," *Adv. Drug Deliv. Rev.* 29:249-271, Elsevier Science B.V. (1998).

Forsyth, C. J., et al., "Thalidomide responsive chronic pulmonary GVHD," *Bone Marrow Transplantation* 17:291-293, Stockton Press (1996).

Fujiwara, T., et al., "A Retroviral Wild-Type p53 Expression Vector Penetrates Human Lung Cancer Spheroids and Inhibits Growth by Inducing Apoptosis," *Cancer Res.* 53:4129-4133, American Association for Cancer Research (1993).

Fujiwara, T., et al., "Induction of Chemosensitivity in Human Lung Cancer Cells in vivo by Adenovirus-mediated Transfer of the Wild-Type *p53* Gene," *Cancer Res.* 54:2287-2291, American Association for Cancer Research (1994).

Grayback, J.T., et al., "Analysis of Specific Proteins in Prostatic Fluid for Detecting Prostatic Malignancy," *J. Urol.* 121:295-299, The Williams & Wilkins Co. (1979).

Gershon, H., et al., "Mode of formation and structural features of DNA-cationic liposome complexes used for transfection," *Biochemistry* 32:7143-7151, American Chemical Society (1993).

Hamanda, K., et al., "Growth Inhibition of Human Cervical Cancer Cells with the Recombinant Adenovirus p53 in Vitro," *Gynecol. Oncol.* 60:373-379, Academic Press, Inc. (1996).

Hamada, K., et al., "Adenovirus-mediated Transfer of a Wild-Type *p53* Gene and induction of Apoptosis in Cervical Cancer," *Cancer Res.* 56:3047-3054, American Association for Cancer Research (1996).

Hamel, E., et al., "Antitumor 2,3-Dihydro-2-(aryl)-4(1H)-quinazolinone Derivatives. Interactions with Tubulin," *Biochemical Pharmacology* 51:53-59, Elsevier Science Ltd. (1995).

Reere-Ress, E., et al.,"Thalidomide Enhances the Anti-Tumor Activity of Standard Chemotherapy in a Human Melanoma Xenotransplantation Model," *J Invest Dermatol* 125:201-206, The Society for Investigative Dermatology, Inc. (2005).

Hour, M.-J,, et al., "6-Alkylamino- and 2,3-Dihydro-3'-methoxy-2-phenyl-4-quinazolinones and Related Compounds: Their Synthesis, Cytotoxicity, and Inhibition of Tubulin Polymerization," *J. Med. Chem.* 43: 4479-4487, American Chemical Society (2000).

Huwyler, J., et al., "Brain drug delivery of small molecules using immunoliposomes," *Proc. Natl. Acad. Sci. USA* 93:14164-14169, National Academy of Sciences (1996).

Jacobson, J. M., et al., "Thalidomide for the Treatment of Oral Aphthous Ulcers in Patients with Human Immunodeficiency Virus Infection," *New England Journal of Medicine* 336:1487-1493, Massachusetts Medical Society (1997).

Jiang, A., et al., "Cell-Type-Specific Gene Transfer into Human Cells with Retroviral Vectors that Display Single-Chain Antibodies," *J. Virol.* 72:10148-10156, American Society for Microbiology (Dec. 1998).

Johnson, P., et al., "Expression of Wild-Type p53 is Not Compatible with Continued Growth of p53-Negative Tumor Cells," *Mol. Cell Biol.* 11:1-11, American Society for Microbiology (1991).

Keer, H.N., et al., "Elevated Transferrin receptor Content in Human Prostate Cancer Cell Lines Assessed In Vitro and In Vivo,"*J. Urol* 143:381-385, American Urological Association, Inc. (1990).

Kenyon, B.M., et al., "Effects of Thalidomide and Related Metabolites in a Mouse Corneal Model of Neovascularization," *Exp. Eye Res.* 64:971-978, Academic Press Limited 1997.

Kerr, J.F.R., et al., "Apoptosis: Its Significance in Cancer and Cancer Therapy," *Cancer* 73:2013-2026, Wiley (1994).

Kirpotin, D., et al., "Sterically Stabilized Anti-HER2 Immunoliposomes: Design and Targeting to Human Breast Cancer Cells in Vitro," *Biochemistry* 36:66-75, American Chemical Society (1997).

(56) References Cited

OTHER PUBLICATIONS

Kobatake, E., et al., "A Flouroimmunoassay Based on Immunoliposomes Containing Genetically Engineered Lipid-Tagged Antibody," *Anal. Chem.* 69:1295-1298, American Chemical Society (1997).

Koning, G.A., et al., "Selective transfer of a lipophilic prodrug of 5-fluorodeoxyuridine from immunoliposomes to colon cancer cells," *Biochim. Biophys. Acts* 1420:153-167, Elsevier Science B.V. (Aug. 1999).

Koning, G.A., et al., "Antiproliferative effect of immunoliposomes containing 5-fluorodeoxyuridine-dipalmitate on colon cancer cells," *Br. J. Cancer* 80:1718-1725, Cancer Research Campaign (Aug. 1999).

Konishi, H., et al., "Targeting Strategy for Gene Delivery to Carcinoembryonic Antigen-Producing Cancer Cells by Retrovirus Displaying a Single-Chain Variable Fragment Antibody," *Hum. Gene Ther.* 9:235-248, Mary Ann Liebert, Inc. (1998).

Lasic, D.D., et al., "Sterically stabilized liposomes in cancer therapy and gene delivery," *Curr. Opin. Mol. Ther.* 1:177-185, Current Drugs Ltd. (Apr. 1999).

Lasic. D.D., and Papahadjopoulos, D., "Liposomes Revisited," *Science* 267:1275-1276, American Association for the Advancement of Science (1995).

Laukkanen, M.-L., et al., "Functional Immunoliposomes Harboring a Biosynthetically Lipid-Tagged Single-Chain Antibody," *Biochemistry* 33:11664-11670, American Chemical Society (1994).

Lee, R.J. and Huang, L., "Folate-targeted, Anionic Liposome-entrapped Polylysine-condensed DNA for Tumor Cell-specific Gene Transfer," *J. Biol. Chem.* 271:8481-8487, American Society for Biochemistry and Molecular Biology, Inc. (1996).

Lee, Y.J., et al., "Docetaxel and cisplatin as primary chemotherapy for treatment of locally advanced breast cancers," *Clin Breast Cancer* 5:371-376, Cancer Information Group (2004).

Lesoon-Wood, L.A., et al., "Systemic gene therapy with p53 reduces growth and metastases of a malignant human breast cancer in nude mice," *Hum. Gene Ther.* 6:395-405, M.A. Liebert (1995).

Lewis, J.G., et al., "A serum-resistant cytofectin for cellular delivery of antisense oligodeoxynucleotides and plasmid DNA," *Proc. Natl. Acad. Sci. USA* 93:3176-3181, National Academy of Sciences (1996).

Li, S., and Huang, L., "Functional Pleomorphism of Liposomal Gene Delivery Vectors—Lipoplex and Lipopolyplex," in *Liposomes-Rational Design*, Janoff, A.S., ed., Marcel Dekker, Inc., New York, NY, pp. 89-124 (1998).

Lima, L. M., et al.,"Synthesis and anti-inflammatory activity of phthalimide derivatives, designed as new thalidomide analogues," *Bioorg. Med. Chem.* 10:3067-3073, Elsevier Science Ltd. (2002).

Liu, T.J., et al., "Growth Suppression of Human Head and Neck Cancer Cells by the Introduction of a Wild-Type *p53* Gene via a Recombinant Adenovirus," *Cancer Res.* 54:3662-3667, American Association for Cancer Research (1994).

Lowe, S.W., "Cancer therapy and *p53*," *Curr. Opin. Oncol.* 7:547-553, Rapid Science Publishers (1995).

Maclean, A.L., et al., "Immunoliposomes as targeted delivery vehicles for cancer therapeutics (Review)," *Int. J. Oncol.* 11:325-332, D.A. Spandidos (1997).

Marinina, J., et al., "Stabilization of vinca alkaloids encapsulated in poly(lactide-co-glycolide) microspheres," *Pharmaceutical Research* 17:677-683, Kluwer Academic (2000).

Mamot, et al., "Targeting the epidermal growth factor receptor (EGFR)—a new therapeutic option in oncology?," *Swiss Med. Wkly.* 136:4-12, EMH Swiss Medical Publishers Ltd. (Jan. 2006).

artin, F.J. and Papahadjopoulos, D., "Irreversible coupling of immunoglobulin fragments to preformed vesicles. An improved method for liposome targeting," *J. Biol. Chem.* 257:286-288, American Society for Biochemistty and Molecular Biology (1982).

Martin, F., et al., "Retroviral Vector Targeting to Melanoma Cells by Single-Chain Antibody Incorporation in Envelope," *Human Gene Ther.* 9:737-746, Mary Ann Liebert, Inc. (1998).

Massing, U., "Cancer therapy with liposomal formulations of anticancer drugs," *Int. J. Clin. Pharmacol. Ther.* 35:87-90, Dustri-Verlag Dr. K. Feistle (1997).

Mastrobattista, E., et al., Immunoliposomes for the targeted delivery of antitumor drugs, *Adv Drug Deily Rev.* 40:103-127, Elsevier Science Ltd. (1999).

Matlashewski, G., "p53: Twenty years on, Meeting Review," *Oncogene Rev.* 18:7618-7620, Stockton Press (Dec. 1999).

Mattioli, R., et al., "Long-survival in Responding Patients with Metastatic Breast Cancer Treated with Doxorubicin-Docetaxel Combination. A Multicentre Phase II Trial," *Anticancer Res.* 24:3257-3262, J.G. Delinassios (2004).

May, P. and May, E., "Twenty years of p53 research: structural and functional aspects of the p53 protein," *Oncogene Reviews* 18:7621-7636, Stockton Press (1999).

McCarthy, D.M., et al., "Thalidomide for the therapy of graft-*versus*-host disease following allogeneic bone marrow transplantation," *Biomed. & Pharmacother.* 43:693-697, Elsevier Science Ltd. (1989).

Miller, K.D. and Sledge Jr., G.W., "Taxanes in the Treatment of Breast Cancer: A Prodigy Comes of Age," *Cancer Investigation* 17:121-136, Taylor & Francis (1999).

Miyamoto, T., et al., "Transferrin receptor in oral tumors," *Int. J. Oral Maxillofac. Surg.* 23:430-433, Munksgaard (1994).

Miyashita, T., et al., "Tumor suppressor p53 is a regulator of *bcl-2* and *bax* gene expression in vitro and in vivo," *Oncogene* 9:1799-1805, Macmillan Press Ltd. (1994).

Morishige, H., et al., "In vitro cytostatic effect of TNF (tumor necrosis factor) entrapped in immunoliposomes on cells normally insensitive to TNF," *Biochim. Biophys. Acta* 1151:59-68, Elsevier Science B.V. (1993).

Nag, A., et al., "A Colorimetric Estimation of Polyethyleneglycol-Conjugated Phospholipid in Stealth Liposomes," *Anal. Biochem.* 250:35-43, Academic Press (1997).

Nam, S.M., et al., "Sterically stabilized anti-$G_{M3}$, anti-Le$^x$ immunoliposomes: targeting to B16BL6, HRT-18 cancer cells," *Oncol. Res.* 11:9-16, Cognizant Communication (Jul. 1999).

Ng, K.-Y., et al., "The effects of polyethyleneglycol (PEG)-derived lipid on the activity of target-sensitive immunoliposome," *Int. J. Pharma.* 193:157-166, Elsevier Science B.V. (Jan. 2000).

Ng, S. S.W., et al., "Antiangiogenic Activity of N-substituted and Tetrafluorinated Thalidomide Analogues," *Cancer Res.* 63: 3189-3194, American Association for Cancer Research (2003).

Nguyen, M., "Thalidomide and chemotherapy combination: preliminary results of preclinical and clinical studies," *Int J Oncol* 10:965-969, D.A. Spandidos (1997).

Nicholson, D. W., et al., "Identification and inhibition of the ICE/CED-3 protease necessary for mammalian apoptosis," *Nature* 376:37-43, Nature Publishing Group (1995).

Nicholson, I.C., et al., "Construction and Characterisation of a Functional CD19 Specific Single Chain Fv Fragment for Immunotherapy of B Lineage Leukaemia and Lymphoma," *Mol. Immunol.* 34:1157-1165, Elsevier Science Ltd. (1997).

Nilsson, B., et al., "Fusion proteins in biotechnology and structural biology," *Curr. Opin. Struct. Biol.* 2:569-575, Current Biology Ltd. (1992).

Pagnan, G., et al., "GD2-Mediated Melanoma Cell Targeting and Cytotoxicity of Liposome-Entrapped Fenretinide," *Int. J. Cancer* 81:268-274, Wiley-Liss, Inc. (Apr. 1999).

Park, J.W., et al., "Development of anti-p185$^{HER2}$ immunoliposornes for cancer therapy," *Proc. Natl. Acad. Sci. USA* 92:1327-1331, National Academy of Sciences (1995).

Park, J.W., et al., "Immunoliposomes for cancer treatment," *Adv. Pharmacol.* 40:399-435, Academic Press (1997).

Park, J.W., et al., "Tumor targeting using anti-her2 immunoliposomes," *J. Control. Rel.* 74:95-113, Elsevier Science B.V. (Jul. 2001).

Pirollo, K.F., et al., "p53 mediated sensitization of squamous cell carcinoma of the head and neck to radiotherapy," *Oncogene* 14:1735-1746, Stockton Press (1997).

Pirollo, K.F., et al., "Immunoliposomes: A Targeted Delivery Tool for Cancer Treatment," in *Vector Targeting for Therapeutic Gene Delivery*, Curiet, D.T, and Douglas, J.T., eds., Wiley-Liss, Inc., Hoboken, NJ, pp. 33-62 (Aug. 2002).

(56) References Cited

OTHER PUBLICATIONS

Poon, R.Y.M, "Advances in Monoclonal Antibody Applications: Bispecific Antibodies" in *Biotechnology International: International Developments in the Biotechnology Industry*, Fox, F., and Connor. T.H., eds., Universal Medical Press, Inc., San Francisco, CA, pp. 113-128 (1997).

Rait, A.S., et al., "Inhibitory effects of the combination of HER-2 antisense oligonucleotide and chemotherapeutic agents used for the treatment of human breast cancer," *Cancer Gene Ther.* 8:728-739, Nature Publishing Group (Oct. 2001).

Reyes-Terán, G., et al., "Effects of thalidomide on HIV-associated wasting syndrome: a randomized, double-blind, placebo-controlled clinical trial," *AIDS 10*:1501-1507, Rapid Science Publishers (1996).

Roh, H., et al.,"Her2/neu antisense targetting of human breast carcinoma," *Oncogene 19*:6138-6143, Macmillan Publishers Ltd. (2000).

Rossi, M.C. and Zetter, B.R., "Selective stimulation of prostatic carcinoma cell proliferation by transferrin," *Proc. Natl. Acad. Sci. USA 89*:6197-6201, National Academy of Sciences (1992).

Rowinsky, E.K. and Donehower, R.C., "Paclitaxel (Taxol)," *New England Journal of Medicine 332*:1004-1014, Massachusetts Medical Society (1995).

Ruley, H.E., "p53 and Response to Chemotherapy and Radiotherapy," in *Important Adv. Oncol. 1996*, DeVita, V.T., et al., eds., Lippincott-Raven Publishers, Philadelphia, PA, pp. 37-56 (1996).

Sachdeva, M. S., "Drug targeting systems for cancer chemotherapy," *Exp. Opin. Invest. Drugs 7*:1849-1864, Ashley Publications Ltd. (1998).

Sapra, P., et al., "Improved Therapeutic Responses in a Xenograft Model of Human B Lymphoma (Namalwa) for Liposomal Vincristine *versus* Liposomal Doxorubicin Targeted via Anti-CD19 IgG2a or Fab' Fragments," *Clin. Cancer Res. 10*:1100-1111, American Association for Cancer Research (2004).

Schier, R., et al., "In vitro and in vivo characterization of a human anti-c-erbB-2 single-chain Fv isolated from a filamentous phage antibody library," *Immunotechnology 1*:73-81, Elsevier Science B.V. (1995).

Sidransky, D., and Hollstein, M., "Clinical implications of the p53 gene," *Annu. Rev. Med. 47*:285-301, Annual Reviews, Inc. (1996).

Shahinian, S., et al., "A novel strategy affords high-yield coupling of antibody Fab' fragments to liposomes," *Biochimica et Biophysica Acta 1239*:157-167, Elsevier Science B.V. (1995).

Spragg, D.D., et al., "Immunotargeting of Liposomes to activated vascular endothelial cells: A strategy for site-selective delivery in the cardiovascular system," *Proc. Natl. Acad. Sci. USA 94*:8795-8800, National Academy of Sciences (1997).

Srivastava, S., et al., "Recombinant Adenovirus Vector Expressing Wild-type p53 is a Potent Inhibitor of Prostate Cancer Cell Proliferation," *Urology 46*:843-848, Excerpta Medica, Inc. (1995).

Suzuki, S., et al., "Modulation of doxorubicin resistance in a doxorubicin-resistant human leukaemia cell by an immunoliposome targeting transferring receptor," *Br. J. Cancer 76*:83-89, Cancer Research Campaign (1997).

Tewari, M., et al., "Yarna/CPP32β, a Mammalian Homolog of CED-3, is a CrmA-Inhibitable Protease That Cleaves the Death Substrate Poly(ADP-Ribose) Polymerase," *Cell 81*: 801-809, Cell Press (1995).

The Journal of Gene Medicine Clinical Trials Database, "Gene Therapy Clinical Trials Worldwide," available online at .wiley.co.uk/wileychi/genmed/clinical, John Wiley and Sons, Ltd., 2 pages (accessed Sep. 2001).

Thierry, A.R., et al., "Systemic gene therapy: Biodistribution and long-term expression of a transgene in mice," *Proc. Natl. Acad. Sci. USA 92*:9742-9746, National Academy of Science (1995).

Thorstensen, K. and Romslo, I., "The Transferrin Receptor: Its Diagnostic Value and its Potential as Therapeutic Target," *Scand. J. Clin. Lab. Invest. 53*:113-120, Universitetsforlaget (1993).

Tseng, S., et al., "Rediscovering thalidomide: A review of its mechanism of action, side effects, and potential uses," *Journal of the American Academy of Dermatology 35*:969-979, Mosby (1996).

Turk, M.J., et al., "Characterization of a novel pH-sensitive peptide that enhances drug release from folate-targeted liposomes at endosomal pHs," *Biochimica et Biophysica Acta 1559*: 56-68, Elsevier Science B.V. (2002).

Venugopalan, P., et al., "pH-Sensitive liposomes: mechanism of triggered release to drug and gene delivery prospects," *Pharmazie 57*:659-671, Govi-Verlag Pharmazeutischer Verlag GmbH (2002).

Vertut-doï, A., et al., "Binding and uptake of liposomes containing a poly(ethylene glycol) derivative of cholesterol (stealth liposomes) by the macrophage cell line J774: influence of PEG content and its molecular weight," *Biochim. Biophys. Acta 1278*:19-28, Elsevier Science B.V. (1996).

Vogelsang, G.B., et al., "Treatment and Prevention of Acute Graft-Versus-Host Disease with Thalidomide in a Rat Model," *Transplantation 41*:644-647, The Williams & Wilkins Co. (1986).

Volpert, O.V., et al., "Sequential development of an angiogenic phenotype by human fibroblasts progressing to tumorigenicity," *Oncogene 14*:1495-1502, Stockton Press (1997).

Wang, D., et al., "Generation and Characterization of an Anti-CD19 Single-Chain Fv Immunotoxin Composed of C-Terminal Disulfide-Linked dgRTA," *Bioconjugate Chem. 8*:878-884, American Chemical Society (1997).

Weinberg, E.D., "Roles of Iron in Neoplasia: Promotion, Prevention, and Therapy," *Biol. Trace Element Res. 34*:123-140, Humana Press, Inc. (1992).

Wright, S.E., and Huang, L., "Bilayer stabilization of phosphatidylethanolamine by N-biotinylphosphatidylethanolamine," *Biochim. Biophys. Acta 1103*:172-178, Elsevier Science B.V.(1992).

Xu, L., et al., "Transferrin-Liposome-Mediated p53 Sensitization of Squamous Cell Carcinoma of the Head and Neck to Radiation In Vitro," *Human Gene Therapy 8*:467-475, M.A. Liebert (1997).

Xu, L., et al., "Systemic p53 gene therapy in combination with radiation results in human tumor regression," *Tumor Targeting 4*:92-104, Stockton Press (Jul. 1999).

Xu, L. et al., "Transferrin-Liposome-Mediated Systemic p53 Gene Therapy in Combination with Radiation Results in Regression of Human Head and Neck Cancer Xenografts," *Hum. Gene Ther. 10*:2941-2952, Mary Ann Liebert, Inc. (Dec. 1999).

Xu, L., et al., "Tumor-targeted p53-gene therapy enhances the efficacy of conventional chemo/radiotherapy," *Journal of Controlled Release 74*:115-128, Elsevier Science Ltd. (2001).

Xu, L., et al., "Systemic p53 Gene Therapy of Cancer with Immunolipoplexes Targeted by Anti-Transferrin Receptor scFv," *Molecular Medicine 7*:723-734, The Picower Institute Press (2001).

Xu, L., et al., "Self-Assembly of a Virus-Mimicking Nanostructure System for Efficient Tumor-Targeted Gene Delivery," *Hum. Gene Ther. 13*:469-481, Mary Ann Liebert, Inc. (Feb. 2002).

Xu, L. et al., "Systemic Tumor-targeted Gene Delivery by Anti-Transferrin Receptor scFv-Immunoliposomes," *Mol. Cancer Ther. 1*:337-346, American Association for Cancer Research, Inc. (2002).

Yang, C., et al., "Adenovirus-mediated Wild-Type *p53* Expression Induces Apoptosis and Suppresses Tumorigenesis of Prostatic Tumor Cells," *Cancer Res. 55*:4210-4213, American Association for Cancer Research (1995).

Yazdi, P.T., et al., "Influence of Cellular Trafficking on Protein Synthesis Inhibition of Immunotoxins Directed against the Transferrin Receptor," *Cancer Res. 55*:3763-3771, American Association for Cancer Research (1995).

Yoshida, J., et al., "Simple Preparation and Characterization of cationic Liposomes Associated with a Monoclonal Antibody Against Glioma-Associated Antigen (Immunoliposomes)," *J Liposome Res 5*:981-995, Taylor & Francis (1995).

Yu, W., et al., "Enhanced transfection efficiency of a systemically delivered tumor-targeting immunolipoplex by inclusion of a pH-sensitive histidylated oligolysine peptide," *Nucleic Acids Research 32*: e48, Oxford University Press (2004).

Yu, D., et al., "Liposome-mediated in vivo EIA gene transfer suppressed dissemination of ovarian cancer cells that overexpress HER-2/neu," *Oncogene 11*:1383-1388, Stockton Press (1995).

Zhang, W.-W., et al., "Advances in Cancer Gene Therapy," *Adv. Pharmacol. 32*:289-341, Academic Press, Inc. (1995).

(56) References Cited

OTHER PUBLICATIONS

Database Medline, Accession No. NLM7621238, English language abstract for Zhang, W.W., et al., "High-efficiency gene transfer and high-level expression of wild-type p53 in human lung cancer cells mediated by recombinant adenovirus," *Cancer Gene Ther. 1*:5-13, Nature Publishing Group (1994).
Zignani, M., et al., "In vitro characterization of a novel polymeric-based pH-sensitive liposome system," Biochimica et Biophysica Acta 1463: 383-394, Elsevier Science B.V. (2000).
International Search Report for International Application No. PCT/US07/11407, ISA/US, Alexandria, VA, mailed on Oct. 10, 2007.
Office Action in related U.S. Appl. No. 09/914,046, mailed on Nov. 29, 2004.
Office Action in related U.S. Appl. No. 09/914,046, mailed on Jul. 28, 2005.
Office Action in related U.S. Appl. No. 09/914,046, mailed on Jun. 9, 2006.
Office Action in related U.S. Appl. No. 09/914,046, mailed on Dec. 6, 2006.
Office Action in related U.S. Appl. No. 09/914,046, mailed on Jul. 26, 2007.
Office Action in related U.S. Appl. No. 10/113,927 mailed on Feb. 7, 2008.
Office Action in related U.S. Appl. No. 10/113,927 mailed on Nov. 6, 2007.
Office Action in related U.S. Appl. No. 10/113,927 mailed on Jul. 27, 2007.
Office Action in related U.S. Appl. No. 10/113,927 mailed on Dec. 5, 2006.
Office Action in related U.S. Appl. No. 10/113,927 mailed on Sep. 22, 2005.
Aigner, A.: "Delivery Systems for the Direct Application of siRNAs to Induce RNA Interference (RNAi) In Vivo", Journal of Biomedicine and Biotechnology, vol. 2006, Article ID 71659, pp. 1-15, 2006.
Kobstake, Elry, et al.: "A Fluoroimmunoassay Based on Immunoliposomes Containing Genetically Engineered Lipid-Tagged Antibody", Analytical Chemistry, vol. 69(7), pp. 1295-1298, 1997.
de Kruif, John, et al.: "Biosynthetically Lipid-Modified Human scFv Fragments From Phage Display Libraries as Targeting Molecules for Immunoliposomes", FEBS Letters 399, pp. 232-236, 1996.
Lesoon-Wood, Leslie A., et al.: "Systemic Gene Therapy with p53 Reduces Growth and Metastases of a Malignant Human Breast Cancer in Nude Mice", Human Gene Therapy, vol. 6, pp. 395-405, 1995.
Morishige, Hideaki, et al.: "In Vitro Cytostatic Effect of TNF (Tumor Necrosis Factor) Entrapped in Immunoliposomes on Cells Normally Insenstive to TNF", Biochimica et Biophysica Acta, vol. 1151, pp. 59-68, 1993.
Park, John W., et al.: "Immunoliposomes for Cancer Treatment", Advances in Pharmacology, vol. 40, pp. 399-435, 1997.

Simoes, S., et al.: "Enhancement of Cationic Liposome-Mediated Gene Delivery by Transferrin and Fusogenic Peptides", The $24^{th}$ International Symposium on Controlled Release of Bioactive Materials, 24, pp. 659-660, 1997.
Thorstensen, Ketil, et al.: "The Transferrin Receptor: Its Diagnostic Value and its Potential as Therapeutic Target", Scandinavian Journal of Clinical and Laboratory Investigation, vol. 53 (Suppl 215), pp. 113-120, 1993.
Xu, Liang, et al.: "Transferrin-Liposome-Mediated p53 Sensitization of Squamous Cell Carcinoma of the Head and Neck to Radiation In Vitro", Human Gene Therapy, vol. 8, pp. 467-475, 1997.
DiBrino, M. Non-Final Office Action dated Sep. 22, 2005 issued in U.S. Appl. No. 10/113,927.
DiBrino, M. Non-Final Office Action dated Dec. 5, 2006 issued in U.S. Appl. No. 10/113,927.
DiBrino, M. Final Office Action dated Jul. 27, 2007 issued in U.S. Appl. No. 10/113,927.
DiBrino, M. Non-Final Office Action dated Feb. 7, 2008 issued in U.S. Appl. No. 10/113,927.
DiBrino, M. Final Office Action dated Nov. 25, 2008 issued in U.S. Appl. No. 10/113,927.
DiBrino, M. Notice of Allowance dated Mar. 23, 2010 issued in U.S. Appl. No. 10/113,927.
DiBrino, M., Non-Final Office Action dated Aug. 3, 2010 issued in U.S. Appl. No. 11/520,796.
Office Action in related co-pending U.S. Appl. No. 11/520,796 mailed Apr. 11, 2011.
Office Action in related co-pending U.S. Appl. No. 12/820,800, mailed Nov. 22, 2011, 12 pages.
Hamada, K., et al.: "Adenovirus-Mediated Transfer of HPV 16 E6/E7 Antisense RNA to Human Cervical Cancer Cells," Gynecological Ocology, vol. 63, pp. 219-227, 1996.
Office Action in related U.S. Appl. No. 10/113,927, now Patent No. 7,780,882 mailed May 31, 2006.
Office Action in related co-pending U.S. Appl. No. 11/520,796 mailed Jun. 30, 2010.
Office Action in related co-pending U.S. Appl. No. 12/820,800 mailed Mar. 17, 2011.
Masamitsu Harata, et al., CD19-targeting liposomes containing imatinib efficiently kill Philadelphia chromosome—positive acute lymphoblastic leukemia cells, Blood, Prepublished online May 20, 2004, 7 pages, vol. 104, No. 5, p. 1442-1449, American Society of Hematology, Washington DC, USA.
Yukimasa Shiotsu, Current Screening for Molecular Target Therapy of Cancer, Japan J Cancer Chemother, Nov. 2003, vol. 30, p. 1863-1872, Japan.
Mercé Rodriguez, et al., Development and Effects of Immunoliposomes Carrying an Antisense Oligonucleotide Against DHFR RNA and Directed Toward Human Breast Cancer Cells Overexpressing HER2, Antiserise and Nucleic Acid Drug Development, 2002, vol. 12, p. 311-325, Mary Ann Liebert, Inc., USA.

* cited by examiner

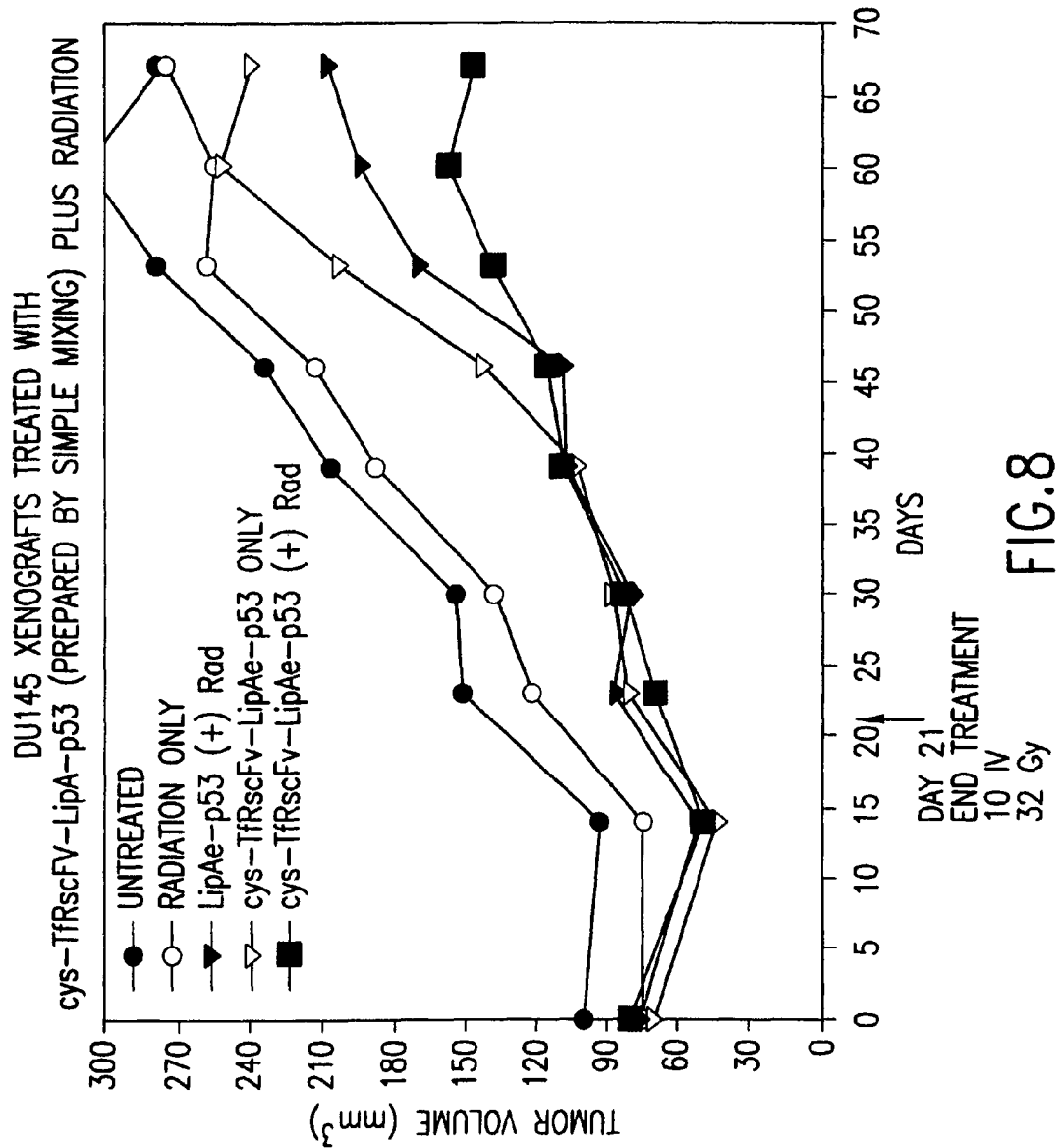

Ratio: TfRscFv/LipA-HoKC/GMC-5-193=0.17 ug/7 nmol/X nmol

Ratio: TfRscFv/LipA-HoKC/GMC-5-193=0.17 ug/7 nmol/7 nmol

Effect of Nanoimmunocomplex (scL-HK/GMC) on Sensitization of MDA-MB-435 Human Melanoma Cells to Doxorubicin

|  | IC$_{50}$: |
|---|---|
| UT | 400 ng/mL |
| LipA-HoKC | 420 ng/mL |
| GMC-5-193 | 300 ng/mL |
| TfRscFv/LipA-HoKC/GMC-5-193 | 8 ng/mL |
|  | Fold Sensitization (compared to UT) |
| LipA-HoKC | 1.0 |
| GMC-5-193 | 1.3 |
| TfRscFv/LipA-HoKC/GMC-5-193 | 50.0 |

Effect of TfRscFv/LipA/GMC-5-193 Nanoimmunocomplex On Sensitization of MDA-MB-435 Human Melanoma Cells to Doxorubicin

| | $IC_{50}$: |
|---|---|
| Doxorubicin only | 700 nM |
| Free GMC-5-193 | 620 nM |
| TfRscFv/LipA/GMC-5-193 | 73 nM |

| | Fold Sensitization (compared to Doxorubicin) |
|---|---|
| Free GMC-5-193 | 1.1 |
| TfRscFv/LipA/GMC-5-193 | 9.6 |

Effect of tumor targeting liposomal delivery of GMC-5-193 on sensitization of B16/F10 mouse melanoma cells to Cisplatin

|  | IC$_{50}$: |
|---|---|
| Cisplatin only | 64 µM |
| LipA only | 70 µM |
| Free GMC-5-193 | 64 µM |
| TfRscFv/LipA/GMC-5-193 | 62 µM |

|  | Fold Sensitization (compared to Cisplatin) |
|---|---|
| LipA only | 0.9 |
| Free GMC-5-193 | 1.0 |
| TfRscFv/LipA/GMC-5-193 | 1.0 |

48 h incubation
9h XTT, 1.25 µM GMC-5-193

Plate5 B16 031706

1.25uM GMC-5-193

Effect of tumor targeting liposomal delivery of GMC-5-193 on sensitization of B16/F10 mouse melanoma cells to Cisplatin

|  | IC$_{50}$: |
|---|---|
| Cisplatin only | 72 μM |
| LipA only | 80 μM |
| Free GMC-5-193 | 70 μM |
| TfRscFv/LipA/GMC-5-193 | 11 μM |

| | Fold Sensitization (compared to Cisplatin) |
|---|---|
| LipA only | 0.9 |
| Free GMC-5-193 | 1.0 |
| TfRscFv/LipA/GMC-5-193 | 6.5 |

48 h incubation
7h XTT, 2 μM GMC-5-193

Plate3 B16 032406

2uM GMC-5-193

Effect of tumor targeting liposomal delivery of GMC-5-193 on sensitization of B16/F10 mouse melanoma cells to Cisplatin

|  | $IC_{50}$: |
|---|---|
| Cisplatin only | 74 µM |
| LipA only | 73 µM |
| Free GMC-5-193 | 24 µM |
| TfRscFv/LipA/GMC-5-193 | 9 µM |
|  | Fold Sensitization (compared to Cisplatin) |
| LipA only | 1.0 |
| Free GMC-5-193 | 3.1 |
| TfRscFv/LipA/GMC-5-193 | 8.2 |

48 h incubation
9h XTT, 2.5 µM GMC-5-193

Plate7 B16 031706

2uM GMC-5-193

Effect of Tumor Targeting Liposomal Delivery of GMC-5-193 on Sensitization of Normal Human Lung Fibroblasts IMR-90 to Doxorubicin

| | $IC_{50}$: |
|---|---|
| UT | 700 ng/mL |
| LipA-HoKC | 500 ng/mL |
| GMC-5-193 | 320 ng/mL |
| TfRscFv/LipA-HoKC/GMC-5-193 | 200 ng/mL |
| | Fold Sensitization (compared to UT) |
| LipA-HoKC | 1.4 |
| GMC-5-193 | 2.2 |
| TfRscFv/LipA-HoKC/GMC-5-193 | 3.5 |

Effect of tumor targeting liposomal delivery of GMC-5-193 on sensitization of IMR-90 human lung fibroblasts to Doxorubicin

|  | IC$_{50}$: |
|---|---|
| Doxorubicin only | 1100 nM |
| LipA only | 1200 nM |
| Free GMC-5-193 | 1300 nM |
| TfRscFv/LipA/GMC-5-193 | 700 nM |

|  | Fold Sensitization (compared to Doxorubicin) |
|---|---|
| LipA only | 0.9 |
| Free GMC-5-193 | 0.8 |
| TfRscFv/LipA/GMC-5-193 | 1.6 |

Plate3 IMR-90 010706

Effect of tumor targeting liposomal delivery of GMC-5-193 on sensitization of IMR-90 human lung fibroblasts to Mitoxantrone

| | $IC_{50}$: |
|---|---|
| Mitoxantrone only | 350 nM |
| LipA only | 340 nM |
| Free GMC-5-193 | 250 nM |
| TfRscFv/LipA/GMC-5-193 | 190 nM |

| | Fold Sensitization (compared to Mitoxantrone) |
|---|---|
| LipA only | 1.0 |
| Free GMC-5-193 | 1.4 |
| TfRscFv/LipA /GMC-5-193 | 1.8 |

Plate1 IMR-90 010706

Effect of Tumor Targeting Liposomal Delivery of GMC-5-193 on Sensitization of DU145 Prostate Cancer Cells to Docetaxel(TAXOTERE®)

Effect of tumor targeting liposomal delivery of GMC-5-193 on sensitization of DU145 human prostate cancer cells to Mitoxantrone

| | $IC_{50}$: |
|---|---|
| Mitoxantrone only | 35 nM |
| LipA only | 33 nM |
| Free GMC-5-193 | 21 nM |
| TfRscFv/LipA/GMC-5-193 | 11 nM |

| | Fold Sensitization (compared to Mitoxantrone) |
|---|---|
| LipA only | 1.1 |
| Free GMC-5-193 | 1.7 |
| TfRscFv/LipA/GMC-5-193 | 3.2 |

Plate3 DU145 012106

Effect of Tumor Targeting Liposomal Delivery of GMC-5-193 on Sensitization of MDA-MB 435 Human Melanoma Cells to Docetaxel (TAXOTERE®)

The Effect of Tumor Targeting Liposomal Delivery of GMC-5-193 on Sensitization of B16/F10 Mouse Melanoma Cells to CDDP

|  | $IC_{50}$: |
|---|---|
| UT | 52 uM |
| LipA-HoKC | 51 uM |
| GMC-5-193 | 42 uM |
| TfRscFv/LipA-HoKC/GMC-5-193 | 20 uM |

|  | Fold Sensitization (compared to UT) |
|---|---|
| LipA-HoKC | 1.0 |
| GMC-5-193 | 1.2 |
| TfRscFv/LipA-HoKC/GMC-5-193 | 2.6 |

*In Vitro* Comparison of Free GMC-5-193 or TfRscFv/LipA/GMC-5-193 Complex Uptake in MDA-MB-435 Cells

*In Vitro* Comparison of Free or Nanoimmunocomplexed (scLHK-GMC) GMC Uptake in MDA-MB-435 Cells Incorporation of a Fluorescent GMC in the Nanoimmunocomplex Enhances Tumor Specific Uptake After Systemic Administration BF = Brightfield; Fl = Fluorescence of identical area Enhanced Tumor Specific Uptake After Systemic Administration by Incorporation of a Fluorescent Small Molecule in TfRscFv/LipA-HoKC/GMC-5-193 Complex Incorporation of a Fluorescent GMC in the Nanoimmunocomplex Enhances Tumor Specific Uptake After Systemic Administration Inhibition of Melanoma Tumor Growth in Syngeneic Mice after Treatment with the GMC Nanoimmunocomplex (scL-GMC, scLHK-GMC)

Inhibition of Tumor Growth in Tumor ($B_{16}/F_{10}$)
Bearing Syngeneic Mice after Treatment with the
Combination of TfRscFv/LipA-HoKC/GMC-5-193
Complex plus CDDP Inhibition of Tumor Growth in Tumor Bearing Syngenic Mice after Treatment with the Combination of TfRscFv/LipA/GMC-5-193 Complex plus Cisplatin Cleaved Caspase-3 in the Serum of Tumor Bearing Syngeneic Mice After Treatment with the Combination of TfRscFv/Liposome/GMC-5-193 Complex plus CDDP

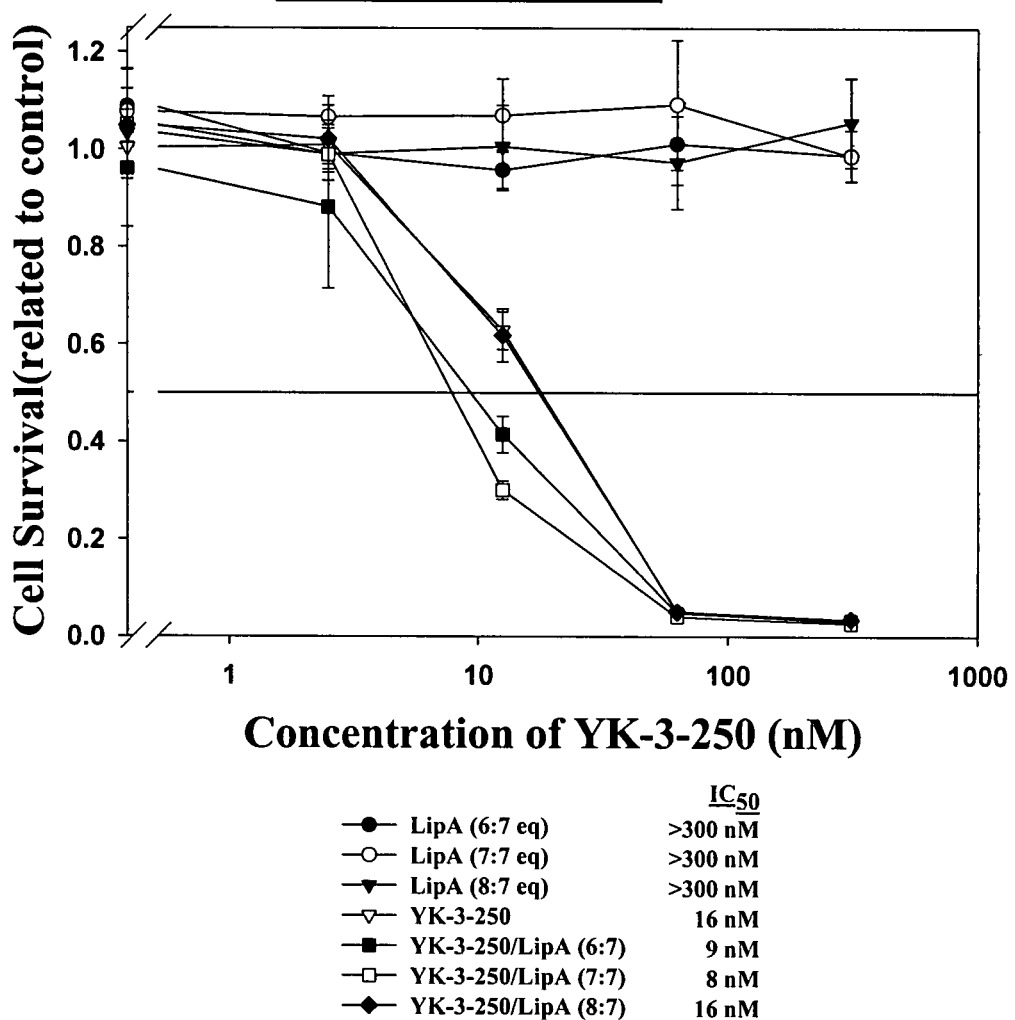

Comparison of the Effect of Nanoimmunocomplex
Delivered and Free Imatinib mesylate (GLEEVEC®)
on Human Prostate Cancer Cells

| | $IC_{50}$ |
|---|---|
| Imatinib mesylate (GLEEVEC®) in DMSO | >200 μM |
| Imatinib mesylate (GLEEVEC®) in Water | >200 μM |
| TfRscFv/LipA/ Imatinib mesylate (GLEEVEC®) in DMSO | 38 μM |
| TfRscFv/LipA/ Imatinib mesylate (GLEEVEC®) in Water | 35 μM |

Comparison of the Effect of Nanoimmunocomplex Delivered and Imatinib mesylate (GLEEVEC®) on MDA-MB-435 Human Melanoma Cells Effect of TfRscFv/LipA/Imatinib mesylate (GLEEVEC®) complex on B16-F10 cell line

| | $IC_{50}$ |
|---|---|
| TfRscFv/LipA/Imatinib mesylate (GLEEVEC®) | 32 µM |
| Imatinib mesylate (GLEEVEC®) | 60 µM |

Effect of Tumor Targeting Liposomal Delivery of Imatinib mesylate (GLEEVEC®) on Sensitization of MDA-MB 435 Human Melanoma Cells to Docetaxel (TAXOTERE®)

20uM Imatinib mesylate (GLEEVEC®)

Effect of Tumor Targeting Liposomal Delivery of Imatinib mesylate (GLEEVEC®) on Sensitization of MDA-MB 435 Human Melanoma Cells to Docetaxel (TAXOTERE®)

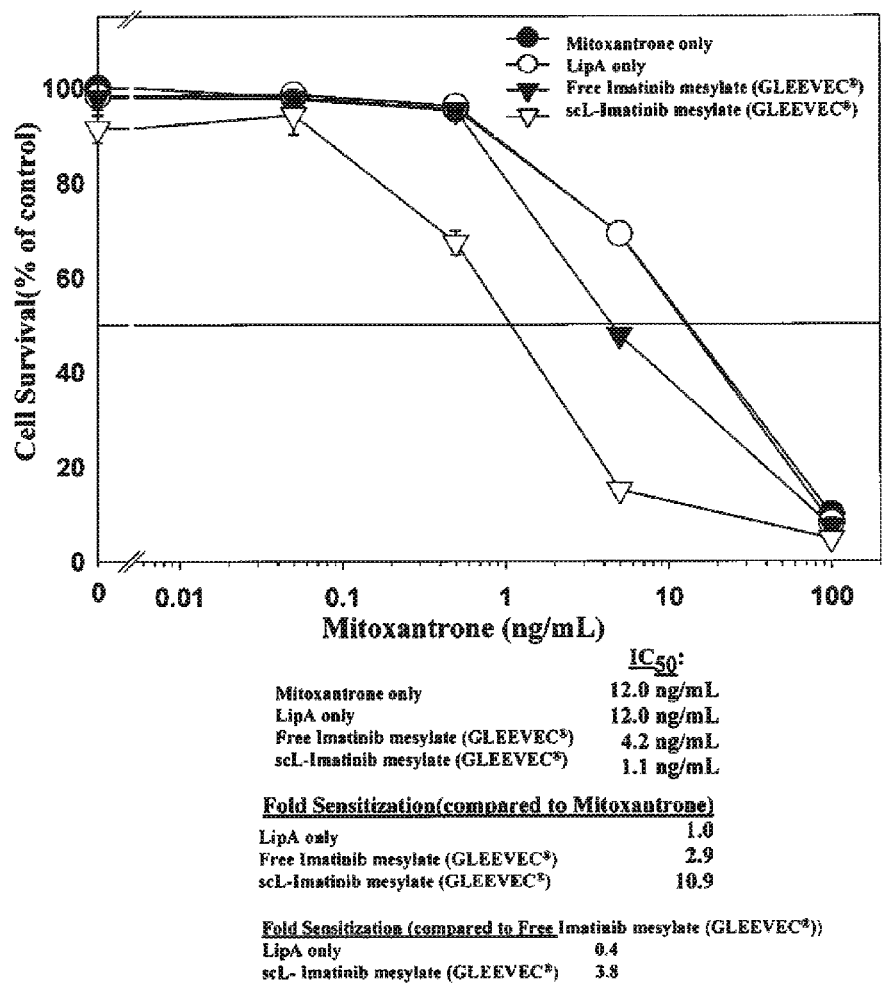

Fig. 26A

Effect of Tumor Targeting Liposomal Delivery of Imatinib mesylate (GLEEVEC®) on Sensitization of DU145 Human Prostate Cancer Cells to Mitoxantrone

$IC_{50}$:

| | |
|---|---|
| Mitoxantrone only | 12.0 ng/mL |
| LipA only | 12.0 ng/mL |
| Free Imatinib mesylate (GLEEVEC®) | 4.2 ng/mL |
| scL-Imatinib mesylate (GLEEVEC®) | 1.1 ng/mL |

Fold Sensitization (compared to Mitoxantrone)

| | |
|---|---|
| LipA only | 1.0 |
| Free Imatinib mesylate (GLEEVEC®) | 2.9 |
| scL-Imatinib mesylate (GLEEVEC®) | 10.9 |

Fold Sensitization (compared to Free Imatinib mesylate (GLEEVEC®))

| | |
|---|---|
| LipA only | 0.4 |
| scL-Imatinib mesylate (GLEEVEC®) | 3.8 |

20uM Imatinib mesylate (GLEEVEC®)

Fig. 26B

Effect of Tumor Targeting Liposomal Delivery of Imatinib mesylate (GLEEVEC®) on Sensitization of DU145 Human Prostate Cancer Cells to Mitoxantrone

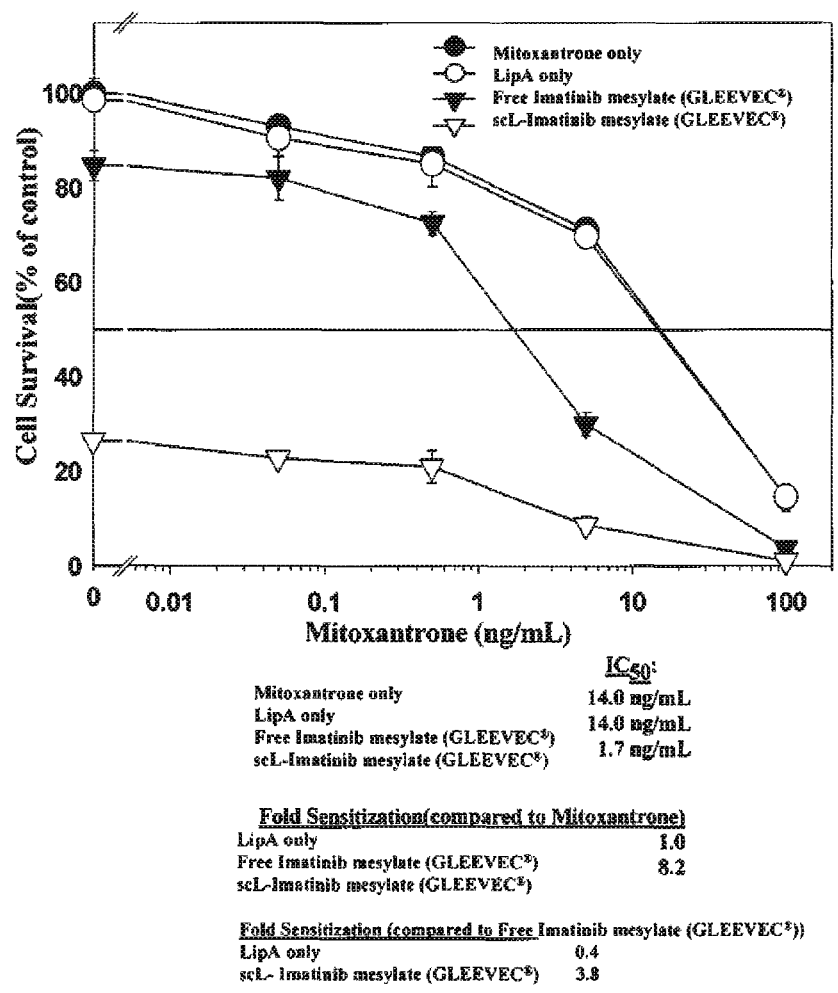

| | $IC_{50}$: |
|---|---|
| Mitoxantrone only | 14.0 ng/mL |
| LipA only | |
| Free Imatinib mesylate (GLEEVEC®) | 14.0 ng/mL |
| scL-Imatinib mesylate (GLEEVEC®) | 1.7 ng/mL |

| Fold Sensitization (compared to Mitoxantrone) | |
|---|---|
| LipA only | 1.0 |
| Free Imatinib mesylate (GLEEVEC®) | |
| scL-Imatinib mesylate (GLEEVEC®) | 8.2 |

| Fold Sensitization (compared to Free Imatinib mesylate (GLEEVEC®)) | |
|---|---|
| LipA only | 0.4 |
| scL- Imatinib mesylate (GLEEVEC®) | 3.8 |

30uM Imatinib mesylate (GLEEVEC®)

Effect of Tumor Targeting Liposomal Delivery of Imatinib mesylate (GLEEVEC®) on Sensitization of Panc-1 Human Pancreatic Cancer Cells to Gemcitabine (GEMZAR®)

20uM Imatinib mesylate (GLEEVEC®)

Effect of Tumor Targeting Liposomal Delivery of Imatinib mesylate (GLEEVEC®) on Sensitization of Panc-1 Human Pancreatic Cancer Cells to Gemcitabine (GEMZAR®)

30uM Imatinib mesylate (GLEEVEC®)

Effect of Tumor Targeting Liposomal Delivery of Imatinib mesylate (GLEEVEC®) on Sensitization of B16-F10 Mouse Melanoma Cells to Cisplatin

|  | $IC_{50}$: |
|---|---|
| Cisplatin only | 89 μM |
| LipA only | 68 μM |
| Free Imatinib mesylate (GLEEVEC®) | |
| TfRscFv/LipA/ Imatinib mesylate (GLEEVEC®) | |

30uM Imatinib mesylate (GLEEVEC®)

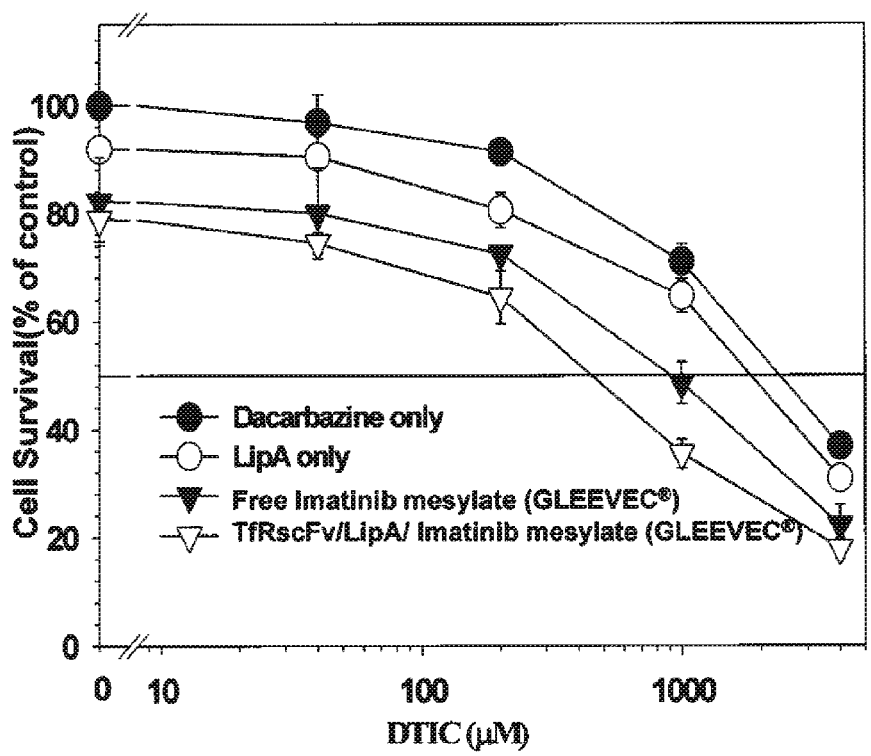

Fig. 29A

Effect of Tumor Targeting Liposomal Delivery of Imatinib Mesylate (GLEEVEC®) on Sensitization of B16-F10 Mouse Melanoma Cells to Dacarbazine (DTIC)

|  | $IC_{50}$: |
|---|---|
| DTIC only | 2300 μM |
| LipA only | 1800 μM |
| Free Imatinib mesylate (GLEEVEC®) | 900 μM |
| TfRscFv/LipA/ Imatinib mesylate (GLEEVEC®) | 430 μM |
| Fold Sensitization (compared to DTIC) | |
| LipA only | 1.3 |
| Free Imatinib mesylate (GLEEVEC®) | 2.6 |
| TfRscFv/LipA/Imatinib mesylate (GLEEVEC®) | 5.3 |
| Fold Sensitization (compared to Free Imatinib mesylate (GLEEVEC®)) | |
| LipA only | 0.5 |
| TfRscFv/LipA/Imatinib mesylate (GLEEVEC®) | 2.1 |

15 μM Imatinib mesylate (GLEEVEC®)

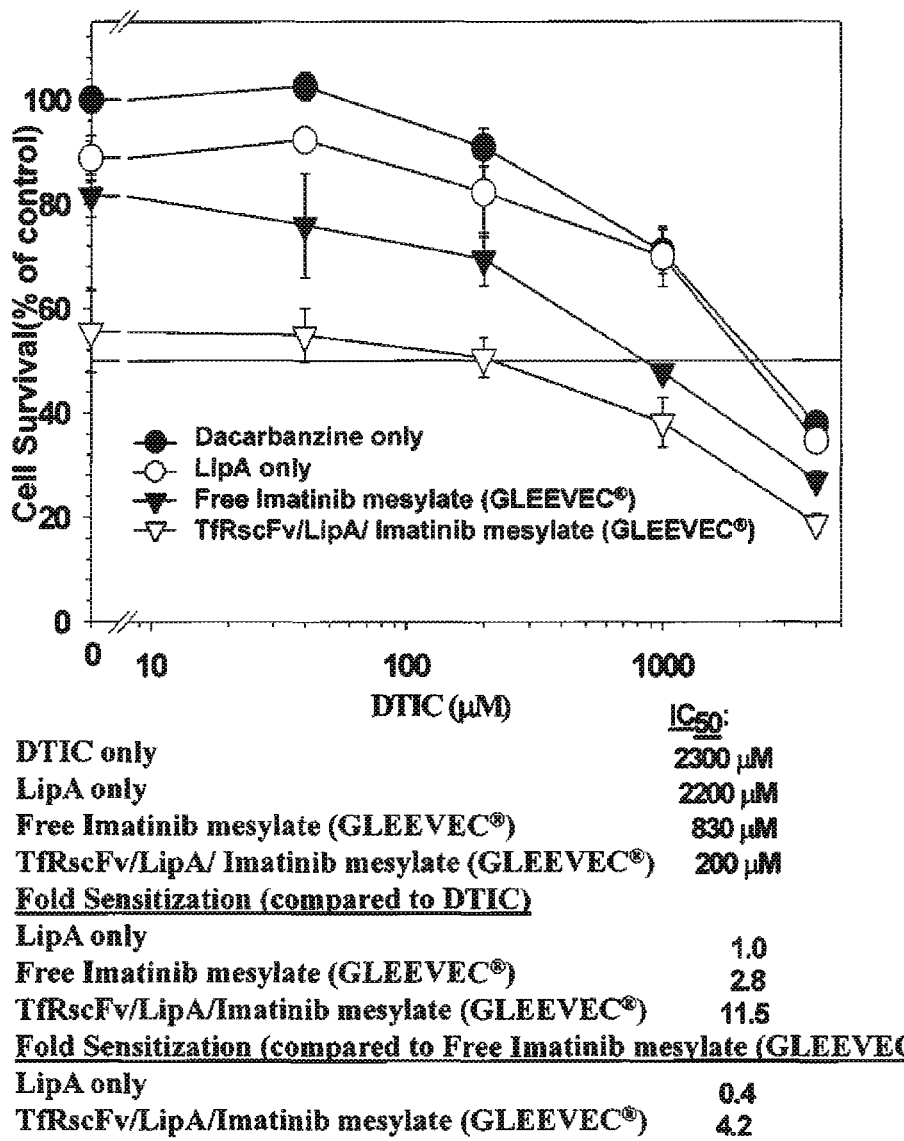

Fig. 29B

Effect of Tumor Targeting Liposomal Delivery of Imatinib Mesylate (GLEEVEC®) on Sensitization of B16-F10 Mouse Melanoma Cells to Dacarbazine (DTIC)

| | IC$_{50}$: |
|---|---|
| DTIC only | 2300 µM |
| LipA only | 2200 µM |
| Free Imatinib mesylate (GLEEVEC®) | 830 µM |
| TfRscFv/LipA/ Imatinib mesylate (GLEEVEC®) | 200 µM |

Fold Sensitization (compared to DTIC)

| | |
|---|---|
| LipA only | 1.0 |
| Free Imatinib mesylate (GLEEVEC®) | 2.8 |
| TfRscFv/LipA/Imatinib mesylate (GLEEVEC®) | 11.5 |

Fold Sensitization (compared to Free Imatinib mesylate (GLEEVEC®))

| | |
|---|---|
| LipA only | 0.4 |
| TfRscFv/LipA/Imatinib mesylate (GLEEVEC®) | 4.2 |

20 µM Imatinib mesylate (GLEEVEC®)

Effect of Tumor Targeting Liposomal Delivery of Imatinib Mesylate (GLEEVEC®) on Sensitization of B16-F10 Mouse Melanoma Cells to Dacarbazine (DTIC)

15 µM Imatinib mesylate (GLEEVEC®)

Effect of Tumor Targeting Liposomal Delivery of Imatinib Mesylate (GLEEVEC®) on Sensitization of B16-F10 Mouse Melanoma Cells to Dacarbazine (DTIC)

20 μM Imatinib mesylate (GLEEVEC®)

Effect of Tumor Targeting Liposomal Delivery of Imatinib Mesylate (GLEEVEC®) on Sensitization of H500 Human Normal Skin Fibroblasts Mitoxantrone

| | $IC_{50}$: |
|---|---|
| UT | > 100 ng/mL |
| LipA only | > 100 ng/mL |
| Free Imatinib mesylate (GLEEVEC®) | > 100 ng/mL |
| TfRscFv/LipA/ Imatinib mesylate (GLEEVEC®) | > 100 ng/mL |

20 µM Imatinib mesylate (GLEEVEC®)

Effect of Tumor Targeting Liposomal Delivery of Imatinib Mesylate (GLEEVEC®) on Sensitization of H500 Human Normal Skin Fibroblasts Docetaxel (TAXOTERE®)

| | $IC_{50}$: |
|---|---|
| UT | >100 nM |
| LipA only | >100 nM |
| Free Imatinib mesylate (GLEEVEC®) | >100 nM |
| TfRscFv/LipA/ Imatinib mesylate (GLEEVEC®) | >100 nM |

20 µM Imatinib mesylate (GLEEVEC®)

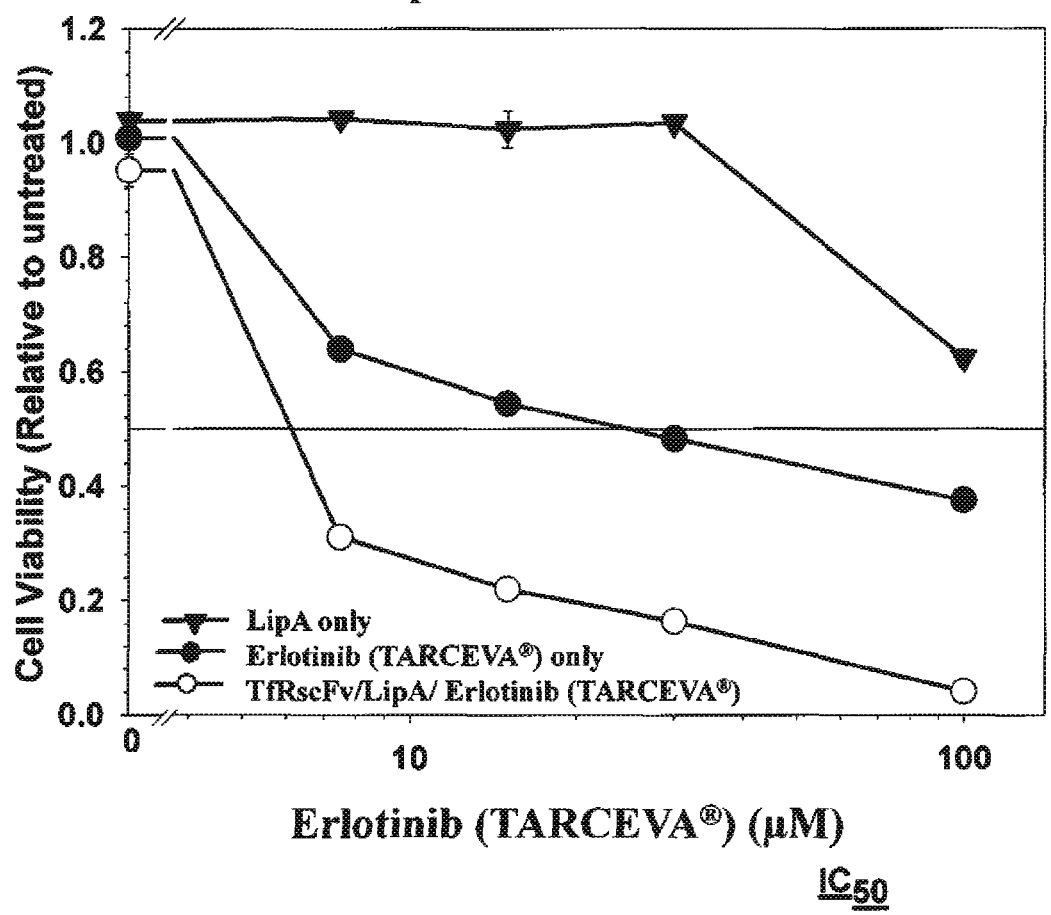

Effect of TfRscFv/LipA/Erlotinib (TARCEVA®) Complexes on 435G Cells

| | IC$_{50}$ |
|---|---|
| LipA only | > 100 µM |
| Erlotinib (TARCEVA®) only | = 40 µM |
| TfRscFv/LipA/ Erlotinib (TARCEVA®) | = 18 µM |

Fig. 33A

Effect of Tumor Targeting Liposomal Delivery of
Erlotinib (TARCEVA®) on Sensitization of DU 145
Human Prostate Cancer Cells to Mitoxantrone

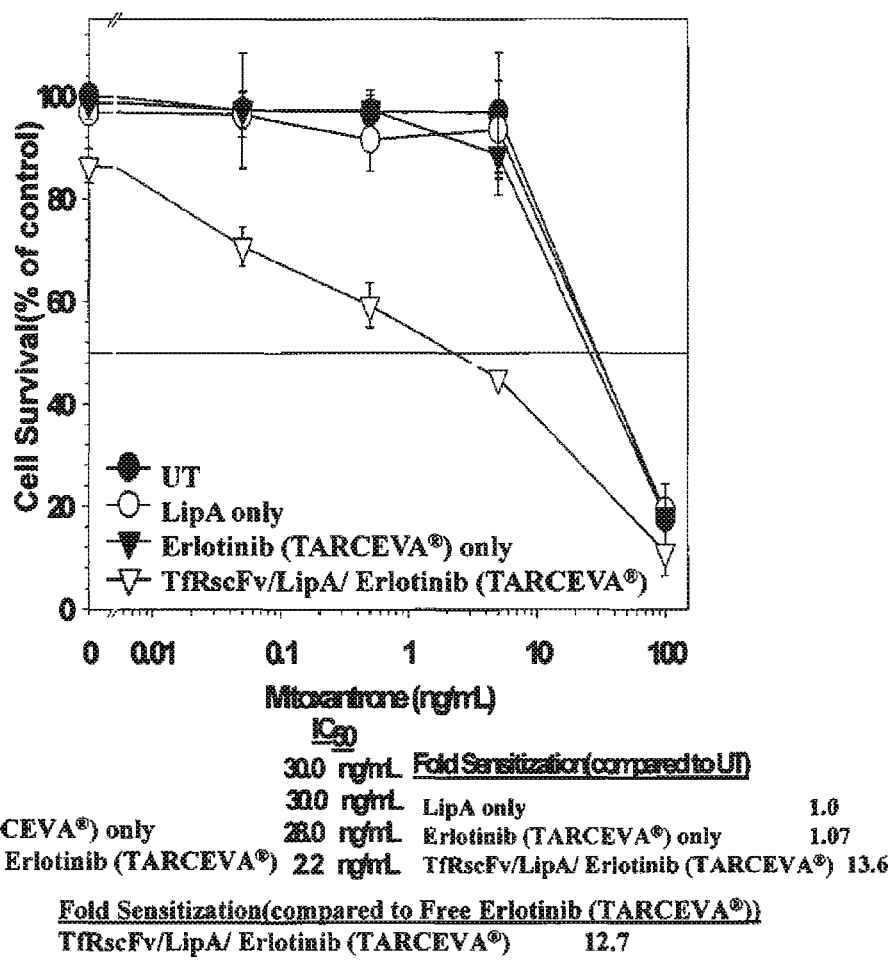

| | $IC_{50}$ | Fold Sensitization (compared to UT) | |
|---|---|---|---|
| UT | 30.0 ng/mL | | |
| LipA only | 30.0 ng/mL | LipA only | 1.0 |
| Erlotinib (TARCEVA®) only | 28.0 ng/mL | Erlotinib (TARCEVA®) only | 1.07 |
| TfRscFv/LipA/ Erlotinib (TARCEVA®) | 2.2 ng/mL | TfRscFv/LipA/ Erlotinib (TARCEVA®) | 13.6 |

Fold Sensitization (compared to Free Erlotinib (TARCEVA®))
TfRscFv/LipA/ Erlotinib (TARCEVA®)        12.7

3.75 µM Erlotinib (TARCEVA®)

Effect of Tumor Targeting Liposomal Delivery of Erlotinib (TARCEVA®) on Sensitization of DU 145 Human Prostate Cancer Cells to Mitoxantrone 7 μM Erlotinib (TARCEVA®)

Fig. 34A

Effect of Tumor Targeting Delivery of Erlotinib (TARCEVA®) on Sensitization of MDA-MB 435 Human Melanoma Cells to Docetaxel (TAXOTERE®)

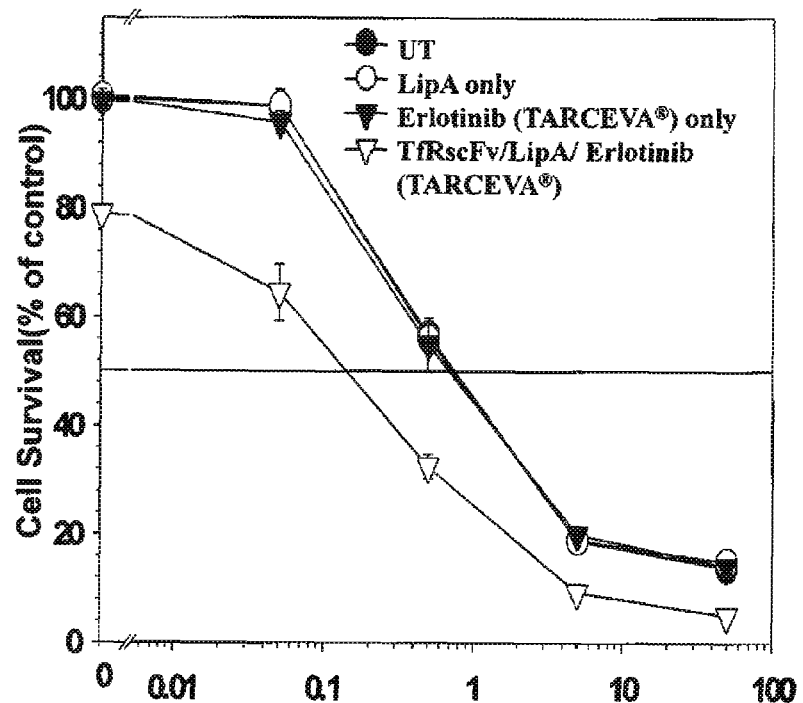

| | $IC_{50}$: Docetaxel (TAXOTERE®) (nM) | Fold Sensitization(compared to UT) | |
|---|---|---|---|
| UT | 0.75 nM | | |
| LipA only | 0.75 nM | LipA only | 1.0 |
| Erlotinib (TARCEVA®) only | 0.70 nM | Erlotinib (TARCEVA®) only | 1.07 |
| TfRscFv/LipA/ Erlotinib (TARCEVA®) | 0.15 nM | TfRscFv/LipA/ Erlotinib (TARCEVA®) | 5.0 |

Fold Sensitization(compared to Free Erlotinib (TARCEVA®))
TfRscFv/LipA/ Erlotinib (TARCEVA®)    4.6

3.75 µM Erlotinib (TARCEVA®)

Effect of Tumor Targeting Delivery of Erlotinib (TARCEVA®) on Sensitization of MDA-MB 435 Human Melanoma Cells to Docetaxel (TAXOTERE®)

| | IC₅₀ | Fold Sensitization (compared to UT) | |
|---|---|---|---|
| UT | 0.85 nM | | |
| LipA only | 0.80 nM | LipA only | 1.06 |
| Erlotinib (TARCEVA®) only | 0.50 nM | Erlotinib (TARCEVA®) only | 1.7 |
| TfRscFv/LipA/ Erlotinib (TARCEVA®) | <0.006 nM | TfRscFv/LipA/ Erlotinib (TARCEVA®) | >140 |

7.5 µM Erlotinib (TARCEVA®)

Fig. 35

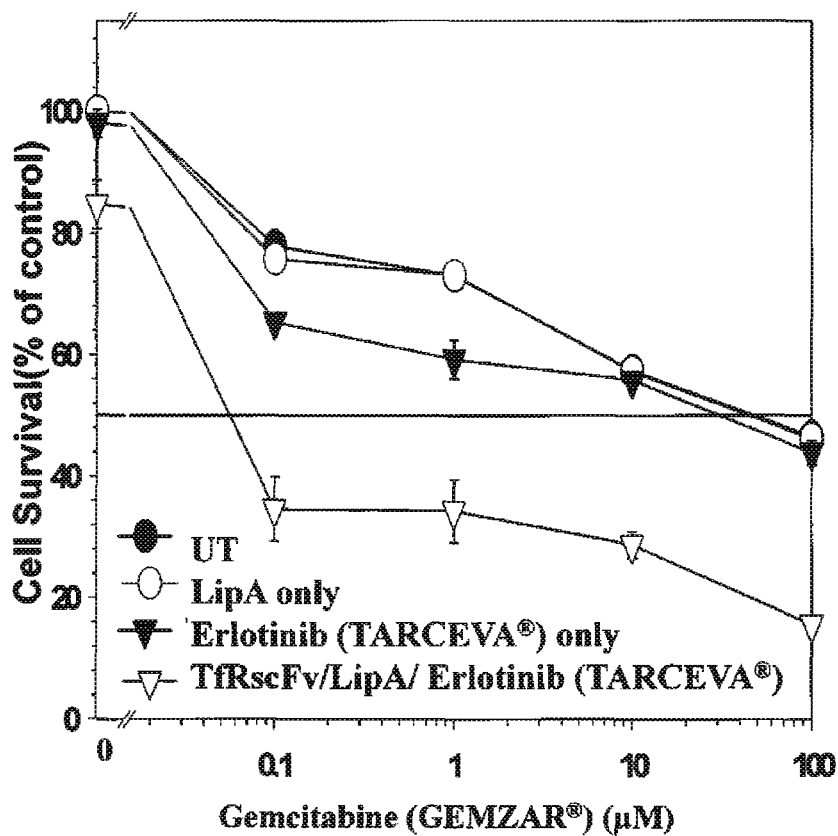

Effect of Tumor Targeting Delivery of Erlotinib (TARCEVA®) on Sensitization of MDA-MB 435 Human Melanoma Cells to Gemcitabine (GEMZAR®)

| | $IC_{50}$ | Fold Sensitization (compared to UT) | |
|---|---|---|---|
| UT | 450 µM | | |
| LipA only | 450 µM | LipA only | 1.0 |
| Erlotinib (TARCEVA®) only | 300 µM | Erlotinib (TARCEVA®) only | 1.5 |
| TfRscFv/LipA/ Erlotinib (TARCEVA®) | 0.055 µM | TfRscFv/LipA/ Erlotinib (TARCEVA®) | 818.0 |

Fold Sensitization(compared to Free Erlotinib (TARCEVA®))
TfRscFv/LipA/ Erlotinib (TARCEVA®)   545.0

7.5 µM Erlotinib (TARCEVA®)

Effect of Tumor Targeting Liposomal Delivery of Erlotinib (TARCEVA®) on Sensitization of H500 Human Skin Fibroblast to Mixoxantrone

| | IC$_{50}$: |
|---|---|
| UT | >100 ng/mL |
| LipA only | >100 ng/mL |
| Erlotinib (TARCEVA®) only | >100 ng/mL |
| TfRscFv/LipA/ Erlotinib (TARCEVA®) | >100 ng/mL |

Effect of Tumor Targeting Liposomal Delivery of Erlotinib (TARCEVA®) on Sensitization of H500 Human Skin Fibroblast to Docetaxel (TAXOTERE®)

Effect of Tumor Targeting Liposomal Delivery of Erlotinib (TARCEVA®) on Sensitization of H500 Human Skin Fibroblast to Gemcitabine (GEMZAR®)

| | $IC_{50}$: |
|---|---|
| UT | >100 μM |
| LipA only | >100 μM |
| Erlotinib (TARCEVA®) only | >100 μM |
| TfRscFv/LipA/ Erlotinib (TARCEVA®) | >100 μM |

Effect of Different Sunitinib (SUTENT®)/LipA Ratios in the TfRscFv/LipA/Sunitinib (SUTENT®) Complex on DU 145 Human Prostate Cancer Cells

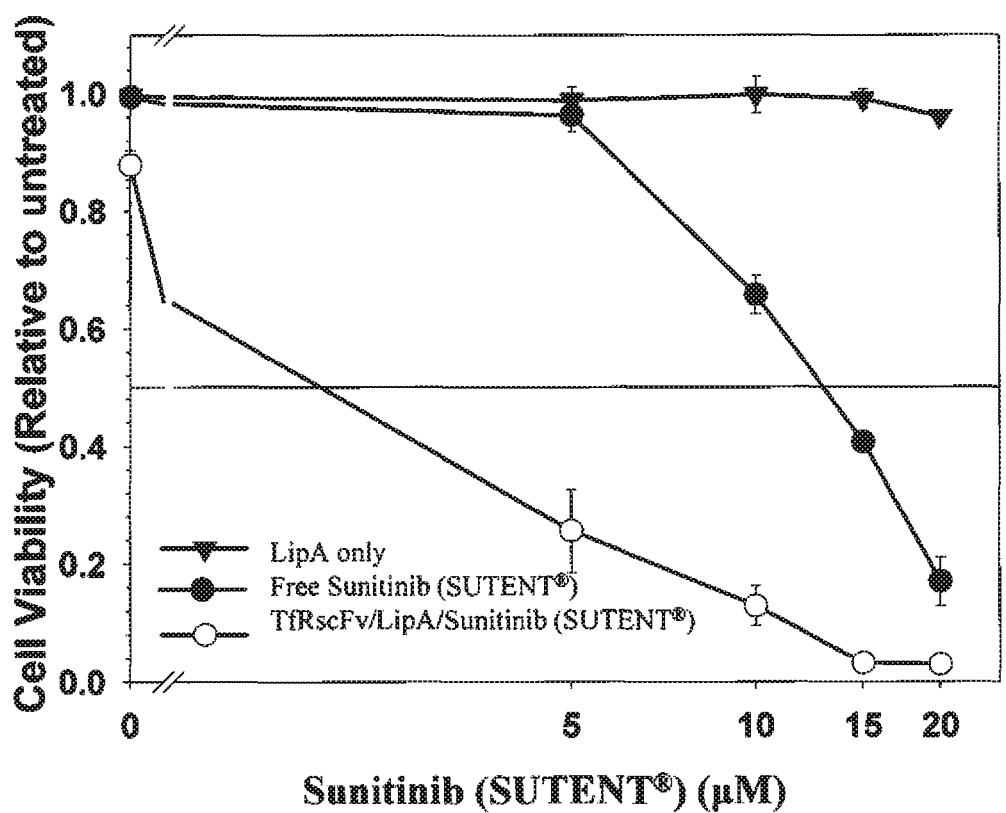

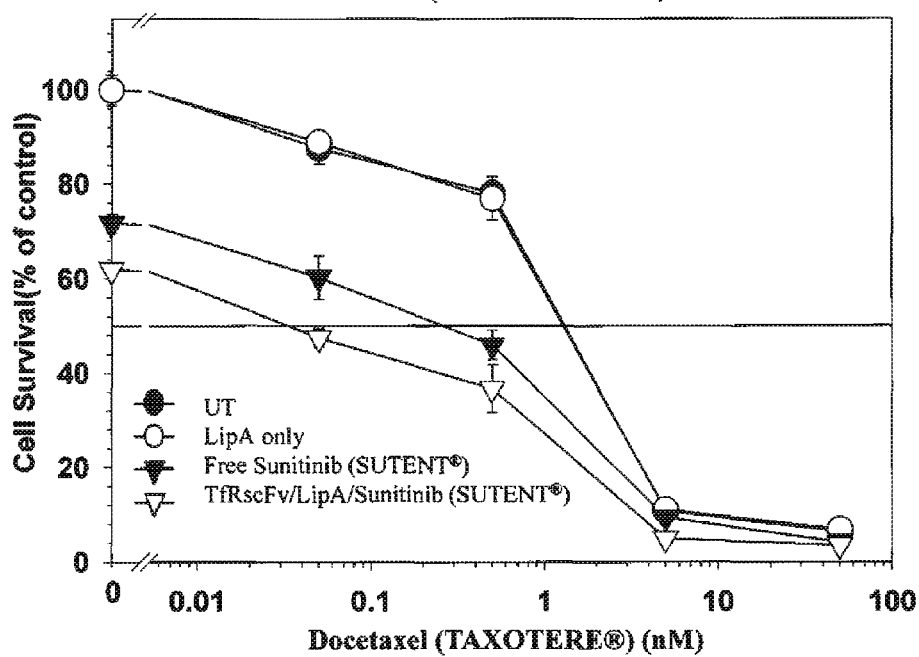

Fig 39A

Effect of Tumor Targeting Liposomal Delivery of Sunitinib (SUTENT®) on Sensitization of MDA-MB-435 Human Melanoma Cells to Docetaxel (TAXOTERE®)

|  | IC$_{50}$: |
|---|---|
| UT | 1.3nM |
| LipA only | 1.3nM |
| Free Sunitinib (SUTENT®) | 0.25 nM |
| TfRscFv/LipA/Sunitinib (SUTENT®) | 0.03 nM |
| Fold Sensitization (compared to UT) | |
| LipA only | 1.0 |
| Free Sunitinib (SUTENT®) | 5.2 |
| TfRscFv/LipA/Sunitinib (SUTENT®) | 0.03 |
| Fold Sensitization (compared to Free Sunitinib (SUTENT®)) | |
| TfRscFv/LipA/Sunitinib (SUTENT®) | 8.3 |

2.5 μM Sunitinib (SUTENT®)

Effect of Tumor Targeting Liposomal Delivery of Sunitinib (SUTENT®) on Sensitization of MDA-MB-435G Human Melanoma Cells to Docetaxel (TAXOTERE®)

|  | IC$_{50}$: |
|---|---|
| UT | 2.0 nM |
| LipA only | 2.0 nM |
| Free Sunitinib (SUTENT®) | 0.06 nM |
| TfRscFv/LipA/Sunitinib (SUTENT®) | |

|  | Fold Sensitization (compared to UT) |
|---|---|
| LipA only | 1.0 |
| Free Sunitinib (SUTENT®) | 50.0 |
| TfRscFv/LipA/Sunitinib (SUTENT®) | >300 |

5 µM Sunitinib (SUTENT®)

Effect of Tumor Targeting Liposomal Delivery of Sunitinib (SUTENT®) on Sensitization of DU 145 Human Prostate Cancer Cells to Mitoxantrone 5 μM Sunitinib (SUTENT®)

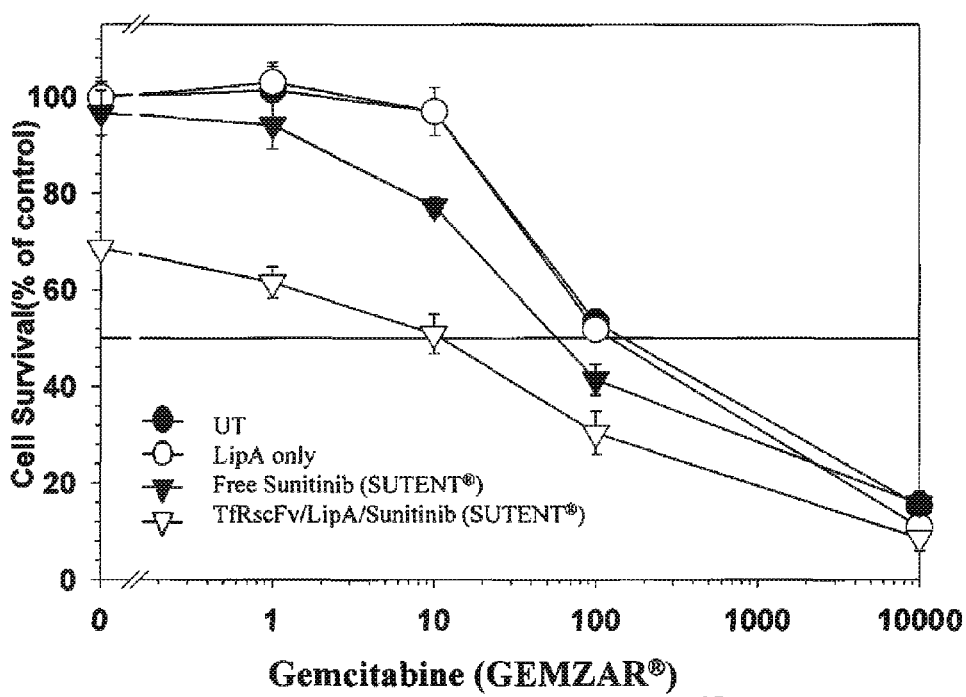

Fig. 41

Effect of Tumor Targeting Liposomal Delivery of Sunitinib (SUTENT®) on Sensitization of PANC-1 Human Pancreatic Cancer Cells to Gemcitabine (GEMZAR®)

|  | IC$_{50}$ |
|---|---|
| UT | 150nM |
| LipA only | 130nM |
| Free Sunitinib (SUTENT®) | 65 nM |
| TfRscFv/LipA/Sunitinib (SUTENT®) | 11 nM |
| Fold Sensitization (compared to UT) | |
| LipA only | 1.2 |
| Free Sunitinib (SUTENT®) | 5.2 |
| TfRscFv/LipA/Sunitinib (SUTENT®) | 13.6 |
| Fold Sensitization (compared to Free Sunitinib (SUTENT®)) | |
| TfRscFv/LipA/Sunitinib (SUTENT®) | 5.9 |

Effect of Tumor Targeting Liposomal Delivery of Sunitinib (SUTENT®) on Sensitization of H500 Normal Skin Fibroblasts to Mitoxantrone

| | $IC_{50}$: |
|---|---|
| UT | > 100 ng/mL |
| LipA only | > 100 ng/mL |
| Free Sunitinib (SUTENT®) | > 100 ng/mL |
| TfRscFv/LipA/Sunitinib (SUTENT®) | > 100 ng/mL |

2.5 µM Sunitinib (SUTENT®)

Effect of Tumor Targeting Liposomal Delivery of Sunitinib (SUTENT®) on Sensitization of H500 Normal Skin Fibroblasts to Docetaxel (TAXOTERE®)

| | $IC_{50}$: |
|---|---|
| UT | >100 nM |
| LipA only | >100 nM |
| Free Sunitinib (SUTENT®) | >100 nM |
| TfRscFv/LipA/Sunitinib (SUTENT®) | >100 nM |

2.5 µM Sunitinib (SUTENT®)

Effect of Tumor Targeting Liposomal Delivery of Sunitinib (SUTENT®) on Sensitization of IMR-90 Human Normal Lung Fibroblasts to Mitoxantrone

| | $IC_{50}$: |
|---|---|
| UT | > 100 ng/mL |
| LipA only | > 100 ng/mL |
| Free Sunitinib (SUTENT®) | > 100 ng/mL |
| TfRscFv/LipA/Sunitinib (SUTENT®) | > 100 ng/mL |

2.5 µM Sunitinib (SUTENT®)

Effect of Tumor Targeting Liposomal Delivery of Sunitinib (SUTENT®) on Sensitization of IMR-90 Human Normal Lung Fibroblasts to Docetaxel (TAXOTERE®)

| | $IC_{50}$: |
|---|---|
| UT | 42 nM |
| LipA only | 32 nM |
| Free Sunitinib (SUTENT®) | > 100 nM |
| TfRscFv/LipA/Sunitinib (SUTENT®) | > 100 nM |

2.5 µM Sunitinib (SUTENT®)

Effect of Tumor Targeting Liposomal Delivery of Sunitinib (SUTENT®) on Sensitization of IMR-90 Human Normal Lung Fibroblasts to Gemcitabine (GEMZAR®)

|  | IC$_{50}$: |
|---|---|
| UT | >10000 nM |
| LipA only | >10000 nM |
| Free Sunitinib (SUTENT®) | >10000 nM |
| TfRscFv/LipA/Sunitinib (SUTENT®) | >10000 nM |

2.5 µM Sunitinib (SUTENT®)

Comparison of Effects of TfRscFv/LipA/Gefitinib (IRESSA®) Complexes at Different Ratios of Gefitinib (IRESSA®) to Lip/A in MDA-MB-231 cells

| | $IC_{50}$: |
|---|---|
| Free Gefitinib (IRESSA®) | 26 μM |
| Gefitinib (IRESSA®)/LipA (14:7) | 22 μM |
| Gefitinib (IRESSA®)/LipA (7:7) | 14 μM |
| Gefitinib (IRESSA®)/LipA (3.5:7) | 12 μM |

Effect of TfRscFv/LipA/Gefitinib (IRESSA®) Complex on MDA-MB-231 Cell Survival

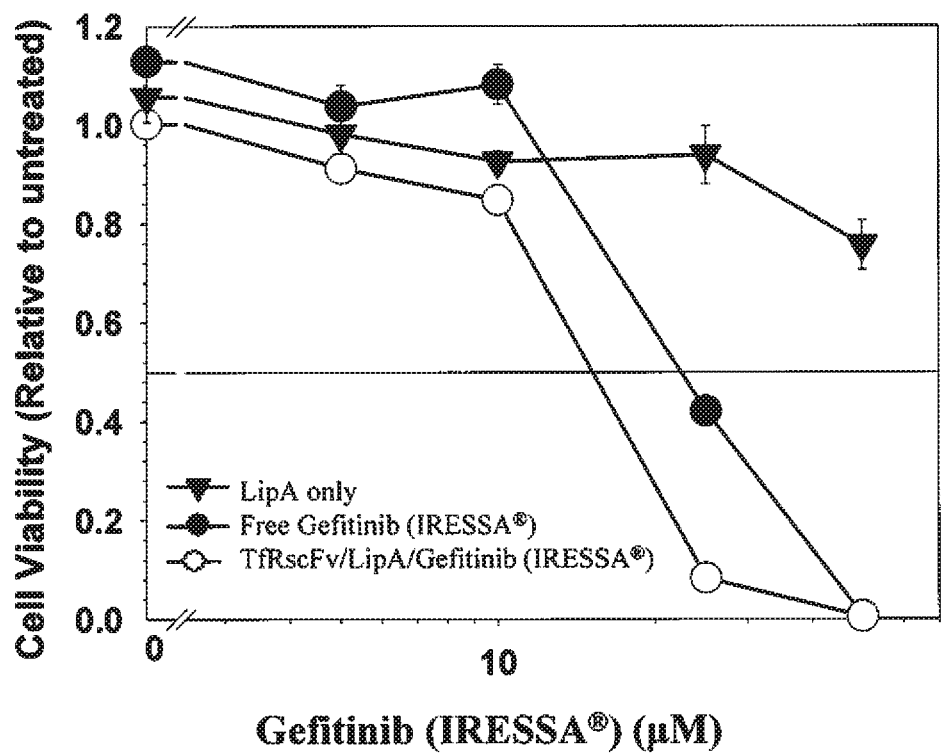

Fig. 46A

Effect of Tumor Tageting TfRscFv/LipA/Gefitinib (IRESSA®) Complex on Sensitization of MDA-MB-231 Human Breast Cancer Cells to Docetaxel (TAXOTERE®)

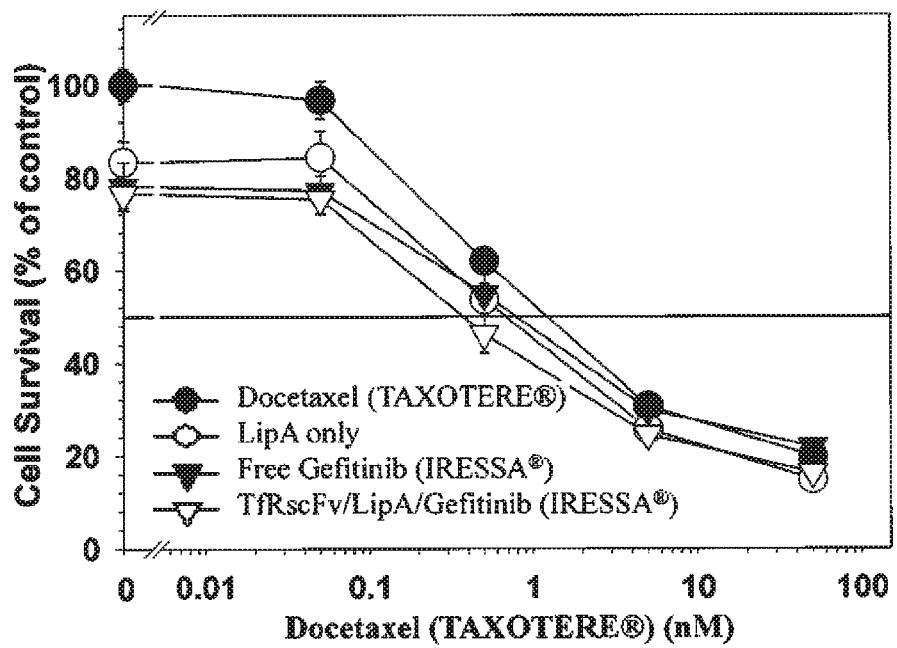

|  | IC$_{50}$: |
|---|---|
| Taxotere only | 1.2 nM |
| LipA only | 0.7 nM |
| Free Gefitinib (IRESSA®) | 0.8 nM |
| TfRscFv/LipA/Gefitinib (IRESSA®) | 0.35 nM |
| Fold Sensitization (compare to Docetaxel (TAXOTERE®)) | |
| LipA only | 1.7 |
| Free Gefitinib (IRESSA®) | 1.5 |
| TfRscFv/LipA/Gefitinib (IRESSA®) | 3.4 |
| Fold Sensitization (compare to Gefitinib (IRESSA®)) | |
| TfRscFv/LipA/Gefitinib (IRESSA®) | 2.3 |

12 µM Gefitinib (IRESSA®)

Fig. 46B

Effect of Tumor Tageting TfRscFv/LipA/Gefitinib (IRESSA®) Complex on Sensitization of MDA-MB-435 Human Melanoma Cells to Docetaxel (TAXOTERE®)

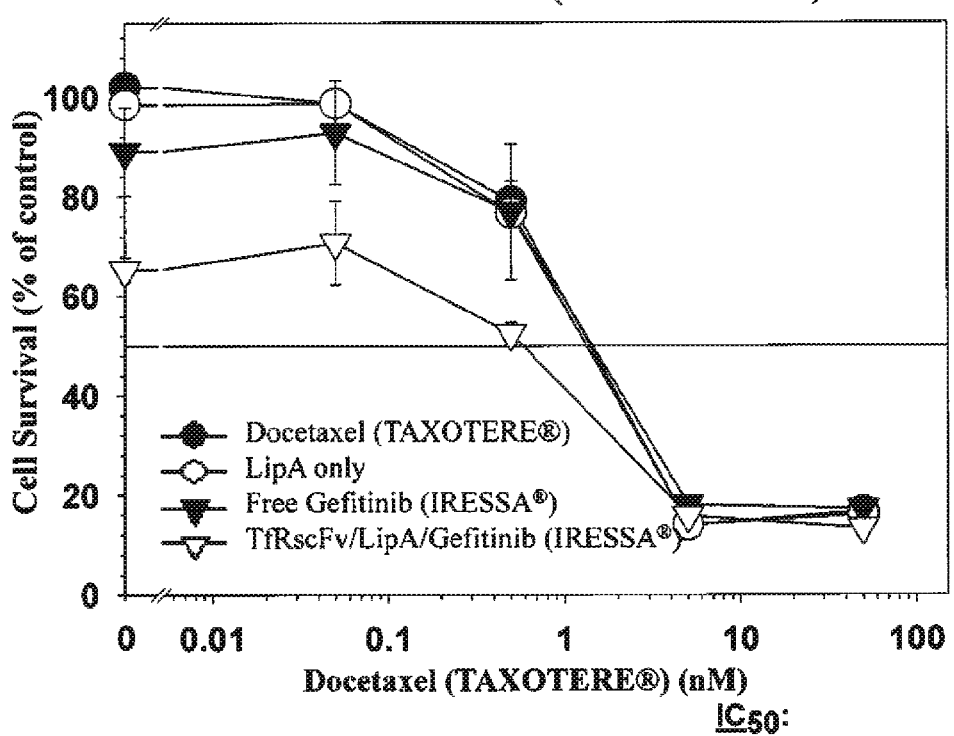

| | $IC_{50}$: |
|---|---|
| Taxotere only | 1.4 nM |
| LipA only | 1.4 nM |
| Free Gefitinib (IRESSA®) | 1.3 nM |
| TfRscFv/LipA/Gefitinib (IRESSA®) | 0.6 nM |
| Fold Sensitization (compare to Docetaxel (TAXOTERE®)) | |
| LipA only | 1.0 |
| Free Gefitinib (IRESSA®) | 1.1 |
| TfRscFv/LipA/Gefitinib (IRESSA®) | 2.3 |
| Fold Sensitization (compare to Gefitinib (IRESSA®)) | |
| TfRscFv/LipA/Gefitinib (IRESSA®) | 2.2 |

15 µM Gefitinib (IRESSA®)

Fig. 46C

Effect of Tumor Tageting TfRscFv/LipA/Gefitinib (IRESSA®) Complex on Sensitization of MDA-MB-435 Human Melanoma Cells to Mitoxantrone

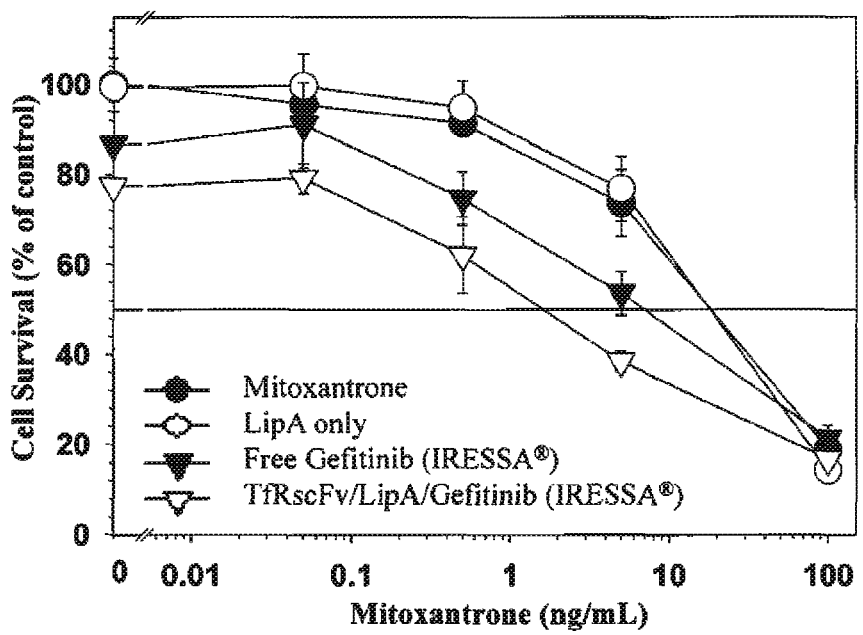

| | $IC_{50}$: |
|---|---|
| Mitoxantrone only | 1.4 ng/mL |
| LipA only | 1.4 ng/mL |
| Free Gefitinib (IRESSA®) | 1.3 ng/mL |
| TfRscFv/LipA/Gefitinib (IRESSA®) | 0.6 ng/mL |
| Fold Sensitization (compare to Mitoxantrone) | |
| LipA only | 1.0 |
| Free Gefitinib (IRESSA®) | 1.1 |
| TfRscFv/LipA/Gefitinib (IRESSA®) | 2.3 |
| Fold Sensitization (compare to Gefitinib (IRESSA®)) | |
| TfRscFv/LipA/Gefitinib (IRESSA®) | 2.2 |

8 µM Gefitinib (IRESSA®)

PREPARATION OF ANTIBODY OR AN ANTIBODY FRAGMENT-TARGETED IMMUNOLIPOSOMES FOR SYSTEMIC ADMINISTRATION OF THERAPEUTIC OR DIAGNOSTIC AGENTS AND USES THEREOF

CROSS REFERENCE TO RELATED APPLICATIONS

The present application is a continuation-in-part of U.S. application Ser. No. 10/113,927, filed Apr. 2, 2002, now U.S. Pat. No. 7,780,882, which is a continuation-in-part of U.S. application Ser. No. 09/914,046, filed Oct. 1, 2001, now U.S. Pat. No. 7,479,276. U.S. application Ser. No. 09/914,046, is a U.S. National Phase Application under 35 U.S.C. §371 of PCT/US00/04392, filed Feb. 22, 2000, which claims the benefit of U.S. Provisional Application No. 60/121,133, filed Feb. 22, 1999. U.S. application Ser. No. 10/113,927 also claims the benefit of U.S. Provisional Application No. 60/280,134, filed Apr. 2, 2001. The present application also claims the benefit of U.S. Provisional Application Nos. 60/800,163, filed May 15, 2006 and 60/844,352, filed Sep. 14, 2006. The disclosures of each of these applications are incorporated by reference herein in their entireties for all purposes.

BACKGROUND OF THE INVENTION

1. Field of the Invention

This invention provides a method of making antibody- or antibody fragment-targeted immunoliposomes and antibody- or antibody fragment-targeted polymers useful for the systemic delivery of molecules to treat diseases. The liposome and polymer complexes are useful for carrying out delivery of small molecules, as well as targeted gene delivery and efficient gene expression after systemic administration. The specificity of the delivery system is derived from the targeting antibodies or antibody fragments.

2. Related Art

The ideal therapeutic for cancer would be one that selectively targets a cellular pathway responsible for the tumor phenotype and would be nontoxic to normal cells. To date, the ideal therapeutic remains just that—an ideal. While cancer treatments involving gene therapy have substantial promise, there are many issues that need to be addressed before this promise can be realized. Perhaps foremost among the issues associated with macromolecular treatments is the efficient delivery of the therapeutic molecules to the site(s) in the body where they are needed. The ideal delivery vehicle would be one that could be systemically administered and then home to tumor cells wherever they occur in the body. A variety of delivery systems ("vectors") have been tried, including viruses and liposomes. The infectivity that makes viruses attractive as delivery vectors also poses their greatest drawback. Residual viral elements can be immunogenic, cytopathic or recombinogenic. The generation of novel viruses with new targets for infection also raises the theoretical possibility that, once introduced into patients, these viruses could be transformed via genetic alteration into new human pathogens. Consequently, a significant amount of attention has been directed at non-viral vectors for the delivery of molecular therapeutics. The liposome approach offers a number of advantages over viral methodologies for gene delivery. Most significantly, they lack immunogenicity. Moreover, since liposomes are not infectious agents capable of self-replication, they pose no risk of evolving into new classes of infectious human pathogens.

Targeting cancer cells via liposomes can be achieved by modifying the liposomes so that they selectively deliver their payload to tumor cells. Surface molecules can be used to target liposomes to tumor cells, because the molecules that decorate the exterior of tumor cells differ from those on normal cells. For example, if a liposome has the protein transferrin (Tf) or an antibody that recognizes transferrin receptor (TfR) on its surface, it will home to cancer cells that have higher levels of the TfR. Such liposomes designed to home to tumors have been likened to "smart" bombs capable of seeking out their target.

Failure to respond to therapy represents an unmet medical need in the treatment of many types of cancer, including prostate cancer. Often when cancer recurs, the tumors have acquired increased resistance to radiation or chemotherapeutic agents. The incorporation into currently used cancer therapies of a new component which results in radio-/chemo-sensitization would have immense clinical relevance. One way in which such sensitization could be achieved is via gene therapy (i.e., delivery of a gene the expression of which results in increased sensitization). In PCT patent application WO 00/50008 (published 31 Aug. 2000), incorporated herein by reference, we provided proof-of-principle that an anti-transferrin receptor single chain antibody (TfRscFv) can be chemically conjugated to a cationic liposome. Moreover, this TfRscFv directed liposome delivery system can deliver genes and other molecules systemically and specifically to tumors.
Immunoliposomes and Cationic Polymers as Gene Transfer Vehicles As noted above, some of the problems associated with using viral vectors could be circumvented by non-viral gene transfer vectors. Progress has been made toward developing non-viral, pharmaceutical formulations of genes for in vivo human therapy, particularly cationic liposome-mediated gene transfer systems (31, 32). Cationic liposomes are composed of positively charged lipid bilayers and can be complexed to negatively charged, naked DNA by simple mixing of lipids and DNA such that the resulting complex has a net positive charge. The complex can be bound and taken up by cells in culture with moderately good transfection efficiency (33). Features of cationic liposomes that make them versatile and attractive for DNA delivery include: simplicity of preparation; the ability to complex large amounts of DNA; versatility in use with any type and size of DNA or RNA; the ability to transfect many different types of cells, including non-dividing cells; and lack of immunogenicity or biohazardous activity (reviewed in 34, 35). More importantly from the perspective of human cancer therapy, cationic liposomes have been proven to be safe and efficient for in vivo gene delivery (33, 34, 36). At least 99 clinical trials have been approved using cationic liposomes for gene delivery (37), and liposomes for delivery of small molecule therapeutics (e.g., antifungal agents) are already on the market.

Researchers also have considered the suitability of cationic polymers as transfer vectors for delivery of therapeutic agents in vivo. For example, Polyethyleneimine (PEI) is the organic macromolecule with the highest cationic-charge-density potential, and a versatile vector for gene and oligonucleotide transfer in vitro and in vivo, as first reported by Boussif et al. (66). Since then, there has been a flurry of research aimed at this polycation and its role in gene therapy (73). Cell-binding ligands can be introduced to the polycation to 1) target specific cell types and 2) enhance intracellular uptake after binding the target cell (13). Erbacher et al. (67) conjugated the integrin-binding peptide 9-mer RGD via a disulfide bridge and showed physical properties of interest for systemic gene delivery.

The transfection efficiency of both cationic liposomes and cationic polymers, such as PEI, can be increased dramatically when they bear a ligand recognized by a cell surface receptor. Receptor-mediated endocytosis represents a highly efficient internalization pathway present in eukaryotic cells (38, 39). The presence of a ligand on a liposome facilitates the entry of DNA into cells through initial binding of ligand by its receptor on the cell surface followed by internalization of the bound complex. Transferrin receptor (TfR) levels are elevated in various types of cancer cells including, but not limited to, breast, pancreatic, head and neck, and prostate cancers (40), even those prostate cell lines derived from human lymph node and bone metastases (40-43). Elevated TfR levels also correlate with the aggressive or proliferative ability of tumor cells (44). Therefore, TfR is a potential target for drug delivery in the therapy of malignant cell growth (45, 46). In our laboratory, we have prepared transferrin-complexed cationic liposomes with tumor cell transfection efficiencies in SCCHN of 60%-70%, as compared to only 5-20% by cationic liposomes without ligand (47). Also see published PCT patent application WO 00/50008.

In addition to the use of ligands that are recognized by receptors on tumor cells, specific antibodies also can be attached to the liposome surface (48) enabling them to be directed to specific tumor surface antigens (including but not limited to receptors) (49). These "immunoliposomes," especially the sterically stabilized immunoliposomes, can deliver therapeutic drugs to a specific target cell population (50). Parks et al. (51) found that anti-HER-2 monoclonal antibody (MAb) Fab fragments conjugated to liposomes could bind specifically to a breast cancer cell line, SK-BR-3, that overexpresses HER-2. The immunoliposomes were found to be internalized efficiently by receptor-mediated endocytosis via the coated pit pathway and also possibly by membrane fusion. Moreover, the anchoring of anti-HER-2 Fab fragments enhanced their inhibitory effects. More recently, Park et al. (23) used an anti-HER-2 immunoliposome composed of long circulating liposomes chemically conjugated to anti-HER-2 monoclonal antibody scFv fragments to deliver doxorubicin to breast cancer tumors even though HER-2 was not overexpressed. A number of other studies have been published which have employed antibodies against tumor specific antigens coupled to liposomes, primarily sterically stabilized liposomes, to target tumor cells for delivery of prodrugs and drugs in vitro or in vivo (52-56). These studies demonstrated the utility of immunoliposomes for tumor-targeting drug delivery. The combination of cationic liposome-gene transfer and immunoliposome techniques appears to be a promising system for targeted gene therapy and is the subject of this application.

Progress in biotechnology has allowed the derivation of specific recognition domains from MAb (57). The recombination of the variable regions of heavy and light chains and their integration into a single polypeptide provides the possibility of employing single-chain antibody derivatives (designated scFv) for targeting purposes. Thus, a scFv based on the anti-TfR MAb 5E9 (52) contains the complete antibody binding site for the epitope of the TfR recognized by this MAb as a single polypeptide chain of approximate molecular weight 26,000. This TfRscFv is formed by connecting the component VH and VL variable domains from the heavy and light chains, respectively, with an appropriately designed peptide. The peptide bridges the C-terminus of the first variable region and N-terminus of the second, ordered as either VH-peptide-VL or VL-peptide-VH. The binding site of an scFv can replicate both the affinity and specificity of its parent antibody combining site.

The TfRscFv has advantages in human use over the Tf molecule itself or even an entire MAb to target liposomes or cationic polymers to cancer cells with elevated levels of the TfR for a number of reasons. First, the size of the scFv (~28 kDa) is much smaller than that of the Tf molecule (~80 kDa) or the parental MAb (~150 kDa). The scFv-liposome-therapeutic agent complex or scFv-polymer-therapeutic agent complex thus may exhibit better penetration into small capillaries characteristic of solid tumors. Second, the smaller scFv also has practical advantages related to its production as a recombinant protein. Large scale production of the TfRscFv will be required for the therapy envisioned in this invention to be taken into eventual human trials. Third, the scFv is a recombinant molecule (not a blood product like Tf) and, therefore, presents no issues related to potential contamination with blood borne pathogens. Additional advantages of using the TfRscFv relate to the fact that Tf interacts with the TfR with high affinity only after the ligand is loaded with iron. Large-scale production of liposomes containing iron-loaded Tf may present practical challenges. Thus, use of TfRscFv enables the tumor cell TfR to be targeted by a liposomal therapeutic complex that does not contain iron (itself implicated in cancer (58)). Fourth, without the Fc region of the MAb, the problem of non-antigen-specific binding through Fc receptors is eliminated (57).

p53 Tumor Suppressor Gene and the Pathogenesis of Prostate Cancer

The tumor suppressor gene p53 plays a crucial role in diverse cellular pathways including those activated in response to DNA damage, such as DNA repair, regulation of the cell cycle and programmed cell death (apoptosis) (1). Malfunctions of these critical cell pathways are associated with the process of tumorigenesis. Loss of functional p53, which has been implicated in over 60% of human cancers, can occur either through mutations in the p53 gene itself (the most common occurrence), or through other mechanisms such as amplification of the MDM-2 gene (found in certain sarcomas, and other cancers), or association of p53 with the E6 protein of human papilloma virus (which likely plays a role in cervical carcinoma) (2).

The loss of p53 function is of relevance to a broad array of cancer types, with non-functional p53 associated with, for example, 15-50% of breast cancer, 25-70% of metastatic prostate cancer, 25-75% of lung cancer, and 33-100% of head and neck cancers (3). The presence of mutant p53 also has been associated with an unfavorable prognosis for many human cancers including lung, colon, and breast (3), and mutant p53 is rarely found in some of the most curable forms of cancer e.g., Wilm's tumor, retinoblastoma, testicular cancer, neuroblastoma and acute lymphoblastic leukemia (4). In addition, p53 protein transcriptionally regulates genes involved in angiogenesis, a process required for solid tumor growth (5). Volpert et al. have proposed that development of the angiogenic phenotype for these tumors requires the loss of both p53 alleles (6).

Since it appears that most anti-cancer agents work by inducing apoptosis (20), inhibition of or changes in this pathway may lead to failure of therapeutic regimens. A direct link has been suggested between mutations in p53 and resistance to cytotoxic cancer treatments (both chemo- and radiotherapy (21)). It has also been suggested that the loss of p53 function may contribute to the cross-resistance to anti-cancer agents observed in some tumor cells (22).

Restoration of p53 function could, therefore result in sensitization of primary prostate tumors and even metastases to radio-/chemo-therapy. The introduction of wtp53 has been reported to suppress, both in vitro and in mouse xenograft models, the growth of various types of malignancies, e.g., prostate (23,24), head and neck (25,26), colon (27), cervical (28) and lung (15,29) tumor cells. However, p53 alone, while being able to partially inhibit tumor growth, has not been shown to be able to eliminate established tumors. Significantly, however, we have demonstrated that the combination of systemically delivered liposome-p53 and radiation led to complete long-term tumor regression of established head and neck xenograft tumors (25,30).

In summary, the implication of the p53 gene in a significant fraction of human cancers makes it one of the premiere candidates for cancer gene therapy. Based on a growing body of evidence related to p53 functions, effective restoration of these functions in tumor cells might be expected to re-establish normal cell growth control, restore appropriate responses to DNA-damaging agents (e.g., chemotherapy and radiotherapy), and to impede angiogenesis.

The sensitization of tumors to chemotherapy and radiation could lower the effective dose of both types of anticancer modalities, correspondingly lessening the severe side effects often associated with these treatments. Until now the vast majority of p53 gene therapy protocols have employed wtp53 gene replacement alone. Based upon the current literature and our data (30, 59), it appears that wtp53 replacement alone, while able to inhibit tumor growth to some extent, is insufficient to eliminate tumors long term. Therefore, it appears that a combinatorial approach involving both standard therapy and targeted gene therapy has substantial promise as a novel and more effective clinical modality for cancer treatment. Moreover, the demonstrated tumor cell selectivity of our systemically delivered ligand-liposome wtp53 complex indicates the potential of this method to sensitize even the distant micrometastases that are the ultimate cause of so many prostate cancer deaths.

Components of intracellular signaling pathways including, but not limited to receptor tyrosine kinases (RTKs) and non-receptor tyrosine kinases (non-RTKs), are crucial mediators of many critical pathways including cell proliferation, differentiation, migration, angiogenesis, cell cycle regulation etc. (Baselga, Science 312, 1175-1178 (2006), Arora and Scholar, J Pharmacol Exp Ther 315, 971-979 (2005), Krause and Van Etten N Eng J Med 353, 172-187 (2005)). Many of these crucial pathways are deregulated in cancer cells. Thus, RTKs and non-RTKs are good targets for cancer therapeutics. One class of such therapeutics are small molecules including, but not limited to those that target growth factor receptors and thus affect these signaling pathways (Imai and Takoka, Nature Reviews: Cancer 6, 714-727 (2006)). These inhibitors compete with ATP (ATP mimetics) and inhibit kinase activity. One of the first successful small molecule inhibitors is Imatinib mesylate (GLEEVEC®). This small molecule inactivates the kinase activity of BCR-ABL fusion protein in CML (Druker Trends in Molecular Medicine 8, S14-S18 (2002)), and has shown significant efficacy in the treatment of patients with Philadelphia chromosome positive CML. It is also an inhibitor of other TKs, including KIT and PDGFRα and PDGFRβ KIT is involved in metastatic GISTs and the two platelet derived growth factor receptors are involved in tumors such as glioblastoma and dermatofibrosarcoma protuberans. Because it is a member of the EGF superfamily, EGFR is also a logical target for small molecule inhibitors. Gefitinib (IRESSA®) (Herbst et al Nature reviews Cancer 4, 9560965 (2004)) and erlotinib (TARCEVA®) (Minna and Dowell Nature Reviews Drug Discovery Suppl. S14-S15 (2005)) selectively inhibit EGFR and have shown efficacy against EGFR expressing cancers such as NSCLC and squamous cell carcinomas of the head and neck. They have also shown efficacy in Phase II trials in combination with chemotherapeutic agents. The combination of erlotinib and chemotherapeutic agent gemcitibine (an anti-metabolite) has been approved for use in treating advanced pancreatic cancer. Several Phase III trials of Gefitinib are on going (Chai and Grandis Current Treat Opin Oncol 7, 3-11 (2006)).

Small Molecule agents can translocate through the plasma membrane and interact with the cytoplasmic domain of the cell surface receptors and intracellular signaling molecules. Thus, small molecules are also being developed that affect cancer cell proliferation and survival by inhibiting RAS prenylation, RAF-MEK kinase, PI3Kinase, the mTOR pathway (the mammalian target of rapamycin, and even heat shock protein 9). They can also affect cell adhesion and invasion by inhibiting SRC kinase or matrix metalloproteinases. Inhibition of vascular endothelial growth factor (VEGF) by small molecules can also inhibit neovascularization of tumors.

A new type of small molecule agent, Sorafenib (Nexavar) exerts its inhibitory effect on different isoforms of RAF serine kinase as well as various RTKs (VEGF, EGFR, and PDGF) (Arora and Scholar, J Pharmacol Exp Ther 315, 971-979 (2005)). This "dual-action" kinase inhibitor shows broad-spectrum anti-tumor activity by inhibiting tumor proliferation and angiogenesis (Marx Science 308, 1248-1249 (2005)). Sunitinib malate (SUTENT®) is also a multitargeted TK inhibitor of VEGF, PDGFR, KIT and FLIT3 (Marx Science 308, 1248-1249 (2005)). Potential targets for small molecule agents have also been identified in the ubiquitin-proteosome pathway which is crucial in cell cycle arrest and apoptosis (programmed cell death). A selective, reversible inhibitor of the chymotryptic protease in the 26S proteosome, Bortezomb (Velcade), has been reported to be effective against various cancers, particularly hematological malignancies The anti-EGFR TK inhibitors are synthetic chemicals of ~500 Da that are administered orally, with half-lives of ~46 hours for (IRESSA®) and ~36 hours for TARCEVA®. Because they are administered orally rather than intravenously, plasma concentrations at the same dose of the small molecule therapeutic can vary between patients (Dancy and Sausville Nature Rev Drug Discov 2, 116-124 (2003)). This is a disadvantage of these agents as currently used. Thus encapsulating small molecule agents in a tumor-targeting delivery complex that can be administered intravenously consistently at the same dose, such as that of this invention, would improve their use as therapeutic agents. Furthermore, encapsulation in such a ligand-liposome complex would protect the small molecule agents from degradation further enhancing their efficacy. Untargeted orally administered small molecule agents are not specific for tumor cells, a fact which increases the risk of normal cell toxicity and adverse side effects. While these side effects are generally mild (e.g. rash, acne, dry skin and pruritis) the gastrointestinal toxicities (nausea, vomiting, anorexia and particularly diarrhea) can be dose limiting. The most common side effect, skin rash, is possibly due to non-specific effects on the target kinase in the epidermis (Herbst et al Clin Lung Caner 4, 366-369 (2003)). Thus, delivery by a tumor cell specific agent could decrease this problem. The most severe toxicity reported to date is with IESSA® (gefitinib): interstitial pneumonitis, a form of pneumonia characterized by non-infectious inflammation and fibrosis in the lower respiratory tract. Over 170 patients have died of this disease after treatment with IRESSA® (Arora and Scholar, J Pharmacol Exp Ther 315, 971-979 (2005)). Recently, chest CT and radiographic imaging has shown that gefitinib-related interstitial lung disease is similar to that of pulmonary damage caused by conventional antineoplastic agents and there may be a direct cytotoxic effect. Therefore, the use of a tumor cell specific agent to deliver IRESSA®, or any small molecule agent, directly to the tumor cells might provide a solution to the problem of interstitial pneumonitis and other side effects. Moreover, direct delivery to the site where needed (primary and metastatic disease), including in the brain, by the method of this invention would also result in a decrease in the dose required for effective treatment, a further benefit currently not possible.

BRIEF SUMMARY OF THE INVENTION

In accordance with this invention a variety of immunoliposomes and polymer complexes have been constructed that are capable of tumor-targeted, systemic delivery of a variety of types of therapeutic molecules for use in treating human diseases. The antibody- or antibody fragment-targeted immunoliposomes or polymer complexes are made via a simple and efficient non-chemical conjugation method. These complexes are equally as effective as, or more effective than, similar complexes prepared by chemical conjugation of the antibody or antibody fragment to the liposome or polymer complex. If an antibody fragment is used, the resultant complex is capable of producing a much higher level of transfection efficiency than the same liposome-therapeutic agent or polymer-therapeutic agent complex bearing the complete antibody molecule.

In accordance with the present invention, the single chain protein is not chemically conjugated to the liposome or polymer. Rather, the antibody- or scFv-liposome-therapeutic or diagnostic agent complex or the antibody- or scFv-polymer-therapeutic or diagnostic agent complex is formed by simple mixing of the components in a defined ratio and order. The antibody- or antibody fragment is complexed (e.g., associated, for example via a charge-charge interaction) directly with the liposome. In one embodiment, the antibody or single chain protein first is mixed with the cationic liposome or the polymer at a protein:lipid ratio in the range of about 1:20 to about 1:40 (w:w) or protein:polymer ratio in the range of about 0.1:1 to 10:1 (molar ratio). The antibody- or antibody fragment-liposome or antibody- or antibody fragment-polymer then is mixed with a desired therapeutic or diagnostic agent, such as nucleic acid, at a ratio in the range of about 1:10 to 1:20 (µg therapeutic or diagnostic agent:nmole total lipid) or about 1:1 to 1:40 (ug therapeutic or diagnostic agent:nmole polymer) and incubated for 10-15 minutes at room temperature. In embodiments where the therapeutic or diagnostic agent is a small molecule, the antibody- or antibody fragment-liposome or antibody- or antibody fragment-polymer is mixed with the small molecule at a molar ratio in the range of about 0.2:7 to about 14:7 (small molecule:liposome/polymer complex), suitably at a molar ratio of about 2.8:7 or about 7:7 (small molecule:liposome/polymer complex).

The resultant therapeutic or diagnostic agent-antibody-liposome or therapeutic agent-antibody-polymer complex can be administered to a mammal, preferably a human, to deliver the agent to target cells in the mammal's body. Desirably the complexes are targeted to a site of interest, which can be a cell, including a cancer cell or a non-cancer cell. The targeting agent is an antibody or antibody fragment, which in one exemplary embodiment binds to a transferrin receptor, and the target cell is a cell which expresses or contains the target site of interest. If the antibody or antibody fragment binds to a transferrin receptor, the target cell is a cell which expresses a transferrin receptor. The therapeutic agent can be a small molecule, a nucleic acid, including a DNA molecule and suitably a DNA molecule which encodes a wild type p53 molecule, Rb molecule or Apoptin molecule or an antisense HER-2. The complexes, for example in a therapeutic composition, can be administered systemically, preferably intravenously.

In an additional embodiment, the present invention provides methods of preparing an antibody- or antibody fragment-targeted cationic immunoliposome complex comprising preparing an antibody or antibody fragment; mixing the antibody or antibody fragment with a cationic liposome to form a cationic immunoliposome, wherein the antibody or antibody fragment is not chemically conjugated to the cationic liposome (but is directly complexed/associated with the liposome); and mixing the cationic immunoliposome with a small molecule to form said antibody- or antibody fragment-targeted-cationic immunoliposome complex. In suitable embodiments, the antibody fragment is a single chain Fv fragment, such as an anti-transferrin receptor single chain Fv (TfRscFv).

Suitable lipids useful in preparing the small molecule-comprising cationic immunoliposome complexes of the present invention include mixtures of one or more cationic lipids and one or more neutral or helper lipids. Suitably, the antibody or antibody fragment is mixed with said cationic liposome at a ratio in the range of about 1:20 to about 1:40 (w:w). In embodiments, the cationic liposomes comprise a mixture of dioleoyltrimethylammonium phosphate with dioleoylphosphatidylethanolamine and/or cholesterol; or a mixture of dimethyldioctadecylammonium bromide with dioleoylphosphatidylethanolamine and/or cholesterol. In further embodiments, the cationic immunoliposome is mixed with the small molecule at a molar ratio in the range of about 0.2:7 to about 14:7 (small molecule:immunoliposome), suitably at a molar ratio of about 1:7 to about 12:7, about 1:7 to about 10:7, about 2:7 to about 9:7, about 4:7 to about 8:7, about 5:7 to about 8:7 or about 7:7 (small molecule:immunoliposome).

Small molecules for use in the practice of the present invention suitably will have a molecular weight of less than about 5000 Daltons, more suitably less than about 1000 Daltons, for example about 300 to about 700 Daltons. In additional embodiments, the small molecules have at least one pKa in the range of about 2 to about 9. Suitable small molecules for use in the practice of the present invention include anticancer small molecules, including, but not limited to, GMC-5-193, YK-3-250, imatinib mesylate, erlotinib hydrochloride, sunitinib malate, gefitinib and analogs and derivatives thereof. In a further embodiment, the present invention provides small molecule-comprising cationic immunoliposome complexes prepared by the methods described herein.

In an additional embodiment, the present invention provides antibody- or antibody fragment-targeted cationic immunoliposome complexes comprising a cationic liposome, an antibody or antibody fragment, and a small molecule, wherein the antibody or antibody fragment is not chemically conjugated to said cationic liposome (but is directly associated/complexed with the liposome). The small molecule may be encapsulated within the cationic liposome, contained within a hydrocarbon chain region of the cationic liposome, associated with an inner or outer monolayer of the cationic liposome (including the head-group region), or any combination thereof.

The present invention also provides methods of treating a patient suffering from, or predisposed to, a disease state, such as, but not limited to, cancer, comprising administering the small molecule-comprising cationic immunoliposome complexes of the present invention to the patient. Suitably the complexes are administered via intravenous administration. Alternatively, the complexes can be delivered via other routes of administration, such as intratumoral, intralesional, aerosal, percutaneous, endoscopic, topical, oral, or subcutaneous administration. In embodiments where the patient is suffering from or predisposed to cancer, the methods of the present invention can further comprise administering radiation or a chemotherapeutic agent to the patient, either before, during, or after (e.g., at least 12 hours before, at least 12 hours after, or at the same time) administration of the cationic immunoliposome complex. Suitable chemotherapeutic agents include, but are not limited to, doxorubicin, cisplatin, mitoxantrone, taxotere and CDDP. The present invention also provides methods of enhancing the effectiveness of a chemotherapeutic agent comprising administering the small molecule-comprising cationic immunoliposomes of the present invention in conjunction with the chemotherapeutic agent to a patient, either before, during or after (e.g., at least 12 hours before, at least 12 hours after, or at the same time) administration of the cationic immunoliposome complex.

BRIEF DESCRIPTION OF THE DRAWINGS/FIGURES

FIG. 8 shows the effect of the combination of systemically administered TfRscFv-liposome A-p53 prepared by simple mixing and radiation on DU145 human prostate xenograft tumors.

FIG. 17 A shows the effect of tumor targeting liposomal delivery of GMC-5-193 (TfRscFv/LipA-HoKC/GMC-5-193 complexes) on sensitization of DU145 human prostate cancer cells to (docetaxel) TAXOTERE®.

Figure 17A:
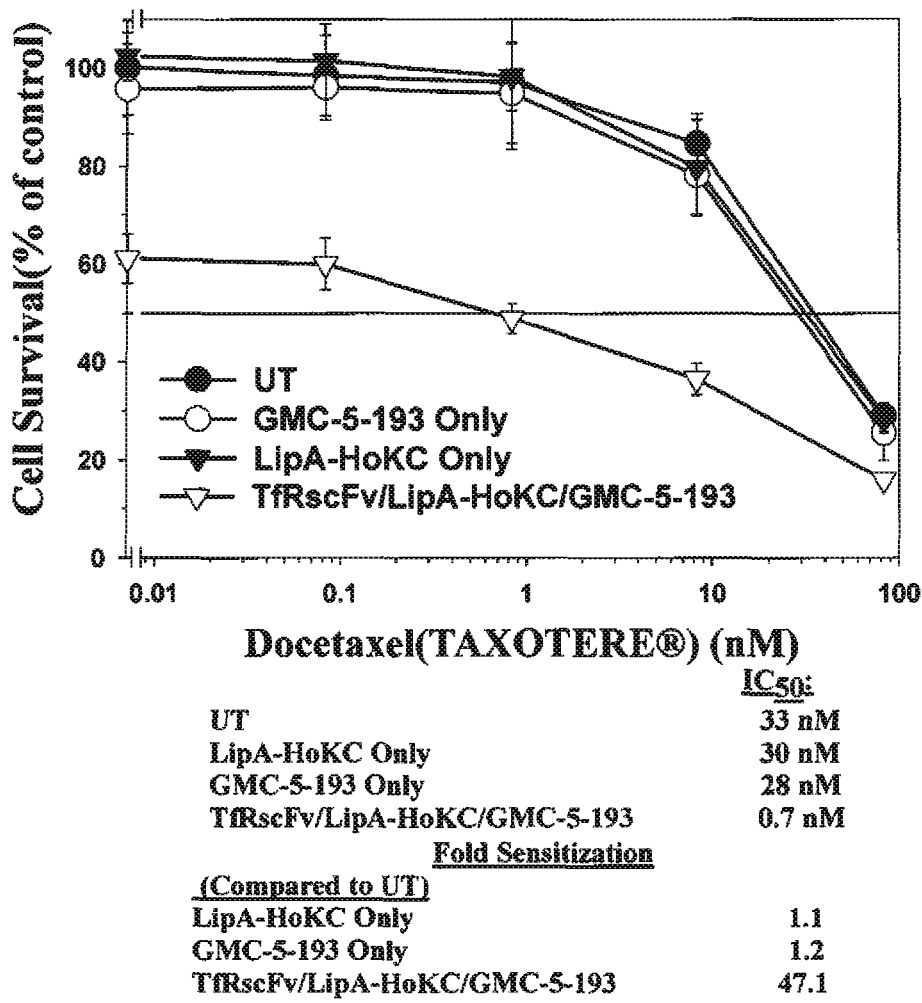
Figure 17B:
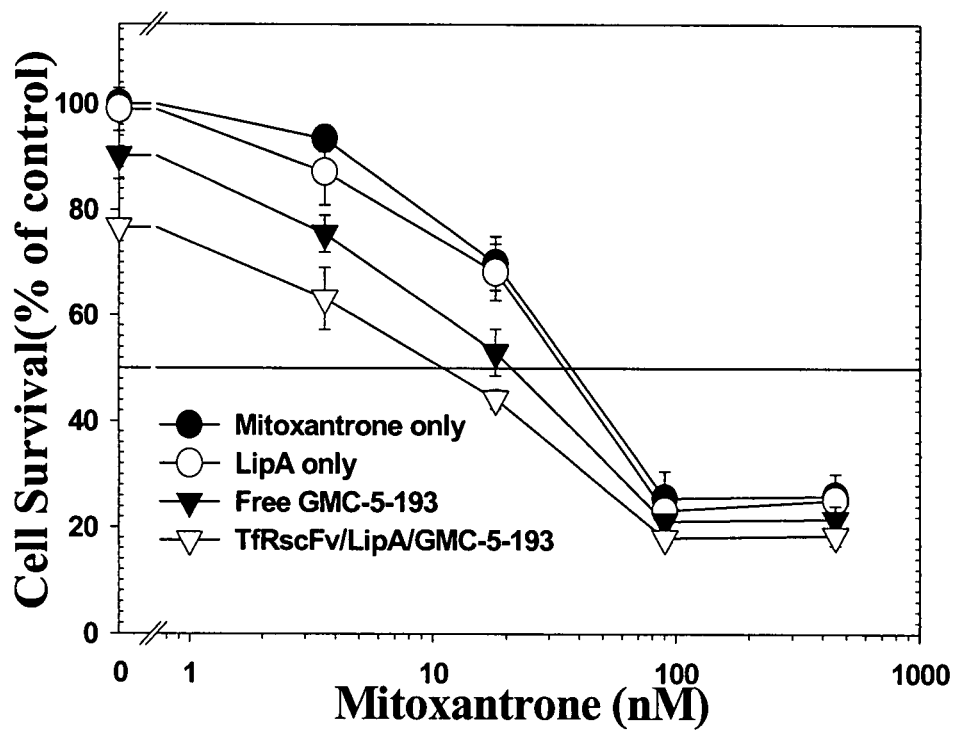

FIG. 17B shows the effect of tumor targeting liposomal delivery of GMC-5-193 (TfRscFv/LipA/GMC-5-193 complexes) on sensitization of DU145 human prostate cancer cells to Mitoxantrone.

Figure 17C:
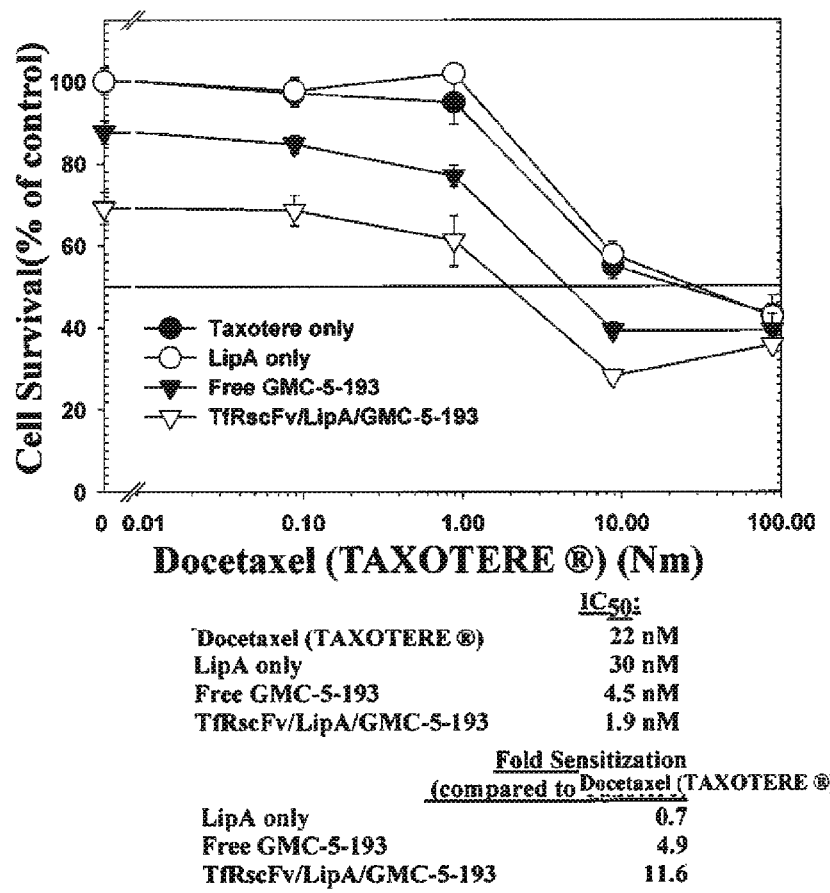

FIG. 17C shows the effect of tumor targeting liposomal delivery of GMC-5-193 (TfRscFv/LipAlGMC-5-193 complexes) on sensitization of MDA-MB-435 human melanoma cells to (docetaxel) TAXOTERE®.

Figure 18:
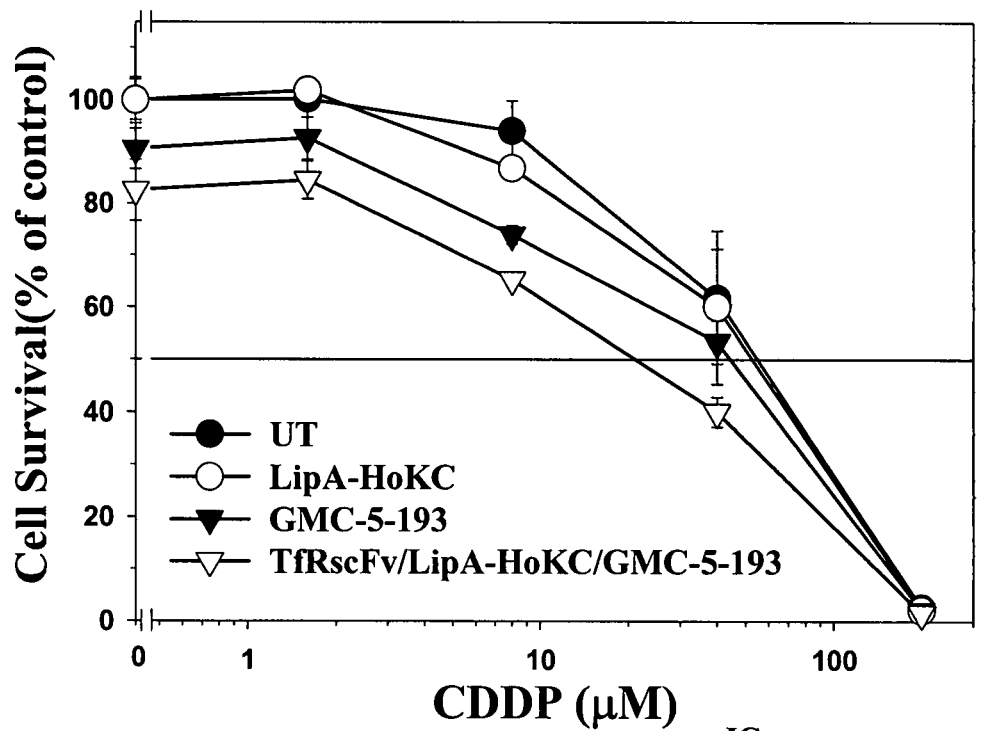

FIG. 18 shows the effect of tumor targeting liposomal delivery of GMC-5-193 on sensitization of B16/F10 mouse melanoma cells to CDDP.

Figure 19A:
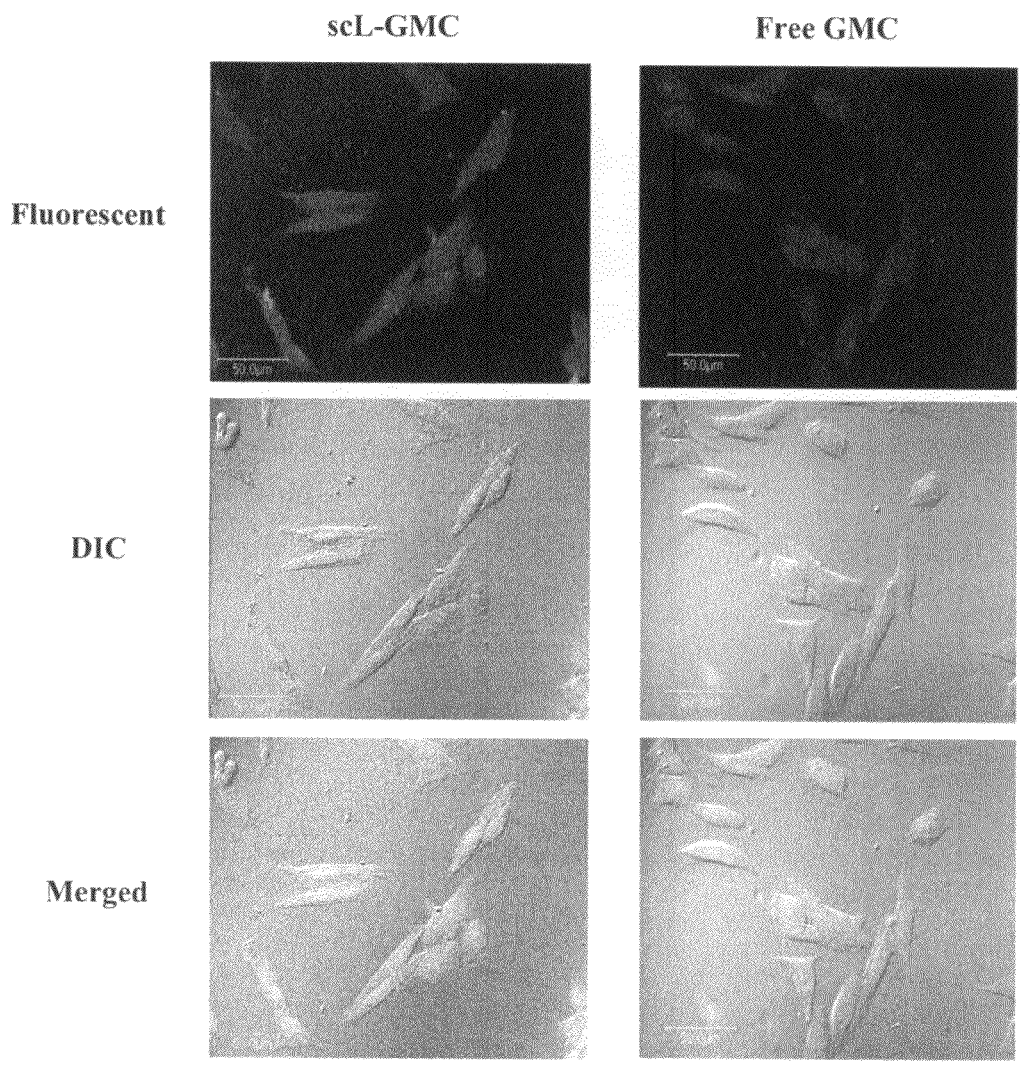

FIG. 19A shows in vitro comparison of free GMC-5-193 or TfRscFv/LipA/GMC-5-193 complex uptake in MDA-MB-435 cells.

Figure 19B:
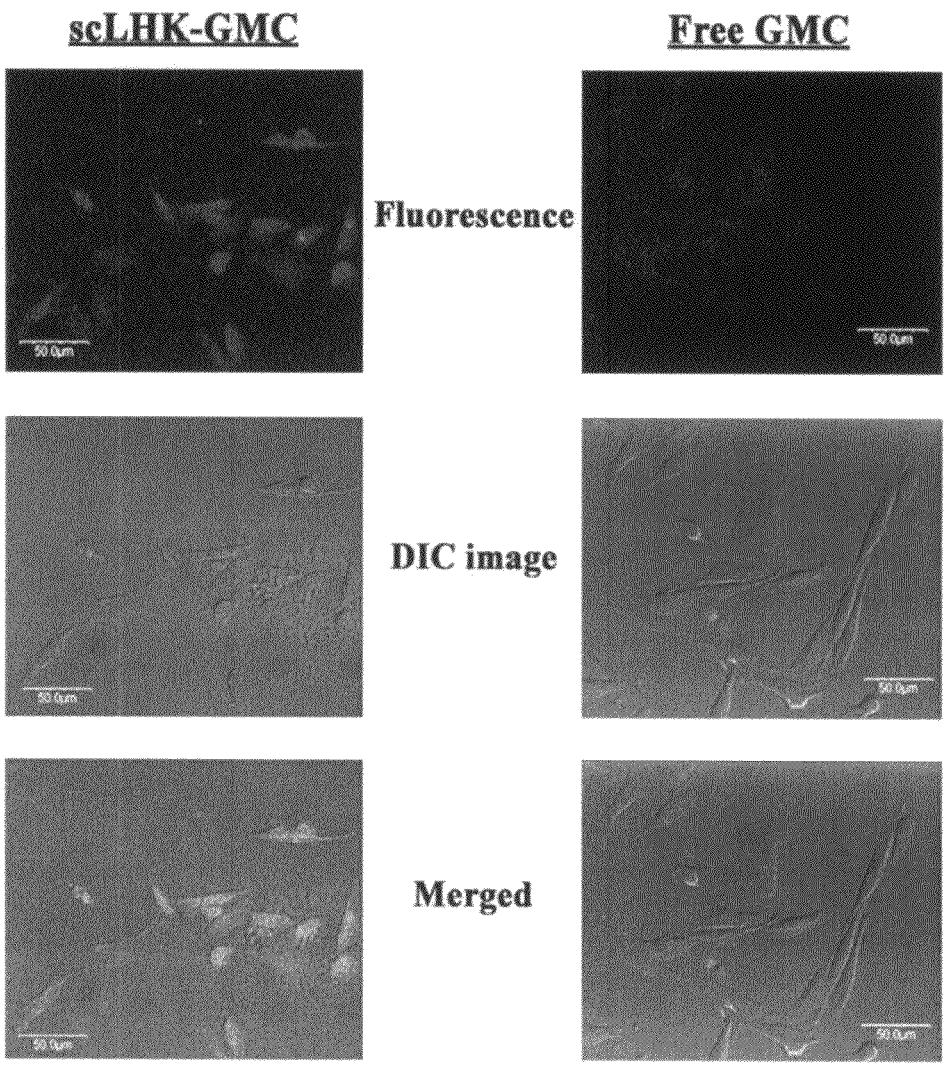

FIG. 19B shows in vitro comparison of free GMC-5-193 or TfRscFv/LipA-HoKC/GMC-5-193 complex uptake in MDA-MB-435 cells.

Figure 20A:
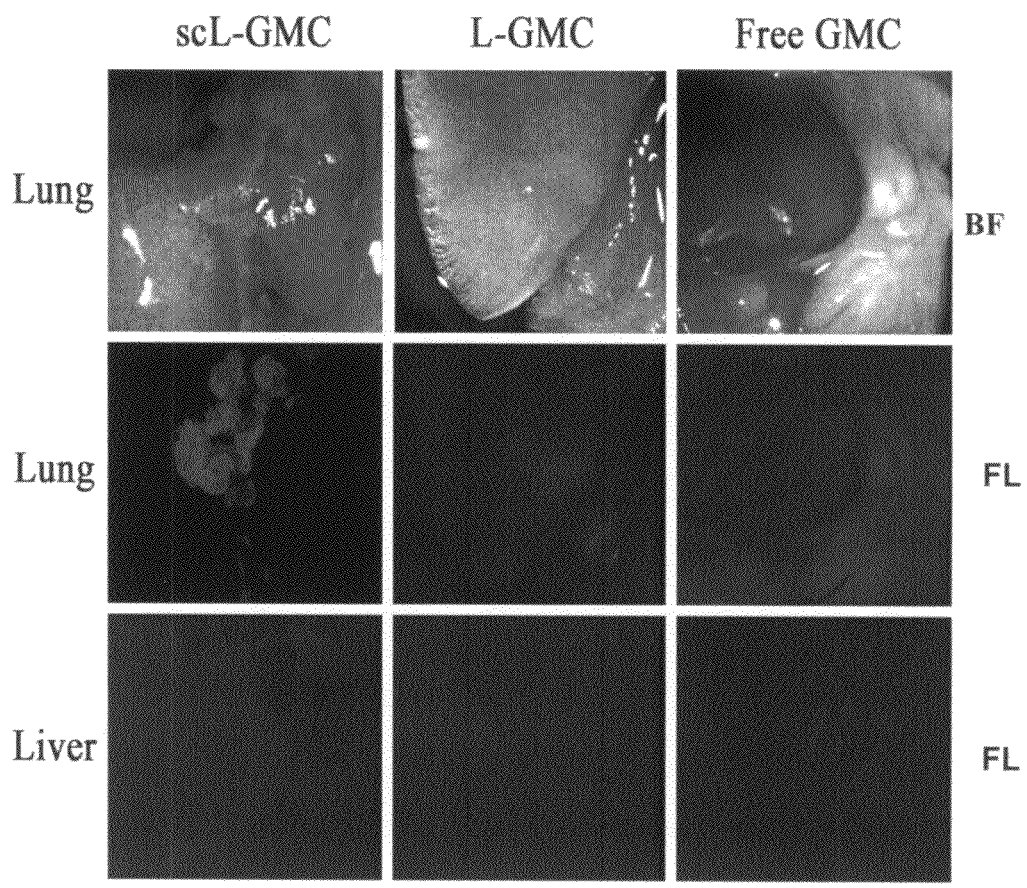

FIG. 20A shows enhanced tumor-specific uptake after systemic administration by incorporation of a fluorescent small molecule in TfRscFv/LipA/GMC-5-193 (scL-GMC) complex.

Figure 20B:
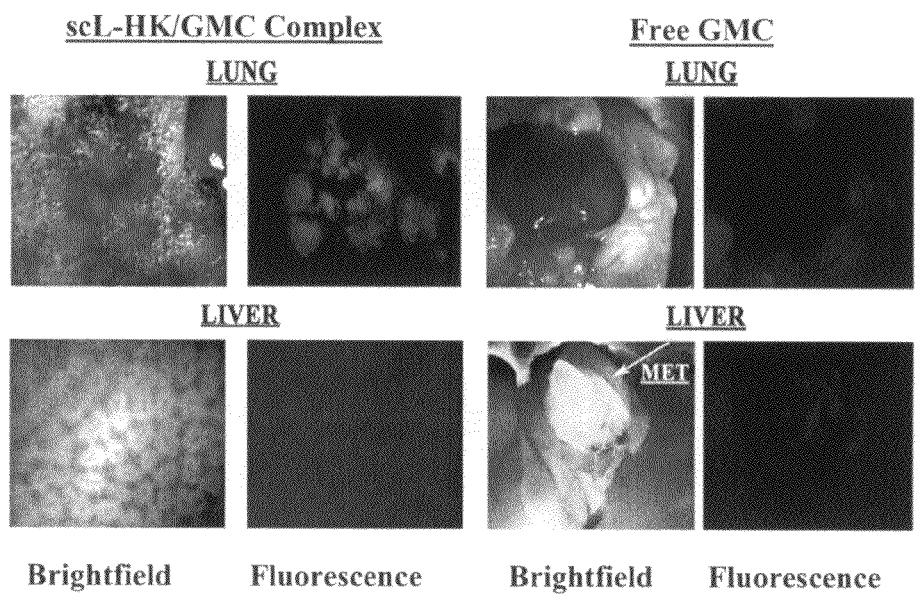

FIG. 20B shows enhanced tumor-specific uptake after systemic administration by incorporation of a fluorescent small molecule in TfRscFv/LipA-HoKC/GMC-5-193 complex.

Figure 20C:
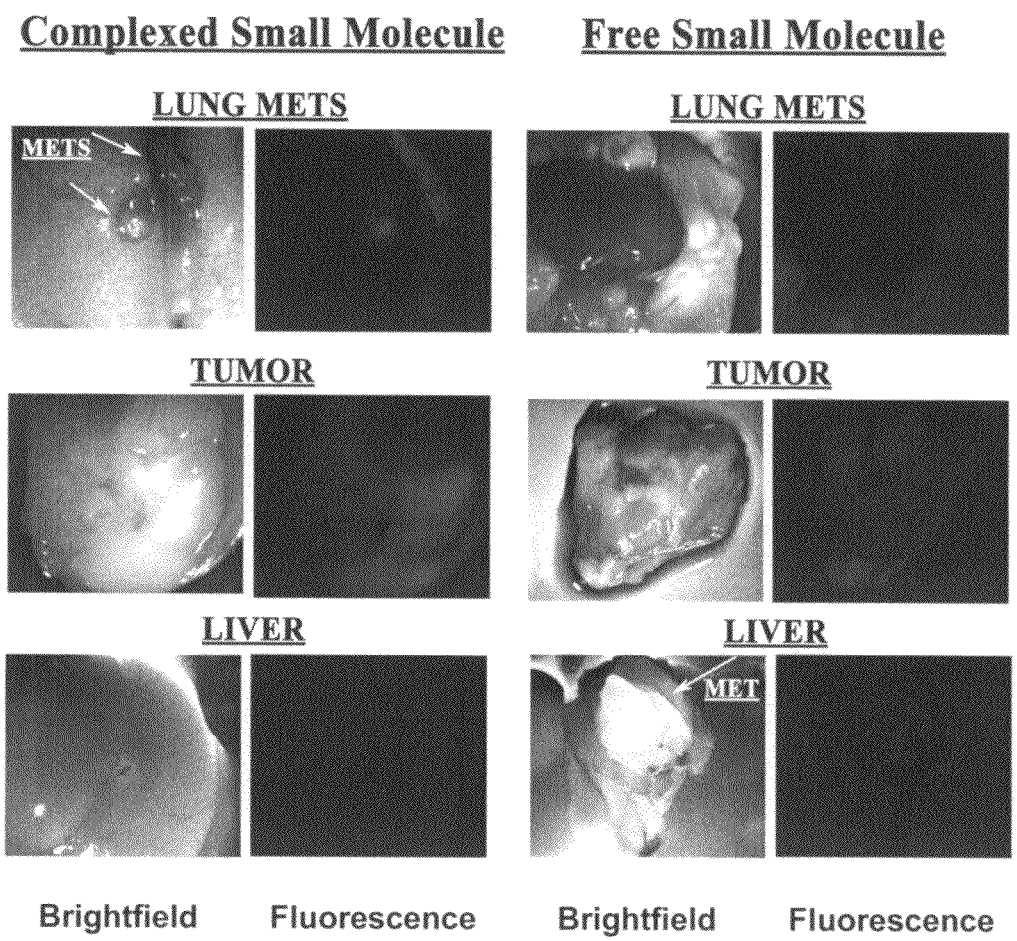

FIG. 20C shows additional data demonstrating enhanced tumor-specific uptake after systemic administration by incorporation of fluorescent GMC-5-193 using the TfRscFv/LipA-HoKC/GMC-5-193 complex.

Figure 21A:
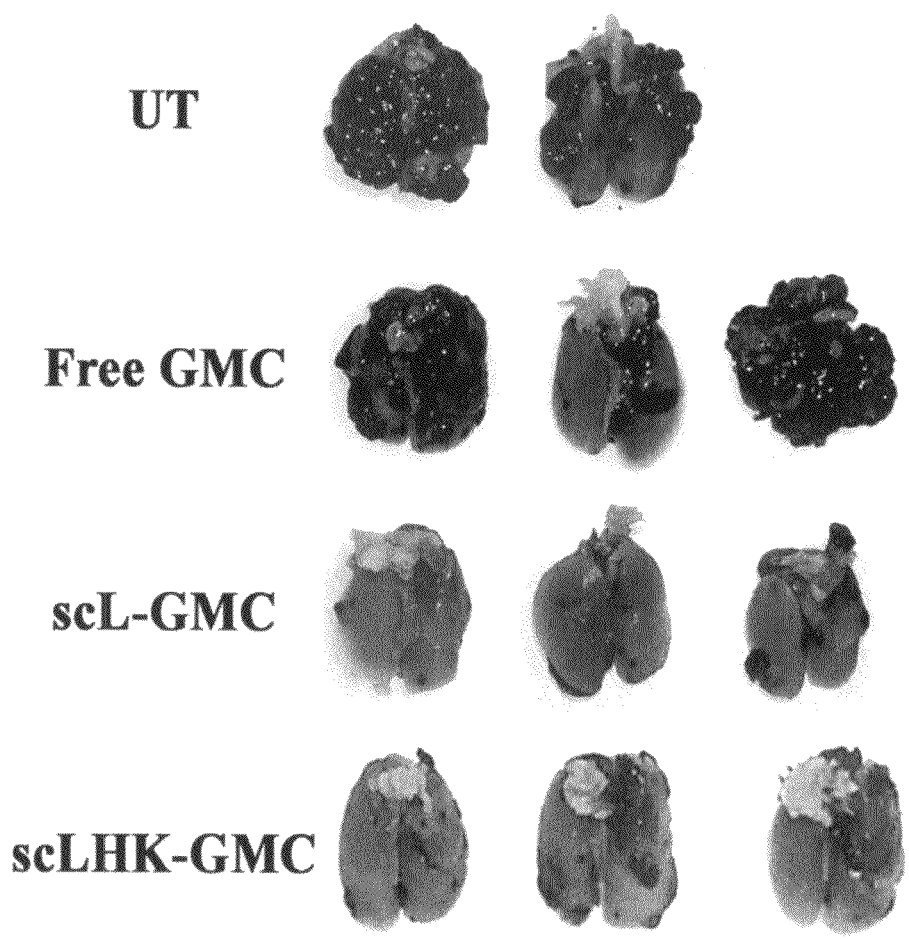

FIG. 21A shows inhibition of tumor growth in B16/F10 lung tumor bearing syngenic mice after treatment with free GMC-5-193, TfRscFv/LipA/GMC-5-193 (scL-GMC) and TfRscFv/LipA-HoKC/GMC-5-193 (scLHK-GMC) complexes.

Figure 21B:
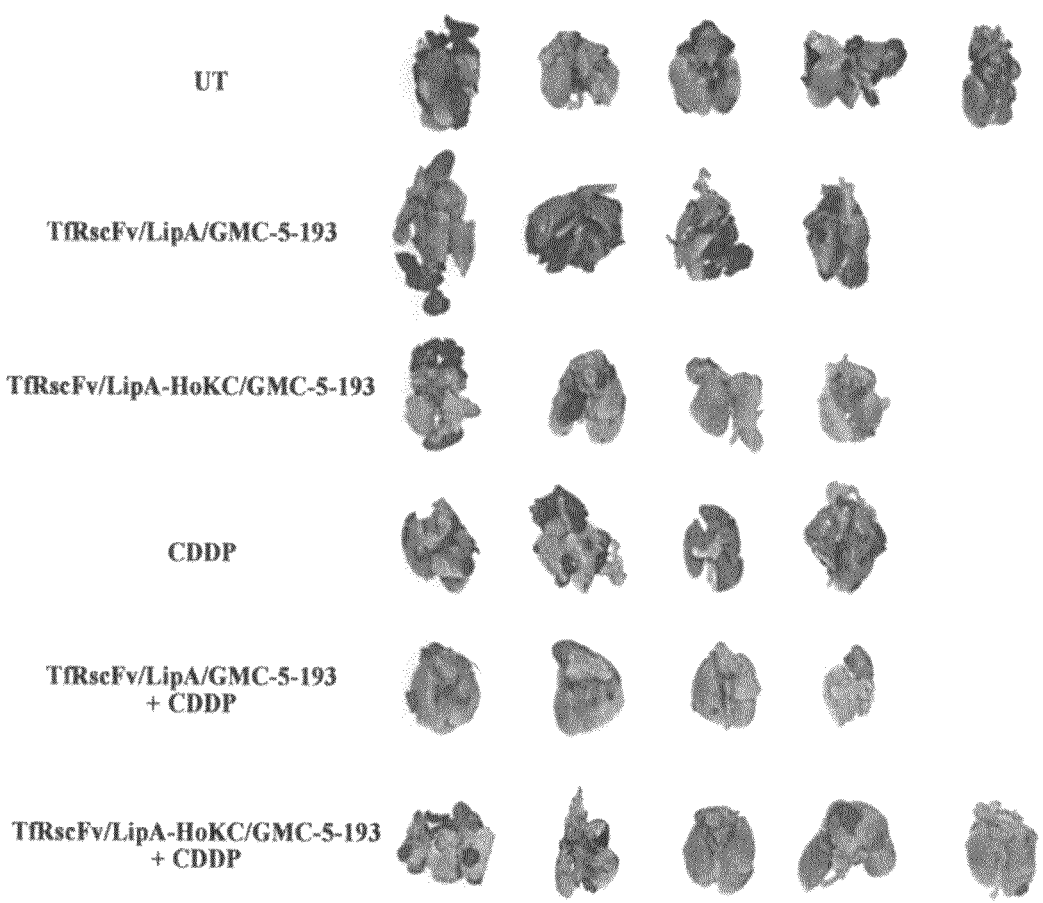

FIG. 21B shows inhibition of tumor growth in B16/F10 lung tumor bearing syngenic mice after treatment with the combination of TfRscFv/LipA/GMC-5-193 (scL-GMC) and TfRscFv/LipA-HoKC/GMC-5-193 (scLHK-GMC) complexes with and without Cisplatin.

Figure 21C:
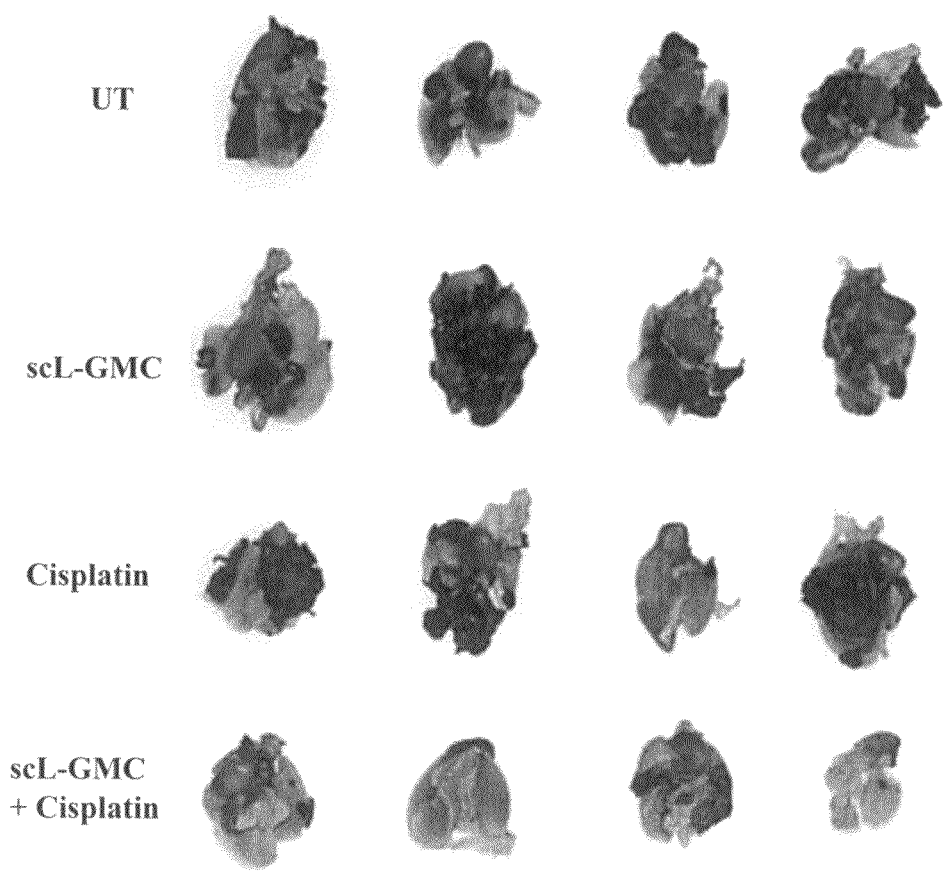

FIG. 21C shows inhibition of tumor growth in B16/F10 lung tumor bearing syngenic mice after treatment with the combination of TfRscFv/LipA/GMC-5-193 and TfRscFv/LipA-HoKC/GMC-5-193 complexes with and without CDDP.

Figure 22:
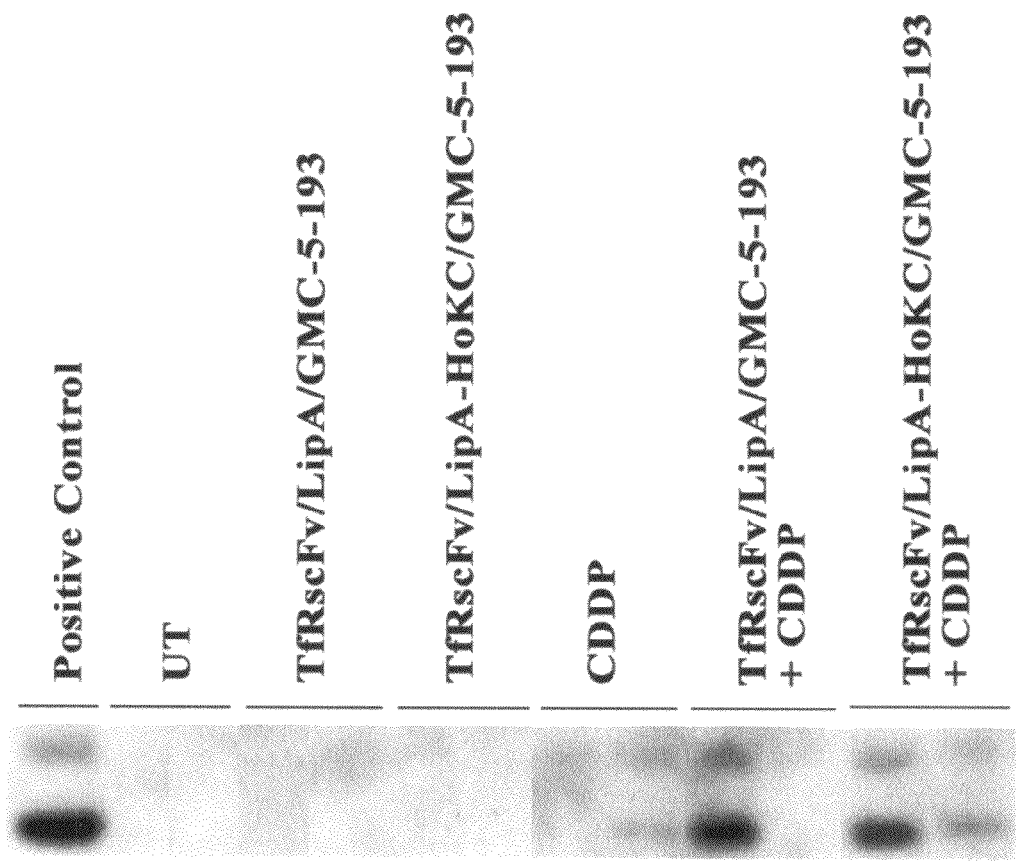

FIG. 22 shows cleaved caspase-3 in the serum of B16/F10 lung tumor bearing syngenic mice after treatment with the combination of TfRscFv/LipA/GMC-5-193 and TfRscFv/LipA-HoKC/GMC-5-193 complexes with and without CDDP.

FIG. 23A shows a comparison of the effects of TfRscFv/LipA/Yk-3-250 complexes at different ratios of YK-3-250 to LipA in MDA-MB-435 cells.

Figure 23B:
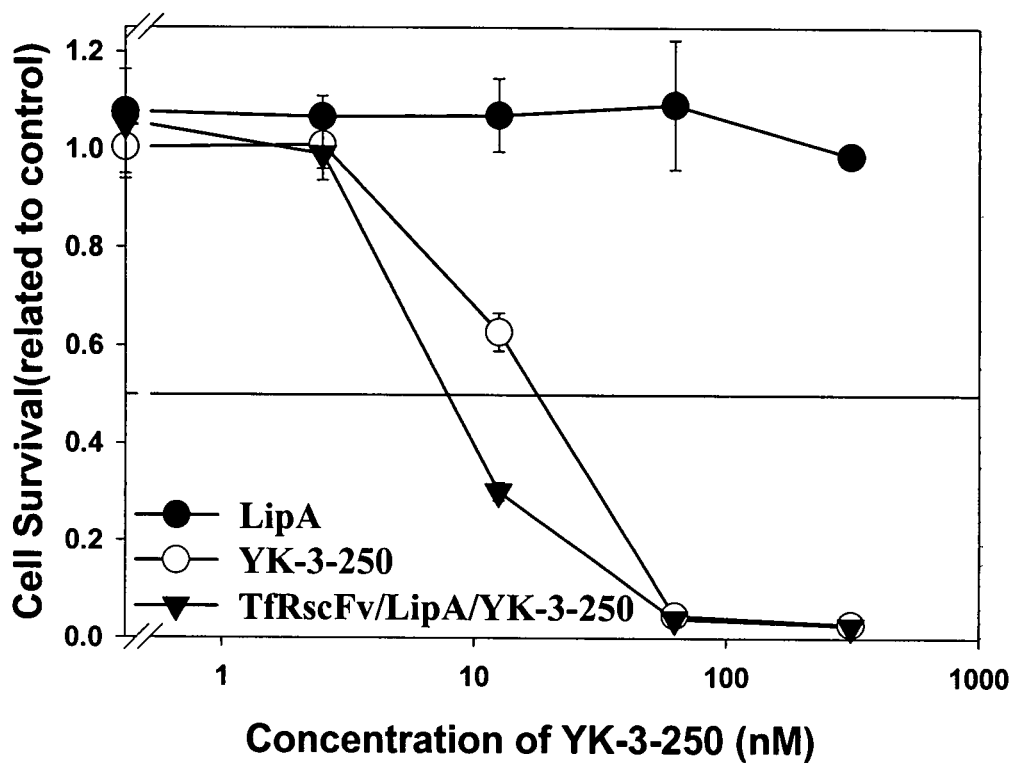

FIG. 23B shows a comparison of the effect of free and complexed YK-3-250 on MDA-MB-435 cells.

Figure 24A:
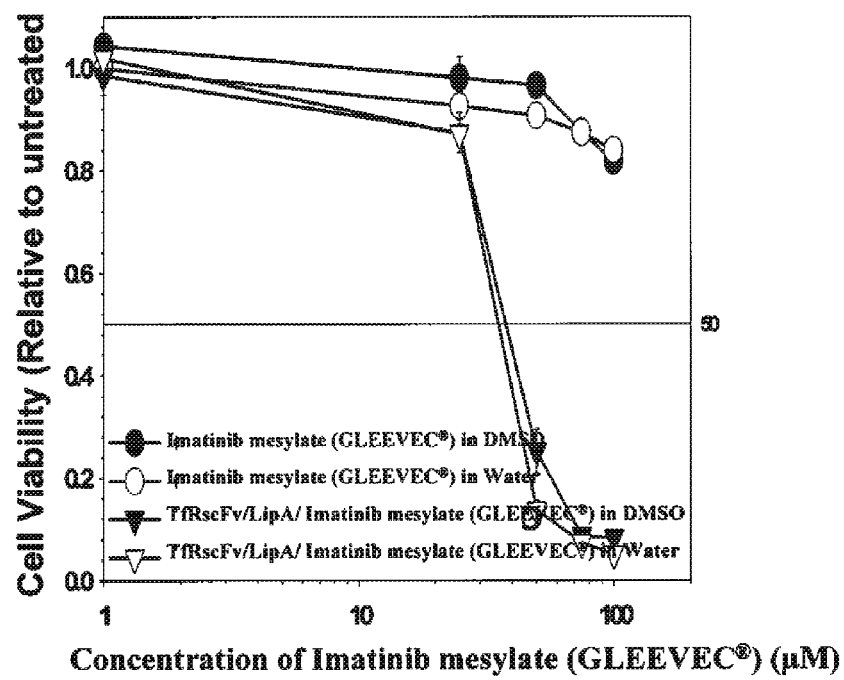

FIG. 24A shows a comparison of the effect of Imatinib Mesylate (GLEEVEC®) delivered via liposome complex and free Imatinib Mesylate (GLEEVEC®) on human prostate cancer cells.

Figure 24B:
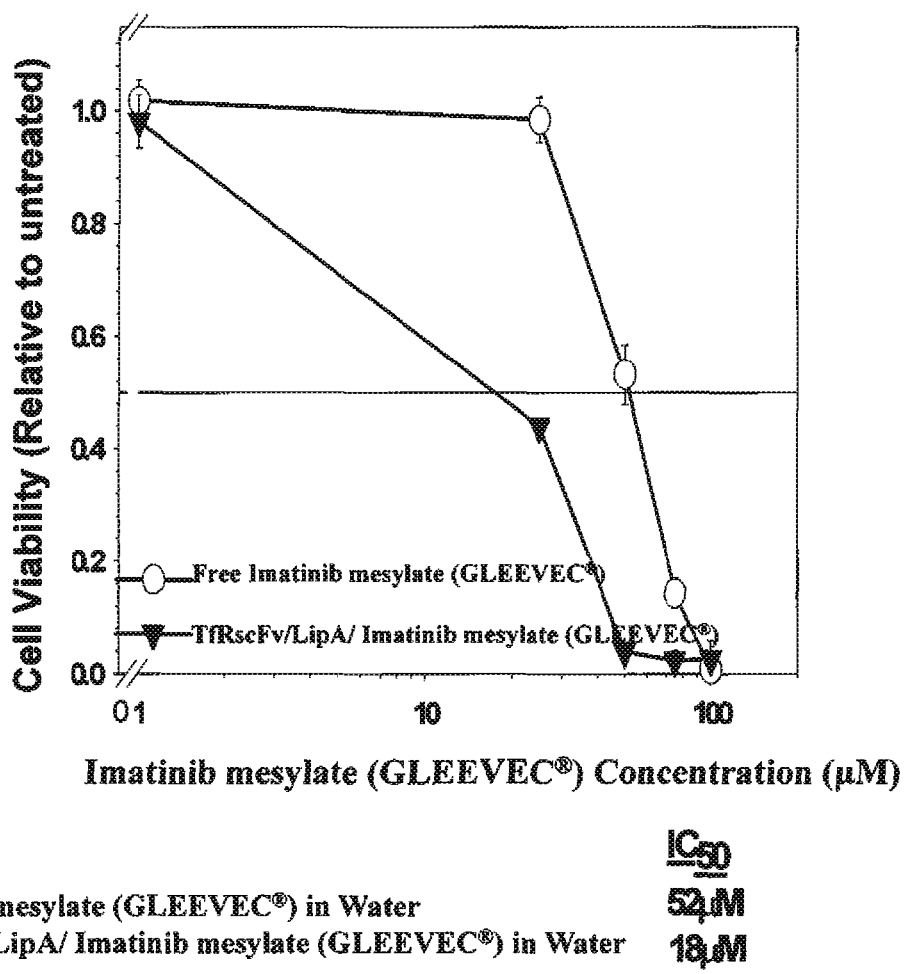

FIG. 24B shows a comparison of the effect of Imatinib Mesylate (GLEEVEC®) delivered via liposome complex and free Imatinib Mesylate (GLEEVEC®) on human melanoma cells.

FIG. 24 C shows a comparison of the effect of Imatinib Mesylate (GLEEVEC®) on B16-F10 cells.

Figure 25A:
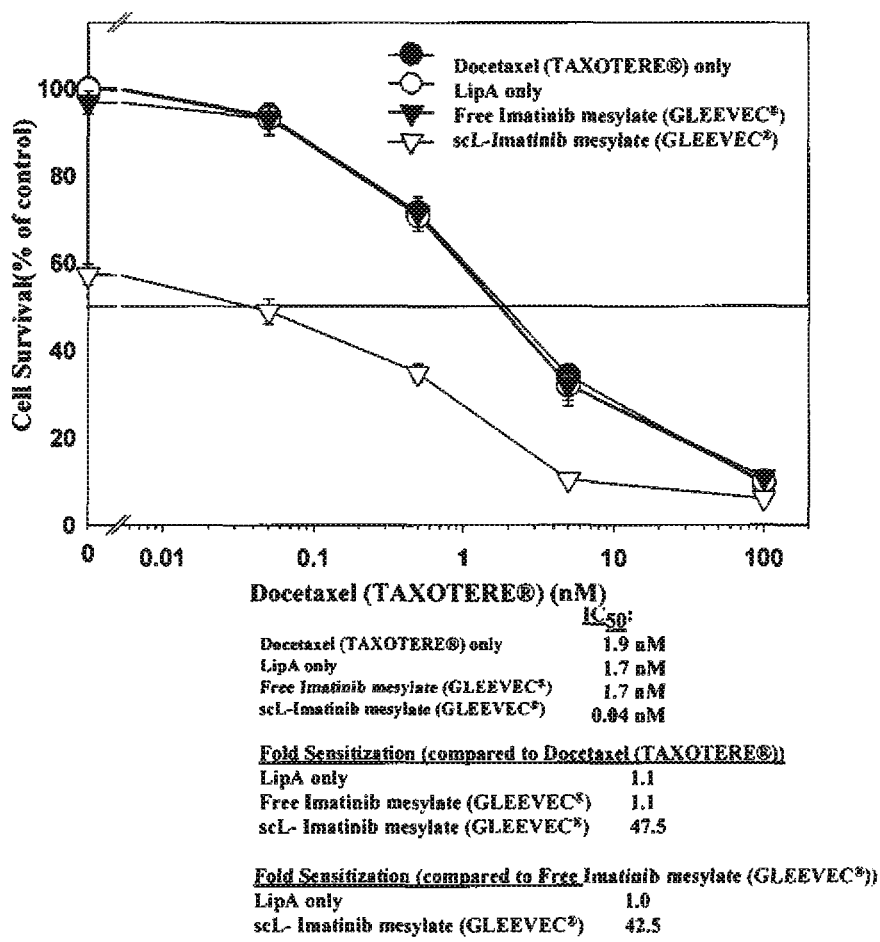

FIG. 25A shows the effect of liposome complex delivery of Imatinib Mesylate (GLEEVEC®) (20 µM) on sensitization of MDA-MB-435 human melanoma cells to Taxotere.

Figure 25B:
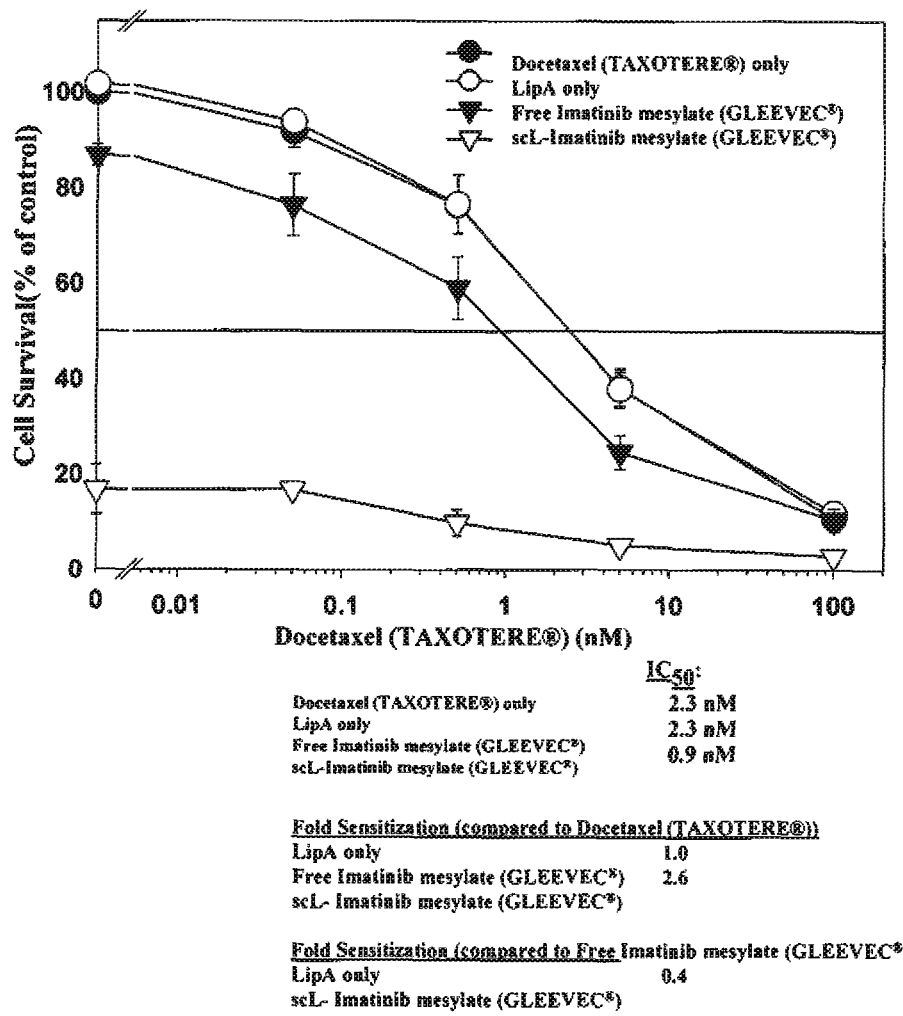

FIG. 25B shows the effect of liposome complex delivery of Imatinib Mesylate (GLEEVEC®) (30 µM) on sensitization of MDA-MB-435 human melanoma cells to (docetaxel) TAXOTERE®.

FIG. 26A shows the effect of liposome complex delivery of Imatinib Mesylate (GLEEVEC®) (20 µM) on sensitization of DU145 human prostate cancer cells to Mitoxantrone.

FIG. 26B shows the effect of liposome complex delivery of Imatinib Mesylate (GLEEVEC®) (30 µM) on sensitization of DU145 human prostate cancer cells to Mitoxantrone.

Figure 27A:
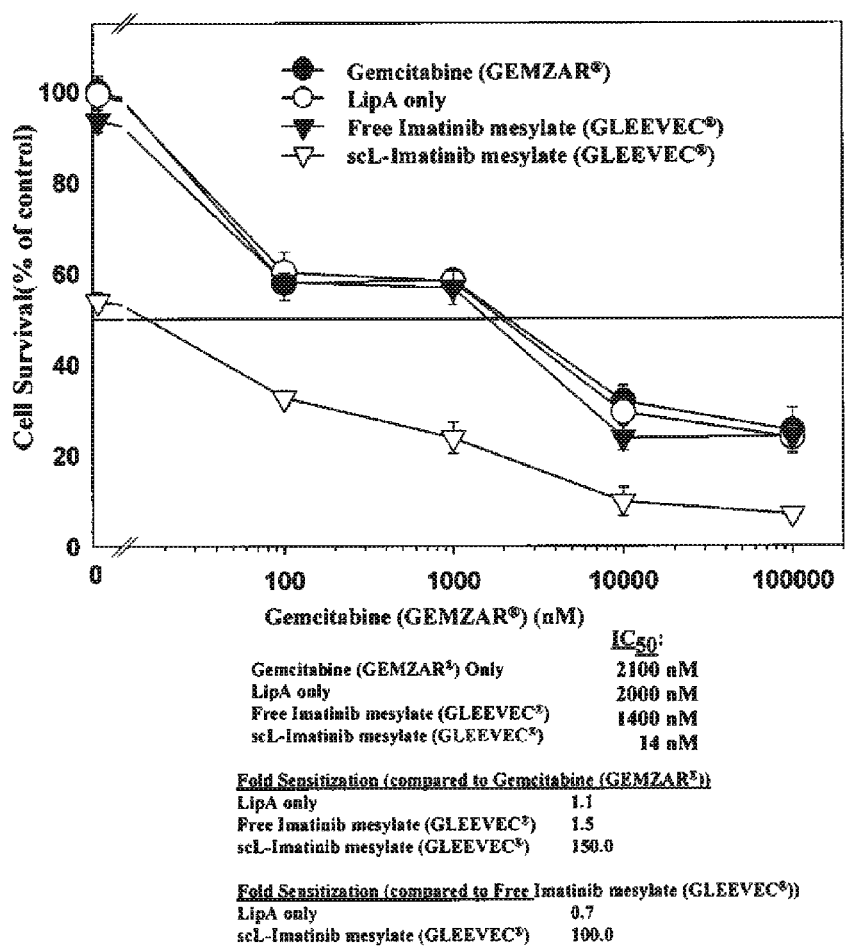

FIG. 27A shows the effect of liposome complex delivery of Imatinib Mesylate (GLEEVEC®) (20 µM) on sensitization of PANC-1 human pancreatic cancer cells to Gemcitabine.

Figure 27B:
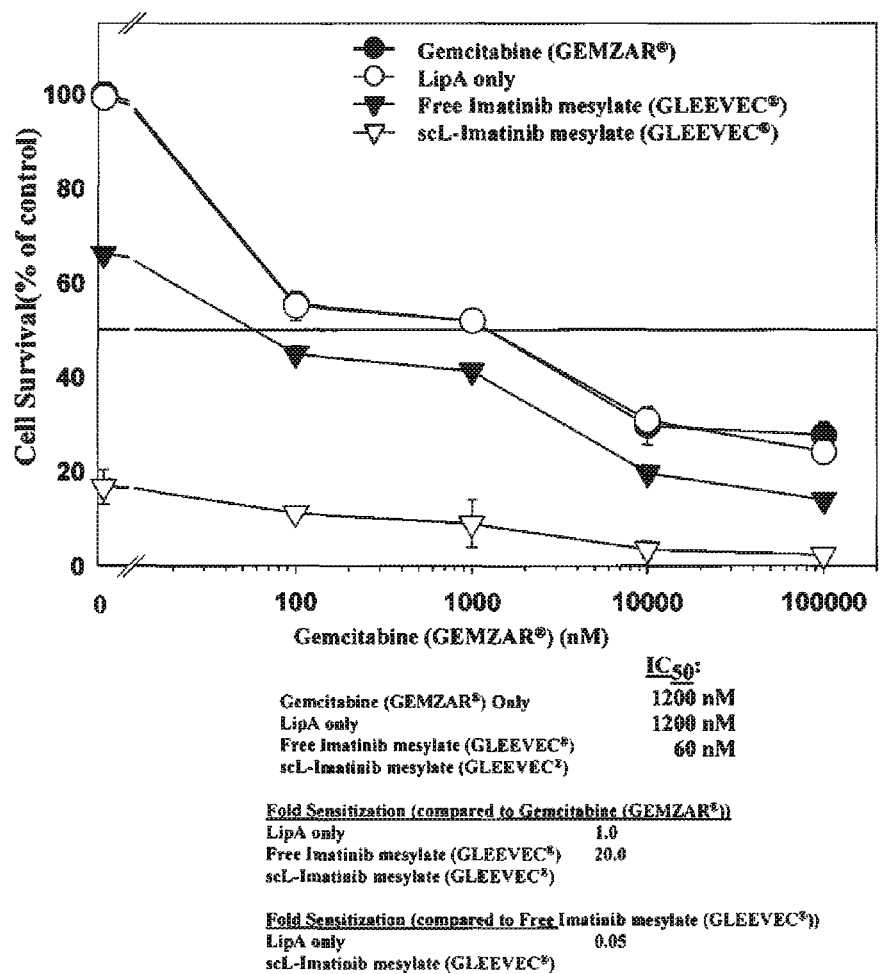

FIG. 27B shows the effect of liposome complex delivery of Imatinib Mesylate (GLEEVEC®) (30 µM) on sensitization of PANC-1 human pancreatic cancer cells to Gemcitabine.

Figure 28A:
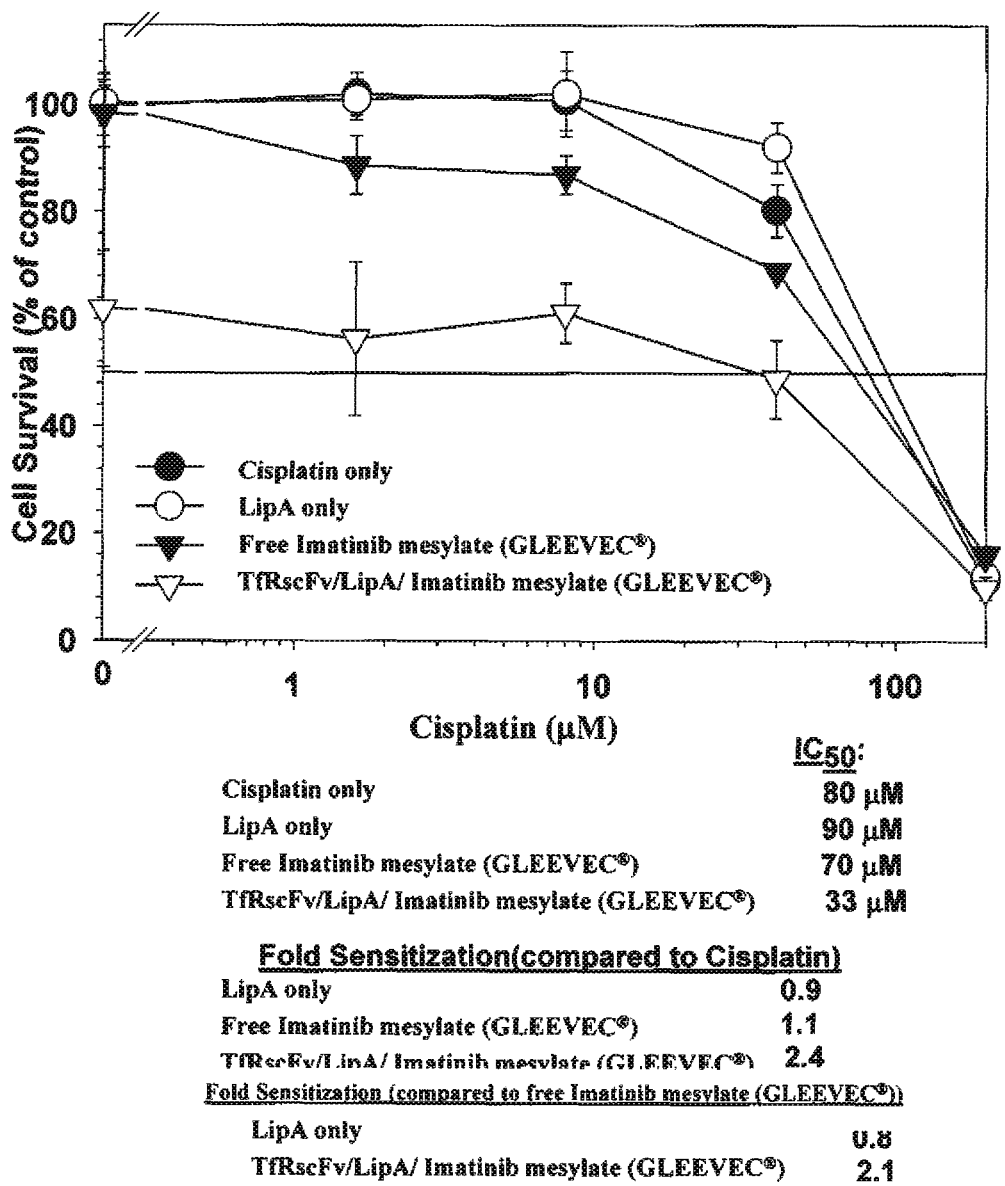

FIG. 28A shows the effect of liposome complex delivery of Imatinib Mesylate (GLEEVEC®) (20 µM) on sensitization of B16/F10 mouse melanoma cells to Cisplatin (CDDP).

Figure 28B:
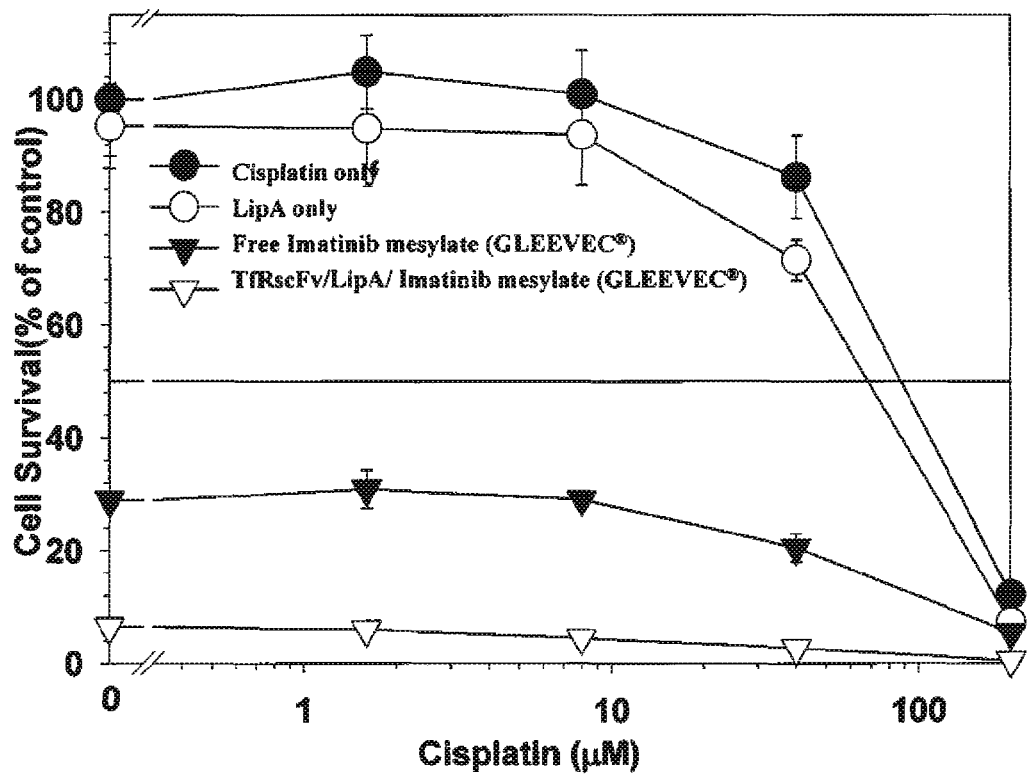

FIG. 28B shows the effect of liposome complex delivery of Imatinib Mesylate (GLEEVEC®) (30 µM) on sensitization of B16/F10 mouse melanoma cells to Cisplatin (CDDP).

FIG. 29A shows the effect of liposome complex delivery of Imatinib Mesylate (GLEEVEC®) (15 µM) on sensitization of B16/F10 mouse melanoma cells to Dacarbazine (DTIC) 24 hours incubation.

FIG. 29B shows the effect of liposome complex delivery of Imatinib Mesylate (GLEEVEC®) (20 µM) on sensitization of B16/F10 mouse melanoma cells to Dacarbazine (DTIC) 24 hours incubation.

Figure 29C:
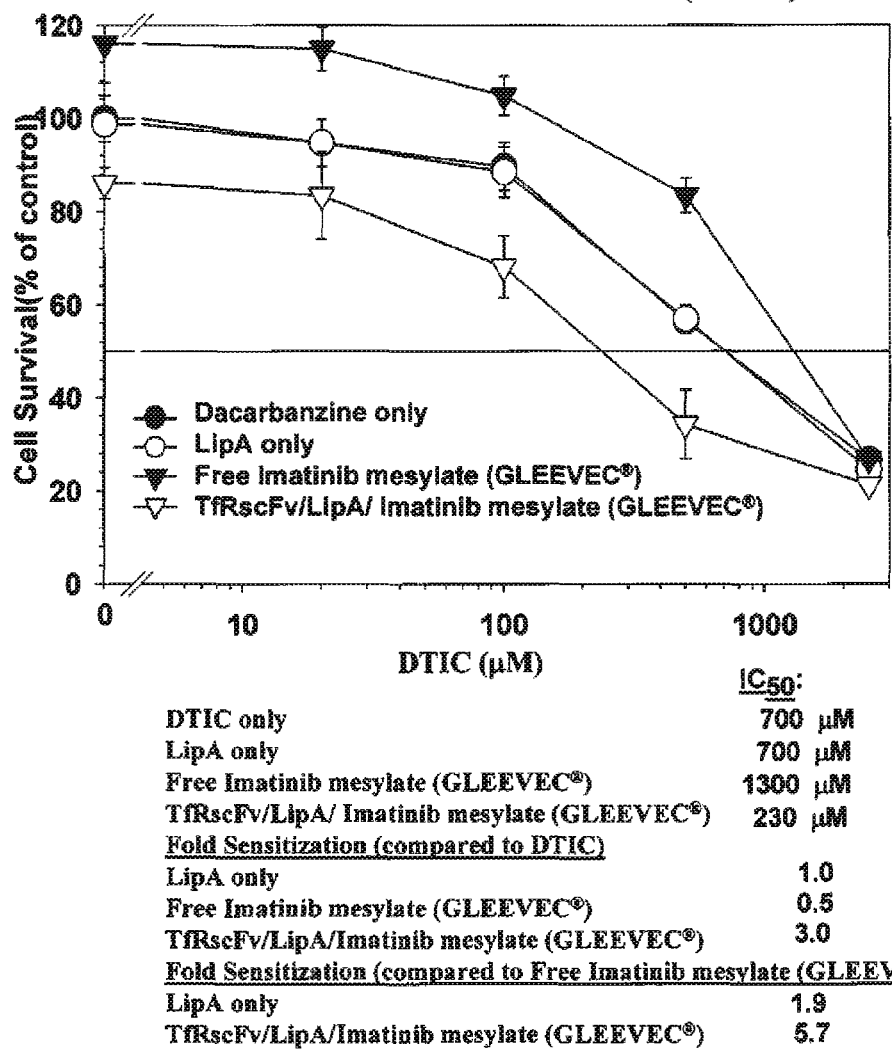

FIG. 29C shows the effect of liposome complex delivery of Imatinib Mesylate (GLEEVEC®) (15 µM) on sensitization of B16/F10 mouse melanoma cells to Dacarbazine (DTIC) 48 hours incubation.

Figure 29D:
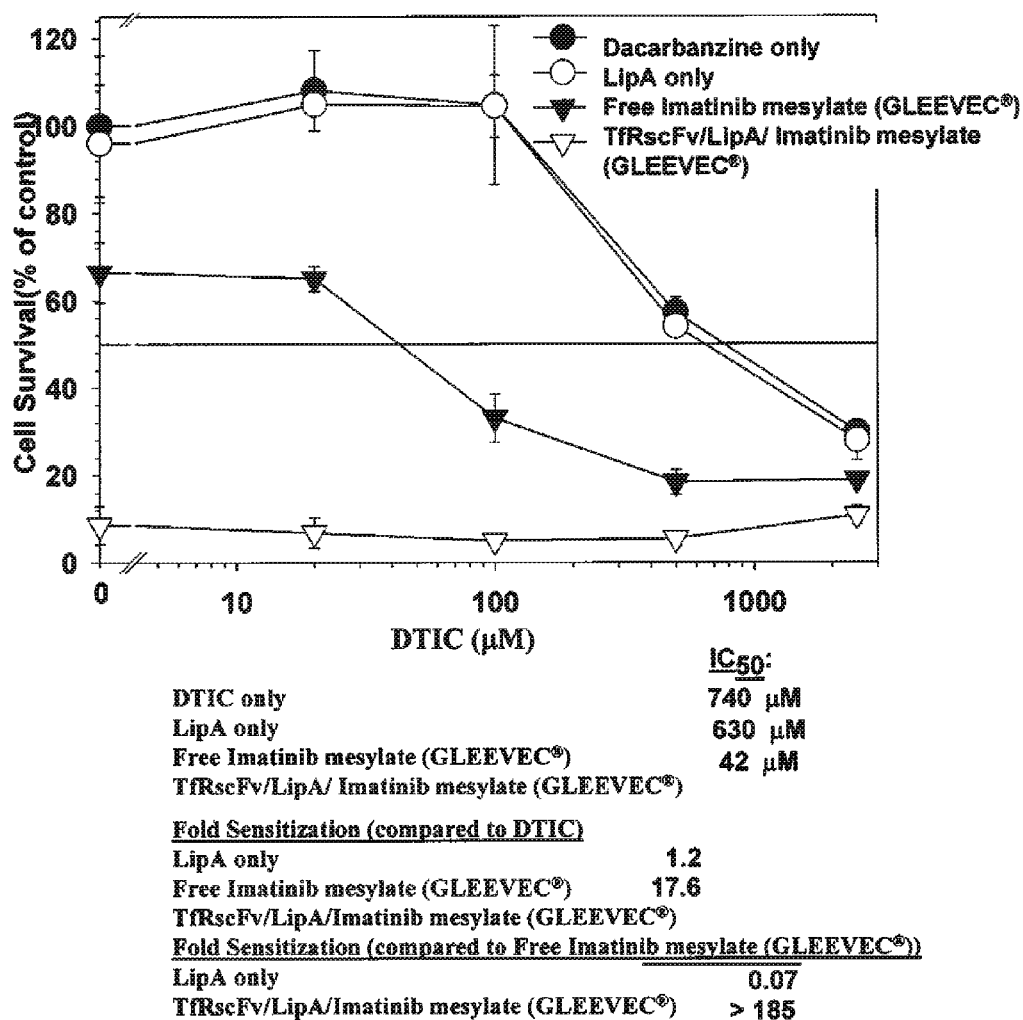

FIG. 29D shows the effect of liposome complex delivery of Imatinib Mesylate (GLEEVEC®) (20 µM) on sensitization of B16/F10 mouse melanoma cells to Dacarbazine (DTIC) 48 hours incubation.

Figure 30A:
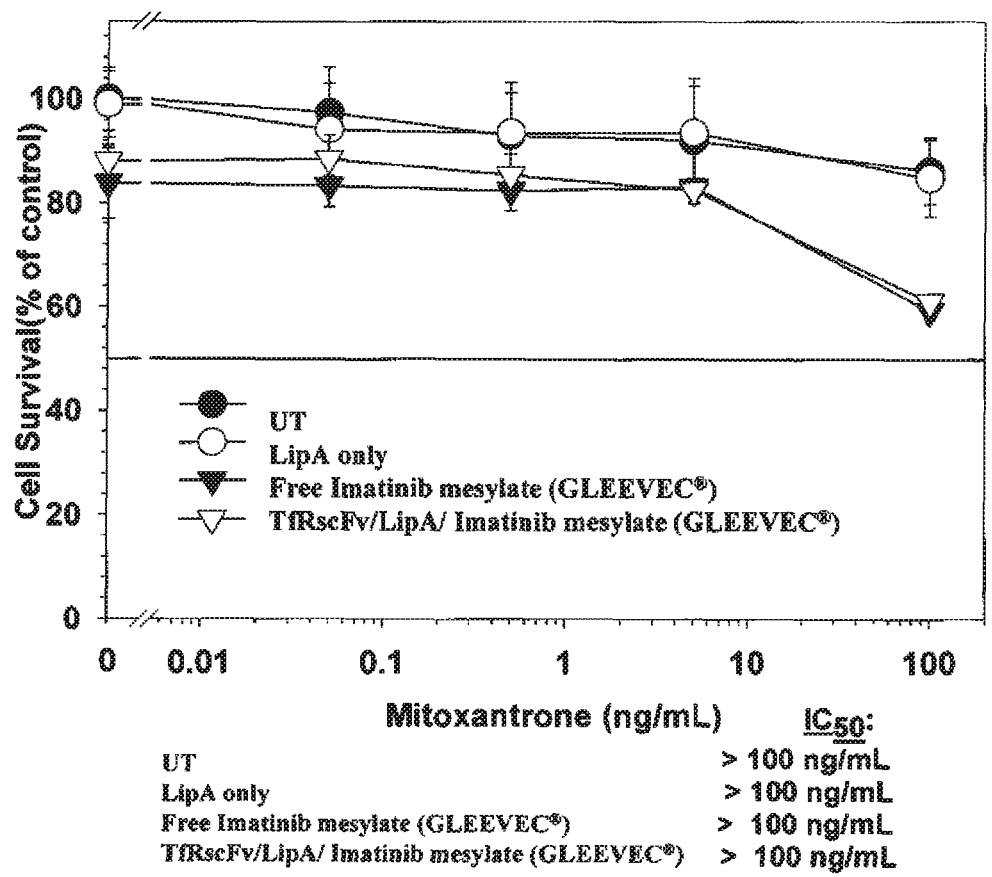
Figure 30B:
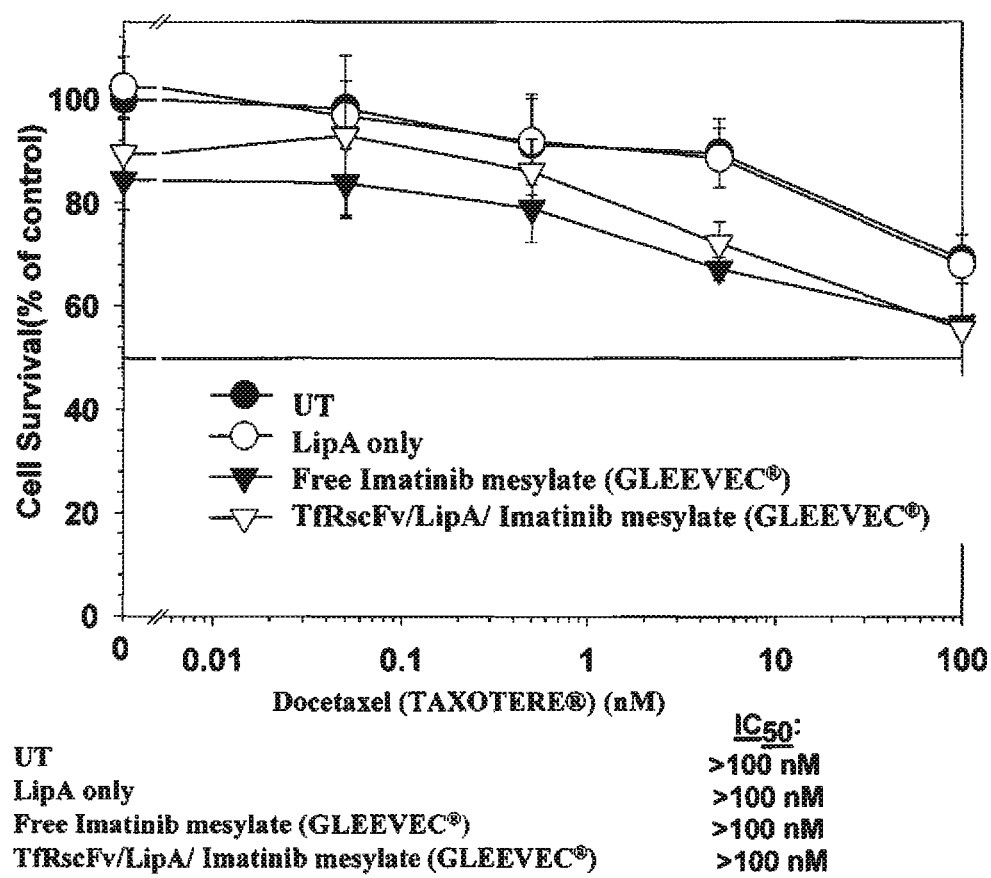

FIG. 30A shows the effect of tumor targeting liposomal delivery of Imatinib Mesylate (GLEEVEC®) (TfRscFv/LipA/Imatinib Mesylate (scL-GLEEVEC®)) on sensitization of normal human fibroblast cell line H500 to mitoxantrone FIG. 30B shows the effect of tumor targeting liposomal delivery of Imatinib Mesylate (GLEEVEC®) (TfRscFv/LipA/Imatinib Mesylate (scL-GLEEVEC®) on sensitization of normal human fibroblast cell line H500 to Taxotere.

Figure 31:
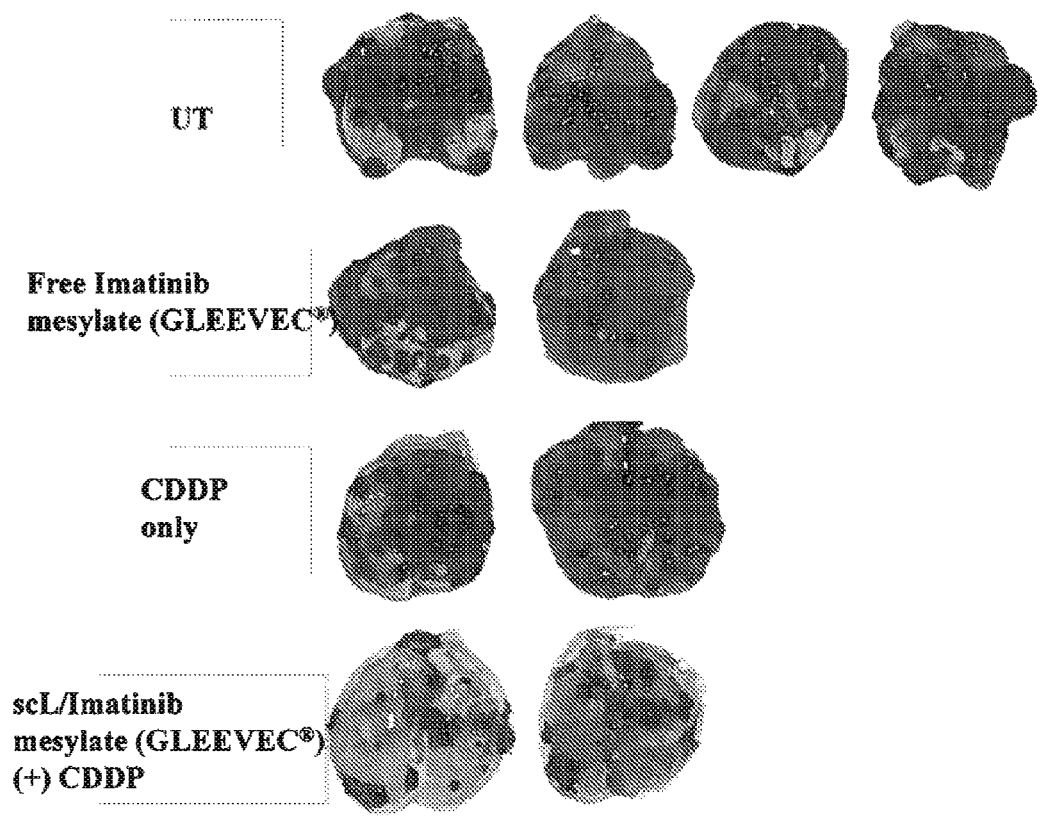

FIG. 31 shows the inhibition of B16/F10 lung tumor growth by the combination of TfRscFv/LipA/Imatinib Mesylate (scL-GLEEVEC®) plus CDDP.

FIG. 32A shows the comparison of the effects of Erlotinib (TARCEVA®) delivered by the ligand-liposome complex (TfRscFv/LipA/Erlotinib (scL-TARCEVA®)) and free Erlotinib on human prostate cancer cells (DU145)

Figure 32B:
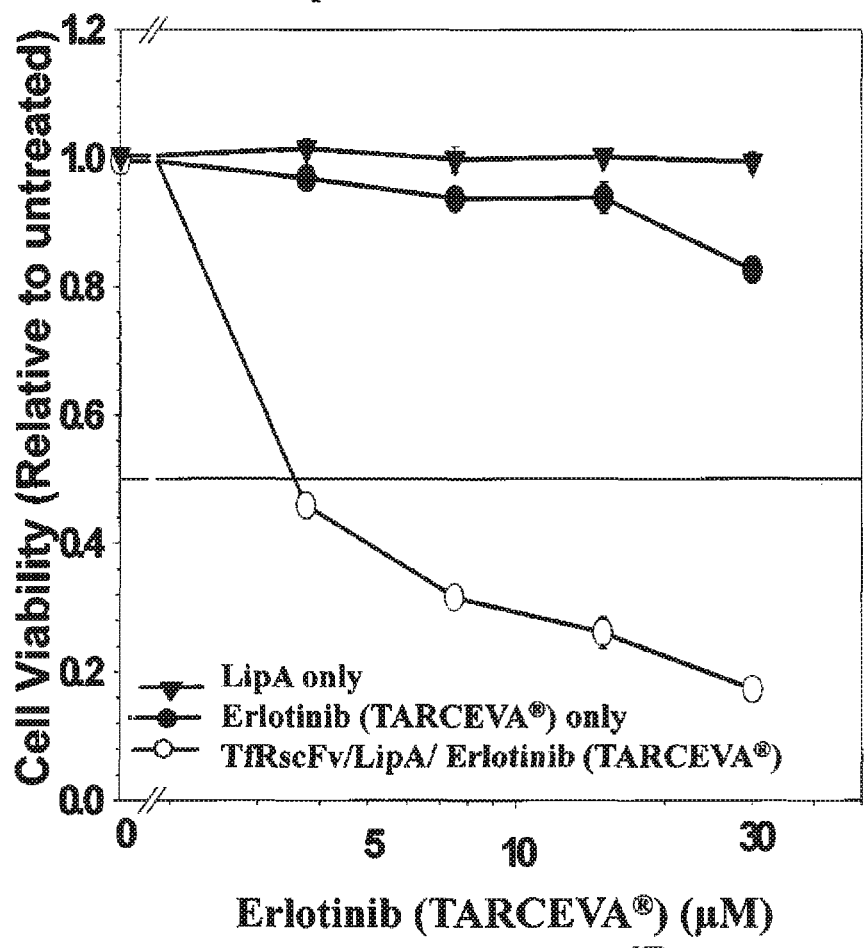

FIG. 32B shows the comparison of the effects of Erlotinib (TARCEVA®) delivered by the ligand-liposome complex (TfRscFv/LipA/Erlotinib (scL-TARCEVA®)) and free Erlotinib on human pancreatic cancer cells (PANC-1).

Figure 32C:
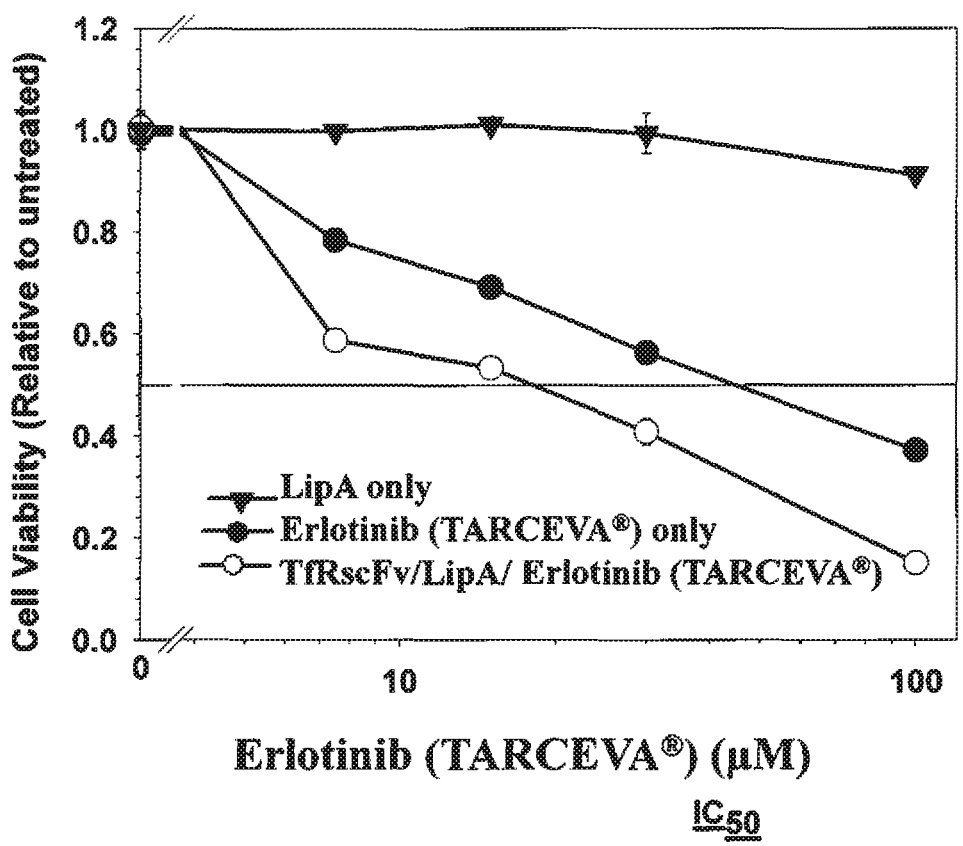

FIG. 32C shows the comparison of the effects of Erlotinib (TARCEVA®) delivered by the ligand-liposome complex (TfRscFv/LipA/Erlotinib (scL-TARCEVA®)) and free Erlotinib on human melanoma cells (MDA-MB-435).

FIG. 33A shows the effect of TfRscFv/LipA (scL) complex delivery of Erlotinib at a concentration of 3.75 uM on sensitization of human prostate cancer cell line DU145 to mitoxantrone as compared to free Erlotinib (TARCEVA®).

Figure 33B:
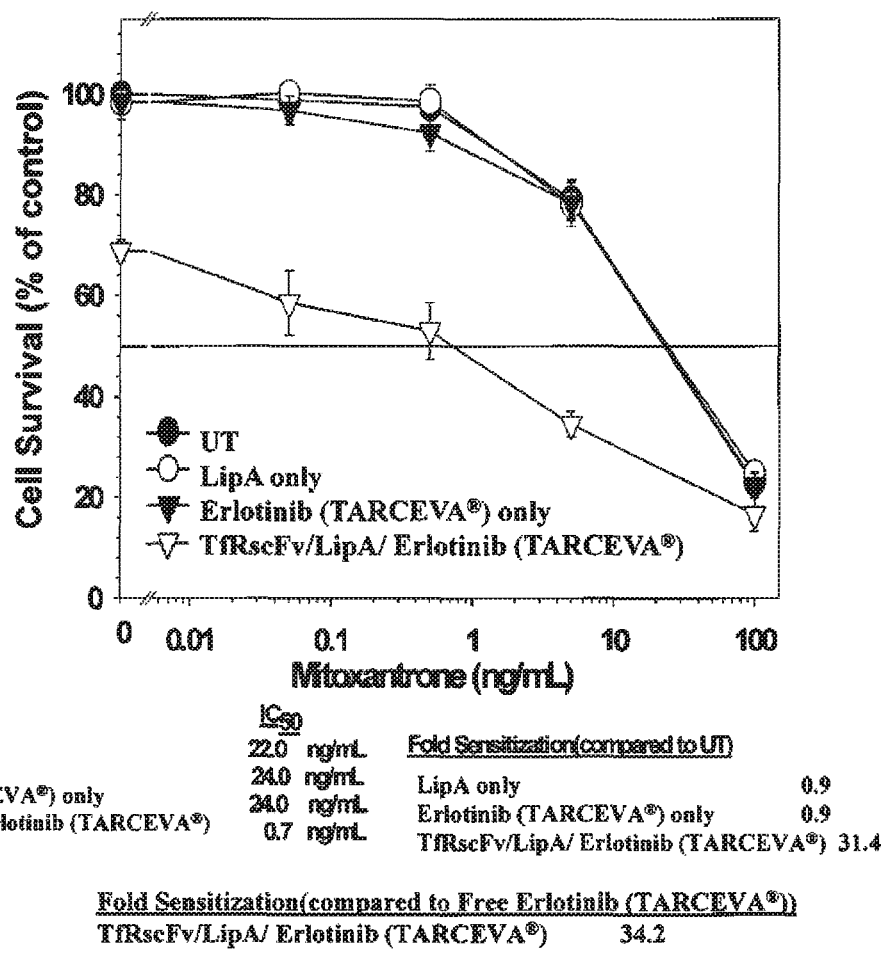

FIG. 33B shows the effect of TfRscFv/LipA (scL) complex delivery of Erlotinib at a concentration of 7.5 uM on sensitization of human prostate cancer cell line DU145 to mitoxantrone as compared to free Erlotinib (TARCEVA®).

FIG. 34A shows the effect of TfRscFv/LipA (scL) complex delivery of Erlotinib at a concentration of 3.75 uM on sensitization of human melanoma cells to docetaxel (Taxotere) as compared to free Erlotinib (TARCEVA®).

Figure 34B:
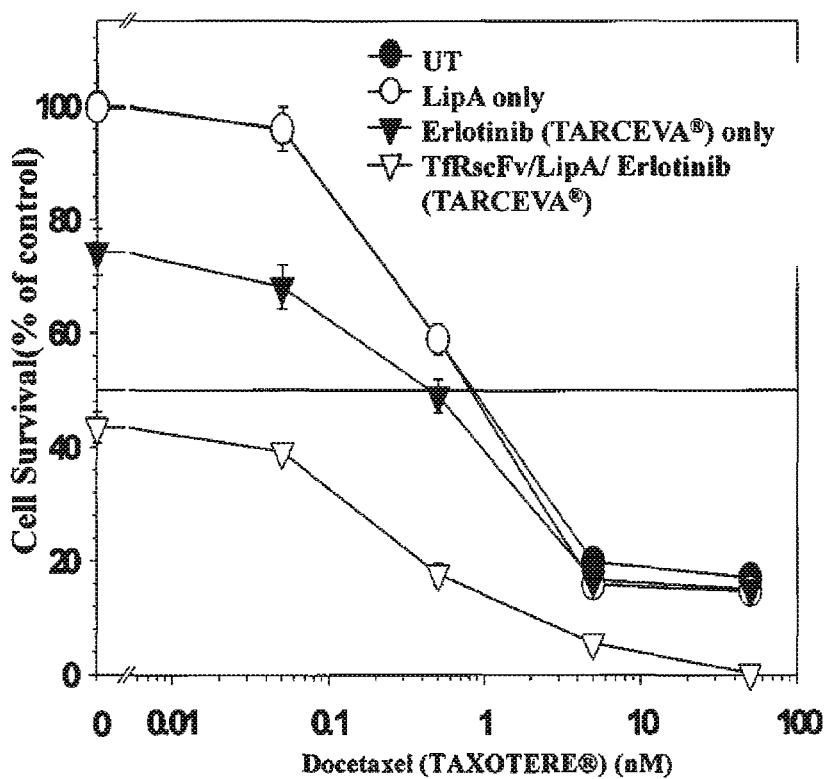

FIG. 34B shows the effect of TfRscFv/LipA (scL) complex delivery of Erlotinib at a concentration of 7.5 uM on sensitization of human melanoma cells to docetaxel (Taxotere) as compared to free Erlotinib (TARCEVA®).

FIG. 35 shows the effect of TfRscFv/LipA (scL) complex delivery of Erlotinib at a concentration of 7.5 uM on sensitization of human pancreatic cancer cells PANC-1 to gemcitabine (GEMZAR®) as compared to free Erlotinib (TARCEVA®).

Figure 36A:
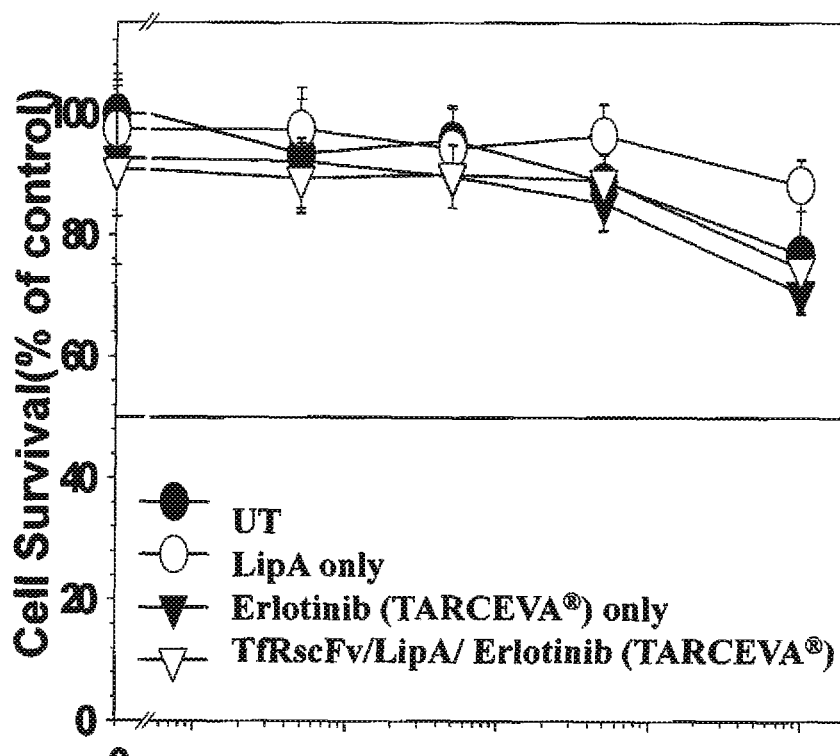

FIG. 36A shows the effect of tumor targeting liposomal delivery of Erlotinib (TARCEVA®) (TfRscFv/LipA/Erlotinib (scL-TARCEVA®)) on sensitization of normal human fibroblast cell line H500 to Mitoxantrone.

Figure 36B:
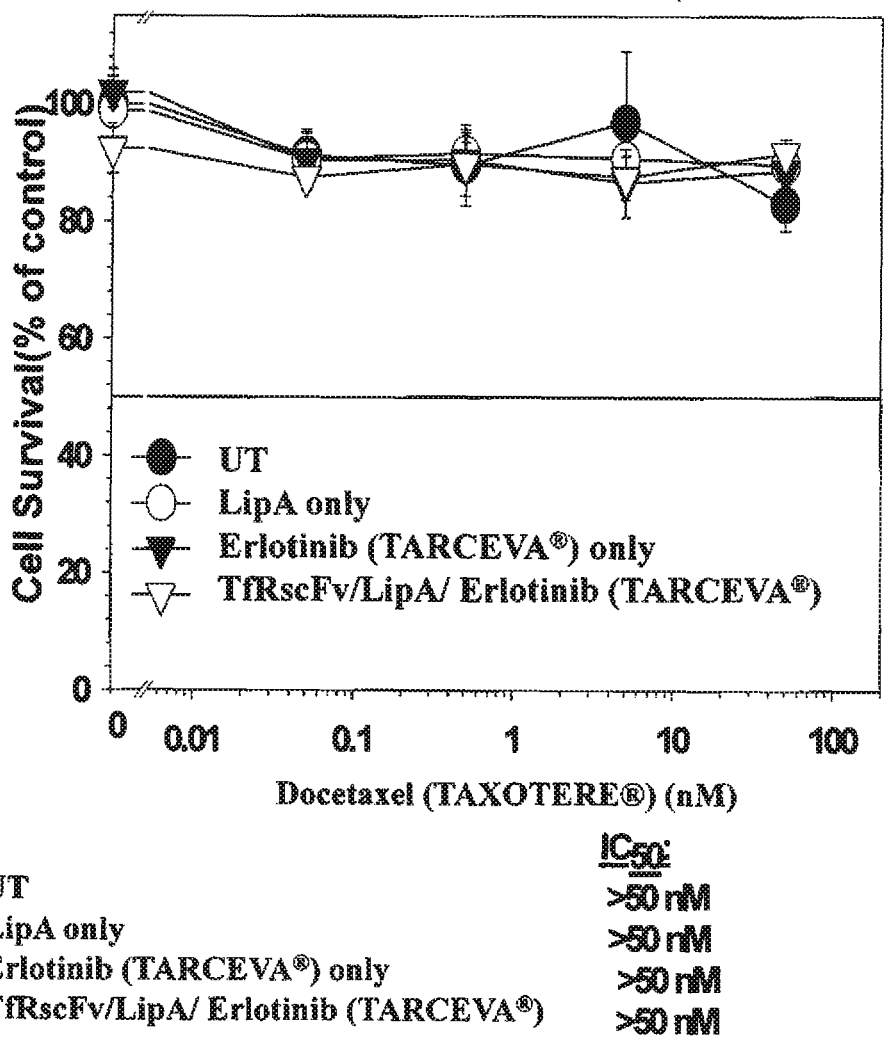

FIG. 36B shows the effect of tumor targeting liposomal delivery of Erlotinib (TARCEVA®) (TfRscFv/LipA/Erlotinib (scL-TARCEVA®) on sensitization of normal human fibroblast cell line H500 to (docetaxel) TAXOTERE®.

Figure 36C:
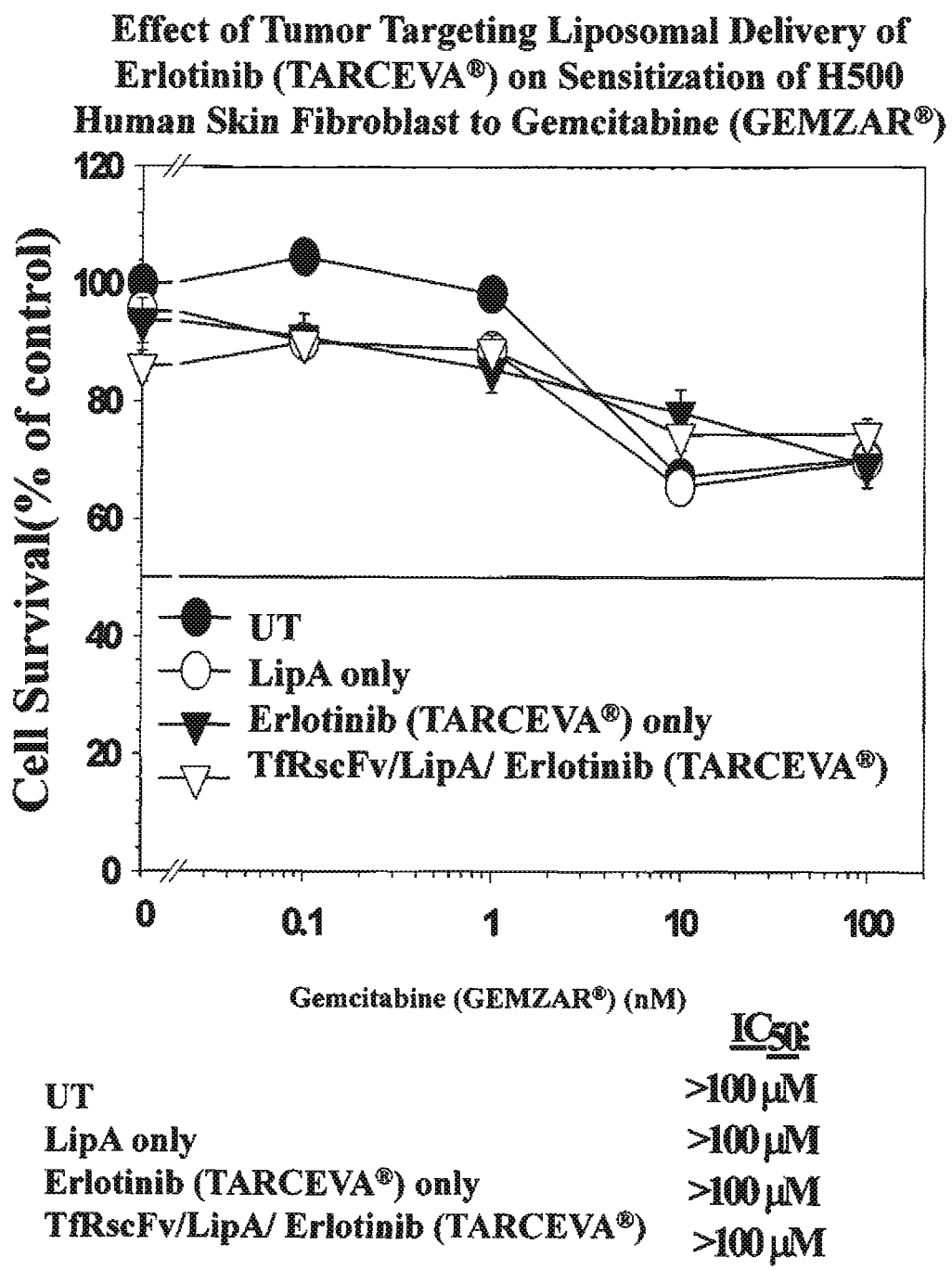

FIG. 36C shows the effect of tumor targeting liposomal delivery of Erlotinib (TARCEVA®) (TfRscFv/LipA/Erlotinib (scL-TARCEVA®)) on sensitization of normal human fibroblast cell line H500 to Gemcitabine (GEMZAR®).

Figure 37:
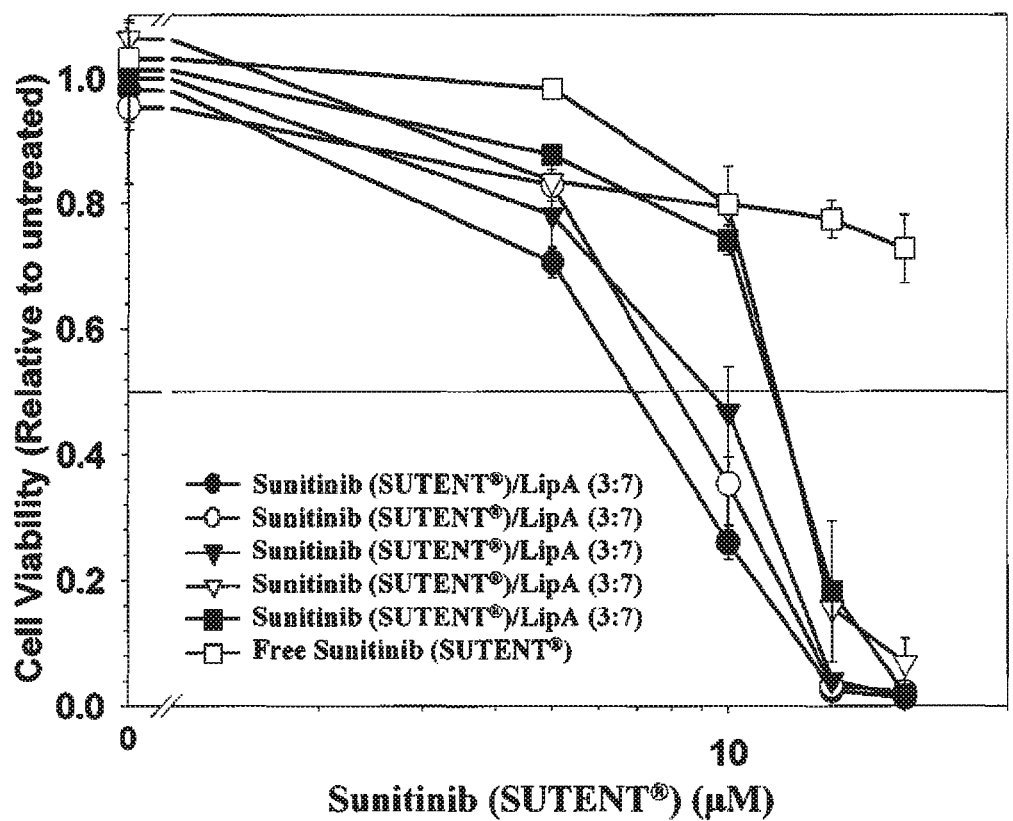

FIG. 37 shows the effect of different ratios of Sunitinib (SUTENT®)/LipA in the TfRscFv/LipA/Sunitinib complex on DU145 human prostate cancer cells as compared to free Sunitinib.

Figure 38A:
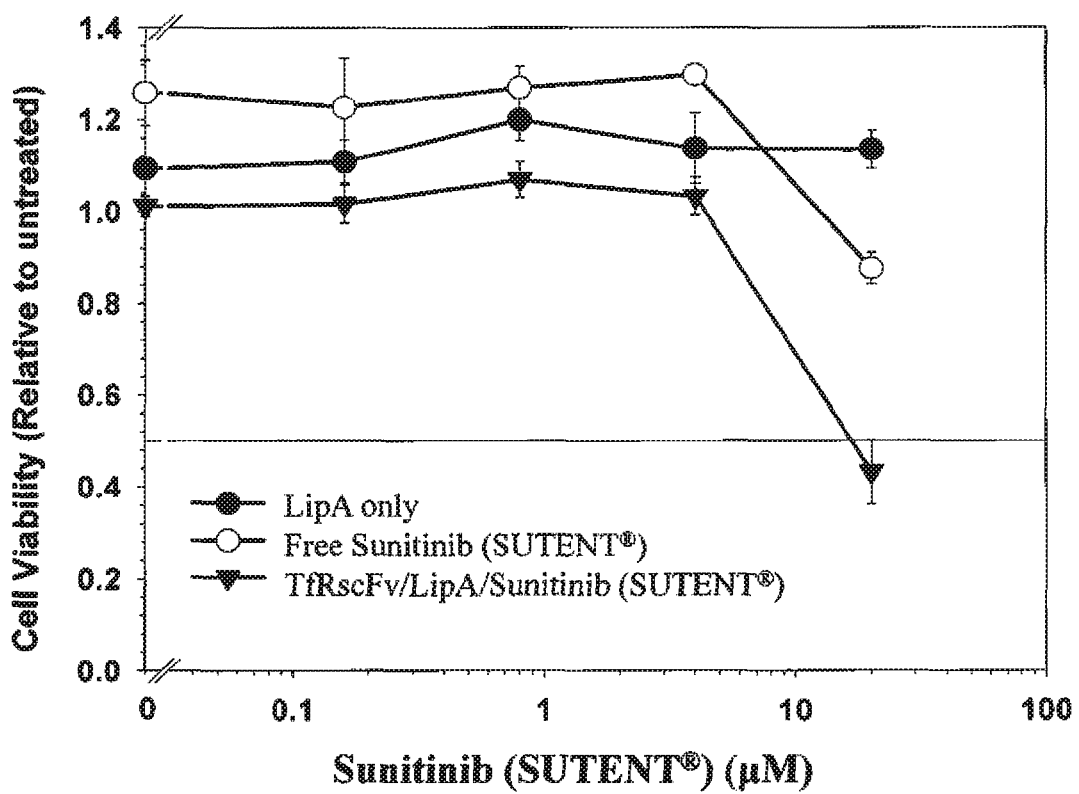

FIG. 38A shows the comparison of the effects of Sunitinib (SUTENT®) delivered by the ligand-liposome complex (TfRscFv/LipA/Sunitinib (scL-SUTENT®)) and free Sunitinib on human prostate cancer cells (DU145).

FIG. 38B shows the comparison of the effects of Sunitinib (SUTENT®) delivered by the ligand-liposome complex (TfRscFv/LipA/Sunitinib (scL-SUTENT®)) and free Sunitinib on human pancreatic cancer cells (PANC-1).

FIG. 39A shows the effect of TfRscFv/LipA (scL) complex delivery of Sunitinib at a concentration of 2.5 uM on sensitization of human melanoma cell line MDA-MB-435 to Docetaxel (Taxotere) as compared to free Sunitinib (SUTENT®).

Figure 39B:
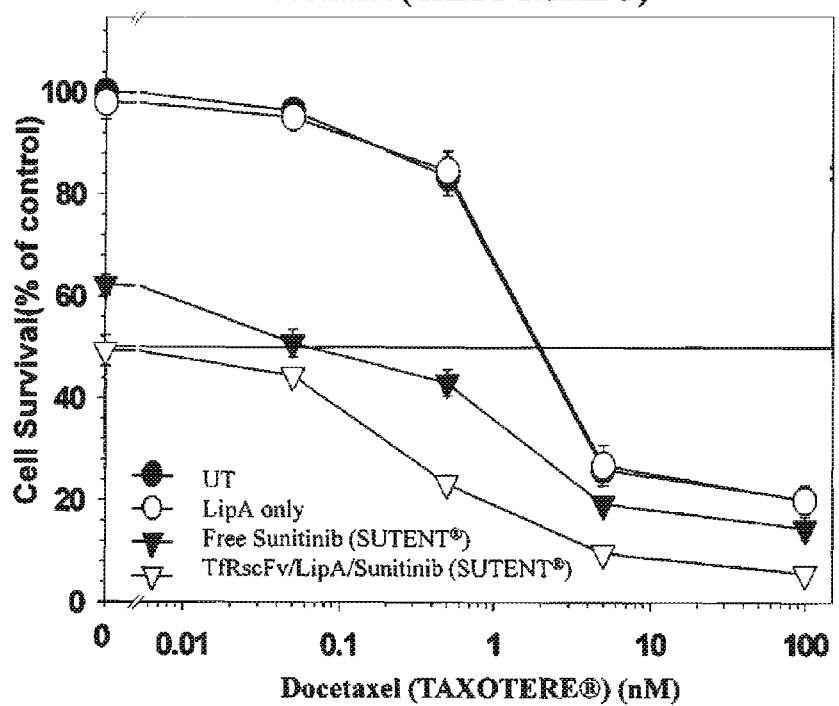

FIG. 39B shows the effect of TfRscFv/LipA (scL) complex delivery of Sunitinib at a concentration of 5 uM on sensitization of human melanoma cell line MDA-MB-435 to Docetaxel (Taxotere) as compared to free Sunitinib (SUTENT®)

Figure 40:
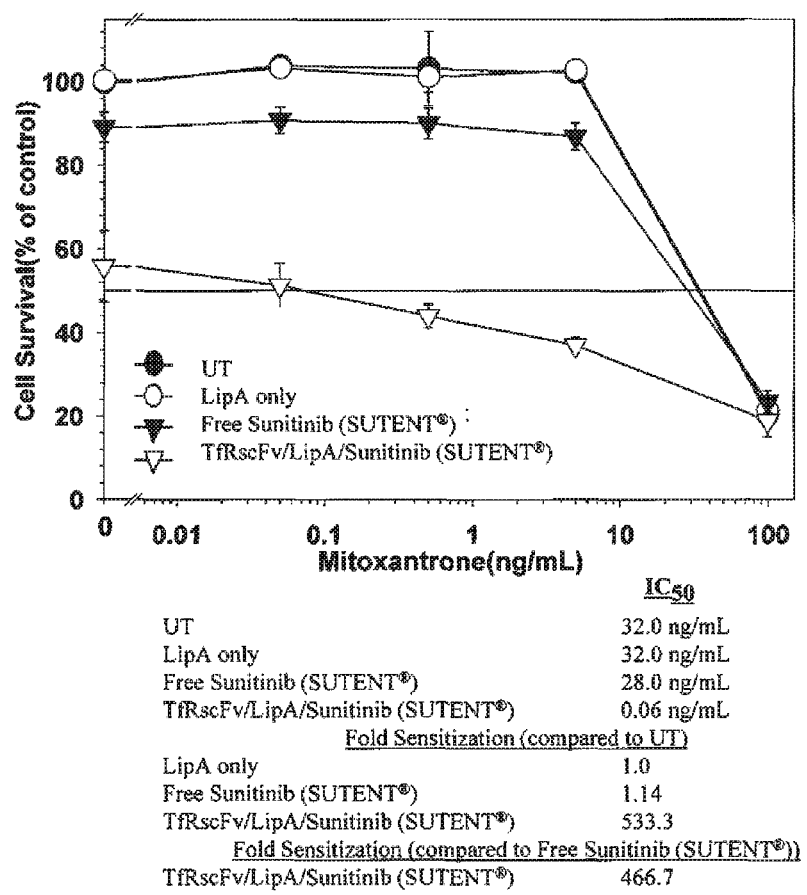

FIG. 40 shows the effect of TfRscFv/LipA (scL) complex delivery of Sunitinib at a concentration of 5 uM on sensitization of human prostate cancer cell line DU145 to mitoxantrone as compared to free Sunitinib (SUTENT®)

FIG. 41 shows the effect of TfRscFv/LipA (scL) complex delivery of Sunitinib at a concentration of 2.5 uM on sensitization of human pancreatic cancer cell line PANC-1 to gemcitabine (GEMZAR®) as compared to free Sunitinib (SUTENT®).

Figure 42A:
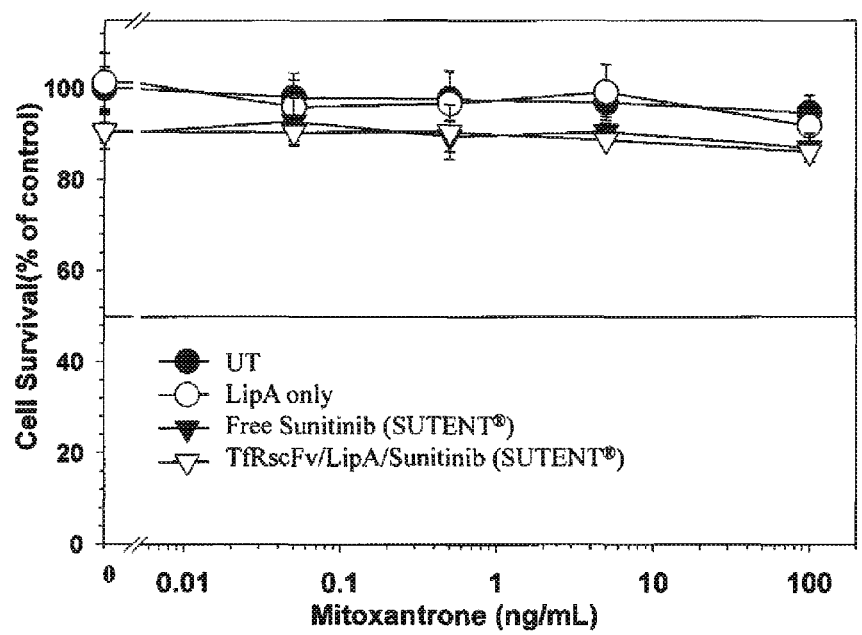

FIG. 42A shows the effect of tumor targeting liposomal delivery of Sunitinib (SUTENT®) (TfRscFv/LipA/Sunitinib (scL-SUTENT®)) on sensitization of normal human fibroblast cell line H500 to Mitoxantrone.

Figure 42B:
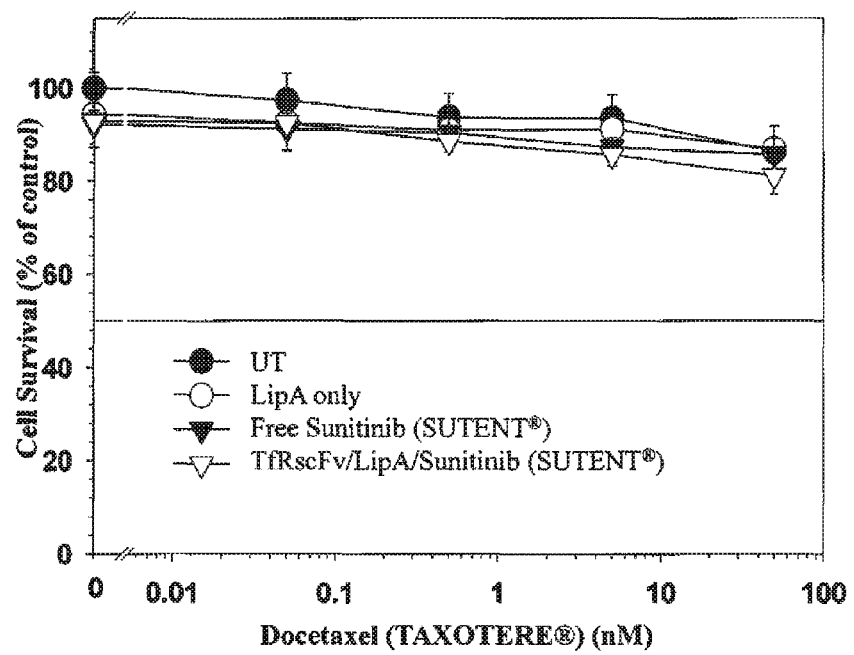

FIG. 42B shows the effect of tumor targeting liposomal delivery of Sunitinib (SUTENT®) (TfRscFv/LipA/Sunitinib (scL-SUTENT~) on sensitization of normal human fibroblast cell line H500 to docetaxel (TAXOTERE®).

Figure 42C:
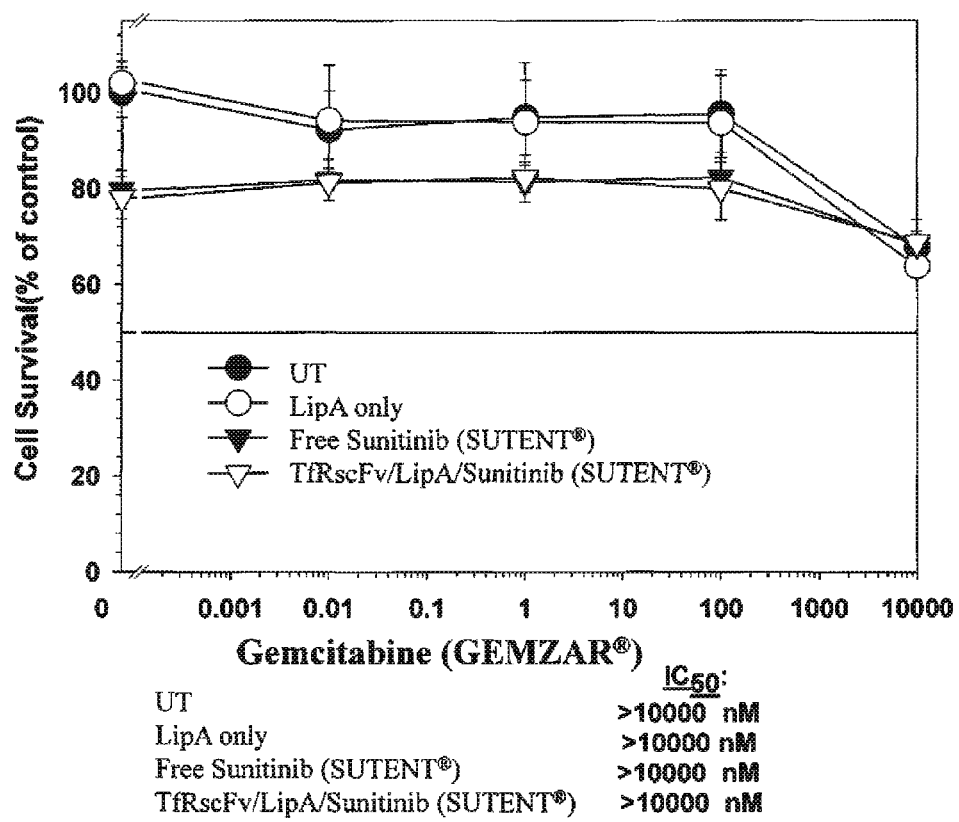

FIG. 42C shows the effect of tumor targeting liposomal delivery of Sunitinib (SUTENT®) (TfRscFv/LipA/Sunitinib (scL-SUTENT®)) on sensitization of normal human fibroblast cell line H500 to Gemcitabine (GEMZAR®).

Figure 43A:
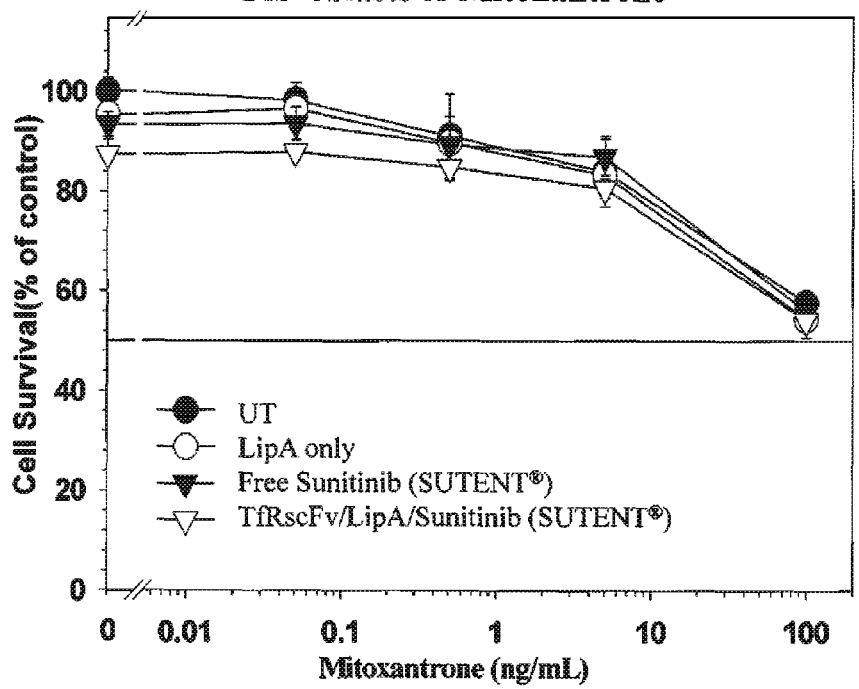

FIG. 43A shows the effect of tumor targeting liposomal delivery of Sunitinib (SUTENT®) (TfRscFv/LipA/Sunitinib (scL-SUTENT®)) on sensitization of normal human lung fibroblast cell line IMR90 to Mitoxantrone.

Figure 43B:
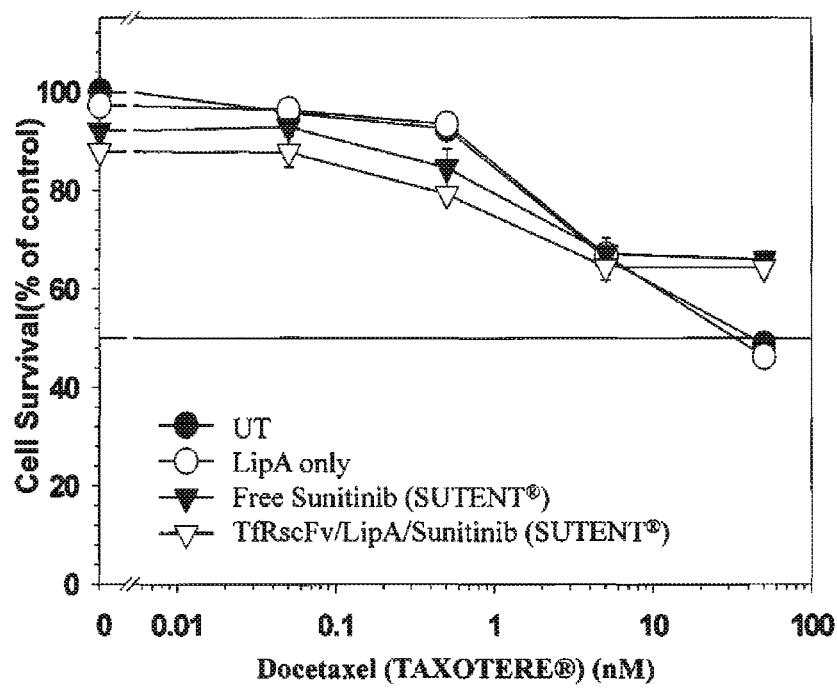

FIG. 43B shows the effect of tumor targeting liposomal delivery of Sunitinib (SUTENT®) (TfRscFv/LipA/Sunitinib (scL-SUTENT®) on sensitization of normal human lung fibroblast cell line IMR90 to docetaxel (TAXOTERE®).

Figure 43C:
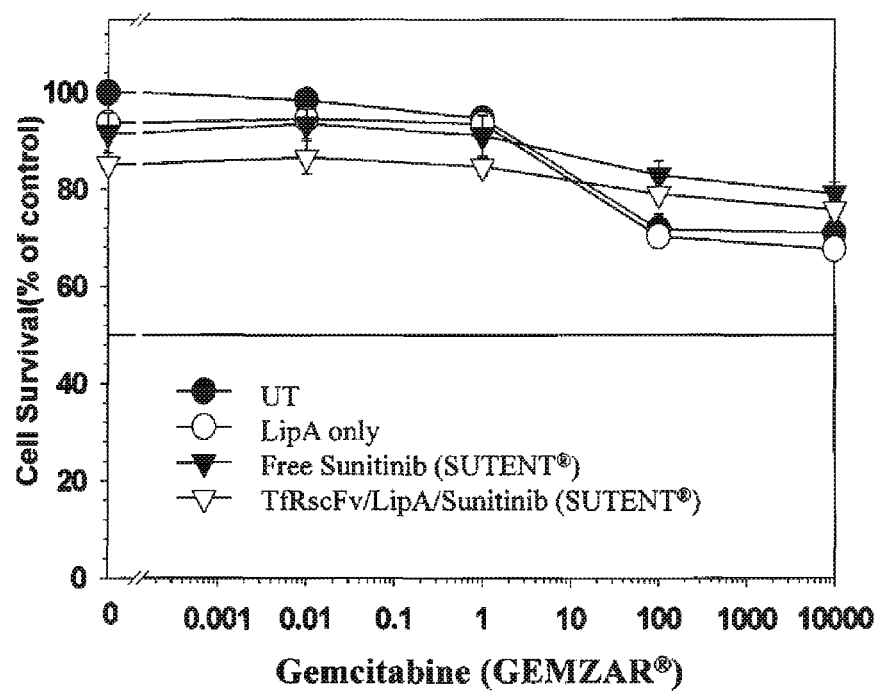

FIG. 43C shows the effect of tumor targeting liposomal delivery of Sunitinib (SUTENT®) (TfRscFv/LipA/Sunitinib (scL-SUTENT®)) on sensitization of normal human lung fibroblast cell line IMR90 to gemcitabine (GEMZAR®).

Figure 44:
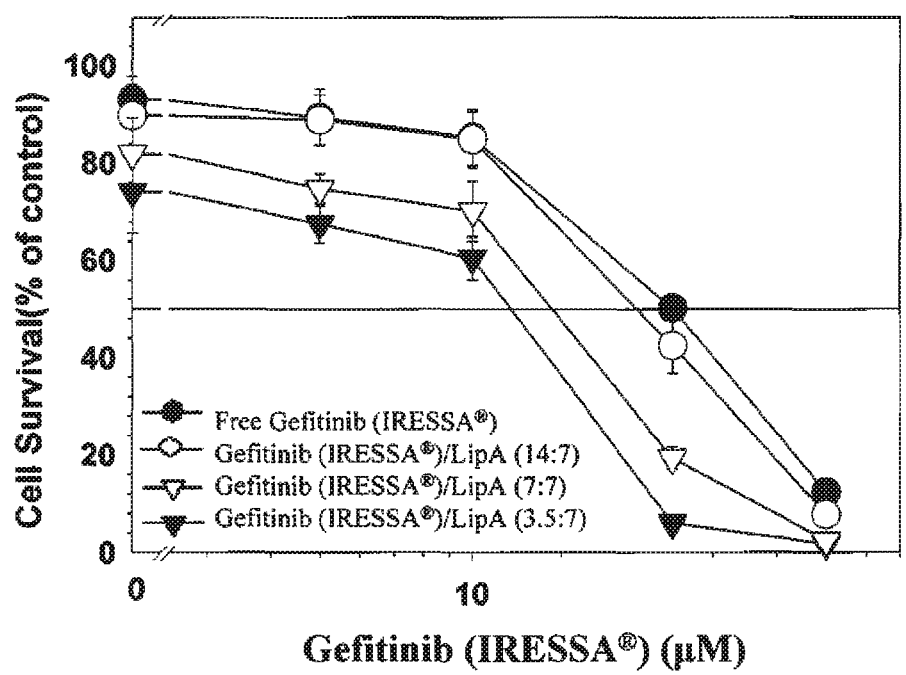

FIG. 44 shows the effect of different ratios of Gefitinib (IRESSA®)/LipA in the TfRscFv/LipA/Gefitinib complex on MDA-MB-231 human breast cancer cells as compared to free Gefitinib (IRESSA®).

Figure 45A:
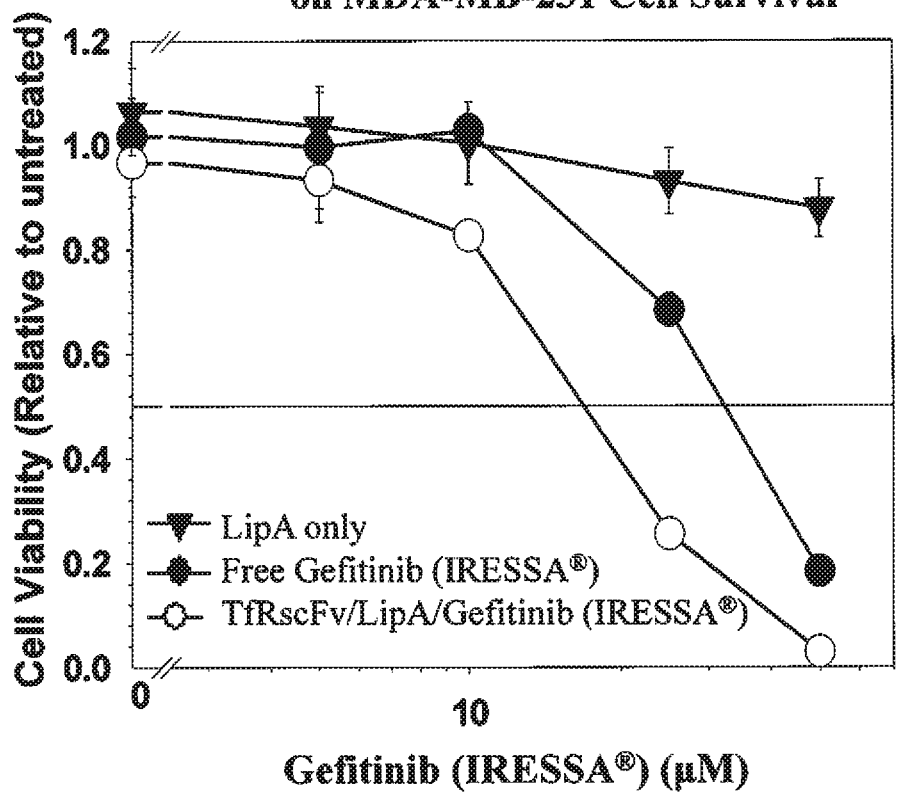

FIG. 45A shows the comparison of the effects of Gefitinib (IRESSA®) delivered by the ligand-liposome complex (TfRscFv/LipA/Gefitinib (scL-Gefitinib)) and free Gefitinib on human breast cancer cells (MDA-MB-231)

FIG. 45B shows the comparison of the effects of Gefitinib (IRESSA®) delivered by the ligand-liposome complex (TfRscFv/LipA/Gefitinib (scL-Gefitinib)) and free Gefitinib on human melanoma cells (MDA-MB-435)

Figure 45C:
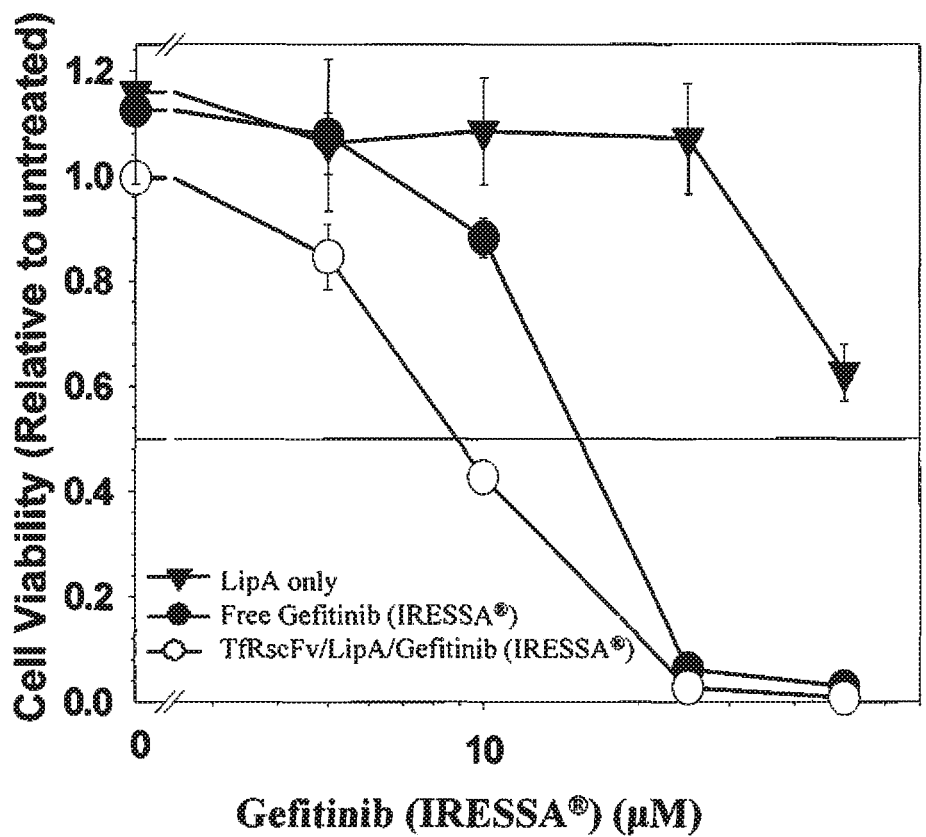

FIG. 45C shows the comparison of the effects of Gefitinib (IRESSA®) delivered by the ligand-liposome complex (TfRscFv/LipA/Gefitinib (scL-Gefitinib)) and free Gefitinib on human prostate cancer cells (DU145)

FIG. 46A shows the effect of TfRscFv/LipA (scL) complex delivery of Gefitinib at a concentration of 12 uM on sensitization of human breast cancer cell line MDA-MB-231 to docetaxel (Taxotere) as compared to free Gefitinib (IRESSA®).

FIG. 46B shows the effect of TfRscFv/LipA (scL) complex delivery of Gefitinib at a concentration of 15 uM on sensitization of human melanoma cells to docetaxel (Taxotere) as compared to free Gefitinib (IRESSA®)

FIG. 46C shows the effect of TfRscFv/LipA (scL) complex delivery of Gefitinib at a concentration of 8 uM on sensitization of human prostate cancer cell line (DU145) to mitoxantrone as compared to free Gefitinib (IRESSA®)

DETAILED DESCRIPTION OF THE INVENTION

Antibody- or antibody fragment-targeted cationic liposome or cationic polymer complexes in accordance with this invention are made by a simple and efficient non chemical conjugation method in which the components of the desired complex are mixed together in a defined ratio and in a defined order. Unexpectedly, the resultant complexes are as effective as, or more effective than, similar complexes in which the antibody or antibody fragment is chemically conjugated to the liposome or polymer.

Either a whole antibody or an antibody fragment can be used to make the complexes of this invention. In an exemplary embodiment, an antibody fragment is used. Suitably, the antibody fragment is a single chain Fv fragment of an antibody. One exemplary antibody is an anti-TfR monoclonal antibody, and a suitably antibody fragment is an scFv based on an anti-TfR monoclonal antibody. A suitable anti-TfR monoclonal antibody is 5E9. An scFv based on this antibody contains the complete antibody binding site for the epitope of the TfR recognized by this MAb as a single polypeptide chain of approximate molecular weight 26,000. An scFv is formed by connecting the component VH and VL variable domains from the heavy and light chains, respectively, with an appropriately designed peptide, which bridges the C-terminus of the first variable region and N-terminus of the second, ordered as either VH-peptide-VL or VL-peptide-VH. Another exemplary antibody is an anti-HER-2 monoclonal antibody, and another preferred antibody fragment is an scFv based on an anti-HER-2 monoclonal antibody.

In a preferred embodiment, a cysteine moiety is added to the C-terminus of the scFv. Although not wishing to be bound by theory, it is believed that the cysteine, which provides a free sulfhydryl group, may enhance the formation of the complex between the antibody and the liposome. With or without the cysteine, the protein can be expressed in E. coli inclusion bodies and then refolded to produce the antibody fragment in active form, as described in detail in the Examples below.

Unless it is desired to use a sterically stabilized immunoliposome in the formation of the complex, a first step in making the complex comprises mixing a cationic liposome or combination of liposomes or small polymer with the antibody or antibody fragment of choice. A wide variety of cationic liposomes are useful in the preparation of the complexes of this invention. Published PCT application WO99/25320 describes the preparation of several cationic liposomes. Examples of desirable liposomes include those that comprise a mixture of dioleoyltrimethylammonium phosphate (DOTAP) and dioleoylphosphatidylethanolamine (DOPE) and/or cholesterol (chol), a mixture of dimethyldioctadecylammonium bromide (DDAB) and DOPE and/or chol. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio). In addition, the liposomes can also comprise endosomal disrupting peptides, such as the K[K(H)KKK]$_5$-K(H)KKC (HoKC) (SEQ ID NO: 2) peptide manufactured by Sigma-Genosys (The Woodlands, Tex.). The endosomal disrupting peptide HoKC may help the release of agents in the cytoplasm of the cells.

Suitable polymers are DNA binding cationic polymers that are capable of mediating DNA compaction and can also mediate endosome release. A preferred polymer is polyethyleneimine. Other useful polymers include polysine, protamine and polyamidoamine dendrimers.

The antibody or antibody fragment is one which will bind to the surface of the target cell, and preferably to a receptor that is differentially expressed on the target cell. The antibody or antibody fragment is mixed with the cationic liposome or polymer at room temperature and at a protein:lipid ratio in the range of about 1:20 to about 1:40 (w:w) or a protein polymer ratio in the range of about 0.1:1 to 10:1 (molar ratio).

The antibody or antibody fragment and the liposome or polymer are allowed to incubate at room temperature for a short period of time, typically for about 10-15 minutes, then the mixture is mixed with a therapeutic or diagnostic agent of choice. Examples of therapeutic molecules or agents which can be complexed to the antibody and liposome include genes, high molecular weight DNA (genomic DNA), plasmid DNA, antisense oligonucleotides, siRNA, peptides, ribozymes, nucleic acids, small molecules, viral particles, immunomodulating agents, proteins, imaging agents and chemical agents. Preferred therapeutic molecules include genes encoding p53, Rb94 or Apoptin. RB94 is a variant of the retinoblastoma tumor suppressor gene. Apoptin is a gene that induces apoptosis in tumor cells only. In another preferred embodiment, the agent is an antisense oligonucleotide, such as HER-2. A preferred HER-2 antisense oligonucleotide has the sequence 5'-TCC ATG GTG CTC ACT-3' (Seq. ID No: 1). A third type of preferred agent is a diagnostic imaging agent, such as an MRI imaging agent, such as a Gd-DTPA agent. If the agent is DNA, such as the coding region of p53, it can be positioned under the control of a strong constitutive promoter, such as an RSV or a CMV promoter.

The antibody or antibody fragment and liposome combination is mixed with the therapeutic or diagnostic agent at a ratio in the range of about 1:10 to 1:20 (μg of agent:nmole of total lipid) or about 1:10 to 1:40 (ug of agent:nmole of total polymer) and incubated at room temperature for a short period of time, typically about 10 to 15 minutes. The size of the liposome complex is typically within the range of about 50-500 nm as measured by dynamic light scattering using a Malvern ZETASIZER® 3000.

In one embodiment of this invention, the liposome used to form the complex is a sterically stabilized liposome. Sterically stabilized liposomes are liposomes into which a hydrophilic polymer, such as PEG, poly(2-ethylacrylic acid), or poly(n-isopropylacrylamide (PNIPAM) have been integrated. Such modified liposomes can be particularly useful when complexed with therapeutic or diagnostic agents, as they typically are not cleared from the blood stream by the reticuloendothelial system as quickly as are comparable liposomes that have not been so modified. To make a sterically stabilized liposome complex of the present invention, the order of mixing the antibody or antibody fragment, the liposome and the therapeutic or diagnostic agent is reversed from the order set forth above. In a first step, a cationic liposome as described above is first mixed with a therapeutic or diagnostic agent as described above at a ratio in the range of about 1:10 to 1:20 (μg of agent:nmole of lipid). To this lipoplex is added a solution of a PEG polymer in a physiologically acceptable buffer and the resultant solution is incubated at room temperature for a time sufficient to allow the polymer to integrate into the liposome complex. The antibody or antibody fragment then is mixed with the stabilized liposome complex at room temperature and at a protein:lipid ratio in the range of about 1:5 to about 1:30 (w:w).

The liposomal or polymer complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a human patient to be benefited by administration of the therapeutic or diagnostic molecule of the complex. The complexes are sized appropriately so that they are distributed throughout the body following i.v. administration. Alternatively, the complexes can be delivered via other routes of administration, such as intratumoral, oral, intralesional, aerosal, percutaneous, endoscopic, topical, intraperitoneal or subcutaneous administration.

In one embodiment, compositions comprising the antibody- or antibody fragment-targeted liposome (or polymer) and therapeutic agent complexes are administered to effect human gene therapy. The therapeutic agent component of the complex comprises a therapeutic gene under the control of an appropriate regulatory sequence. Gene therapy for various forms of human cancers can be accomplished by the systemic delivery of antibody or antibody fragment-targeted liposome or polymer complexes which contain a nucleic acid encoding wt p53. The complexes can specifically target and sensitize tumor cells, both primary and metastatic tumors, to radiation and/or chemotherapy both in vitro and in vivo.

The complexes can be optimized for target cell type through the choice and ratio of lipids, the ratio of antibody or antibody fragment to liposome, the ratio of antibody or antibody fragment and liposome to the therapeutic or diagnostic agent, and the choice of antibody or antibody fragment and therapeutic or diagnostic agent.

In one embodiment, the target cells are cancer cells. Although any tissue having malignant cell growth can be a target, head and neck, breast, prostate, pancreatic, glioblastoma, renal, hepatic, cervical, lung, liposarcoma, rhabdomyosarcoma, choriocarcinoma, melanoma, retinoblastoma, ovarian, gastric and colorectal cancers are preferred targets.

The complexes made by the method of this invention also can be used to target non-tumor cells for delivery of a therapeutic molecule. While any normal cell can be a target, preferred cells are dendritic cells, endothelial cells of the blood vessels, lung cells, breast cells, bone marrow cells, spleen cells, thymus cells, cells of the nasal passage and liver cells. Undesirable, but benign, cells can be targeted, such as benign prostatic hyperplasia cells, over-active thyroid cells, lipoma cells, and cells relating to autoimmune diseases, such as B cells that produce antibodies involved in arthritis, lupus, myasthenia gravis, squamous metaplasia, dysplasia and the like.

The complexes can be administered in combination with another therapeutic agent, such as either a radiation or chemotherapeutic agent. The therapeutic agent, or a combination of therapeutic agents, can be administered before or subsequent to the administration of the complex, for example within about 12 hours to about 7 days. Chemotherapeutic agents include, but are not limited to, for example, doxorubicin, 5-fluorouracil (5FU), cisplatin (CDDP), docetaxel. gemcitabine, pacletaxel, vinblastine, etoposide (VP-16), camptothecia, actinomycin-D, mitoxantrone and mitomycin C. Radiation therapies include gamma radiation, X-rays, LN irradiation, microwaves, electronic emissions and the like.

Diagnostic agents also can be delivered to targeted cells via the liposome or polymer complexes. Agents which can be detected in vivo following administration can be used. Exemplary diagnostic agents include electron dense materials, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. Imaging agents disclosed by Low et al. in U.S. Pat. No. 5,688,488, incorporated herein by reference, are useful in the present invention.

The complexes made in accordance with the method of this invention can be provided in the form of kits for use in the systemic delivery of a therapeutic molecule by the complex. Suitable kits can comprise, in separate, suitable containers, the liposome, the antibody or antibody fragment, and the therapeutic or diagnostic agent. The components can be mixed under sterile conditions in the appropriate order and administered to a patient within a reasonable period of time, generally from about 30 minutes to about 24 hours, after preparation. The kit components preferably are provided as solutions or as dried powders. Components provided in solution form preferably are formulated in sterile water-for-injection, along with appropriate buffers, osmolarity control agents, etc.

In a further embodiment, the present invention provides liposomal complexes wherein the diagnostic and/or therapeutic agents are one or more small molecules encapsulated within the interior of the liposome, contained within the hydrocarbon chain region of the bilayer, complexed/associated with the inner and/or outer monolayer (e.g., via static interaction or chemical/covalent interaction), or a combination of any or all of these possibilities. As used herein, the term "small molecule" refers to a low molecular-weight pharmaceutical, therapeutic and/or diagnostic agent (examples of the latter being markers, dyes, etc.), that generally has a molecular weight of less than about 10 kD, suitably less than about 5000 Daltons, and more suitably less than about 1000 Daltons, for example about 100 to about 900 Daltons, about 200 to about 800 Daltons, about 300 to about 700 Daltons, about 400 to about 600 Daltons, or about 500 Daltons, as well as salts, esters, and other pharmaceutically acceptable forms of such compounds.

Examples of small molecules include compounds useful for treating patients that are suffering from or pre-disposed to any disease state, including, but not limited to, cancers (e.g., a breast cancer, a uterine cancer, an ovarian cancer, a prostate cancer, a testicular cancer, a lung cancer, a leukemia, a lymphoma, a colon cancer, a gastrointestinal cancer, a pancreatic cancer, a bladder cancer, a kidney cancer, a bone cancer, a neurological cancer, a head and neck cancer, a skin cancer, a sarcoma, an adenoma, a carcinoma and a myeloma); infectious diseases (e.g, bacterial diseases, fungal diseases, parasitic diseases and viral diseases (such as a viral hepatitis, a disease caused by a cardiotropic virus; HIV/AIDS, flu, SARS, and the like)); and genetic disorders (e.g., anemia, neutropenia, thrombocytopenia, hemophilia, dwarfism and severe combined immunodeficiency disease ("SCID"); autoimmune disorders (e.g., psoriasis, systemic lupus erythematosus and rheumatoid arthritis) and neurodegenerative disorders (e.g., various forms and stages of multiple sclerosis, Creutzfeldt-Jakob Disease, Alzheimer's Disease, and the like).

Exemplary small molecules useful for treatment of cancers (i.e. anticancer small molecules) include, but are not limited to small molecules that inhibit tubulin polymerization, anti-angiogenic small molecules, kinase inhibitors, and the like. Small molecules for use in the present invention suitably have a pKa of about 2 to about 9, and in many cases, will have several pKas (i.e., 2, 3, 4, etc) within this range. Small molecules for use in the practice of the present invention can be water-soluble, slightly water-soluble, or poorly water soluble (including compounds that are not soluble in water).

In suitable embodiments, the small molecules for use in the practice of the present invention include, but are not limited to tubulin polymerization inhibitors, such as GMC-5-193 (and analogs thereof) and YK-3-250 (and analogs thereof).

GMC-5-193 (and analogs thereof) is a thalidomide analog which has antimicrotubule and anti-angiogenic effects in several cancer cell lines. GMC-5-193 inhibits human cancer cell proliferation with antiproliferative activities. The potency of this molecule is similar to that of vincristine, a well-known antimitotic agent. Several studies suggest that the antiproliferative effect may be due to inhibition of tubulin polymerization in several types of cancer cells. These analogs initiated mitotic accumulation and formation of abnormal mitotic spindles in cancer cells.

From the x-ray structure, it has been confirmed that GMC-5-193 docks right into the area of greatest amino acid difference near the taxol and colchicines binding sites in PIII human tubulin. However, in examining in vivo efficacy, the poor water solubility of this small molecule hinders its administration. Solubility is an important consideration in terms of systemic drug bioavailability, because insolubility further limits drug efficacy and the subsequent need for increased dosage compromises patient tolerance. To circumvent this problem, a tumor-targeting liposomal delivery system for this molecule, using tumor-targeted ligand (TfRscFv) and cationic liposome conjugated with (or without) HoKC, a synthetic pH-sensitive histidylated oligolysine was utilized. HoKC was included in the complex to improve the anticancer effect of the targeting complex, designed to aid in endosomal escape. The drug is expected to diffuse into the cytoplasm from where it is transferred to the nucleus exerting its cytotoxic effects or released into the extracellular compartment, where it can have cytotoxic effects on other tumor cells (bystander effect).

Additional small molecules for use in the practice of the present invention include tyrosine kinase inhibitors, such as, but not limited to:

imatinib mesylate (GLEEVEC®):

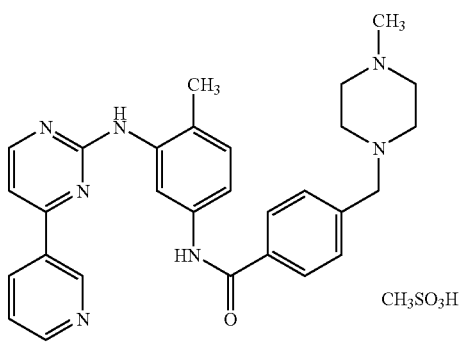

$C_{29}H_{31}N_7O$ (MW = 589.7), pKa = 7.5, 3.0, 2.7;

Erlotinib hydrochloride (TARCEVA®):

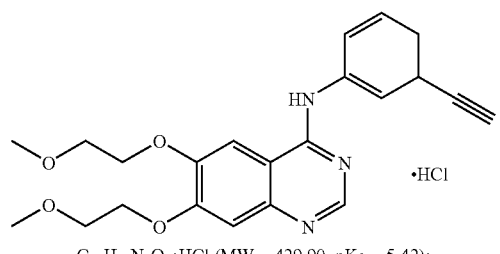

$C_{22}H_{23}N_3O_4 \cdot HCl$ (MW = 429.90, pKa = 5.42);

Sunitinib Malate (SU11248, SUTENT®):

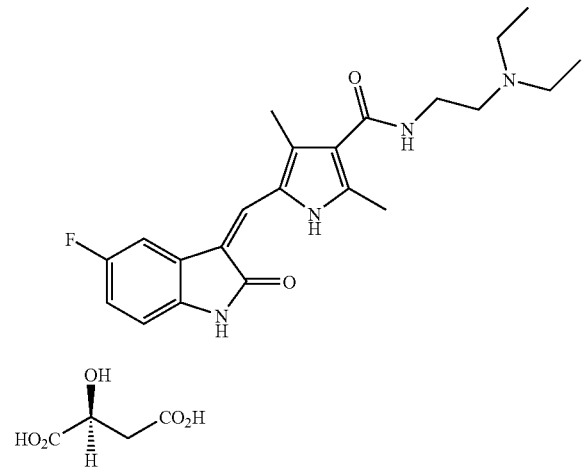

$C_{22}H_{27}FN_4O_2 \cdot C_4H_6O_5$ (MW = 532.6, pKa = 8.95); and

Gefitinib (IRESSA®):

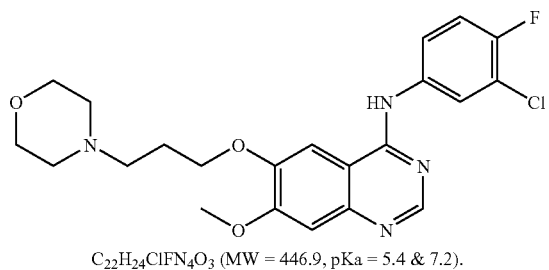 [SMILES: COc1cc2ncnc(Nc3ccc(F)c(Cl)c3)c2cc1OCCCN1CCOCC1]

$C_{22}H_{24}ClFN_4O_3$ (MW = 446.9, pKa = 5.4 & 7.2).

Additional small molecules for use in the practice of the present invention include pharmaceutical compounds, as well as marker dyes and other molecules for diagnosis. Examples of such small molecules are well known and easily identified by those skilled in the art, and many can be found on databases such as Pharmabase (National Center for Research Sources, National Institutes of Health). General classes of pharmaceutical small molecules that can be used in the practice of the present invention include, but are not limited to, compounds involved in regulating membrane transport (e.g., channels, pumps, receptors, transporters); compounds involved in metabolism (such as ATP inhibitors, electron transport controllers, inhibitors of amino acid or fatty acid synthesis, ceramide analogs, etc.); intracellular messengers (e.g., kinase inhibitors, etc); compounds involved in regulating cell signaling; compounds involved in regulating cellular area; as well as other well known classes of small molecules. Additional examples of small molecule classes and compounds can be found throughout U.S. Pat. Nos. 7,041,651, 7,033,775, 7,005,255 and 6,900,198, the disclosures of each of which are incorporated by reference herein in their entireties.

As described herein, small molecules are suitably encapsulated, contained or complexed/associated with the liposome complexes of the present invention by simply mixing the one or more small molecules with the liposomes during processing. Suitable ratios of small molecule:liposome complexes are readily determined by the ordinarily skilled artisan. For example, the molar ratio of small molecules to liposome complex is suitably in the range of about 0.2:7 to about 14:7 (small molecule:liposome), suitably at a molar ratio of about 1:7 to about 12:7, about 1:7 to about 10:7, about 2:7 to about 9:7, about 4:7 to about 8:7, about 5:7 to about 8:7, about 2.8:7 or about 7:7 (small molecule:liposome). As described throughout, examples of desirable cationic liposomes for delivery of small molecules include those that comprise a mixture of dioleoyltrimethylammonium phosphate (DOTAP) and dioleoylphosphatidylethanolamine (DOPE) and/or cholesterol (chol), a mixture of dimethyldioctadecylammonium bromide (DDAB) and DOPE and/or chol. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably about 1:(1-2) (molar ratio). Examples of ratios of various lipids include, but are not limited to:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |

| | | |
|---|---|---|
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol)

In one embodiment, the present invention provides methods of preparing small molecule-comprising antibody- or antibody fragment-targeted cationic immunoliposome complexes comprising preparing an antibody or antibody fragment; mixing the antibody or antibody fragment with a cationic liposome to form a cationic immunoliposome, wherein the antibody or antibody fragment is not chemically conjugated to the cationic liposome; and mixing the cationic immunoliposome with a small molecule to form said antibody- or antibody fragment-targeted-cationic immunoliposome complex. While not chemically conjugated to the cationic liposome, the antibody or antibody fragment directly associates/complexes with the liposome, e.g., via a charge-charge, or other non-chemical conjugation interaction, to form the immunoliposomes.

In suitable embodiments, the antibody fragment is a single chain Fv fragment, for example, an anti-transferrin receptor single chain Fv (TfRscFv). Examples of suitable lipids for use in preparing the small molecule-comprising cationic immunoliposomes are described herein, and include, mixtures of dioleoyltrimethylammonium phosphate with dioleoylphosphatidylethanolamine and/or cholesterol; and mixtures of dimethyldioctadecylammonium bromide with dioleoylphosphatidylethanolamine and/or cholesterol. Suitably, the cationic immunoliposome is mixed with the small molecule at a molar ratio in the range of about 0.2:7 to about 14:7 (small molecule:immunoliposome), suitably at a molar ratio of about 1:7 to about 12:7, about 1:7 to about 10:7, about 2:7 to about 9:7, about 4:7 to about 8:7, about 5:7 to about 8:7 or about 7:7 (small molecule:immunoliposome). Exemplary small molecules for use in the practice of the present invention include those described herein, as well as additional small molecules known in the art and readily identifiable by the ordinarily skilled artisan. Suitably, the small molecules are anticancer small molecules, such as, but not limited to, GMC-5-193, YK-3-250, imatinib mesylate, erlotinib hydrochloride, sunitinib malate, gefitinib and analogs and derivatives thereof, as well as others described herein and/or that will be familiar to the ordinarily skilled artisan. In a further embodiment, the present invention provides small molecule-comprising cationic immunoliposome complexes prepared by the methods described herein.

In a further embodiment, the present invention provides antibody- or antibody fragment-targeted cationic immunoliposome complexes comprising a cationic liposome, an antibody or antibody fragment, and a small molecule, wherein the antibody or antibody fragment is not chemically conjugated to the cationic liposome. The small molecule(s) can be encapsulated within the cationic liposome, contained with a hydrocarbon chain region of the cationic liposome, associated with an inner or outer monolayer of the cationic liposome (including the head-group region), or any combination thereof. Suitably, the cationic immunoliposomes of the present invention are unilamellar liposomes (i.e. a single bilayer), though multilamellar liposomes which comprise several concentric bilayers can also be used. Single bilayer cationic immunoliposomes of the present invention comprise an interior aqueous volume in which agents (e.g., small molecules) can be encapsulated (suitably water-soluble agents). They also comprise a single bilayer which has a hydrocarbon chain region (i.e., the lipid chain region of the lipids) in which agents (e.g., small molecules) can be contained (suitably lipid-soluble agents). In addition, agents (e.g., small molecules) can be complexed or associated with either, or both, the inner monolayer and/or the outer monolayer of the liposome membrane (i.e., the headgroup region of the lipids). In further embodiments, agents (e.g., small molecules) can be encapsulated/associated/complexed in any or all of these regions of the cationic immunoliposome complexes of the present invention.

In a still further embodiment, the present invention provides methods of treating a patient suffering from, or predisposed to, a disease state, comprising administering the small molecule-comprising cationic immunoliposome complexes of the present invention to the patient. The immunoliposome complexes can be administered via any desired route, including, but not limited to, intravenous, oral, topical, via inhalation, intramuscular injection, intratumoral injection, intralesional injection, aerosal, percutaneous, endoscopic, topical, intraperitoneal, or subcutaneous administration or other injection routes. As used herein, the term patient includes both animal patients (e.g., mammals such as dogs, cats, pigs, sheep, etc) as well as humans.

Suitably, the methods of the present invention are used to treat patients suffering from, or predisposed to, cancer. In further embodiments, the methods of treating patients suffering from, or predisposed to, cancer can further comprise administering a chemotherapeutic agent to the patient in addition to the administration of the small molecule-comprising immunoliposome complex. In suitable embodiments, the methods of the present invention comprise administering an immunoliposome complex comprising a small molecule selected from the group consisting of GMC-5-193, YK-3-250, imatinib mesylate, erlotinib hydrochloride, sunitinib malate, gefitinib and analogs and derivatives thereof, along with a chemotherapeutic agent selected from the group consisting of doxorubicin, cisplatin, mitoxantrone, taxotere and CDDP. The small molecule-comprising immunoliposome complex and the chemotherapeutic agent can be administered at the same time, or can be administered at different times (e.g., before or after one another). Suitably, the chemotherapeutic agent is administered before or after the small molecule-comprising immunoliposome complex, (e.g., at least 6 hours before or after, at least 12 hours before or after, at least 24 hours before or after, at least 48 hours before or after, etc., administration of the cationic immunoliposome complex). In further embodiments, the chemotherapeutic agent and the small molecule-comprising immunoliposome complex are administered at the same time to the patient. Appropriate dosages and timings or administration of the small molecule-comprising immunoliposome complexes and the chemotherapeutic agents are easily determined by those of skill in the art, based on information contained herein and that is readily available in the art.

In a further embodiment, the present invention provides methods of enhancing the effectiveness of a chemotherapeutic agent comprising administering a cationic immunoliposome complex of the present invention (e.g., a cationic immunoliposome complex comprising a small molecule) in conjunction with the chemotherapeutic agent to a patient. Suitable small molecules and chemotherapeutic agents include those described throughout as well as those known in the art. The small molecule-comprising immunoliposome complex and the chemotherapeutic agent can be administered at the same time, or can be administered at different times. Suitably, the chemotherapeutic agent is administered before or after the small molecule-comprising immunoliposome complex, (e.g., at least 6 hours before or after, at least 12 hours before or after, at least 24 hours before or after, at least 48 hours before or after, etc., administration of the cationic immunoliposome complex). In further embodiments, the chemotherapeutic agent and the small molecule-comprising immunoliposome complex are administered at the same time to the patient.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Construction and Purification of TfRscFv with a 3'-cysteine

Plasmid expression vector pDFH2T-vecOK was obtained from Dr. David Fitzgerald, NCI. This vector encodes the single chain fragment for the 5E9 antibody, which recognizes the human transferrin receptor (CD71). The VH-linker-Vκ TfRscFv was obtained by PCR amplification of the desired fragment. A cysteine moiety was added at the 3' end of the TfRscFv protein. Two forms of this vector were constructed. The first contains a pelB leader signal sequence, for transport to the periplasmic space, and a H is Tag. The presence of the His Tag aids in detection of the protein, thus simplifying development of the purification protocol. Although this form was used for the initial testing, FDA guidelines recommend that no extraneous sequences be present for use in clinical trials. Therefore, a second form minus both of these sequences also was made.

Using PCR amplification the nucleotide sequence for the cysteine residue and a NotI restriction site were introduced at the 3' end. Similarly, a 5' NcoI site also was incorporated. The PCR product was cloned into NcoI and NotI sites of the commercial vector pET26b(+) (Novagen) thus producing a protein product containing both the pelB leader signal sequence and the His Tag. Growth in bacterial culture containing IPTG yielded an approximate 100 fold increase in single chain protein expression which was maximum at approximately 10 hours of IPTG induction. This protein was found primarily in the insoluble fraction (inclusion bodies).

The above construct also was modified to eliminate both the His Tag and pelB sequences in the final protein product. To accomplish this, the pET26b(+) vector was cut at the Nde I enzyme site 5' of the pelB sequence. PCR amplification inserted an Nde I site at the 5' end of the VH-linker-Vκ scFv for the TfR sequence. In addition to the nucleotide sequence for the cysteine residue and the NotI restriction site at the 3' end, a DNA stop codon was introduced adjacent to the cysteine sequence and before the NotI site. The PCR product was cloned into the NdeI and NotI sites of commercial expression vector pET26b(+) (Novogen). Thus, the protein product of this construct will not contain either the pelB sequence or the His-tag.

The majority of the cys-TfRscFv protein (approximately 90%) was found not to be soluble but to be contained within inclusion bodies. Therefore, the protein from the constructs described above was isolated from the inclusion bodies by sonication, treatment with 6 M guanidine-HCl, 200 mM NaCl (6 M GuHCl buffer) and purified via SEPHACRYL® S-200 gel filtration column chromatography. Refolding of the cys-TfRscFv protein was accomplished by dialysis at 4° C. against decreasing concentrations of guanidine-HCl. Alternatively, the cys-TfRscFv protein was prepared by isolation of the inclusion bodies by sonication with Triton X-100 followed by solubilization in 6 M Guanidine-HCl, 0.1 M tris-HCI pH=8.0, 2 mM EDTA pH=8.0 and dithioerythritol. Refolding was accomplished by mixing with a buffer composed of 0.1 M Tris-HCI pH=8.0, 0.5M L-arginine-HCI, 2 mM EDTA and 0.9 mM glutathionine and holding at 4° C. for 36-48 hours, followed by dialysis at 4° C. for 20-24 hours against 20 mM Tris-HCI (pH=9.0), 100 mM Urea, and 2 mM EDTA (pH=8.0). After dialysis, the cys-TfRscFv was purified by ion exchange chromatography with Q-sepharose, followed by concentration (using an AMICON® ultrafiltration device) and dialysis at 4° C. for 30 hours against PBS (pH=7.4) plus 0.06 M sodium chloride. After purification, SDS-PAGE showed a single band of the solublized, refolded cys-TfRscFv protein with the correct molecular weight of approximately 28-30 kDa (as described in WO 00/50008). The cys TfRscFv protein is stored at −80° C.

EXAMPLE 2

Preparation of Cys-Tfrscfv-Liposome by Simple Mixing

Published PCT application WO 99/25320, incorporated herein by reference, describes the preparation of several cationic liposomes. The cationic liposomes prepared are clear solutions, their compositions and ratios are as follows:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol)

It is well known by those knowledgeable in the field that conjugated TfRscFv-immunoliposome retains its immunologic activity. We have established that the cys-TfRscFv can be chemically conjugated to lipoplex (PCT application WO 00/50008) and can efficiently transfect human prostate tumor cells in vitro and in vivo. It is common practice for single chain antibody fragments to be attached to liposomes using various chemical conjugation methods. We performed studies to determine if a simple mixing of the cys-TfRscFv and the cationic liposome (which does not contain any lipid with a reducible group such as Maleimide DOPE or any reducible group), instead of chemical conjugation, would result in formation of an immunologically active complex that could still efficiently bind to and transfect tumor cells. A series of cys-TfRscFv-immunoliposome complexes was prepared by mixing the cys-TfRscFv with liposome A at defined ratios of single chain protein to liposome ranging from 1/25 to 1/36 (w/w). Based upon the ELISA data with the conjugated cys-TfRscFv complex the ratio of DNA to nmoles total lipid in the mixed complex also was varied from 1/8 to 1/18. The preparation of the complexes was in accordance with the following general procedure: The appropriate amount of 2 mM liposome (A-H described above) is mixed with any water required to give a desired volume and inverted to mix. To the liposome-water the appropriate amount of cys-TfRscFv is added to give the desired ratio and mixed by gentle inversion 5-10 seconds. This mixture is kept at room temperature for 10 minutes (again inverted gently for 5-10 seconds after approximately 5 minutes). At the same time, the appropriate amount of DNA is mixed by inversion for 5-10 seconds with any water required to give a desired volume. Typically, for use in an in vitro assay, it is desirable that the concentration of DNA is in the range of about 0.01 µg to about 2 µg per well; for in vivo use, it is desirable to provide about 5 µg to about 100 µg of DNA per injection. The DNA solution is quickly added to the cys-TfRscFv-liposome solution and the mixture is inverted for 5-10 seconds. The final mixture is kept at room temperature for 10 minutes, gently inverting again for 5-10 seconds after approximately 5 minutes. For use in vivo 50% dextrose or 50% sucrose is added to a final concentration of 5-10% (V:V) and mixed by gentle inversion for 5-10 seconds. A specific example at a preferred ratio of 1:30 (cys-TfRscFv:liposome, w:w) and 1:14 (µg DNA:n mole total Lipid) is as follows: For 40 µg of DNA in a final volume of 800 µl mix 183 µl water with 280 µl of 2 mM liposome solution. Add 34 µl of cys-TfRscFv (with a concentration of 0.4 µg/ml). Mix 183 µl water with 40 µl of 1 µg/1 µl DNA. Add 801 of 50% Dextrose as the last step.

The size of the final complex prepared by the method of this invention is between 100 and 400 (number value) with a zeta potential of between 25 and 35 as determined by dynamic light scattering using a Malvern Zetasizer 3000. This size is small enough to efficiently pass through the tumor capillary bed and reach the tumor cells.

Figure 1:
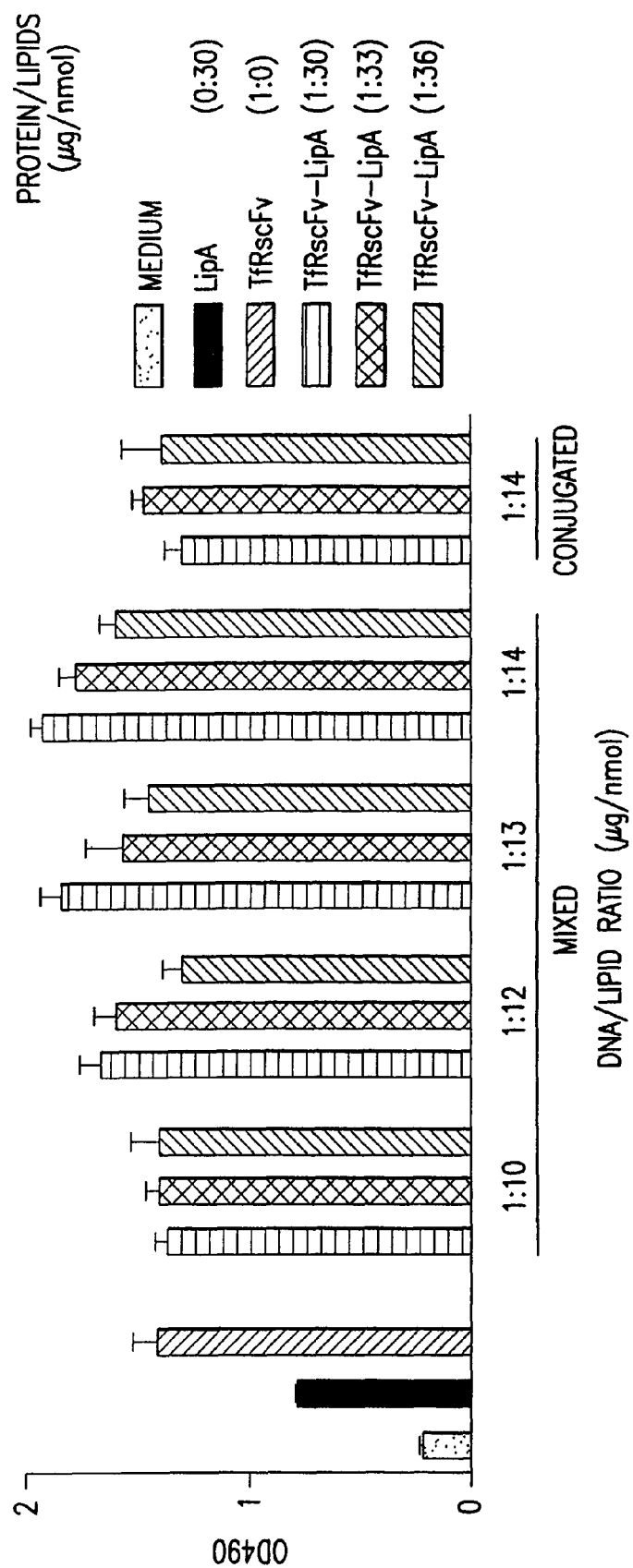
FIG. 1 shows the results of an ELISA assay showing binding of TfRscFv-liposome-DNA complex, made by simple mixing, to DU145 cells at various ratios of protein/lipid and DNA/lipid.
Figure 2:
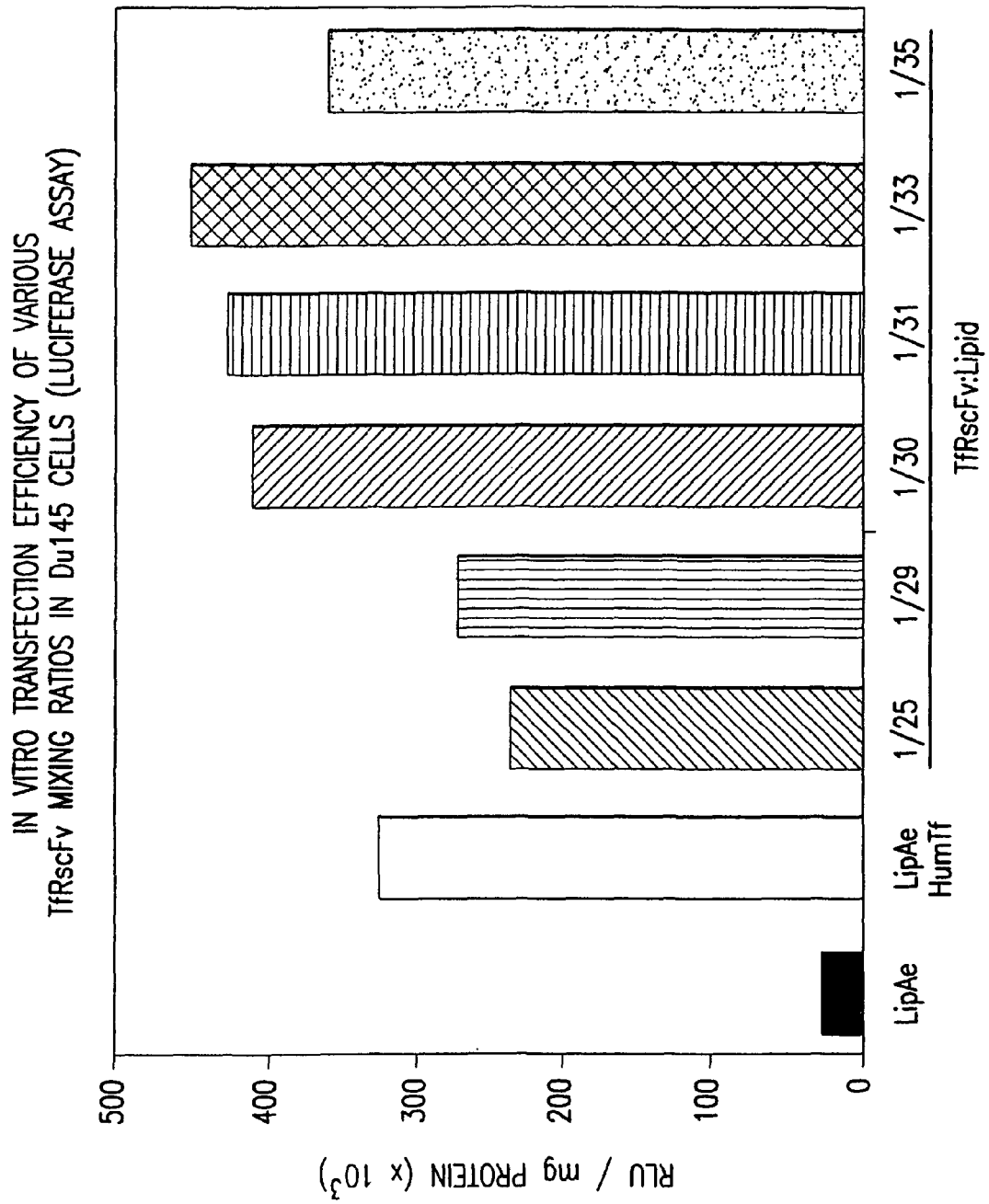
FIG. 2 shows the results of an in vitro transfection assay using different mixing ratios of TfRscFv:lipid in DU145 cells (Luciferase assay).
Figure 3:
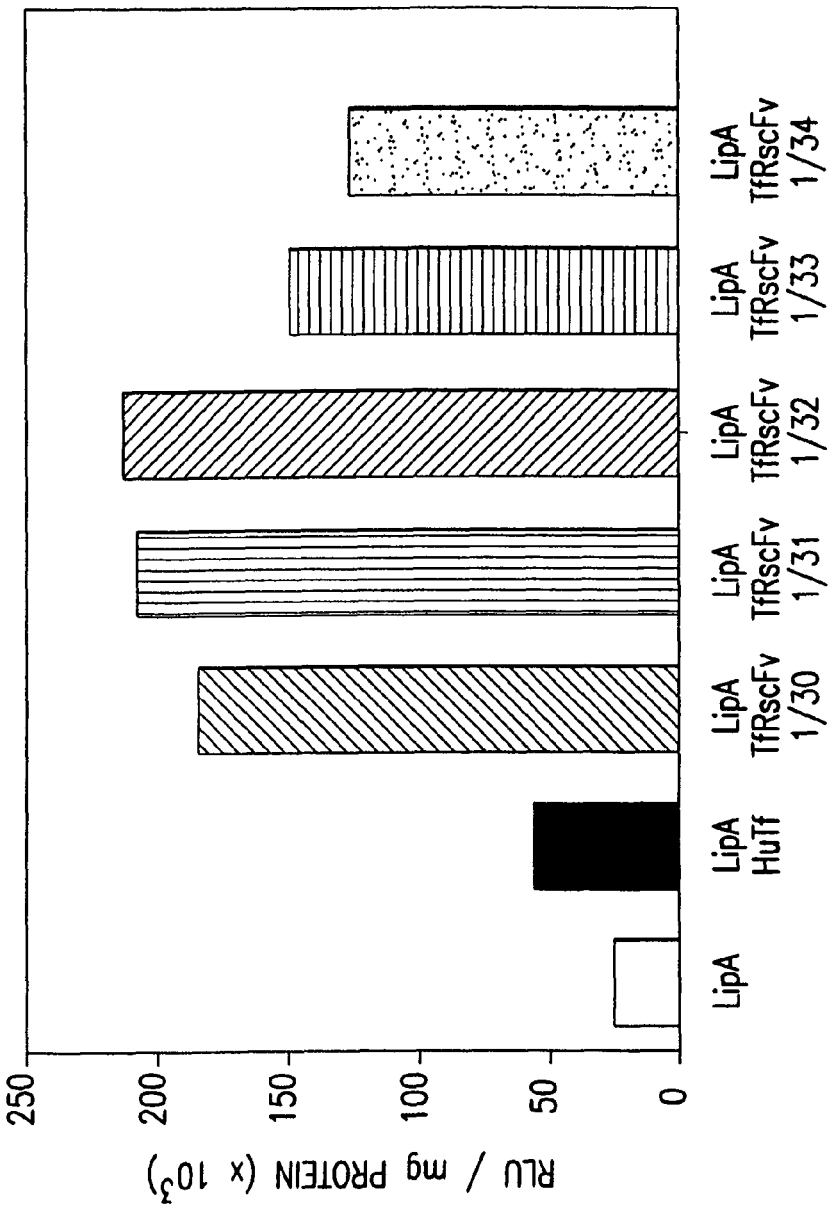
FIG. 3 shows the results of an in vitro transfection assay using different mixing ratios of TfRscFv:lipid in rat C6 cells (Luciferase assay).

An ELISA assay to assess the binding ability of the mixed complex to human prostate cancer DU145 cells was performed. For comparison, the complexes made with the conjugated immunoliposome were also included in the assay. The results shown in FIG. 1 clearly demonstrate that the immunoliposome complex prepared by simple mixing of the cys-TfRscFv protein with the cationic liposome binds to DU145 cells at least as well as those prepared through conjugation. Similar to the conjugated complex, a ratio of 1/30 protein to lipid and 1/14 DNA to lipid was found to have the highest binding ability. As was also previously observed with the conjugated complexes, the binding decreased in a DNA dose dependent manner. These findings indicate that simple mixing of components can form a complex that retains its immunologic activity. Identical optimal ratios were found in human prostate DU145 cells, and RAT C6 cells using the Luciferase assay (FIG. 2 and 3) and in human pancreatic cancer cell line Panc I (Table I, II) using enhanced green fluorescence protein (EGFP) to assess the transfection efficiency.

TABLE I

Transfection Efficiency of cys-TfRscFv-Liposome A in Panc I Cells Prepared by Simple Mixing Assessed Using the EGFP Reporter Gene I

| Ratio DNA:Total Lipids (µg:nmoles) | % Fluorescent Cells |
|---|---|
| 1:8 | 20 |
| 1:10 | 22 |
| 1:12 | 35 |
| 1:14 | 50 |
| 1:16 | 24 |
| 1:18 | 20 |

The ratio of cys-TfRscFv:Liposome was 1:3 (w:w)

TABLE II

Transfection Efficiency of cys-TfRscFv-Liposome A in Panc I Cells Prepared by Simple Mixing Assessed Using the EGFP Reporter Gene II

| Ratio cys-TfRscFv:Lipids (w:w) | % Fluorescent Cells |
|---|---|
| 1:26 | 14 |
| 1:28 | 14 |
| 1:30 | 30 |
| 1:32 | 28 |
| 1:34 | 15 |
| 1:36 | 18 |

Figure 4:
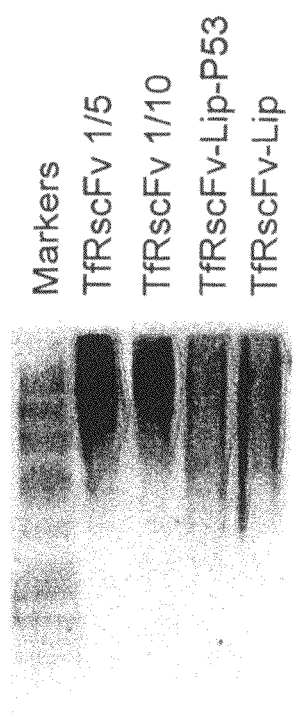
FIG. 4 shows a non-denaturing polyacrylamide gel demonstrating that >95% of the TfRscFv is bound to the liposome or liposome-p53 after simple mixing.

To establish the efficiency of the binding of the cys-TfRscFv to the liposome complex by simple mixing, a non-denaturing polyacylamide gel was used. Mixed cys-TfRscFv-liposome A-p53 complex and cys-TfRscFv-Liposome A without p53 DNA were loaded on the gel along with free cys-TfRscFv in amounts equal to 1/5 or 1/10 the amount of cys-TfRscFv used to prepare the complexes. The complexes were prepared using the ratio of cys-TfRscFv:liposome of 1:30 (w:w) and DNA:total lipid of 1:14 (µg:n mol total lipid). The free cys-TfRscFv complexes serve as quantitation standards, since under non-denaturing conditions the complex can not enter the gel, only free, unbound cys-TfRscFv can migrate into it. After transferring to membrane, the gel was probed with an anti-cys-TfRscFv antibody using the ECL Western Blot detection kit (Amersham). Comparison of the low signal level for the two complexes (with and without p53 DNA) shown in FIG. 4 with the signals from the free cys-TfRscFv standards indicates that greater than 95% of the cys-TfRscFv is incorporated into the complex by simple mixing of the components.

EXAMPLE 3

In Vitro Chemosensitization of Human Cancer Cell Lines by cys-TfRscFv-Immunoliposome Delivered wtp53

Figure 5A:
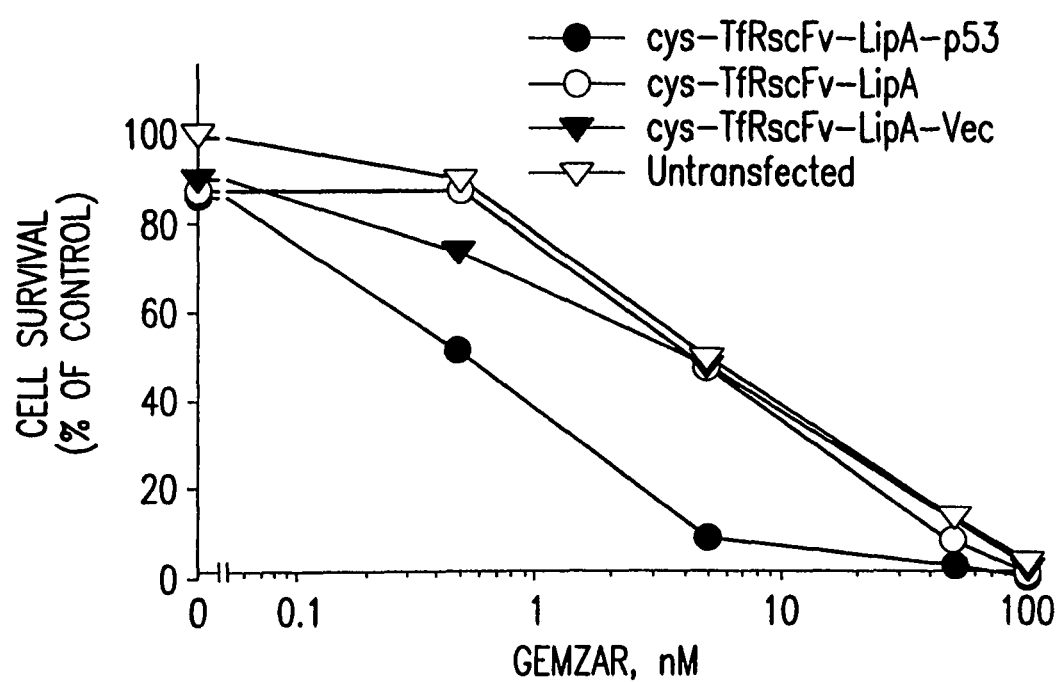
FIG. 5A shows the results of an XTT cytotoxicity assay showing the chemosensitivity to GEMZAR® fgemcitabine) induced in DU145 cells treated with TfRscFv-liposome-p53 prepared by simple mixing.

Experiments were performed to determine how effective the cys-TfRscFv-Liposome-p53 complex prepared by simple mixing would be in sensitizing prostate tumor cells to the drugs GEMZAR® (gemcitabine HCl; manufactured by Eli Lilly and Co.) and NOVANTRONE® (mitoxantrone, Immunex Corp.) both of which currently are used for the treatment of prostate cancer. The prostate tumor cell line DU145, which harbors mutant p53, was employed in these studies. The XTT cytotoxicity assay (66) was used to establish the level of chemosensitivity induced by the cys-TfRscFv-Liposome-p53 complex of this invention. $5 \times 10^3$ DU145 cells were plated/well of a 96 well plate. After 24 hours, the cells were transfected with the mixed cys-TfRscFv-Liposome-p53 complex. The cys-TfRscFv-Liposome-p53 complex was prepared by mixing at a ratio of 1:30 (w:w) (cys-TfRscFv:Liposome A) and 1:14 (µg p53 DNA: nmoles total lipid). One day after transfection, anti-neoplastic agents were added at increasing concentrations (in triplicate). The XTT assay was performed approximately 3 days later and $IC_{50}$ values, the drug concentration yielding 50% growth inhibition, calculated. As shown in FIG. 5A, treatment with the cys-TfRscFv-Liposome-p53 complex increased the sensitivity of the cells to GEMZAR® by 8-fold. For FIG. 5A, the $IC_{50}$ Values (nM) are as follows:

cys-TfRscFv-LipA-p53: 0.5; cys-TfRscFv-LipA: 4.0; cys-TfRscFv-LipA-Vec: 4.0; Untransfected: 5.0. The fold sensitization for Vec vs p53=8 and for UT vs p53=10.

Figure 5B:
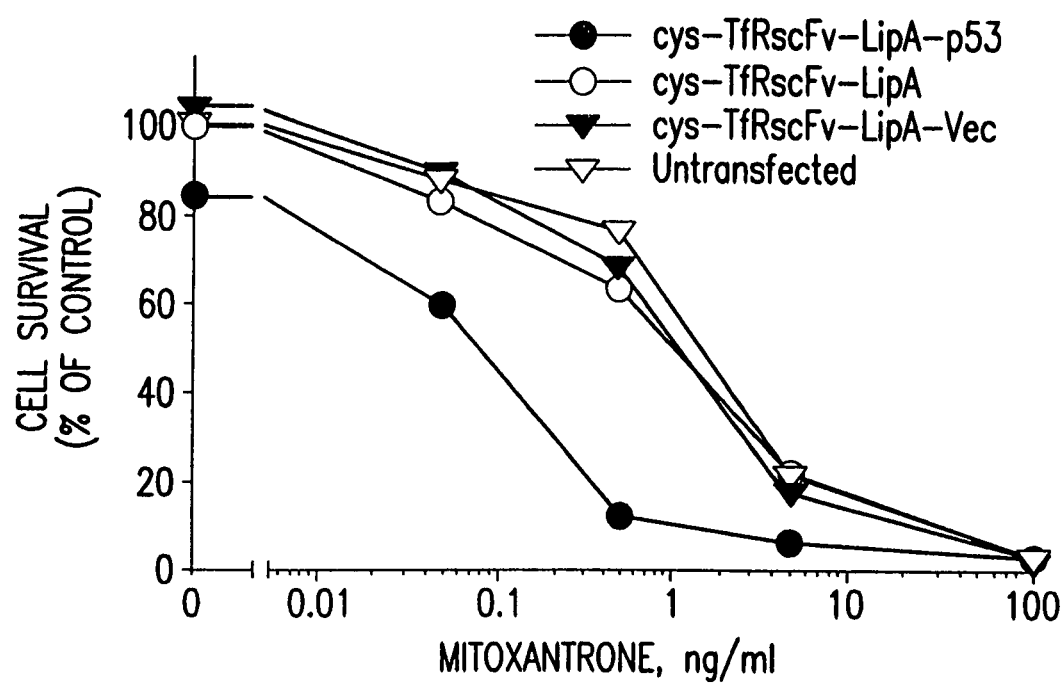
FIG. 5B shows the results of an XTT cytotoxicity assay showing the chemosensitivity to mitoxantrone induced in DU145 cells treated with TfRscFv-liposome-p53 prepared by simple mixing.
Figure 6A:
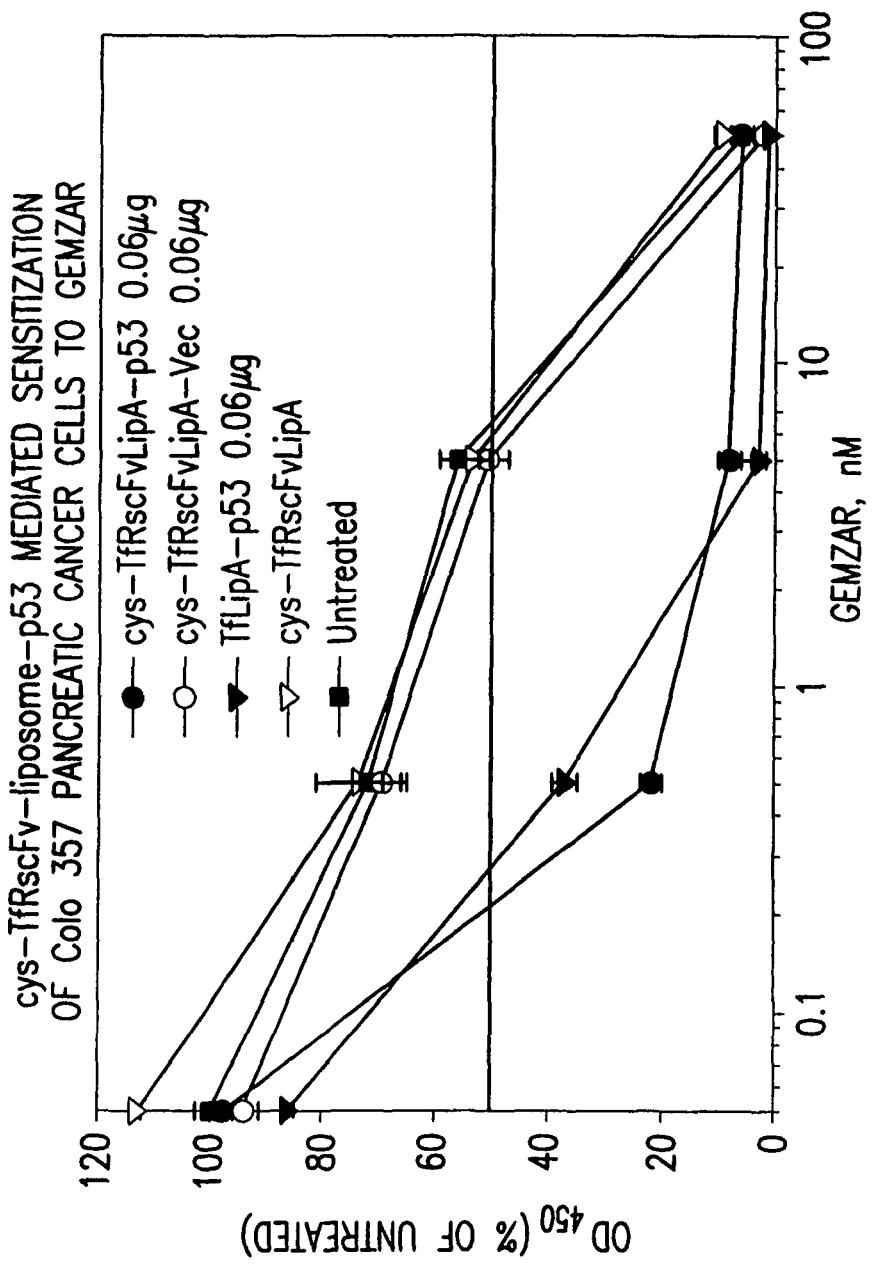
FIGS. 6A and 6B show the results of an XTT cytotoxicity assay showing the chemosensitivity to GEMZAR® (gemcitabine) induced in pancreatic cancer cell lines (Colo 357 and Panc I) treated with TfRscFv-liposome-p53 prepared by simple mixing.
Figure 6B:
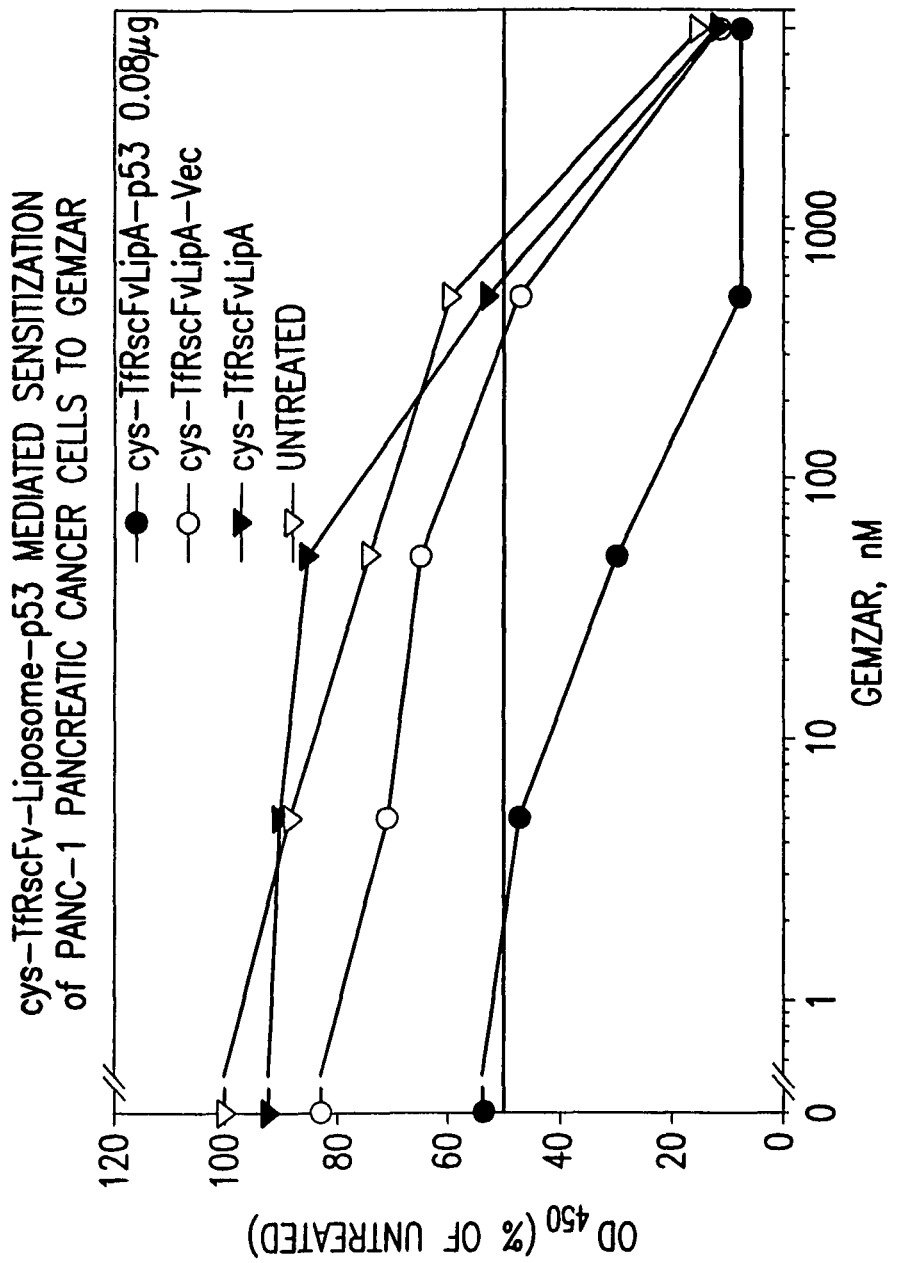

Similarly, DU145 cells were sensitized to the drug mitoxantrone by 17.5-fold (FIG. 5B). For FIG. 5B, the $IC_{50}$ values (ng/ml) were as follows:

cys-TfRscFv-LipA-p53: 0.08; cys-TfRscV-LipA: 1.20; cys-TfRscFv-LipA-Vec: 1.40 and Untransfected: 1.80. The fold sensitization for Vec vs p53=17.5 and for UT vs p53=22.5. Similar studies were performed using human pancreatic cancer cell line Panc I. $4 \times 10^3$ Panc I cells per well were plated, and the XTT assay performed as above. A preferred ratio of 1:30 (cys-TfRscFv:liposome A w:w) and 1:14 (μg p53 DNA: nmoles total lipid) also was used here. As with DU145 there was significant sensitization of the tumor cells to chemotherapeutic agents (FIGS. 6A and B). At a p53 DNA concentration of 0.06 μg/well there was a 23.8 fold increase in sensitization to GEMZAR® using the mixed cys-TfRscFv-liposome DNA complex (FIG. 6A). For FIG. 6A, the IC50 values were as follows: cys-TfRscFvLipA-p53: 0.21 nM; cys-TfRscFvLipA-Vec: 5.00 nM and TfLipA-p53: 0.30 nM. The IC50 of cys-TfRscFvLipA-Vec/IC50 of cys-TfRscFrLipA-p53=23.8. No sensitization was observed when empty vector in place of p53 was used. There was dramatic increase in response of the Panc I cells at a p53 DNA concentration of 0.08 μg DNA/well (FIG. 6B). Here an almost 200 fold increase in sensitization was observed. For FIG. 6B, the IC50 values were as follows: cys-TfRscFvLipA-p53: 1.8 nM;

cys-TfRscFvLipA-Vec: 350 nM; and cys-TfRscFvLipA: 600 nM. The $IC_{50}$ of cys-TfRscFvLipA-Vec/IC50 of cys-TfRscFvLipA-p53=194.44. Therefore, these in vitro studies demonstrate that the cys-TfRscFv-liposome, prepared by simple mixing, can efficiently transfect wtp53 into prostate tumor cells and sensitize them to conventional chemotherapeutic agents.

EXAMPLE 4

In Vivo Tumor Targeting by the cys-TfRscFv-LipA-EGFP Prepared by Simple Mixing

Figure 7A:
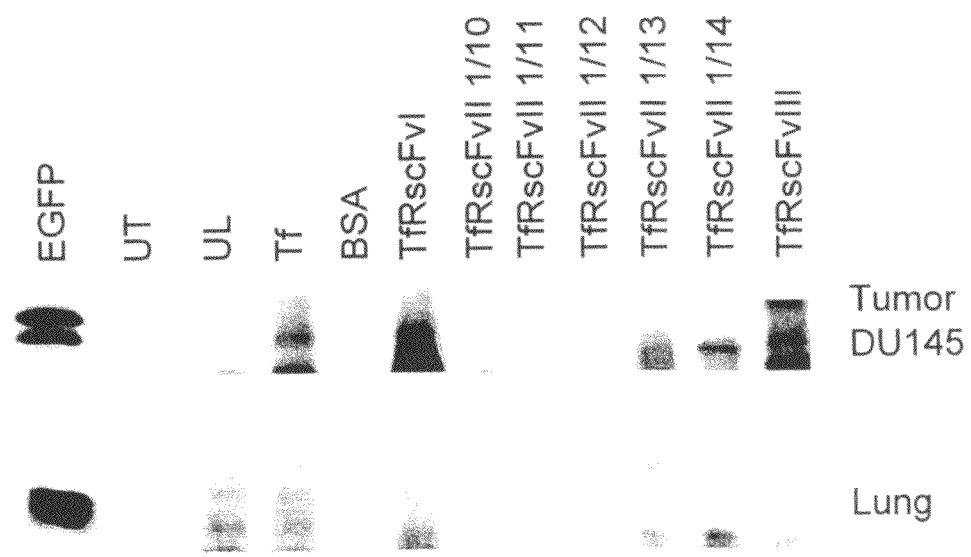
FIG. 7A shows the in vitro tumor targeting ability of the systemically administered TfRscFv-liposome-EGFP complex prepared by simple mixing at various ratios of DNA:lipid

DU145 tumors were subcutaneously induced in female athymic nude (NCR nu/nu) mice. Mice were I.V. tail vein injected three times over a 24 hour period with cys-TfRscFv-LipA-EGFP (enhanced green fluorescence protein) (TfRscFvII) prepared by simple mixing at a scFv:Liposome ratio of 1/30 but at various DNA:total lipid ratios (1/10, 1/11, 1/12, 1/13. 1/14) at 32 ug DNA/injection. For comparison, a complex at 1/30, 1/14 made via the conjugation method (TfRscFv III in FIG. 7B) and a different batch of single chain at 1/30, 1/14 (TfRscFv I in FIG. 7B) also were injected into mice. 60 hours post injection the mice were sacrificed, tumor and lung harvested and protein isolated for Western Blot Analysis using an anti-EGFP antibody. Unliganded LipA-EGFP complex (UL), Tf-LipA-EGFP complex (Tf) and BSA-LipA-EGFP complex (BSA) were injected into mice as controls. FIG. 7A—As shown in the DU145 tumor an EGFP band is observed in the positive controls Tf, TfRscFvIII, and in TfRscFvI. More significantly, a strong EGFP signal was found in TfRscFvII at the DNA to lipid ratio of 1/14. In contrast, only very low level of EGFP expression was evident in normal lung tissue. Therefore, the cys-TfRscFv-Lipoplex prepared by simple mixing can target tumor effectively after systemic administration.

Figure 7B:
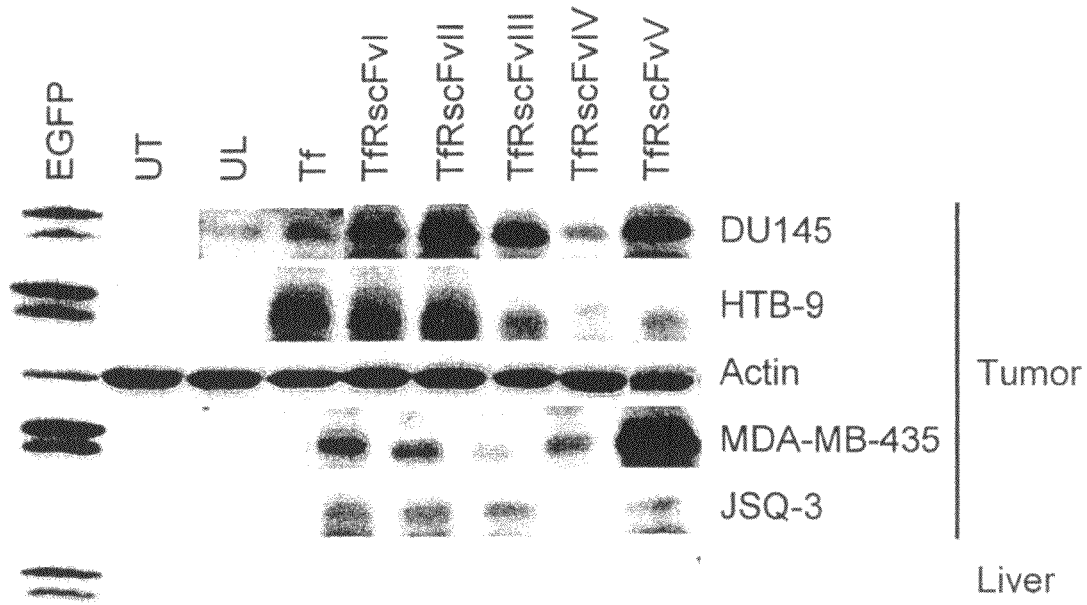
FIG. 7B shows the in vivo tumor targeting ability of the systemically administered TfRscFv-liposome-EGFP complex prepared by simple mixing in four different tumors and using multiple batches of the TfRscFv protein.

To assess the reproducibility of the mixing, different batches of cys-TfRscFv (I to V) were complexed to Liposome A-EGFP by simple mixing at the preferred ratio of 1:30 (scFv:liposome w:w) and 1:14 (μg DNA:nmoles total lipid). Human prostate DU145, bladder HTB-9, breast MDA-MB-435 and head and neck JSQ-3 xenograft tumors were subcutaneously induced as above. The complexes also were I.V. tail vein injected three times over a 24 hour period. Tf-LipA-EGFP(Tf) and unliganded LipA-EGFP complex (UL) were used as controls. 60 hours after injection the mice were sacrificed and the tumor and liver were harvested and analyzed as above. Targeting is evident with all of the mixed complexes in the four tumor types (FIG. 7B). However, there is almost no signal in normal tissue (liver). The identical membrane was probed for Actin levels to show equal loading.

EXAMPLE 5

Radio/Chemosensitization of Human Xenograft Tumors by Systemically Administered cys-TfRscFv-Liposome-p53 Prepared by Simple Mixing Efficacy studies were performed to further confirm the ability of the cys-TfRscFv-immunoliposome complex of this invention to bind and deliver wtp53 efficiently to tumor cells in vivo. Mice bearing subcutaneous DU145 tumors of approximately 60-90 $mm^3$ were injected, via the tail vein, three times a week (a total of 10 injections) with cys-TfRscFv-Liposome-p53. This complex was prepared by simple mixing at a ratio of 1/30 (cys-TfRscFv:LiposomeA, w:w) and 1/14 (μg DNA/nmoles total lipid). The tumor area was selectively exposed to 2.0 Gy daily fractionated doses of γ-radiation to a total of 32 Gy (FIG. 8). The animals treated with the mixed cys-TFRscFv-liposome A complex plus radiation had significant tumor growth inhibition. Similar findings also were observed using the combination of the anticancer drug Gemzar® and the cys-TFRscFv-immunoliposome of this invention delivering tumor suppressor gene Rb94 to a human bladder carcinoma xenograft tumor (HTB-9), and in Panc I xenografts treated with GEMZAR® and cys-TFRscFv-Liposome carrying either another gene inducing apoptosis (Apoptin) or p53.

These findings demonstrate that a complex made by the method of this invention can comprise a variety of genes (incorporated into plasmid vectors) for effective delivery in vivo to cancer cells as a therapeutic treatment.

EXAMPLE 6

Figure 9:
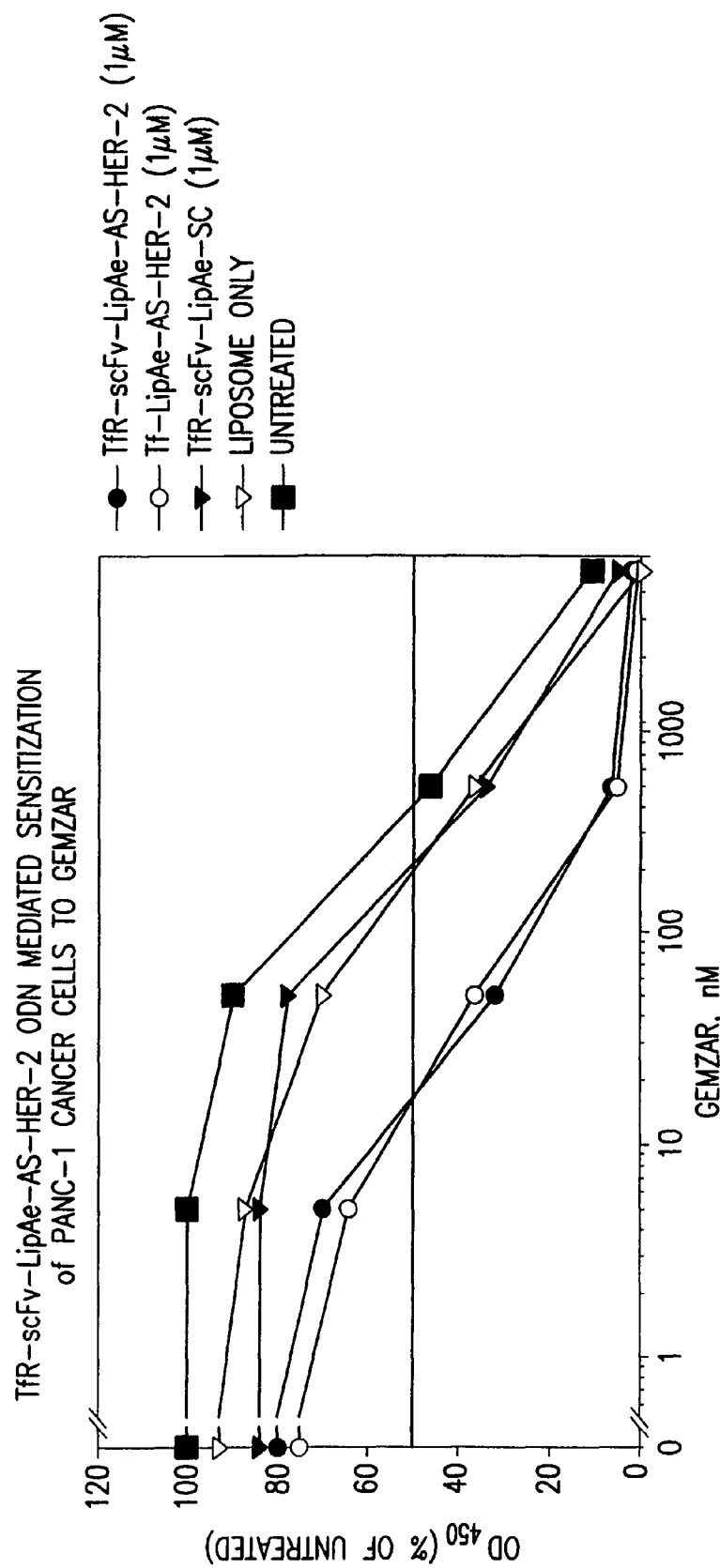
FIG. 9 shows the results of an XTT cytotoxicity assay showing chemosensitivity to GEMZAR® (gemcitabine) induced Panc I cells treated with TfRscFv-liposome-AS HER-2 ODN.

Chemosensitization of Pancreatic Cancer Cells In Vitro by Antisense HER-2 Oligonucleotides Delivered by cys-TFRscFv-Liposome a Prepared by Simple Mixing This example demonstrates the usefulness of this invention in efficiently delivering molecules other than genes to tumor cells for therapeutic treatment. The complex was prepared as in Example 2, however, the DNA encapsulated here was an 18 mer phosphorothioated oligonucleotide (ODN) directed against the initiation codon of the HER-2 gene (AS HER-2) (51). The ratio used was as above for plasmid DNA 1:30 (cys-TfRscFv: liposome, w:w) and 1:14 (nmoles ODN: n mole total lipids). Panc I cells, at $4 \times 10^3$ cells/well, were seeded in a 96 well plate. The cells were transfected 24 hours later by cys-TfRscFv-LipA-AS HER-2 prepared by the method of this invention. Tf-LipA-AS HER-2 and cys-TfRscFv-LipA-SC ODN were used as controls. SC ODN is a scrambled ODN that has the same nucleotide composition as the AS HER-2 ODN but in random order. As shown in FIG. 9 the cys-TfRscFv-Lip A-AS HER-2 complex prepared by the method of this invention was able to sensitize pancreatic cancer cell line Panc I to the effects of chemotherapeutic agent GEMZAR® by over 11 fold. This increase in sensitization is identical to that resulting from transfection with the positive control Tf-LipA-AS HER2 complex. For FIG. 9, the $IC_{50}$ values were as follows:

TfRscFv-LipA3-AS-HER-2: 16 nM; Tf-LipAe-AS-HER-2: 14 nM and TfR-scFv-LipAe-SC: 200 nM. The $IC_{50}$ of TfR-scFv-LipAe-SC/$IC_{50}$ of TfR-scFv-LipAe-AS-HER-2-12.5.

EXAMPLE 7

Figure 10A:
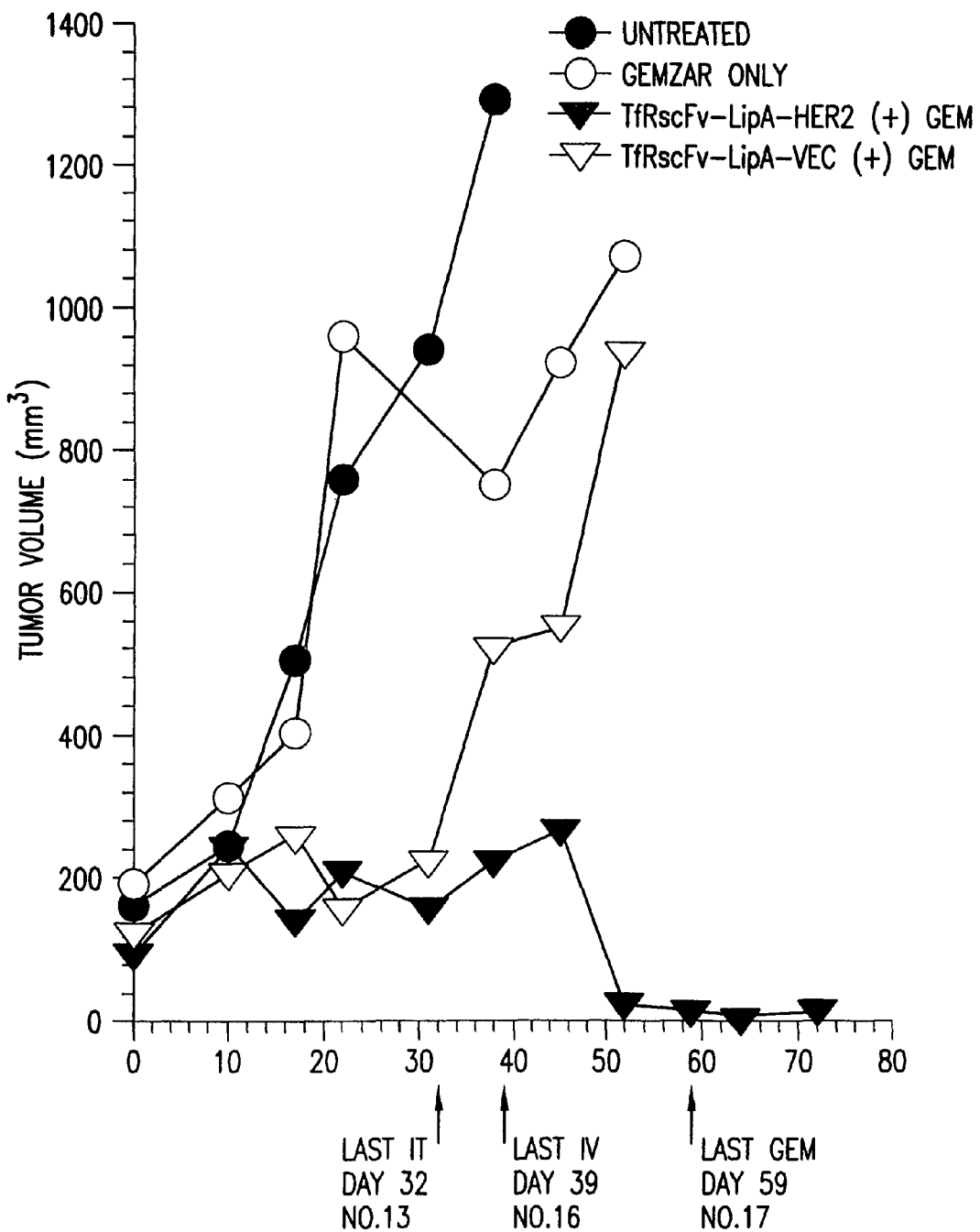
FIG. 10A shows the effect of the combination of systemically administered TfRscFv-liposome A-AS HER-2 ODN and GEMZAR® (gemcitabine) on Pane I human pancreatic xenograft tumors.

In Vivo Chemosensitization of Human Xenograft Tumors by Systemically Delivered cys-TFRscFv-LipA-AS HER-2 ODN Prepared by Simple Mixing In this example, the ability of the cys-TfRscFv liposome-DNA complex prepared by the method of this invention to deliver an antisense molecule to tumor cells in vivo after systemic delivery is demonstrated. To show the universality of this delivery system two different human xenograft mouse tumor models (pancreatic cancer and breast cancer) were employed. In the first (FIG. 10A) Panc I subcutaneous xenograft tumors were induced in female athymic nude (NCR nu/nu) mice. When the tumors were 100-200 mm$^3$ in size the animals were injected with the chemotherapeutic agent GEMZAR® (intraperitoneally) and with cys-TfRscFv-LipA AS HER-2 prepared by the method of this invention (I.V.). The complex was made using the ratio of 1:30 (cys-TfRscFv: liposome, w:w) and 1:15 (n mole ODN: n mole total lipid). In addition to the I.V. injections the complex described above also was intratumorally injected. One group of animals received GEMZAR® only and a second control group received GEMZAR® plus the complex carrying empty vector. Treatment with GEMZAR® alone was not able to significantly inhibit pancreatic tumor growth. In contrast (FIG. 10A), the combination of GEMZAR® and AS-HER-2 ODN delivered by the cys-TfRscFv-Lip A complex prepared by the method of this invention not only significantly inhibited tumor growth but also resulted in tumor regression.

Figure 10B:
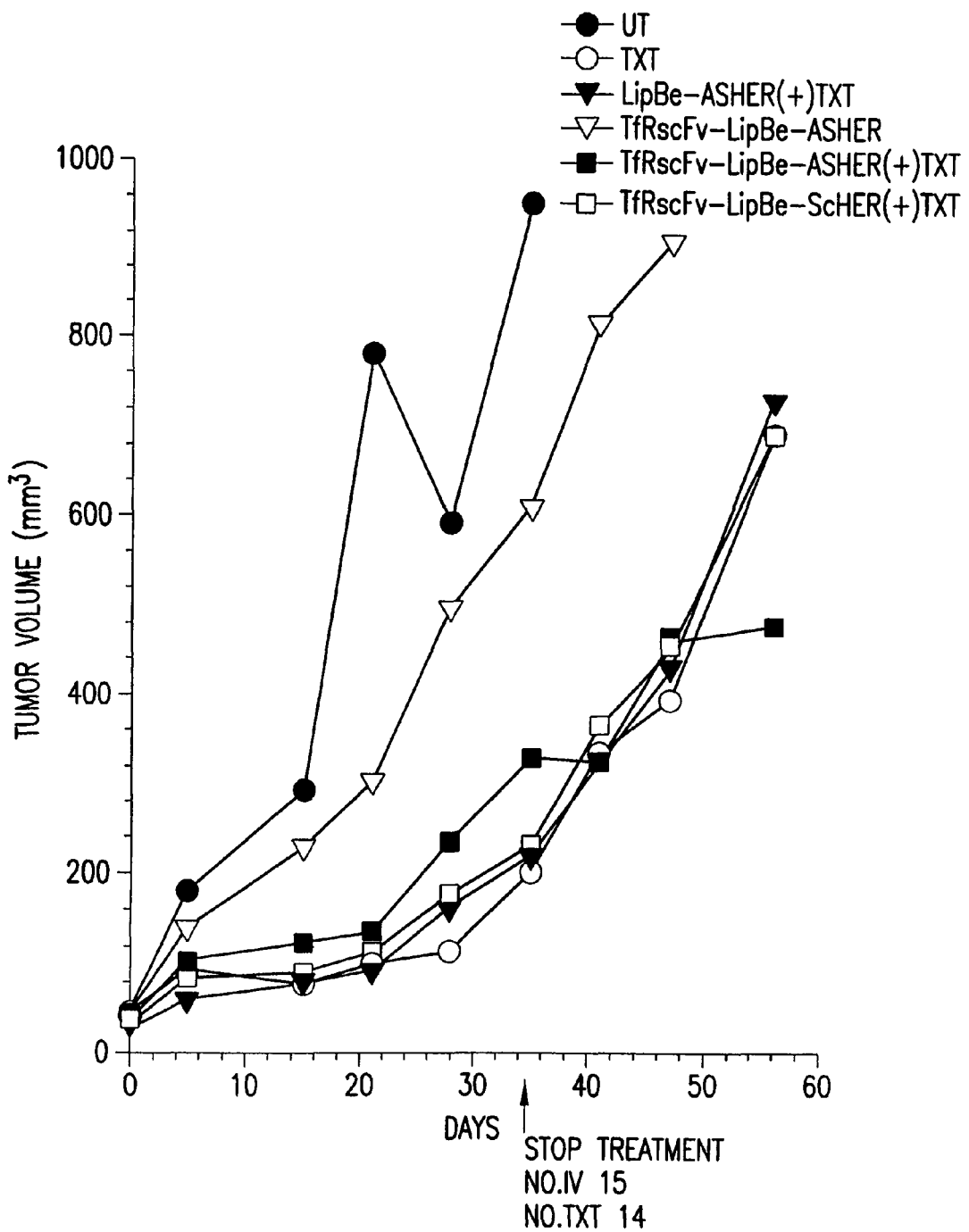
FIG. 10B shows the effect of the combination of systemically administered TfRscFv-liposome B-AS HER-2 ODN and (docetaxel) TAXOTERE® on MDA-MB-435 human breast xenograft tumors.

Significant tumor growth inhibition of human breast cancer xenograft tumors also was observed with the combination of the drug TAXOTERE® (docetaxel; manufactured by Aventis Pharmaceuticals, Collegeville, Pa.) and I.V. administered cys-TfRscFv-LipB AS HER-2 prepared by the method of this invention (FIG. 10B). While liposome formulation B was used in the breast tumor, the same ratios as described above for Panc I were employed.

EXAMPLE 8

Enhancement of MRI Image by Delivery of Imaging Agent MAGNEVIST® by cys-TFRscFv-Liposome a Prepared by Simple Mixing This example demonstrates the ability to encapsulate MRI imaging agents and form a cys-TfRscFv-Liposome-imaging agent complex by the method of this invention. The complex prepared by the method of this invention can be administered intravenously resulting in increased enhancement of the tumor image for both primary tumor and metastases. These imaging agents can include, but are not limited to, MAGNEVIST® (Gd-DTPA) (Schering AG). The ratios used to form the complex by simple mixing are the preferred ratios of 1:30 (cys-TfRscFv:liposome, w:w) and 1:14 (ug imaging agent: nmoles lipid). In these studies 16 ul of MAGNEVIST® were used in the complex.

Figure 11:
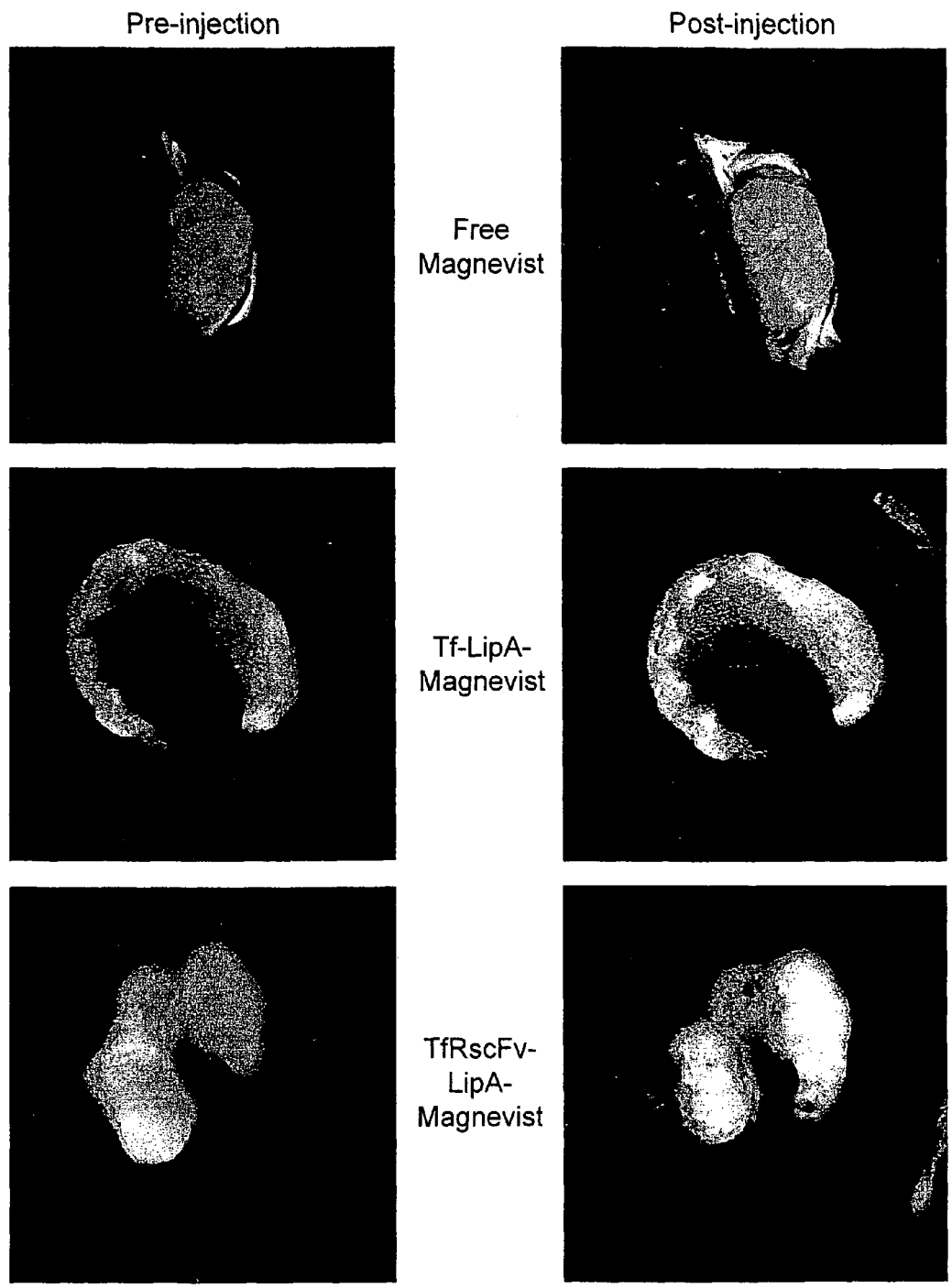
FIG. 11 shows the enhanced tumor imaging resulting from the systemic administration of the TfRscFv-liposome-MAGNEVIST® (Gd-DTPA) complex.

FIG. 11 shows the results from one I.V. injection of the cys-TfRscFv-LipA-MAGNEVIST® made by the method of this invention into mice bearing subcutaneous xenograft tumors of human head and neck (top panel), breast (middle panel) or prostate (bottom panel) origin. A higher level of imaging agent enhancement is evident in the tumor that received the cys-TfRscFv-LipA-MAGNEVIST® as compared to that receiving free MAGNEVIST® demonstrating the benefit of administering the imaging agent using the complex prepared by the method of this invention. In other experiments an increased uptake in the tumor as compared to the surrounding normal tissue also was observed.

Similar enhancement also was observed using syngenetic mouse lung metastasis model. $B_{16}/F_{10}$ mouse melanoma cells were injected intravenously into C57BL/6 mice. These cells form tumor nodules in the mouse lungs. The cys-TfRscFv-Liposome-MAGNEVIST® complex was prepared by the method of this invention also using the preferred ratios of 1:30 and 1:14. The complex was I.V. administered and the tumor modules imaged via MRI. Compared to free MAGNEVIST®, the encapsulated imaging agent also has a prolonged uptake in the tumor since the peak enhancement with the complex is later than that of the free MAGNEVIST®.

EXAMPLE 9

Preparation of Sterically Stabilized Immunoliposomes by Simple Mixing

Liposomal complexes are rapidly cleared from the blood stream by the reticuloendothelial system. In an effort to prolong this circulation time sterically stabilized liposomes have been formulated that have a hydrophilic polymer such as PEG integrated into the liposome complex. Various methods have been devised to include a targeting ligand such as an antibody or antibody fragment in the PEG-liposome complex. Most, if not all, of these methodologies involve a chemical conjugation step to link the antibody or antibody fragment to the PEG. Such harsh chemical reactions and the method used to form the complex can result in loss or masking of antibody activity. In this example, we demonstrate that the cys-TfRscFv protein can be linked to a PEG-liposome molecule by simple mixing and that the resultant complex can more efficiently transfect human tumor cells.

To form this complex, a lipoplex consisting of one of the cationic lipid formulations given in Example 2 was mixed with nucleic acid at a ratio of 1:14 (ug DNA:nmoles lipid) as described in Example 2. To this lipoplex was added the commercially available NHS-PEG-MAL polymer (2%) in 25 mM HEPE Buffer (pH 7.2). The solution was gently inverted for 3-5 seconds and incubated at room temperature for 1.5 hours. To form the cys-TfRscFv-PEG-Liposome-DNA complex, the cys-TfRscFv protein was added to the PEG-lipoplex at a ratio of 1:8 (cys-TfRscFv:liposome, w:w), inverted gently and kept at room temperature for 10 minutes to 1 hour, then used to transfect the cells in vitro. Other ratios in the range of 1:5 to 1:30 (cys-TfRscFv:liposome, w:w) could also be employed to form the complex. For in vivo use, 50% Dextrose was added to a final concentration of 5% after the incubation, mixed gently by inversion and injected into animals. Alternatively, the final complex could have been stored at 4° C. overnight (12-18 hr).

Figure 12:
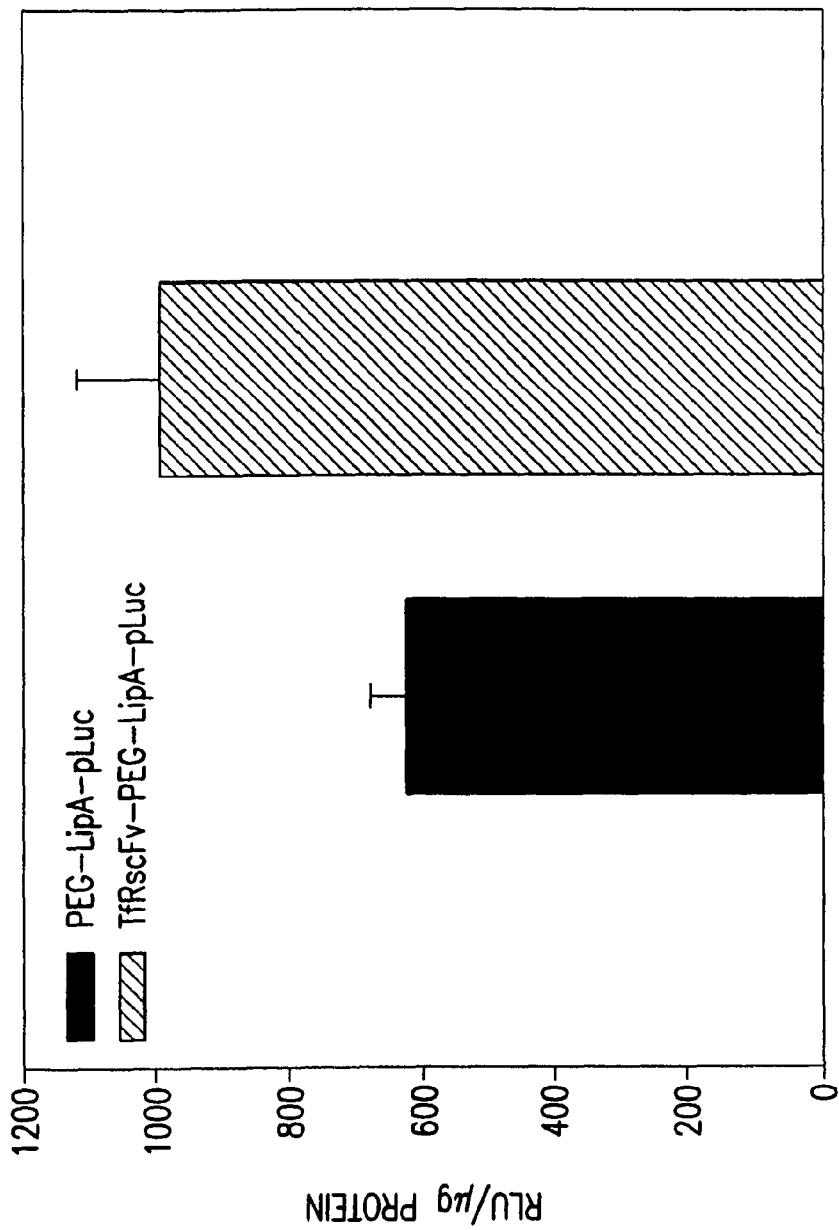
FIG. 12 shows the results of an in vitro transfection assay of sterically stabilized TfRscFv-PEG-liposome A-pLuc in MDA-MB-435 cells (Luciferase assay).

In the experiment shown here the nucleic acid was pLuc, a plasmid DNA that codes for the firefly luciferase gene. Human melanoma cells MDA-MB-435 were plated at $5 \times 10^4$ cells/well. Twenty-four hours later they were transfected with the cys-TfRscFv-PEG-LipA-pLuc as described in Example 3 and the transfection efficiency assessed by the level of luciferase activity. As shown in FIG. 12 the cys-TfRscFv-PEG-LipA-pLuc complex prepared by the method of this invention was able to transfect the target cells with better efficiency than the PEG-LipA-pLuc without the targeting cys-TfRscF protein.

Thus the method of simple mixing described here also can be used as a simple, non-destructive means of preparing sterically stabilized targeted immunoliposomes.

EXAMPLE 10

Preparation and Characterization of Small Molecule (GMC-5-193)-Comprising-Immunoliposomes by Simple Mixing To improve the in vitro and in vivo anticancer effects of the small molecule GMC-5-193, a tumor-targeting liposomal complex comprising the small molecule was prepared. In addition to a TfRscFv/LipA complex, a cationic liposome conjugated with endosomal disrupting peptide (LipA-HoKC) was also prepared. The endosomal disrupting peptide HoKC may help the release of GMC-5-193 in the cytoplasm of the cells to affect tubulin polymerization in cytoplasm. The ligand-liposome complex preferentially targets tumor cells due to elevated levels of the corresponding receptor on their surface. High levels of expression of the ligand-liposome delivered gene were evident in primary tumors and metastasis, but not in normal tissue such as liver, lung, bone marrow, and intestinal crypts. In this Example, a liposome complex of the present invention, comprising the transferrin receptor single chain (TfRscFv), was used to deliver GMC-5-193 to cancer cells in vitro and in vivo to evaluate the in vitro and in vivo bio-efficacy of the lipoplex comprising GMC-5-193.

Materials and Methods 1,2-Dioeoyl-3-trimethylammonium propane (DOTAP), dioleolylphosphatidyl ethanolamine (DOPE), and N-maleimido-phenylbutyrate DOPE (MPB-DOPE) were purchased from Avanti Polar Lipids (Alabaster, Ala.). The K[K(H)KKK]$_5$-K(H)KKC (HoKC) (SEQ ID NO: 2) peptide was manufactured by Sigma-Genosys (The Woodlands, Tex.).

Synthesis of GMC-5-193

The compound GMC-5-193 was synthesized at the department of Chemistry, University of Virginia. It has a molecular weight of 359.4 Da and its structure was confirmed by mass spectrometry and NMR. The pKa values of amide proton and amine proton were 15 and 9, respectively. 2.5 mg/mL stock solution of the compound was prepared in DMSO.

Cell Lines and Culture

The human prostate cancer cell line DU145 (HTB-81) and mouse melanoma cell line B16/F10 (CRL-6475) were obtained from the American Type Culture Collection (ATCC; Manassas, Va.). DU145 was cultured in Eagle minimum essential medium with Earls salts (EMEM) supplemented with 10% heat-inactivated fetal bovine serum (FBS), 2 mM L-glutamine, and 50 µg/mL each of penicillin, streptomycin, and neomycin. B16/F10 (ATCC, CRL-6475) was cultured in Dulbecco modified Eagle medium (DMEM) supplemented with 10% heat-inactivated FBS, 2 mM L-glutamine, and 50 µg/mL each of penicillin, streptomycin, and neomycin. The human melanoma cell line MDA-MB-435, human breast cancer cell line MDA-MB-231, and human pancreatic cancer cell line PANC-1 were cultured in improved MEM (IMEM) supplemented with 10% heat-inactivated FBS, 2 mM L-glutamine, and 50 µg/mL each of penicillin, streptomycin, and neomycin. The metastatic cell line MDA435/LCC6, was developed from MDA-MB-435 ascites. MDA435/LCC6 was cultured in IMEM supplemented with 5% heat-inactivated FBS, 2 mM L-glutamine, and 50 µg/mL each of penicillin, streptomycin, and neomycin. Normal human lung fibroblast IMR-90 cells, a gift from Dr. I. Panyutin (Nuclear Medicine Department, National Institutes of Health, Bethesda, Md.), were cultured in EMEM supplemented with 10% heat-inactivated FBS, 2 mM L-glutamine, 0.1 mM nonessential amino acids, 1 mM sodium pyruvate, and 50 µg/mL each of penicillin, streptomycin, and neomycin. Normal (non-cancerous) skin fibroblast cell line H500 was cultured in EMEM supplemented with 1 mM Sodium pryuvate, 1 mM Non-essential amino acids plus 10% heat inactivated fetal bovine serum, 2 mM L-glutamine and 50 µg/mL each of penicillin, streptomycin, and neomycin. EMEM was purchased from MediaTech (Herndon, Va.) and the other cell culture media and ingredients were obtained from Biofluids (Rockville, Md.).

Preparation of TfRscFv/LipA/GMC-5-193 Complexes

Cationic liposomal formulation LipA (DOTAP: DOPE or DDAB:DOPE at a 1:1 to 1:2 molar ratio) were prepared using the ethanol injection method as described throughout, and in U.S. patent application Ser. No. 09/914,046, the disclosure of which is incorporated by reference herein in its entirety. TfRscFv/LipA/GMC-5-193 complexes were prepared as follows. After 10 minutes incubation with rotation or stirring at room temperature of a mixture of LipA and TfRscFv (ratio of TfRscFv to LipA, 1:1 to 1:40 (wt/wt), more suitably 1:10 to 1:30 wt/wt), the GMC-5-193 at the appropriate concentration was added mixed by inversion or stirring at room temperature and incubated for 10 minutes. For animal injection, dextrose or sucrose was added to each sample to a final concentration of 1% to 20%, more suitably 5-10%. The molar ratio of GMC-5-193 to Liposome was from 0.2:7 to 14:7, more suitably 2:7 to 8:7, most suitably 7:7 or 2.8:7. The sizes of the complexes were determined by dynamic light scattering at 25° C. with a ZETASIZER® 3000HS system (Malvern, United Kingdom).

Preparation of TfRscFv/LipA-HoKC/GMC-5-193 Complexes

Cationic liposomal formulations for use with the HoKC peptide and LipA-MPB (DOTAP: DOPE: MPB-DOPE or DDAB:DOPE:MPB-DOPE at a 1:1:0.1 to 1:2:0.1 molar ratios) were prepared using the ethanol injection method. The LipA-HoKC liposome was then prepared using the coupling reaction between the cationic liposomes carrying the maleimide group and the peptide-carrying terminal cysteine group as previously described. Yu, W., et al., "Enhanced transfection efficiency of a systemically delivered tumor-targeting immunolipoplex by inclusion of a pH-sensitive histidylated oligolysine peptide." *Nucleic Acids Research* 32:e48 (2004). An aliquot of 0.1 mmol of the peptide with a free thiol group on cysteine was added to 2 mmol of LipA-MPB in 10 mM HEPES (pH 7.4) solution and rotated at room temperature for 2 hours. The resulting LipA-HoKC had a lipid concentration of 1.4 mM. TfRscFv/LipA-HoKC/GMC-5-193 complexes were prepared as follows. After 10 minutes incubation with rotation or stirring at room temperature of a mixture of LipA-HoKC and TfRscFv (ratio of TfRscFv to LipA-HoKC, 1:1 to 1:40 (wt/wt), more suitably 1:10 to 1:30 (wt/wt)), the GMC-5-193 at the appropriate concentration was added mixed by inversion or stirring at room temperature and incubated for 10 minutes. For animal injection, dextrose or sucrose was added to each sample to a final concentration of 1% to 20%, more suitably 5-10%. The molar ratio of GMC-5-193 to Liposome was from 0.2:7 to 14:7, more suitably 2:7 to 8:7, most suitably 7:7 or 2.8:7. The sizes of the complexes were determined by dynamic light scattering at 25° C. with a ZETASIZER® 3000HS system (Malvern, United Kingdom).

In Vitro Cell Viability and Optimization of the TfRscFv/LipA/GMC-5-193 or TfkscFv/Liposome-HoKC/GMC-5-193 Complexes For in vitro cytotoxicity studies, 5 to $5.5 \times 10^3$ cells/well in 100 µL of the appropriate growth medium of each cell line were plated in a 96-well plate. After 24 hours, the cells were washed with serum-free medium, overlaid with 100 µL of TfRscFv/Liposome/GMC-5-193 complexes (TfRscFv/LipA/GMC-5-193 or TfRscFv/LipA-HoKC/GMC-5-193 as appropriate) or free GMC-5-193 in serum-free medium in increasing concentrations, incubated for 4-6 hours, suitably 5 hours, and then supplemented with FBS. The cells were then incubated for an additional 24-72 hours, suitably 48 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3,4-tetrazolium]-bis(4-methoxy-6-nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

In Vitro Chemosensitization

For the chemosensitization study, $4-5 \times 10^3$ cells/well in 100 µL were seeded in a 96-well plate. After 24 hours, the cells were washed with serum-free medium, overlaid with 100 µL of TfRscFv/Liposome/GMC-5-193 complexes (TfRscFv/LipA/GMC-5-193 or TfRscFv/LipA-HoKC/GMC-5-193 as appropriate) or free GMC-5-193 at 1.25~2.5 µM as GMC-5-193, incubated for 4-6 hours, suitably 5 hours, and then FBS was added to each well. The cells were incubated for an additional 24-72 hours, suitably1 9 hours, followed by the addition of the appropriate supplemented medium with or without chemotherapeutics in increasing concentrations, and incubation continued for approximately 24-72 hours, suitably 48 hours. The chemotherapeutic drugs used were doxorubicin (Bedford Labs, Bedford, Ohio), docetaxel (Taxotere; Aventis Pharmaceuticals, Bridgewater, N.J.), mitoxantrone (NOVANTRONE®, Immunex Corp., Seattle Wash.) and cisplatin (CDDP; Bedford Labs, Bedford, Ohio). The XTT assays were performed to assess the degree of sensitization to the chemotherapeutics, and $IC_{50}$ values of each cell were calculated. Fold sensitization equals the following: $IC_{50}$ untransfected/$IC_{50}$ each complex.

In Vitro Confocal Imaging

For the confocal imaging, $5.0 \times 10^4$ cells/well of MDA-MB-435 were seeded on the glass in a 24-well plate and, after 24 hours, washed with serum-free medium, treated with TfRscFv/Liposome/GMC-5-193 complexes (TfRscFv/LipA/GMC-5-193 or TfRscFv/LipA-HoKC/GMC-5-193 as appropriate) or free GMC-5-193, and incubated for 6 hours. Six hours after treatment, the cells were washed with phosphate-buffered saline (PBS) twice, fixed with 4% paraformaldehyde in PBS, and washed again with PBS. Then, the cells were mounted on the slide glass, using PROLONG® Antifade Kit (Molecular Probes, Eugene, Oreg.). For nuclear staining, DAPI, blue-fluorescent counterstain reagent in Select FX Nuclear Labeling Kit for fixed cells (Molecular Probes) was used according to the manufacturer's protocol. For imaging, an Olympus FLUOVIEW®-300 laser scanning confocal system located in the GUMC Microscopy and Imaging Shared Resource (MISR) was used.

In Vivo Tumor Targeting

Human metastatic cells MDA435/LCC6 ($8 \times 10^6$) suspended in PBS were injected intravenously into the tail vein of athymic nude mice. The mice carrying MDA-MB-435/LCC6 xenograft tumors were injected intravenously with free GMC-5-193, TfRscFv/LipA/GMC-5-193, TfRscFv/LipA-HoKC/GMC-5-193 or LipA/GMC-5-193 (unliganded complex) at 9 mg/kg GMC-5-193 per mouse. This is a molar ratio of 2.8:7 (small molecule to liposome). The ratio of single-chain antibody fragment to liposome in each complex was 1:30 (w:w). Three hours after injection, the liver, lung and any other visible tumor, were excised and examined under a fluorescence microscope (Nikon SMZ-1500 EPI-Fluorescence stereoscope system).

In Vivo Efficacy Studies

Mouse melanoma cells B16/F10 ($1 \times 10^5$) suspended in PBS were injected intravenously into the tail vein of C57BL/6 mice. The mice carrying B16/F10 tumors were intravenously injected with, free GMC-5-193 only, or TfRscFv/Liposome/GMC-5-193 complexes (TfRscFv/LipA/GMC-5-193 or TfRscFv/LipA-HoKC/GMC-5-193 as appropriate) alone or in combination with CDDP at a dose of 3 mg/kg GMC-5-193/injection two to three times a week to at total of 7 injections. The molar ratio of GMC-5-193 to LipA or LipA-HoKC in each complex was 7 to 7. The ratio of single-chain antibody fragment to liposome in each complex was 1:30 (w:w). Certain groups also received CDDP only, given as twice weekly injections to a total of 6 injections. The first two CDDP injections were at 2.5 mg/kg. All subsequent injections were at 2 mg/kg. After 3 weeks of treatment, the mice were sacrificed, the lungs were excised, and the blood from each mouse was withdrawn. The organs were fixed in 10% formaldehyde and preserved in 70% ethanol before being photographed.

Western Blot Analysis of Cleaved Caspase-3 from Mice Serum

The blood collected from the retroorbital sinus of mice was centrifuged at 1,000 rpm for 10 minutes at room temperature after coagulation at room temperature for 1 hr. The serum was transferred to a new tube and centrifuged again at 10,000 g for 20 minutes. The supernatant serum was purified using a P-30 Micro-Bio-Spin Chromatography Column (BIORAD, Hercules, Calif.). Fifteen microliters of the fractions was loaded on a 4% to 12% gradient NuPAGE gel (Invitrogen Life Technologies, Carlsbad, Calif.) and run until the kDa protein marker has run off the gel (approximately 1.5 to 2 hours). After electrophoresis, the proteins were transferred onto a Protran BA 85 nitrocellulose transfer membrane (Schleicher and Schuell, BioScience, Keene, N.H.). Finally, a Western blot analysis for cleaved caspase-3 was performed with cleaved caspase-3 (17 kD) antibody. To block nonspecific binding, the membrane was incubated at room temperature for 1 hour with 5% nonfat dry milk in 10 mM Tris-HCl buffer, pH 8.0, containing 150 mM NaCl and 0.05% Tween 20 (TBST). The blot was probed with cleaved caspase-3 rabbit primary antibody (Cell Signaling Technology, Beverly, Mass.) at 1:1000 dilution, in 5% milk TBST, overnight at 4° C. and then washed three times (15 minutes each) with TBST. The protein was detected using goat antirabbit secondary antibody (Jackson ImmunoResearch Laboratories, West Grove, Pa.), ECL Western blotting detection reagent, and Hyperfilm ECL (Amersham, Piscataway, N.J.).

Results

In Vitro Optimization of the Molar Ratio of TfRscFv/LipA-HoKC/GMC-5-193 Complex

Figure 13:
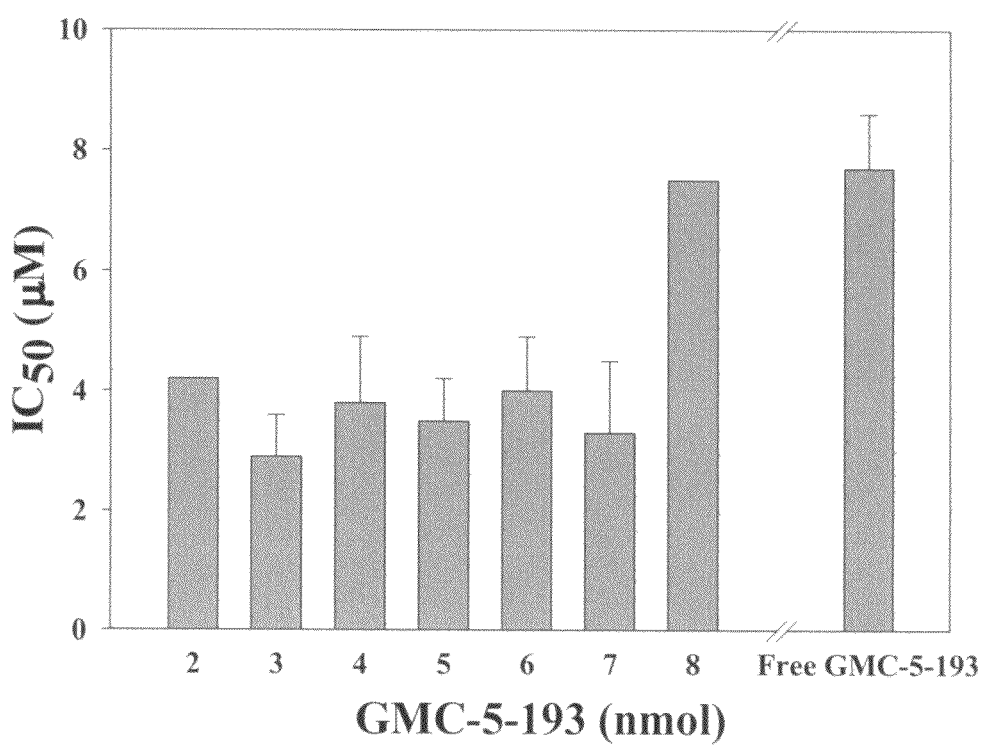
FIG. 13 shows the optimization of the molar ratio of GMC-5-193 to LipA-HoKC, and the effect of TfRscFv/LipA-HoKC/GMC-5-193 complexes at different ratios of GMC-5-193 to LipA-HoKC on DU145 human prostate cancer cells.

The TfRscFv/LipA-HoKC/GMC-5-193 complex was prepared as detailed above and the molar ratio of the small molecule to liposome of the TfRscFv/LipA-HoKC/GMC-5-193 complex was optimized. The cytotoxic effect of complexed GMC-5-193 at different ratios of GMC-5-193 to LipA-HoKC on DU145 human prostate cancer cells was examined. $5.5 \times 10^3$ cells/well were seeded in a 96-well plate and treated after 24 hours with TfRscFv/LipA-HoKC/GMC-5-193 complexes or free GMC-5-193. The XTT assays were performed 48 hours after treatment to assess cytotoxicity, and the $IC_{50}$ values (the drug concentration yielding 50% growth inhibition) were calculated from the concentration-cell viability curve. FIG. 13 shows the $IC_{50}$ values of DU145 cells treated with each complex. The ratio of single-chain antibody fragment to liposome in each complex was 1:30 (w:w). At the range of the molar ratio of GMC-5-193 to liposome of 2:7~7:7, a decrease in the $IC_{50}$ values were observed in cells treated with the complexed GMC-5-193 in comparison with cells treated with free GMC-5-193, reducing the $IC_{50}$ values from 7.7±0.9 µM to 2.2±5 µM. At the molar ratio of GMC-5-193 to liposome of 8:7. The $IC_{50}$ values of cells transfected with either complexed or free GMC-5-193 were similar. The GMC-5-193 complex at the molar ratio of GMC-5-193 to liposome of 7:7 was chosen for further experiment because there was no significant difference in the $IC_{50}$ values of DU145 cells treated with the complexed GMC-5-193 at the range of the molar ratio of GMC-5-193 to liposome of 2:7~7:7. The particle size of the complexed GMC-5-193 at the molar ratio of GMC-5-193 to liposome of 7:7 (i.e. 1:1) was about 300 nm in 5% dextrose.

Figure 14:
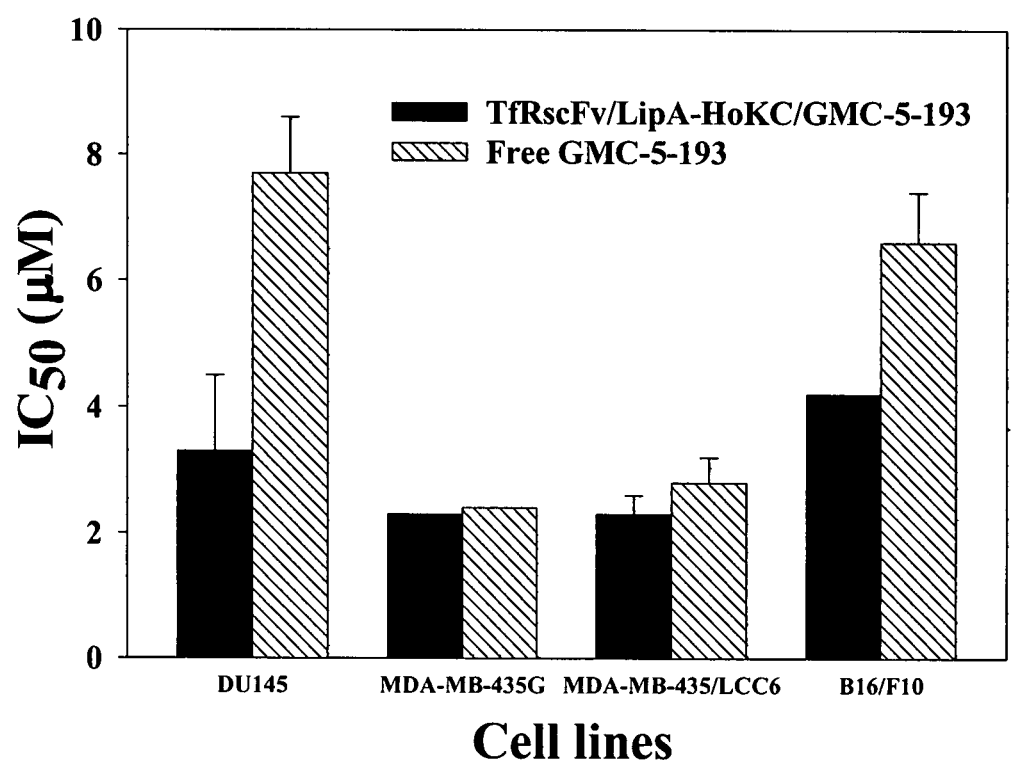
FIG. 14 shows the effect of TfRscFv/LipA-HoKC/GMC-5-193 complexes on different cell lines.

The Effect of Free or Complexed GMC-5-193 on Cell Kill (Sensitivity) in Different Cell Lines FIG. 14 shows the comparison of the level of cell kill of the complexed GMC-5-193 and free GMC-5-193 in different cell lines (DU145, MDA-MB-435, MDA435/LCC6, B16/F10. Here $4~5.5 \times 10^3$ cells/well were seeded in a 96-well plate and after 24 hours, treated with TfRscFv/LipA-HoKC/GMC-5-193 complexes, free GMC-5-193. The concentrations of GMC-5-193 were 50 nM~31.25 µM. The molar ratio of GMC-5-193 to LipA-HoKC in the complexes was 1:1. The ratio of single-chain antibody fragment to liposome in each complex was 1:30 (w:w). The XTT assays were performed 48 hours after treatment to assess cytotoxicity and the $IC_{50}$ values were calculated. The $IC_{50}$ values of DU145, MDA435/LCC6 and B16/F10 cells treated with the TfRscFv/LipA-HoKC/GMC-5-193 were lower than those treated with free GMC-5-193, indicating increased sensitivity to this molecule. MDA-MB-435 showed similar sensitivity to the TfRscFv/LipA-HoKC/GMC-5-193 complex or Free GMC-5-193. The greatest difference in sensitivity between free and complexed GMC-5-193 was seen with DU145 cells (reducing the $IC_{50}$ value from 7.9 uM with free to 3.2 uM with complex) and with B16/F10 cells (reducing the $IC_{50}$ value range from 6.6±0.8 µM to 4.2±0.0 µM).

Table III below shows the results of similar experiments performed comparing free GMC-5-193 and the TfRscFv/LipA/GMC-5-193 complex.

TABLE III

| | $IC_{50}$ values (µM)* obtained with XTT viability assay | |
|---|---|---|
| Cell lines | Free GMC-5-193 | TfRscFv/LipA/GMC-5-193 |
| DU145 | 11.3 ± 0.6 | 3.9 ± 0.5 |
| MDA-MB-435 | 4.0 ± 0.5 | 2.5 ± 0.1 |
| B16-F10 | >31 | 5.7 ± 0.4 |

*Mean of three series of measurements ± S.D.

Thus, complexing GMC-5-193 with the TfRScFv/LipA-HoKC of this invention increases the response of multiple human and mouse cell lines to the small molecule, as compared to the response to the free small molecule as is currently used in the art.

In Vitro Chemosensitization by the TfRscFv/Liposome/GMC-5-193 Complex

Figure 15A:
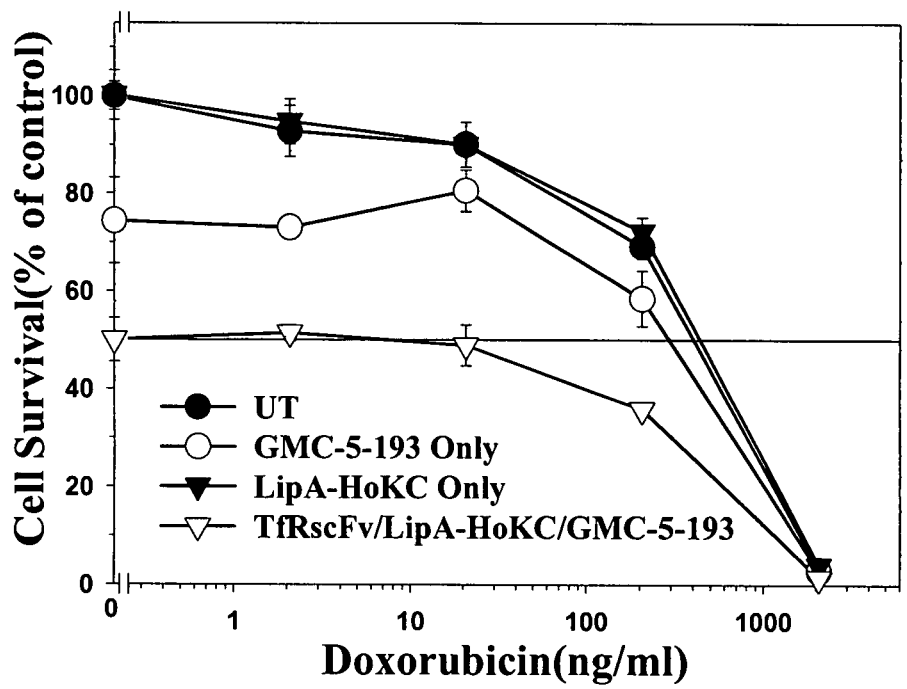
FIG. 15A shows the effect of tumor targeting liposomal delivery of GMC-5-193 on sensitization of MDA-MB-435 human melanoma cells to doxorubicin using TfRscFv/LipA-HoKC/GMC-5-193 complexes compared to free GMC-5-193.

GMC-5-193 has microtubule disruptive and anti-angiogenic effects. The effect of combination therapy of free and ligand/liposome complexed GMC-5-193 with conventional chemotherapeutics was studied in order to determine if the anticancer effect of the conventional chemotherapies could be enhanced and to compare the level of enhancement of the complexed small molecule as compared to free small molecule. The ability of the ligand/liposome/GMC-5-193 (TfRscFv/LipA-HoKC/GMC-5-193) complex to sensitize MDA-MB-435 human melanoma cells to doxorubicin was examined and the results are presented in FIG. 15A. Here, $4.5 \times 10^3$ cells/well were seeded in a 96-well plate and after 24 hours, treated with TfRscFv/LipA-HoKC/GMC-5-193 complex, free GMC-5-193 or LipA-HoKC only. The concentration of GMC-5-193 was 1.25 µM per well. The molar ratio of GMC-5-193 to LipA-HoKC in the complexes was 1:1. The ratio of single-chain antibody fragment to liposome in each complex was 1:30 (w:w). After 24 hours, doxorubicin was added in concentrations increasing from 2.07 to ~2070 ng/mL. After 48 hours, XTT assays were performed to assess cell viability in response to treatments. Each point in FIG. 15A represents the mean of triplicate samples±standard deviation. $IC_{50}$ values represent the concentration of drug resulting in 50% growth inhibition. UT=untransfected. The anthracycline antibiotic doxorubicin was chosen because it is one of the most common of the chemotherapeutics and has been used for combination therapy with the microtubule-targeted, tubulin-polymerizing agents for breast cancer. $IC_{50}$ values were calculated. Cells transfected with LipA-HoKC without GMC-5-193 showed an $IC_{50}$ similar to that of untransfected cells, indicating that the liposomes themselves are nontoxic. Cells treated with free GMC-5-193 exhibited a slightly reduced, but not significantly different, $IC_{50}$, indicating that free GMC-5-193 does not effectively inhibit cell growth. However, a significant (~50-fold) increase in sensitization was observed in cells treated with the complexed GMC-5-193 in comparison with cells treated with free GMC-5-193, with the $IC_{50}$ value declining from 300 to 8 ng/mL.

Figure 15B:
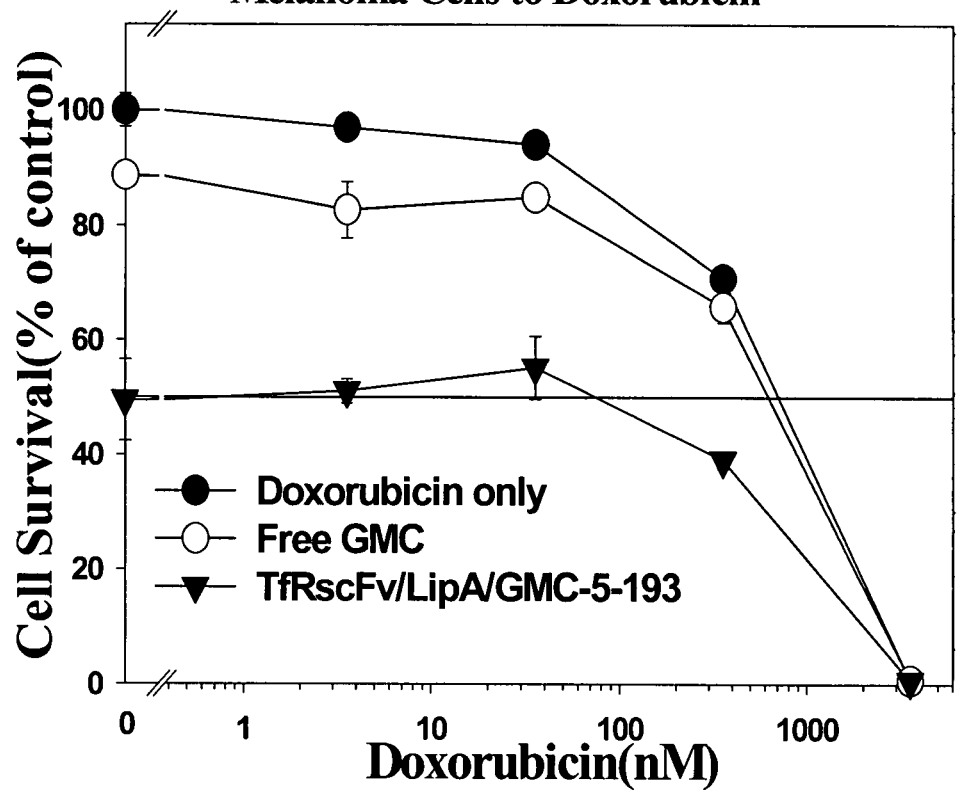
FIG. 15B shows the effect of tumor targeting liposomal delivery of GMC-5-193 on sensitization of MDA-MB-435 human melanoma cells to doxorubicin using TfRscFv/LipA/GMC-5-193 complexes compared to free GMC-5-193.

The results of a similar study examining the effects of doxorubicin only, doxorubicin plus free GMC-5-193 (GMC) and doxorubicin plus TfRscFv/LipA/GMC-5-193 (scL-GMC) complexes (i.e. cationic immunoliposomes without the HOKC peptide) is shown in FIG. 15B. The molar ratio of GMC-5-193 to LipA in the complexes was 1:1. The ratio of single-chain antibody fragment to liposome in each complex was 1:30 (w:w). A ~10 fold increase in sensitization was observed in cells treated with the complexed GMC-5-193 in comparison to both cells treated with doxorubicin only and doxorubicin plus free GMC-5-193.

Figure 15C:
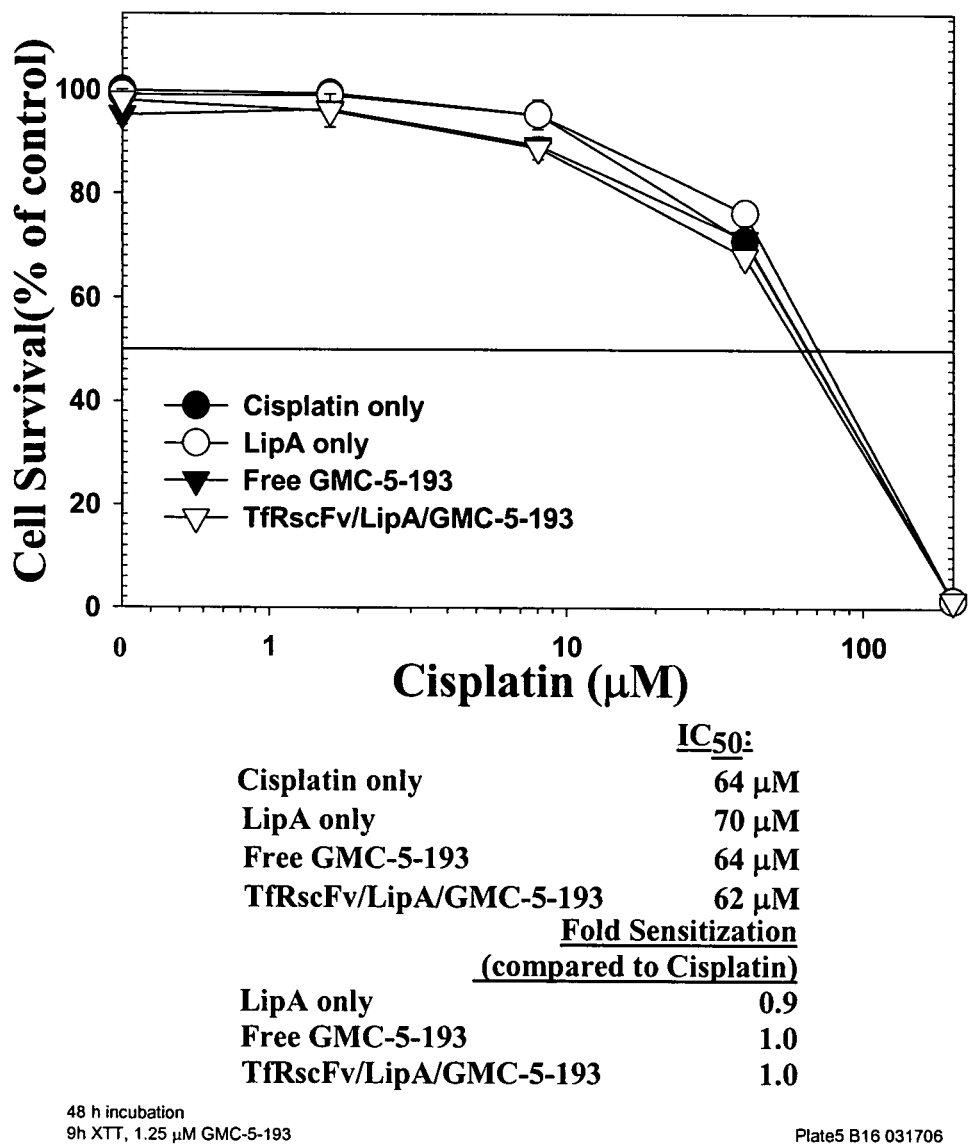
FIG. 15C shows the effect of tumor targeting liposomal delivery of GMC-5-193 (TfRscFv/LipA/GMC-5-193 complexes) on sensitization of B16/F10 mouse melanoma cells to Cisplatin compared to free GMC-5-193, at a concentration of 1.25 µM GMC-5-193.
Figure 15D:
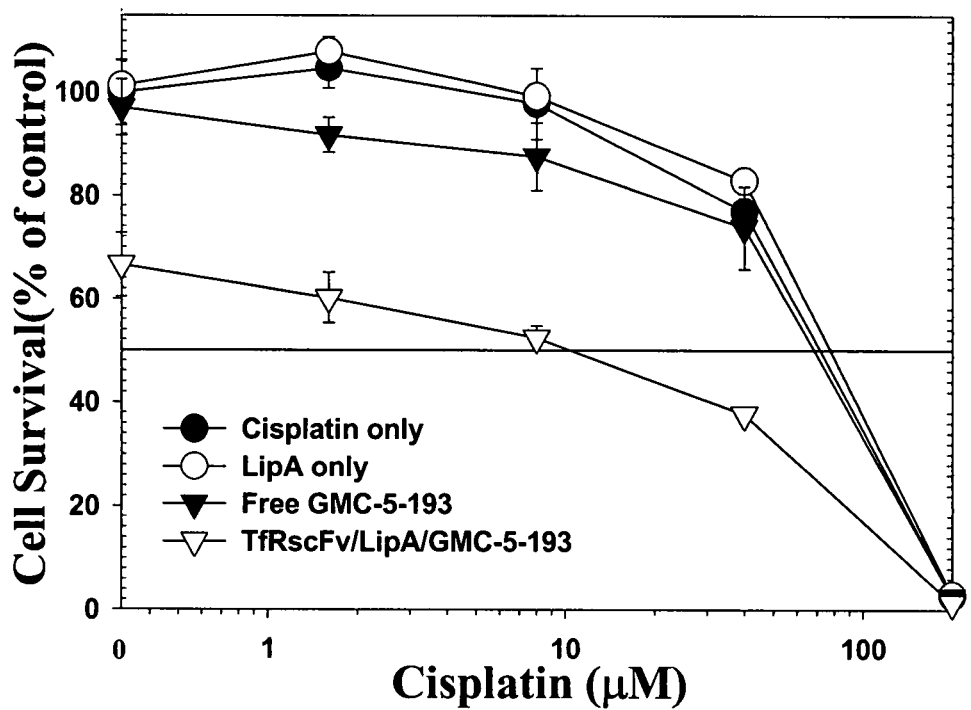
FIG. 15D shows the effect of tumor targeting liposomal delivery of GMC-5-193 (TfRscFv/LipA/GMC-5-193 complexes) on sensitization of B16/F10 mouse melanoma cells to Cisplatin compared to free GMC-5-193, at a concentration of 2 µM GMC-5-193.
Figure 15E:
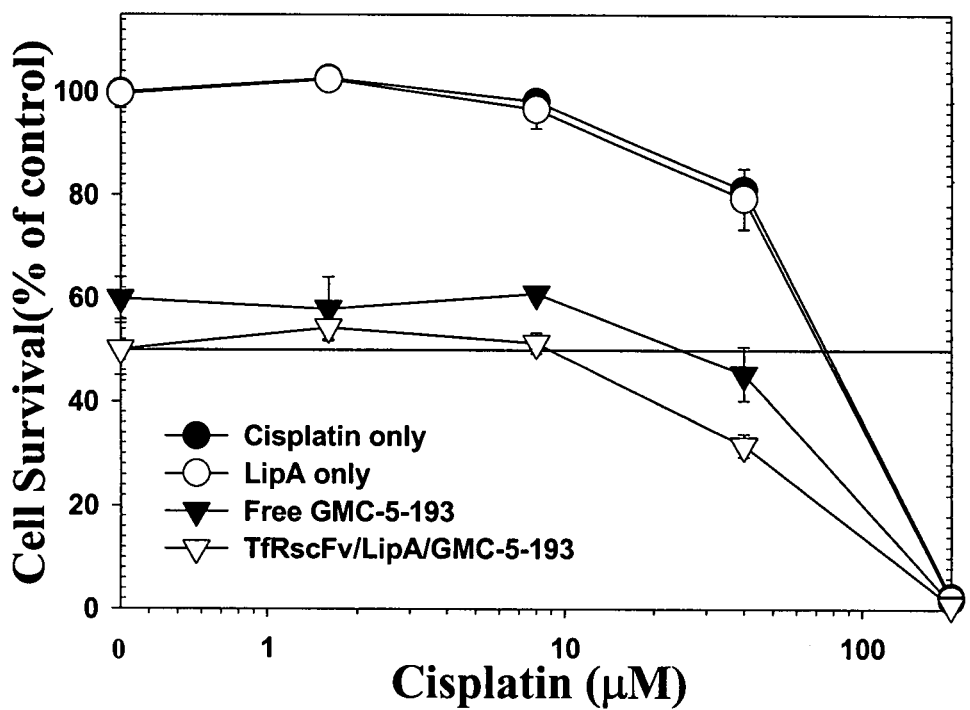
FIG. 15E shows the effect of tumor targeting liposomal delivery of GMC-5-193 (TfRscFv/LipA/GMC-5-193 complexes) on sensitization of B16/F10 mouse melanoma cells to Cisplatin compared to free GMC-5-193, at a concentration of 2.5 µM GMC-5-193.

A study of the effects of increasing doses of GMC-5-193, administered either free or as TfRscFv/LipA/GMC-5-193 complex, on sensitization on B16/F10 cells to cisplatin (CDDP) was performed and is shown in FIG. 15C-E. The concentration of GMC-5-193 was 1.25, 2 and 2.5 uM, respectively. The molar ratio of GMC-5-193 to LipA in the complexes was 1:1. The ratio of single-chain antibody fragment to liposome in each complex was 1:30 (w:w). In FIG. 15C the concentration of GMC-5-193 was 1.25 µM per well and the XTT assay was incubated for 9 hours. In FIG. 15D the concentration of GMC-5-193 was 2 µM per well and the XTT assay was incubated for 7 hours. In FIG. 15E the concentration of GMC-5-193 was 2.5 µM per well and the XTT assay was incubated for 9 hours. At the lowest dose of GMC-5-193 neither the free nor complexed GMC-5-193 enhances the response to CDDP (FIG. 15C). However, the degree of sensitization increases as the doses of GMC-5-193 increases to 2 uM and 2.5 UuM. In both cases the complexed small molecule has an increased effect on the cells as compared to CDDP only and free GMC-5-193. This difference is most pronounced at the 2 uM dose. Thus, under this treatment protocol, an increase in sensitization was observed in cells treated with the complexed GMC-5-193 in comparison to cells treated with free GMC-5-193 at the same concentration, illustrating the beneficial effects of delivery using the complexes. Thus, there is a dose-dependent increase in sensitization with the complex delivered GMC-5-193.

The above series of experiments also demonstrate that an increased response is obtained when either TfRscFv/LipA-HoKC or TfRscFv/LipA are used to deliver the small molecule.

Figure 16:
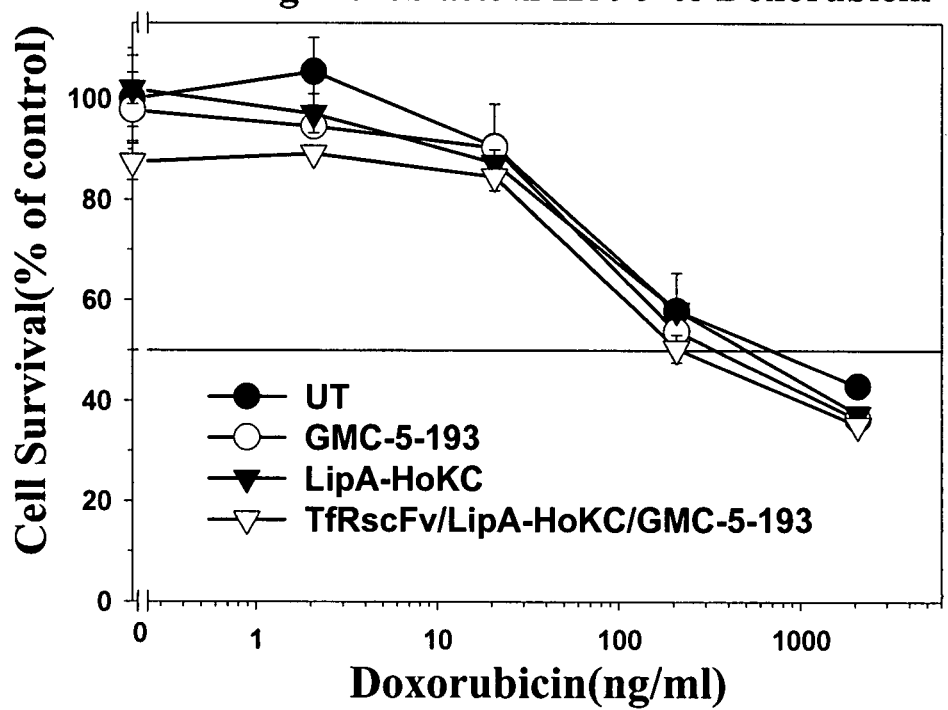
FIG. 16A shows the effect of tumor targeting liposomal delivery of GMC-5-193 on sensitization of normal human lung fibroblasts IMR-90 to doxorubicin using TfRscFv/LipA-HoKC/GMC-5-193 complexes.
FIG. 16B shows the effect of tumor targeting liposomal delivery of GMC-5-193 on sensitization of normal human lung fibroblasts IMR-90 to doxorubicin using TfRscFv/LipA/GMC-5-193 complexes.
FIG. 16C shows the effect of tumor targeting liposomal delivery of GMC-5-193 on sensitization of normal human lung fibroblasts IMR-90 to mitoxantrone using TfRscFv/LipA/GMC-5-193 complexes.

The specificity of the effect of the small molecule when included as part of the complex of this invention is shown if FIG. 16 A-C with normal lung fibroblast cell line IMR-90. The above sensitization results with B16/F10 and MDA-MB-435 were dramatically different from the results with normal human lung fibroblasts IMR-90 under the same conditions. $4.5 \times 10^3$ cells/well were seeded in a 96-well plate and after 24 hours treated with TfRscFv/LipA-HoKC/GMC-5-193 complex, free GMC-5-193 or LipA-HoKC only (FIG. 16A). The concentration of GMC-5-193 was 1.25 µM per well. The molar ratio of GMC-5-193 to LipA-HoKC in the complexes was 1:1. The ratio of single-chain antibody fragment to liposome in each complex was 1:30 (w:w). After 24 hours, doxorubicin was added in increasing concentrations from 2.07 ng/mL to ~2070 ng/mL. After 48 hours, XTT assays were performed to assess cell viability in response to treatments. Each point represents the mean of triplicate samples±standard deviation. $IC_{50}$ values represent concentration of drug resulting in 50% growth inhibition. UT=untransfected. In IMR-90 cells, the fold sensitizations of LipA-HoKC only, free GMC-5-193, and complexed GMC-5-193 were not statistically different, showing little or no effect of GMC-5-193 on normal cells whether administered alone or complexed with the TfRscFv/Lip-HoKC. This is further demonstrated since in IMR-90 the $IC_{50}$ with complexed GMC-5-193 was 200 ng/mL compared with 8 ng/mL in MDA-MB-435 cells, representing a 25-fold difference between the normal and tumor cell lines. In comparison, after treatment with free GMC-5-193, the difference of the $IC_{50}$ values between the two cell lines was only 1.1-fold. Thus GMC-5-193 is specifically more effective on tumor cells when delivered as a component of the TfRscFv/LipA-HoKC complex than when administered as free GMC-5-193.

Figure 16B:
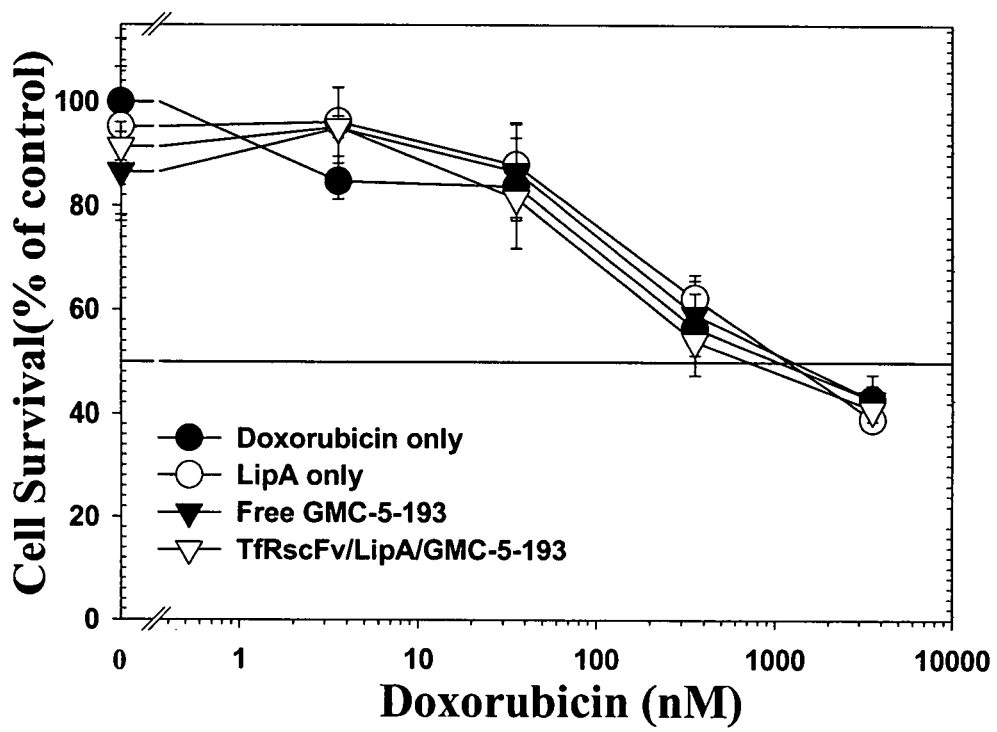

Results of a similar experiment examining the effect of TfRscFV/LipA (without HoKC) delivery of GMC-5-193 on sensitization of normal human lung fibroblasts IMR-90 to doxorubicin are shown in FIG. 16B. Again, administration of the small molecule with the complex did not sensitize the normal cells to the chemotherapeutic agent.

Figure 16C:
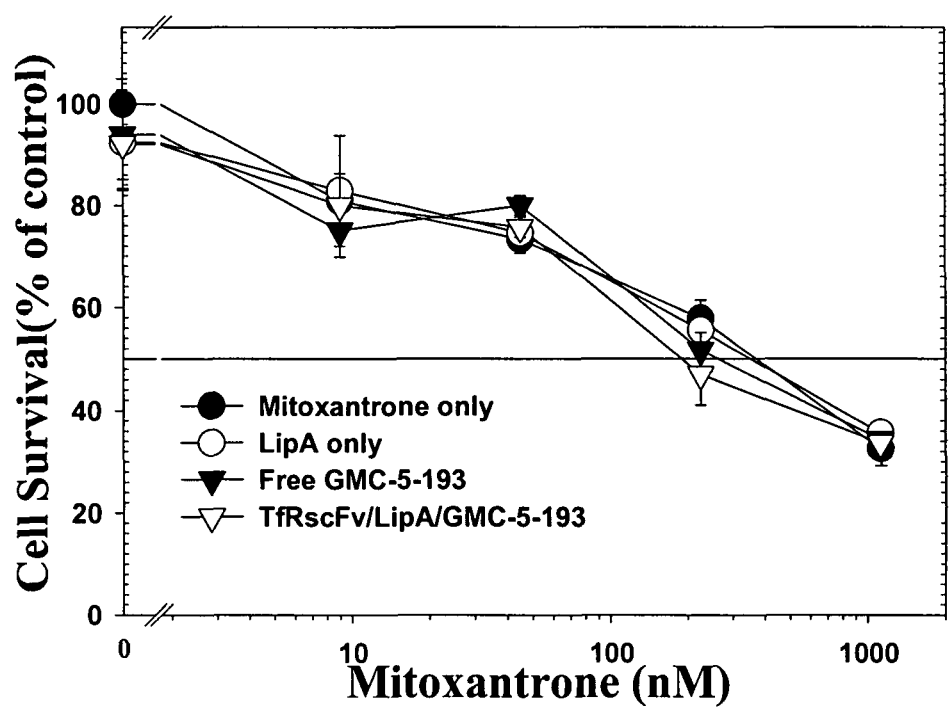

Similarly in a study with IMR-90 and a different chemotherapeutic agent the effect of tumor targeting liposomal delivery of GMC-5-193 (TfRscFv/LipA/GMC-5-193) on sensitization to mitoxantrone was examined (FIG. 16C). Here also complexing the small molecule did not effect the response of normal cells to mitoxantrone.

The effect of the complex on sensitization of another human tumor cell line, DU145 human prostate cancer cells, to Taxotere was also examined (FIG. 17A). $4.5 \times 10^3$ cells/well were seeded in a 96-well plate and after 24 hours treated with TfRscFv/LipA-HoKC/GMC-5-193 complexes. The concentration of GMC-5-193 was 1.25 µM per well. The molar ratio of GMC-5-193 to LipA-HoKC in the complexes was 1:1. The ratio of single-chain antibody fragment to liposome in each complex was 1:30 (w:w). After 24 hours, Taxotere was added in increasing concentrations from 0.08 nM to ~82.7 nM. After 48 hours XTT assays were performed to assess cell viability in response to treatments. Each point represents the mean of triplicate samples±standard deviation. $IC_{50}$ values represent the concentration of drug resulting in 50% growth inhibition. UT=untransfected. Taxotere is a microtubule-targeted, tubulin-polymerizing agent that has been demonstrated to exert a high level of clinical activity. This drug was chosen because it is one of the first-line chemotherapeutics used in combination therapy for prostate cancer. The fold sensitizations of DU145 cells to Taxotere after treatment with LipA-HoKC only, free GMC-5-193, and TfRscFv/LipA-HoKC/GMC-5-193 were 1.1, 1.2, and 47.1, respectively, indicating that the level of response to Taxotere was highly enhanced in cells treated with complexed GMC-5-193.

The results of a similar study with a different chemotherapeutic agent, comparing the degree of sensitization to mitoxantrone by free GMC-5-193, LipA only and TfRscFv/LipA/GMC-5-193 complexes in DU145 human prostate cancer cells is shown in FIG. 17B. The molar ratio of GMC-5-193 to LipA in the complexes was 1:1. The ratio of single-chain antibody fragment to liposome in each complex was 1:30 (w:w). A ~3 fold increase in sensitization was observed in cells treated with the complexed GMC-5-193 in comparison to cells treated with mitoxantrone only, whereas only a 1.7 fold increase was seen with free GMC-5-193. The fold sensitization is doubled when the complex is used.

The results of an additional study comparing the degree of sensitization to taxotere by free GMC-5-193 (GMC), LipA only and TfRscFv/LipA/GMC-5-193 complexes in MDA-MB-435 human melanoma cells is shown in FIG. 17C. The molar ratio of GMC-5-193 to LipA in the complexes was 1:1. The ratio of single-chain antibody fragment to liposome in each complex was 1:30 (w:w). A ~10 fold increase in sensitization was observed in cells treated with the complexed GMC-5-193 in comparison to cells treated with taxotere only, double that with free GMC-5-193.

Next, the comparison of the effect of treatment with the complexed GMC-5-193 and CDDP in the mouse syngeneic lung metastasis model was examined. FIG. 18 shows the effect of the complex on sensitization of B16/F10 cells to CDDP as compared to free GMC-5-193. $3.5 \times 10^3$ cells/well were seeded in a 96-well plate and transfected after 24 hours with LipA-HoKC only, free GMC-5-193 and TfRscFv/LipA-HoKC/GMC-5-193 complex. The concentration of GMC-5-193 was 2 µM per well. The molar ratio of GMC-5-193 to LipA-HoKC in complex was 1:1. The ratio of single-chain antibody fragment to liposome in each complex was 1:30 (w:w). After 24 hours, CDDP was added in increasing concentrations from 0.4 µM~200 µM. The XTT assays were performed 48 hours after CDDP treatment to assess the degree of sensitization to CDDP. Each point is the mean of triplicate samples±standard deviation. $IC_{50}$ values are the drug concentration yielding 50% growth inhibition. UT=untransfected. An increase in sensitization by the complexed GMC-5-193 over free GMC-5-193 was observed, reducing the $IC_{50}$ value from 42 to 20 µM. The fold sensitization of the complex was 2.6, once again double that of free GMC-5-193. Thus, the results from all of the above in vitro experiments support the observation that GMC-5-193 complexed with the targeted liposome, both TfRscFv/LipA and TfRScFv/LipA-HoKC, sensitizes cancer cells more effectively to conventional chemotherapeutics than when delivered as free GMC-5-193 as is currently used in the art.

In Vitro Confocal Imaging

Confocal imaging was used to compare the internalization of the GMC-5-193 when delivered as free GMC-5-193 and when complexed with the targeted liposomes (with and without HoKC peptide), taking advantage of the inherent fluorescence of GMC-5-193. MDA-MB-435 cells were exposed for 6 hours to either free GMC-5-193 or complexed GMC-5-193, then washed with PBS, fixed with 4% paraformaldehyde in PBS, and visualized by confocal microscopy. FIG. 19A shows comparison between uptake of free GMC-5-193 and that delivered to the cells by the TfRscFv/LipA/GMC-5-193 complex; FIG. 19 B shows comparison between uptake of free GMC-5-193 and that delivered by TfRscFv/LipA-HoKC/GMC-5-193 (scLHK-GMC) complex. $5 \times 10^4$ cells/well were seeded on glass slides in a 24-well plate and after 24 hours treated with TfRscFv/Liposome/GMC-5-193 complex or free GMC-5-193. The molar ratio of GMC-5-193 to LipA or LipA-HoKC in the complexes was 1:1. The ratio of single-chain antibody fragment to liposome in each complex was 1:30 (w:w). Six hours after treatment, cells were washed with phosphate-buffered saline (PBS), fixed with 4% paraformaldehyde in PBS, and mounted on the glass slides. The Olympus FLUOVIEW®-300 laser scanning confocal system was used to visualize fluorescence. Significantly increased fluorescence uptake by the cells was observed when the small molecule GMC-5-193 was complexed with either the TfRScFv/LipA or the TfRScFv/LipA-HoKC complexes of this invention when compared to cells treated with free GMC-5-193.

The GMC-5-193 fluorescent distribution pattern was observed throughout the cells, including the cytoplasm and in the nucleus, in cells treated with the complexed GMC-5-193. DIC images revealed that the morphology of cells treated with the GMC-5-193 complexes differed from cells treated with free GMC-5-193. The former showed relatively rounded cells and the latter showed elongated and more spread cells, similar to what is observed with untreated cells. These results indicate that after complexing with the TfRscFv/LopA or TfRScFv/LipA-HoKC GMC-5-193 can be more efficiently taken up by the cancer cells, with greater evidence of it intended cell killing. For further investigation, the nucleus was stained with the nucleus specific dye DAPI (blue fluorescence) and the images analyzed. From the three-dimensional animation of the photographed cells, it was apparent that the GMC-5-193 green fluorescence was distributed equally throughout the cells in cells treated with the either of the GMC-5-193 complexes, whereas the green fluorescence was observed more in the nucleus than in the cytoplasm, in cells treated with free GMC-5-193.

In Vivo Tumor Targeting by the Ligand/Liposome Complex Carrying GMC-5-193

To generate a tumor-bearing animal, MDA435/LCC6 human melanoma cells ($8 \times 10^6$) suspended in PBS were injected intravenously into the tail vein of athymic nude mice.
Using TfRscFv/LipA/GMC-5-193:

Mice carrying MDA435/LCC6 xenograft tumors, primarily in the lung, were injected intravenously with free GMC-5-193, non-targeted LipA/GMC-5-193 (L-GMC) or TfRscFv/LipA/GMC-5-193 (scL-GMC) at 9 mg GMC-5-193/kg per mouse. The molar ratio of GMC-5-193 to LipA in the complexes was 1:2.5 (equivalent to 2.8:7). The ratio of single-chain antibody fragment to liposome in each complex was 1:30 (w:w). Three hours after injection, liver and lung were excised and examined under a fluorescence microscope. The metastases varied in size from microscopic to small visible metastases. FIG. 20A shows the same field photographed in bright-field and with fluorescence. It can be clearly seen that the TfRscFv/LipA-GMC-5-193 complex is able to deliver GMC-5-193 specifically to the tumor cells in the lung. In the bright-field image of the mouse treated with free GMC-5-193, large tumors can be observed around the lung, with metastasis to the liver. However, the fluorescent image shows very weak fluorescence in all the tissues. Untargeted complex (LipA/GMC-5-193 (L-GMC)) showed very weak signals both in lung and liver and no tumor specificity. In contrast, in the mouse injected with the TfRscFv/LipA/GMC-5-193 complex (scL-GMC), the fluorescence signal of GMC-5-193 was much stronger in the lung metastases (distinguishable in the bright-field image by a more dense appearance as compared to the lighter bubbly appearance of the normal lung tissue). In addition, very low background signal was observed in the normal liver of the mouse treated with the complexed GMC-5-193, again demonstrating tumor specificity. These results show that tumor specific uptake of GMC-5-193 after systemic administration is enhanced when GMC-5-193 is incorporated into the TfRscFv/LipA complex.

Using TfRscFv/LipA-HoKC/GMC-5-193

Mice carrying MDA-MB-435/LCC6 xenograft tumors, primarily in the lung, were injected intravenously with free GMC-5-193 (FIG. 20B (PanelB)) or TfRscFv/LipA-HoKC/GMC-5-193 (FIG. 20B (PanelA)) at 9 mg GMC-5-193/kg per mouse. The molar ratio of GMC-5-193 to LipA-HoKC in the complexes was 1:2.5 (equivalent to 2.8:7). The ratio of single-chain antibody fragment to liposome in each complex was 1:30 (w:w). Three hours after injection, liver and lung were excised and examined under a fluorescence microscope. The metastases varied in size from microscopic to small visible metastases. The same field is photographed in bright-field and with fluorescence. It can be clearly seen that the ligand-liposome complex is able to deliver GMC-5-193 specifically to the tumor cells in the lung (FIG. 20B (Left-hand panels)). In the bright-field image of the mouse treated with free GMC-5-193 (FIG. 20B (right-hand panels)), large tumors can be observed around the lung, with metastasis to the liver. However, there was very weak fluorescence in all the tissues, with no fluorescence in the metastases in the liver. These results show that tumor specific uptake of GMC-5-193 after systemic administration is enhanced when GMC-5-193 is incorporated into the TfRscFv/LipA-HoKC complex.

Additional results showing the tumor-specific incorporation of fluorescent GMC-5-193 delivered with TfRscFv/LipA-HoKC/GMC-5-193 complexes is shown in FIG. 20C. The molar ratio of GMC-5-193 to LipA-HoKC in the complexes was 1:2.5 (equivalent to 2.8:7). The ratio of single-chain antibody fragment to liposome in each complex was 1:30 (w:w). Here also the difference between the signal in the mice which received intravenous administration of the TfRscFv/LipA-HoKC/GMC-5-193 and those receiving intravenous free GMC-5-193 is dramatic. Large tumors in the liver and near the spine were present in the mouse that received the free GMC-5-193. However, very little fluorescence was evident in these tumors. In contrast, the fluorescence signal was much stronger in the lung mets and separate tumor from the mouse that received the complexed GMC-5-193. These above experiments clearly demonstrate the efficient tumor targeting and delivery of systemically administered GMC-5-193 when complexed with the ligand/liposome (with and without HoKC peptide) complex of this invention.

In Vivo Efficacy Study

C57BL/6 mice carrying B16/F10 tumors were injected with CDDP or TfRscFv/liposome/GMC-5-193 complexes (TfRscFv/LipA/GMC-5-193 or TfRscFv/LipA-HoKC/GMC-5-193) alone or in combination with CDDP. The molar ratio of GMC-5-193 to LipA or LipA-HoKC in the complexes was 1:1. The ratio of single-chain antibody fragment to liposome in each complex was 1:30 (w:w). FIGS. 21A-21C show the photographs of lung of each mouse after 3 weeks of treatment. Multiple metastases of B16/F10 were observed in the lung of mice who did not undergo treatment (UT). In FIG. 21A mice were given seven intravenous injections of GMC-5-193 at 3 mg GMC-5-193/kg/injection two or three times a week. These results show that the complexed GMC-5-193 (with and without the HoKC peptide) was better than free GMC-5-193 as a single agent treatment. In FIGS. 21B and 21C, the mice also received seven intravenous injections of GMC-5-193 at 3 mg GMC-5-193/kg/injection two or three times a week. In the groups that received CDDP, the CDDP was administered twice weekly to a total of six injections. The initial dose of CDDP was 2.5 mg/kg, while all subsequent doses were 2.0 mg/kg. Mice treated with the combination of TfRscFv/Liposome/GMC-5-193 (TfRscFv/LipA/GMC-5-193) complexes plus CDDP showed a significant decrease in the number of lung metastases (FIG. 21B). In FIG. 21C, mice treated with the combination of TfRscFv/LipA/GMC-5-193 (scL-GMC) or TfRscFv/LipA-HoKC/GMC-5-193 (scL-HK-GMC) complexes plus Cisplatin also showed a significant decrease in the number of lung metastases, compared to single agent treatment (complex or CDDP).

The results of FIG. 21B correlate with those of the Western blot analysis for cleaved caspase-3 as a marker of apoptosis (FIG. 22). In the serum of untreated mice or mice treated with TfRscFv/liposome/GMC-5-193 complexes (with or without HoKC) alone, cleaved caspase-3 was not detected, showing no apoptosis, thus no significant effect of the small molecule therapeutic. Cleaved caspase-3 was detected as only a weak band in the serum of mice that received CDDP alone. Most significantly, mice treated with the combination of the complexed GMC-5-193 (TfRscFv/LipA/GMC-5-193 or TfRscFv/LipA-HoKC/GMC-5-193) plus CDDP showed a high level of cleaved caspase-3, indicating enhancement of programmed cell death by the combination therapy.

Discussion

DU145 cells, B16/F10 cells, and to a lesser extent MDA435/LCC6 cells showed an enhanced sensitivity to the TfRscFv/LipA/GMC-5-193 or TfRscFv/LipA-HoKC/GMC-5-193 complex in comparison to cells treated with free GMC-5-193 (FIG. 14). Complexing GMC-5-193 also resulted in an increased sensitization of multiple tumor cell lines (human and mouse) to various chemotherapeutic agents. Confocal images revealed that GMC-5-193 is more efficiently taken up by MDA-MB-435 cells as the complexed GMC-5-193 than as free GMC-5-193 (FIGS. 19A and 19B). Much stronger green fluorescence was observed in the cells treated with the GMC-5-193 complex, when compared with cells treated with free GMC-5-193. Interestingly, the GMC-5-193 green fluorescence was observed throughout the cells equally in cells treated with the GMC-5-193 complex, whereas in cells treated with free GMC-5-193, the green fluorescence was observed more in the nucleus than in the cytoplasm. Incorporation of GMC-5-193 in the liganded liposome complex elevated cellular uptake and altered the localization pattern of GMC-193 in cells.

GMC-5-193 shows anticancer effect by binding to tubulin in cytoplasm; thus the presence of the small molecule in the cytoplasm is preferable for anticipating an anticancer effect. In addition, the drug release into the cytoplasm is followed by the subsequent release into the extracellular compartment, which can cause the bystander effect. For this reason, enhanced anticancer activity in cells treated with the complexed GMC-5-193 was examined.

As results of in vitro chemosensitization of human melanoma cells MDA-MB 435 to doxorubicin, a significant increase in sensitization was observed in the cells treated with the complexed GMC-5-193 compared with cells treated with free GMC-5-193 (FIGS. 15A-15B). These sensitization results were dramatically different from the results of normal human lung fibroblasts IMR-90 under the same conditions, in which GMC-5-13, either free or complexed had virtually no effect (FIGS. 16A-16B). Increased fold difference between the $IC_{50}$ values in cancer cells were observed when the cells were treated with the complexed GMC-5-193 in comparison with the cells treated with the free GMC-5-193. These findings indicate that TfRscFv targets and efficiently delivers the complex to the cancer cells to increase the cytotoxicity, but not to normal cells, demonstrating combination therapy with complexed GMC-5-193 can increase the therapeutic index. Similar chemosensitization of DU145 human prostate cancer cells to Taxotere was observed (FIGS. 17A-17B). The fold sensitization of B16/F10 metastatic mouse melanoma cells to CDDP was also 2.6 fold higher when the cells were treated with the complex (FIG. 18).

All the results from the in vitro experiments support the observation that GMC-5-193 complexed with the targeted liposome sensitizes cancer cells more effectively to the conventional chemotherapeutics than when delivered as free GMC-5-193.

One interest in this study was in tumor-targeting delivery of GMC-5-193 after systemic administration. When TfRscFv/LipA/GMC-5-193 or TfRscFv/LipA-HoKC/GMC-5-193 is administered intravenously to athymic nude mice carrying MDA-MB-435/LCC6 xenograft tumors primarily in the lung, it can be clearly seen that the ligand-liposome complex delivers GMC-5-193 specifically to the tumor cells in the lung (FIGS. 20A-20C). The green fluorescent signal of GMC-5-193 in the lung metastases was much stronger in these mice than in mice treated with free GMC-5-193. Tumor-specific uptake of GMC-5-193 after systemic administration is enhanced when the small molecule is incorporated into the liganded liposome complexes of this invention prepared by simple mixing of the components. From these results, inclusion of the small molecule in the TfRScFv/LipA or TfRScFV/LipA-HoKC complexes of this invention enhance uptake of the small molecule specifically into the tumor cells whether they are primary tumor or metastases.

This tumor-targeting ability was reflected in in vivo efficacy studies. B16/F10 cells showed enhanced sensitivity when treated with the complexed GMC-5-193, as we described above. Therefore, C57BL/6 mice carrying B16/F10 tumors were selected as animal models for efficacy study. As shown above, mice treated with the combination of TfRscFv/Liposome/GMC-5-193 complexes (with or without the HoKC peptide) plus CDDP showed a significant decrease of metastases in their lung and elevated levels of cleaved caspase-3 in comparison with mice treated with CDDP or TfRscFv/liposome/GMC-5-193 complexes alone.

Caspases involved in apoptosis are divided into two groups: the initiator caspases, which include caspase-2, -8, -9, and -10, and the effector caspases, which include caspase-3, -6, and -7. Activation of effector caspases by initiator caspases is responsible for the proteolytic cleavage of cellular substrates including actin, lamin, poly(ADP-ribose) polymerase (PARP), and inhibitors of deoxyribonuclease (such as DFF45 or ICAD). Cleavage of those substrates degrades the chromosomes into nucleosomal fragments during apoptosis. Caspase-3 has been considered as most directly correlated with apoptosis because of its location in the protease cascade pathway. Caspase-3 is synthesized as a 32-kD precursor that is cleaved to generate the mature form composed of 17-kD subunits through intermediary 20-kD and 12-kD subunits.34-36 Elevated levels of the cleaved caspase-3 of 17-kD is considered a marker of programmed cell deaths.

Thus, specific and efficient targeted drug delivery of the anticancer small molecule GMC-5-193 was achieved. These results show that TfRscFv targets the cationic liposome-GMC-5-193 complex (with or without HoKC) to tumor cells in vitro and in vivo and enhances the antitumor effect of the conventional chemotherapeutics in vitro and in vivo. In particular, the lowering of the effective dose of conventional chemotherapeutic agents, with a concomitant decrease in their toxic effects, was demonstrated.

EXAMPLE 111

Preparation and Characterization of Small Molecule (YK-3-250) Comprising-Immunoliposomes by Simple Mixing To improve the in vitro and in vivo anticancer effects of the small molecule YK-3-250 (a microtubule disruptive compound), a tumor-targeting liposomal complex comprising the small molecule was prepared. In addition to a TfRscFv/LipA complex, a cationic liposome conjugated with endosomal disrupting peptide (LipA-HoKC) can also be prepared and studied as described herein. The endosomal disrupting peptide HoKC may help the release of YK-3-250 in the cytoplasm of the cells to affect tubulin polymerization in cytoplasm. The ligand-liposome complex preferentially targets tumor cells due to elevated levels of the corresponding receptor on their surface. High levels of expression of the ligand-liposome delivered gene were evident in primary tumors and metastasis, but not in normal tissue such as liver, lung, bone marrow, and intestinal crypts. In this Example, a liposome complex of the present invention, comprising the transferrin receptor single chain (TfRscFv), was used to deliver YK-3-250 to cancer cells in vitro to evaluate the in vitro bio-efficacy of the lipoplex comprising YK-3-250.

Materials and Methods 1,2-Dioeoyl-3-trimethylammonium propane (DOTAP), dioleolylphosphatidyl ethanolamine (DOPE), and N-maleimido-phenylbutyrate DOPE (MPB-DOPE) were purchased from Avanti Polar Lipids (Alabaster, Ala.). The K[K(H)KKK]$_5$-K(H)KKC (HOKC) (SEQ ID NO: 2) peptide was manufactured by Sigma-Genosys (The Woodlands, Tex.).

Cell Lines and Culture

The human melanoma cell line MDA-MB-435 was cultured in improved MEM (IMEM) supplemented with 10% heat-inactivated FBS, 2 mM L-glutamine, and 50 μg/mL each of penicillin, streptomycin, and neomycin. EMEM was purchased from MediaTech (Hemdon, Va.) and the other cell culture media and ingredients were obtained from Biofluids (Rockville, Md.).

Preparation of TfRscFv/LipA/YK-3-250 Complexes

Cationic liposomal formulation LipA (DOTAP: DOPE or DDAB:DOPE at a 1:1 to 1:2 molar ratio) were prepared using the ethanol injection method as described herein. The concentration is 2 mM. TfRscFv/LipA/YK-3-250 complexes were prepared as follows: After 10 minutes incubation, suitably at room temperature, with rotation or stirring of a mixture of LipA and TfRscFv (ratio of TfRscFv to LipA, 1:1 to 1:40 (wt/wt), more suitably 1:10 to 1:30 wt/wt), the YK-3-250 at the appropriate concentration was added, mixed by inversion or stirring and incubated for 10 minutes, preferably at room temperature. The molar ratio of YK-3-250 to Liposome was from 0.2:7 to 14:7, more suitably 2:7 to 8:7, most suitably 7:7. The sizes of the complexes were determined by dynamic light scattering at 25° C. with a ZETASIZER® 3000HS system (Malvern, United Kingdom).

Preparation of TfRscFv/LipA-HoKC/YK-3-250 Complexes

Cationic liposomal formulation and LipA-MPB (DOTAP: DOPE: MPB-DOPE or DDAB:DOPE:MPB-DOPE at a 1:1: 0.1 to 1:2:0.1 molar ratios) can be prepared using the ethanol injection method. The LipA-HoKC liposome are then prepared using the coupling reaction between the cationic liposomes carrying the maleimide group and the peptide-carrying terminal cysteine group as previously described herein. An aliquot of 0.1 mmol of the peptide with a free thiol group on cysteine is added to 2 mmol of LipA-MPB in 10 mM HEPES (pH 7.4) solution and rotated at room temperature for 2 hours. The resulting LipA-HoKC will have a lipid concentration of 1.4 mM. TfRscFv/LipA-HoKC/YK-3-250 complexes are prepared as follows: After 10 minutes incubation, preferably at room temperature, with rotation or stirring of a mixture of LipA-HoKC and TfRscFv (ratio of TfRscFv to LipA-HoKC, 1:1 to 1:40 (wt/wt), more suitably 1:10 to 1:30 (wt/wt)), the YK-3-250 at the appropriate concentration is added, mixed by inversion or stirring, and incubated for 10 minutes at room temperature. For animal injection, dextrose or sucrose are added to each sample to a final concentration of 1% to 20%, more suitably 5-10%. The molar ratio of YK-3-250 to Liposome will be from 0.2:7 to 14:7, more suitably 2:7 to 8:7, most suitably 7:7. The sizes of the complexes are determined by dynamic light scattering at 25° C. with a Zetasizer 3000HS system (Malvern, United Kingdom).

In Vitro Cell Viability and Optimization of the TfRscFv/Liposome/YK-3-250 Complex For in vitro cytotoxicity studies, 5 to $5.5 \times 10^3$ cells/well in 100 μL of the appropriate growth medium of each cell line were plated in a 96-well plate. After 24 hours, the cells were washed with serum-free medium, overlaid with 100 μL of TfRscFv/LipA/YK-3-250, Lip A only or free YK-3-250 in serum-free medium in increasing concentrations, incubated for 4-6 hours, preferably 5 hours, and then supplemented with FBS. The cells were then incubated for an additional 24-72 hours, preferably 48 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3, 4-tetrazolium]-bis(4-methoxy-6-nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

Results
In Vitro Optimization of the Molar Ratio of TfRscFv/LipA/YK-3-250 Complex The TfRscFv/LipA/YK-3-250 complex was prepared and the molar ratio of the small molecule to liposome of the TfRscFv/LipA/YK-3-250 complex was optimized. The cell killing effect of complexed and free YK-3-250 at different ratios of YK-3-250 to LipA on MDA-MB-435 cancer cells was compared. The ratio of TfRscFv to LipA was 1:1 to 1:40 (wt/wt), more suitably 1:10 to 1:30 (wt/wt). $5.5 \times 10^3$ cells/well were seeded in a 96-well plate and treated after 24 hours with TfRscFv/LipA/YK-3-250 complexes, LipA only or free YK-3-250. The XTT assays were performed 48 hours after treatment to assess cytotoxicity, and the $IC_{50}$ values (the drug concentration yielding 50% growth inhibition) were calculated from the concentration-cell viability curve. FIG. 23A shows the $IC_{50}$ values of MDA-MB-435 for each treatment. At the range of the molar ratio of YK-3-250 to liposome of 6:7~8:7, a decrease in the $IC_{50}$ values were observed in cells treated with the complexed YK-3-250 in comparison with cells treated with free YK-3-250, or free LipA, reducing the $IC_{50}$ values from >300 nM to 16 nM, down to 8 nM at the molar ratio of YK-3-250 to liposome of 7:7.

FIG. 23 B shows a comparison of the effect of free YK-3-250 and TfRscFv/LipA/YK-3-250 (scL-YK-3-250) complex on MDA-MB-435 cells, using a YK-3-205 to liposome complex (LipA) molar ratio of 7:7, (also equivalent to 1:1). Comparison of the level of cell killing of complexed YK-3-250 as compared to the free small molecule indicates a ~2-fold increase in effectiveness with the complex of this invention.

EXAMPLE 12

Preparation and Characterization of Small Molecule (Imatinib Mesylate (GLEEVEC®)) Comprising-Immunoliposomes by Simple Mixing GLEEVEC® (Imatinib Mesylate; Novartis Pharmaeuticals Corp., East Hanover, N.J.), formerly known as STI-571, is an antiproliferative agent (signal transduction inhibitor), which interferes with the pathways that signal the growth and proliferation of tumor cells. Imatinib Mesylate selectively inhibits a group of receptor tyrosine kinases, including Bcr-Abl, c-KIT and PDGF receptors alpha and beta, leading to disruption in cell growth and eventual cell death.

Imatinib Mesylate has been shown to be effective in inhibiting the activity of Bcr-Abl, a tyrosine kinase protein that is dysfunctional in this disease and signals cells to grow and divide continuously and has been approved for the treatment of patients with KIT (CD117) positive unresectable and/or metastatic malignant Gastrointestinal Stromal Tumors (GIST), a relatively rare form of cancer attributable to the activity of c-KIT tyrosine kinase.

Because protein kinases play a critical role in cellular signal transduction cascades, and thus are directly involved in many diseases including cancer, kinase inhibitors have become the focus for development of a new class of anti-cancer therapeutics. Currently more than 30 other kinase inhibitors in clinical trials. Imatinib Mesylate can also be utilized in the treatment of numerous other cancers, especially those that demonstrate abnormal activity of tyrosine kinases shown to be targeted by Imatinib Mesylate, including PDGF receptors alpha and beta. Initial results have been encouraging, however these drugs are not without their toxic side effects. For Imatinib Mesylate these include hematopoietic suppression, hepatotoxicity, and renal toxicity as well as fluid retention (swelling around the eyes or legs), diarrhea, nausea, vomiting, fatigue, muscle cramps, muscle or bone pain, abdominal pain, and rash. Reducing these side effects would lead to significant improvement in patient quality of life. However, while reduction of these toxicities is important, increased concentration of the therapeutic agent in the tumor cells is even more significant with respect to therapeutic benefit. The experiments described herein demonstrate encapsulation of Imatinib Mesylate in the immunoliposomes of the present invention, and action in human breast, prostate and pancreatic cancer models.

Materials and Methods 1,2-Dioeoyl-3-trimethylammonium propane (DOTAP), dioleolylphosphatidyl ethanolamine (DOPE), and N-maleimido-phenylbutyrate DOPE (MPB-DOPE) were purchased from Avanti Polar Lipids (Alabaster, Ala.).

Cell Lines and Culture

The human prostate cancer cell line DU145 (HTB-81) and mouse melanoma cell line B16/F10 (CRL-6475) were obtained from the American Type Culture Collection (ATCC; Manassas, Va.). DU145 was cultured in Eagle minimum essential medium with Earls salts (EMEM) supplemented with 10% heat-inactivated fetal bovine serum (FBS), 2 mM L-glutamine, and 50 µg/mL each of penicillin, streptomycin, and neomycin. B16/F10 (ATCC, CRL-6475) was cultured in Dulbecco modified Eagle medium (DMEM) supplemented with 10% heat-inactivated FBS, 2 mM L-glutamine, and 50 µg/mL each of penicillin, streptomycin, and neomycin. The human melanoma cell line MDA-MB-435 and human pancreatic cancer cell line PANC-1 were cultured in improved MEM (IMEM) supplemented with 10% heat-inactivated FBS, 2 mM L-glutamine, and 50 µg/mL each of penicillin, streptomycin, and neomycin. Normal (non-cancerous) skin fibroblast cell line H500 was cultured in EMEM supplemented with 1 mM Sodium pryuvate, 1 mM Non-essential amino acids plus 10% heat inactivated fetal bovine serum, 2 mM L-glutamine and 50 µg/mL each of penicillin, streptomycin, and neomycin. EMEM was purchased from MediaTech (Hemdon, Va.) and the other cell culture media and ingredients were obtained from Biofluids (Rockville, Md.).

Preparation of TfRscfv/LipA/Imatinib Mesylate (GLEEVEC®) Complexes

Cationic liposomal formulation LipA (DOTAP: DOPE or DDAB:DOPE at a 1:1 to 1:2 molar ratio) were prepared using the ethanol injection method as described throughout. TfRscFv/LipA/Imatinib Mesylate complexes were prepared as follows. After 10 minutes incubation with rotation or stirring at room temperature of a mixture of LipA and TfRscFv (ratio of TfRscFv to LipA, 1:1 to 1:40 (wt/wt), more suitably 1:10 to 1:30 wt/wt), the Imatinib Mesylate at the appropriate concentration was added mixed by inversion or stirring at room temperature and incubated for 10 minutes. For animal injection, dextrose or sucrose was added to each sample to a final concentration of 1% to 20%, more suitably 5-10%. The molar ratio of Imatinib Mesylate to Liposome was from 0.2:7 to 14:7, more suitably 2:7 to 8:7, most suitably 7:7. The sizes of the complexes were determined by dynamic light scattering at 25° C. with a ZETASIZER® 3000HS system (Malvern, United Kingdom).

In Vitro Cell Viability with the TfRscFv/LipA/Imatinib Mesylate Complex

For in vitro cytotoxicity studies, 2.5 to $5.5 \times 10^3$ cells/well in 100 µL of the appropriate growth medium of each cell line were plated in a 96-well plate. After 24 hours, the cells were washed with serum-free medium, overlaid with 100 µL of TfRscFv/LipA/Imatinib Mesylate complex or free Imatinib Mesylate in serum-free medium in increasing concentrations, incubated for 4-6 hours, suitably 5 hours, and then supplemented with FBS. The cells were then incubated for an additional 24-72 hours, suitably 48 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3,4-tetrazolium]-bis(4-methoxy-6-nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

In Vitro Chemosensitization

For the chemosensitization study, 2.5~5.5×10³ cells/well in 100 μL were seeded in a 96-well plate. After 24 hours, the cells were washed with serum-free medium, overlaid with 100 μL of TfRscFv/LipA/Imatinib Mesylate complex or free Imatinib Mesylate at 15 to 30 μM Imatinib Mesylate, incubated for 4-6 hours, suitably 5 hours, and then FBS was added to each well. The cells were incubated for an additional 24-72 hours, suitably 19 hours, followed by the addition of the appropriate supplemented medium with or without chemotherapeutics in increasing concentrations, and incubation continued for approximately 24-72 hours, suitably 48 hours. The chemotherapeutic drugs used were doxorubicin (Bedford Labs, Bedford, Ohio), docetaxel (Taxotere; Aventis Pharmaceuticals, Bridgewater, N.J.), mitoxantrone (NOVANTRONE®, Immunex Corp., Seattle Wash.), cisplatin (CDDP; Bedford Labs, Bedford, Ohio), gemcitabine (GEMZAR®, Eli Lilly and Co., Indianapolis Ind.) and Dacarbazine (DTIC) (Mayne Pharmaceuticals, Paramus N.J.). The XTT assays were performed to assess the degree of sensitization to the chemotherapeutics, and $IC_{50}$ values of each cell were calculated. Fold sensitization equals the following: $IC_{50}$ untransfected/$IC_{50}$ each complex.

In Vivo Efficacy Studies

Mouse melanoma cells B16/F10 (1×10⁵) suspended in PBS were injected intravenously into the tail vein of C57BL/6 mice. Four days later the mice carrying B16/F10 tumors were intravenously injected with free Imatinib Mesylate; CDDP only or TfRscFv/LipA/Imatinib Mesylate in combination with CDDP at a dose of 0.5 mg/kg Imatinib Mesylate. Injection occurred three times a week to at total of 9 injections. The molar ratio of Imatinib Mesylate to LipA in each complex was 7 to 7. The ratio of single-chain antibody fragment to liposome in each complex was 1:30 (w:w). Certain groups also received CDDP only. CDDP was given as twice weekly injections at 2 mg/kg to a total of 6 injections. After 3 weeks of treatment, the mice were sacrificed, the lungs were excised, The organs were fixed in 10% formaldehyde and preserved in 70% ethanol before being photographed.

Results

Comparison of Encapsulated and Free Imatinib Mesylate

Figure 24C:
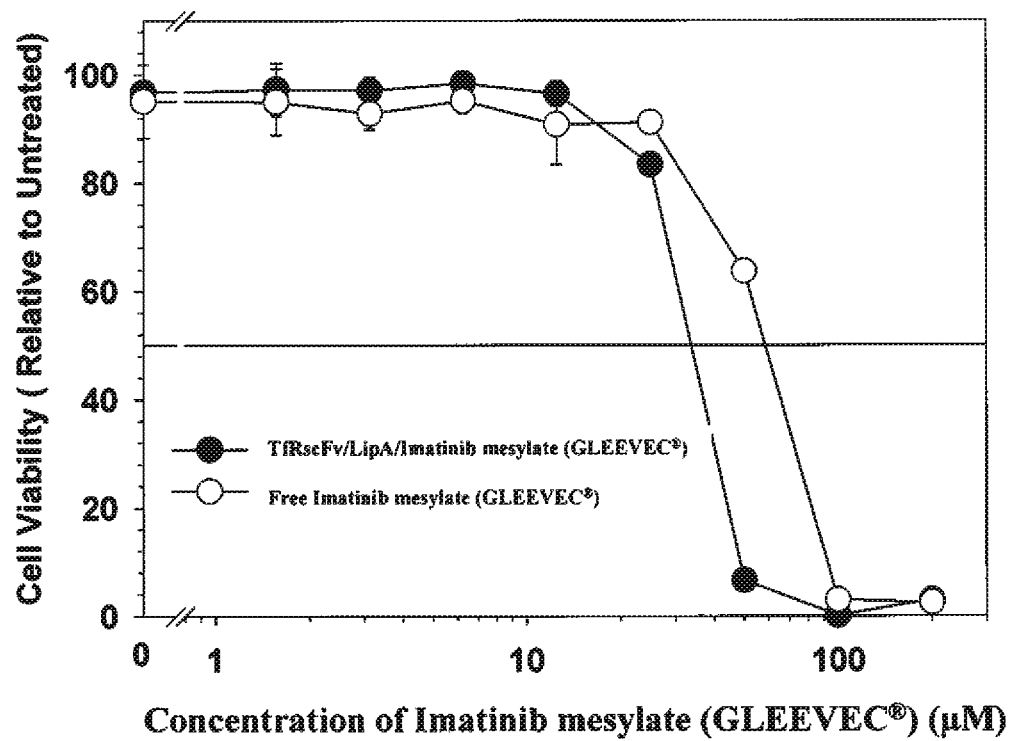

The effectiveness of TfRscFv/LipA/Imatinib Mesylate (GLEEVEC®) compared to that of free Imatinib Mesylate (GLEEVEC®), on cell survival was assessed via XTT assay (as described herein) in both a human prostate cancer cell line (DU145) (FIG. 24A) and a human melanoma cell line (MDA-MB-435) (FIG. 24B), and a mouse melanoma cell line (B16/F10) (FIG. 24C). The molar ratio of Imatinib Mesylate to LipA in each complex was 7 to 7. The ratio of single-chain antibody fragment to liposome in each complex was 1:30 (w:w). Imatinib Mesylate was dissolved in either DMSO or in water. As demonstrated in FIG. 24A, treatment of DU145 cell with liposome complex delivered Imatinib Mesylate resulted in a greater than 5 fold increase in cell killing as compared to free Imatinib Mesylate when dissolved in either DMSO or water.

Similarly, in human melanoma cells, (FIG. 24B) Imatinib Mesylate delivered via the liposome complex had a significantly greater effect on cell kill than when delivered in 'free' form. There was a 3 fold improvement with TfRscFv/LipA/Imatinib Mesylate over free small molecule. The results were identical irrespective of whether Gleevec was dissolved in water or DMSO. Thus subsequent experiments utilized Gleevec that had been dissolved in water.

When the effect of free or TfRScFv/LipA complexed Imatinib Mesylate (scL-Gleevec) was compared in B16/F10 mouse melanoma cells a similar 3 fold increase in cell killing with the scL-Gleevec over that with free Gleevec was observed (FIG. 24C).

Chemosensitization by TfRscFv/LipA/Imatinib Mesylate (scL-Gleevec)

The ability of Imatinib Mesylate, delivered either 'free' or via liposome complex (scL-GLEEVEC®), to sensitize tumor cells (human and mouse) to first line chemotherapeutic agents was also assessed by XTT assay. Human melanoma cell line MDA-MB-435 was treated with 20 μM or 30 μM free or complexed Imatinib Mesylate followed by addition of increasing doses of Taxotere. The molar ratio of Imatinib Mesylate to LipA in each complex was 7 to 7. The ratio of single-chain antibody fragment to liposome in each complex was 1:30 (w:w). As shown in FIG. 25A, at a 20 uM Imatinib Mesylate concentration there is an almost 50 fold increase in response to the chemotherapeutic agent when Imatinib Mesylate is delivered by liposome complex (scL-GLEEVEC®), as compared to administered as free Imatinib Mesylate. At this dose free Imatinib Mesylate does not sensitize the cells to Taxotere. Moreover a dose dependent increase in chemosensitization was observed. At 30 uM Imatinib Mesylate, while free Imatinib Mesylate showed an approximate 4 fold sensitization, the response with liposome complex Imatinib Mesylate was so dramatic that an $IC_{50}$ value could not be determined (FIG. 25B).

Similarly, in human prostate cells (DU145), Imatinib Mesylate delivered by the liposome complex (scL-GLEEVEC®) at 20 μM enhanced the response of the cells to Mitoxantrone by ~4 fold (FIG. 26A) compared to free Imatinib Mesylate. Here also there was a dose response, at 30 μM an $IC_{50}$ value could not be determined with the TfRscFv/LipA/Imatinib Mesylate complex (scL-GLEEVEC®) (FIG. 26B). The molar ratio of Imatinib Mesylate to LipA in each complex was 7 to 7. The ratio of single-chain antibody fragment to liposome in each complex was 1:30 (w:w).

The effect of liposome complex delivery of Imatinib Mesylate was also assessed in human pancreatic cancer cell line PANC-1. The molar ratio of Imatinib Mesylate to LipA in each complex was 7 to 7. The ratio of single-chain antibody fragment to liposome in each complex was 1:30 (w:w). As was observed in the other tumor cells, there was a dose response and a dramatic increase in the level of sensitivity to chemotherapeutic agent GEMZAR® (Gemcitabine HCl) when Imatinib Mesylate was delivered via the liposome complex of the present invention (scL-GLEEVEC®) (FIGS. 27A and B). At 20 μM, there was a 100 fold increase in the response of PANC-1 to Gemcitabine with liposome complex Imatinib Mesylate over that seen with free Imatinib Mesylate (FIG. 27A). As above, at 30 μM no $IC_{50}$ value could be determined (FIG. 27B). In contrast, the $IC_{50}$ value with the free Imatinib Mesylate did not significantly change with increasing dose.

The results with a mouse melanoma cell line, B16/F10, mirror those with the human tumor cells. The comparison of the effect on chemosensitization by free and TfRscFv/LipA/Imatinib Mesylate complex (scL-GLEEVEC®) was shown to be dose and time dependent with two separate chemotherapeutic agents Cisplatin (CDDP and Dacarbazine (DTIC). The molar ratio of Imatinib Mesylate to LipA in each complex was 7 to 7. The ratio of single-chain antibody fragment to liposome in each complex was 1:30 (w:w). With CDDP, transfection with the TfRscFv/LipA/Imatinib Mesylate complex (scL-GLEEVEC®) at a concentration of 20 uM resulted in a two fold increase in sensitization as compared to free Imatinib Mesylate (FIG. 28A). Here again at an Imatinib Mesylate concentration of 30 uM, the level of sensitization to CDDP was so strong that only ~10% of the cells survived at the lowest Imatinib Mesylate dose (FIG. 28B).

Similar experiments were performed to compare the sensitization of B16/F10 cells to another chemotherapeutic agent, Dacarbazine (DTIC), by free or complexed Imatinib Mesylate. The molar ratio of Imatinib Mesylate to LipA in each complex was 7 to 7. The ratio of single-chain antibody fragment to liposome in each complex was 1:30 (w:w). Here also, in addition to a dose dependent enhancement of sensitization with TfRscFv/LipA/Imatinib Mesylate, which is not seen with the free small molecule, there was also an increase in fold sensitization with increasing incubation time after transfection before adding the chemotherapeutic agent (FIG. 29A to D). After 24 hours incubation, at an hnatinib Mesylate concentration of 15 uM, the complexed Imatinib Mesylate resulted in a 2.1 fold increase in response to DTIC as compared to free Imatinib Mesylate (FIG. 29A). This doubled to a 4.2 fold increase in sensitization by the complex of this invention over the free Imatinib Mesylate when the concentration of the small molecule was increased to 20 uM (FIG. 29B). At the longer incubation time (48 hours), the increase in sensitization with the TfRscFv/LipA/Imatinib Mesylate, as compared to free Imatinib Mesylate (concentration=15 uM) was 5.7 fold (FIG. 29C), while at 48 hours with a concentration of 20 uM the response was so great no $IC_{50}$ is obtainable (FIG. 29D). Thus, here again we have shown in multiple tumor cell types and with various chemotherapeutic agents the delivery and efficacy of the small molecule Imatinib Mesylate is enhanced when it is encapsulated in the complex of this invention. Imatinib Mesylate The tumor cell specific nature of the ligand/liposome/Imatinib Mesylate induced chemosensitization is shown in FIGS. 30 A and B. Normal (non-cancerous) skin fibroblast cells (H500) were transfected as above with LipA only, free Imatinib Mesylate and TfRscFv/LipA/Imatinib Mesylate (scL-GLEEVEC®) (at a concentration of 20 uM) prior to the addition of chemotherapeutic agents Mitoxantrone (FIG. 30A) or taxotere (FIG. 30B). The molar ratio of Imatinib Mesylate to LipA in each complex was 7 to 7. The ratio of single-chain antibody fragment to liposome in each complex was 1:30 (w:w). In both experiments no significant increase in sensitization to the chemotherapeutic agents was observed. All $IC_{50}$ values were in the same range as that of the controls, >100 ng/ml for mitoxantrone and >100 nM for Taxotere.
In Vivo Efficacy of the TfRscFv/LipA/Imatinib Mesylate Complex: Enhanced Tumor Growth Inhibition $1 \times 10^5$ B16/F10 mouse melanoma cells, suspended in PBS were injected intravenously into the tail vein of C57BL/6 mice. Four days later, the mice carrying B16/F10 lung metastases were injected with either cisplatin (CDDP) only, free Imatinib Mesylate or TfRscFv/LipA/Imatinib Mesylate (scL-GLEEVEC®) complex in combination with cisplatin. The molar ratio of Imatinib Mesylate to LipA in each complex was 7 to 7. The ratio of single-chain antibody fragment to liposome in each complex was 1:30 (w:w). The mice received three injections a week of free Imatinib Mesylate or scL-GLEEVEC® complex at 0.5 mg Imatinib Mesylate/mouse/injection to a total of 9 injections. CDDP was i.p. twice a week at a dose of 2 mg/kg to a total of 6 injections. After 3 weeks of treatment, the mice were humanely euthanized and the lungs were excised and photographed.

As shown in FIG. 31, there was a significant inhibition of tumor cell growth in the lungs of the mice that received the combination of TfRScFv/Lipa/Imatinib Mesylate plus CDDP compared to those from the animals that received single agent treatment. Thus, this supports the use of the ligand/liposome/small molecule complex of this invention as an anticancer agent, particularly when used in combination with chemotherapeutic agents.

CONCLUSIONS

Imatinib Mesylate has been approved for treating patients with Philadelphia chromosome-positive (Ph+) Chronic Myeloid Leukemia (CML) and for patients with KIT (CD117) positive unresectable and/or metastatic malignant Gastrointestinal Stromal Tumors (GIST). It has been shown in vitro to inhibit a number of tyrosine kinases, including Bcr-Abl, c-KIT and PDGF receptors alpha and beta. Thus, the drug has potential for the treatment of other cancers that express these kinases. In these studies, we have demonstrated that the effectiveness of Imatinib Mesylate in inducing tumor cell death (in breast, prostate and pancreatic cancers) and increasing their response to first line chemotherapeutic agents, is dramatically improved when delivered to the cells via the targeted liposome delivery complexes of the present invention. These results also demonstrate the ability of this nanocomplex to greatly increase the efficacy of Imatinib Mesylate.

EXAMPLE 13

Preparation and Characterization of Small Molecule (Erlotinib (TARCEVA®)) Comprising-Immunoliposomes by Simple Mixing TARCEVA® (Erlotinib, Genentech Inc, So. San Francisco Calif.) is a Human Epidermal Growth Factor Receptor Type 1/Epidermal Growth Factor Receptor (HER1/EGFR) tyrosine kinase inhibitor. This tyrosine kinase is one of the factors critical to cell growth in non-small cell lung and pancreatic cancers.

The epidermal growth factor receptor (EGFR) is a component of the HER (human epidermal growth factor receptor) signaling pathway. The pathway consists of at least four cellular receptors: EGFR/HER1, HER2, HER3, and HER4. Approximately 11 different factors are known to bind and activate these receptors in certain patterns. The HER signaling pathway plays a role in the normal regulation of cell growth, proliferation, migration, and mediating processes, such as wound healing, tissue repair, and maintenance of the skin. In addition to its role in controlling the growth of normal cells, the HER signaling pathway has been shown to have a significant impact on the growth, proliferation, migration, and survival of cancer cells.

EGFR and other components of the HER signaling pathway interact in a complex and tightly regulated manner to regulate cell growth. Alterations in the amount or activity of HER family members may cause or support the inappropriate cell growth that leads to proliferation, migration, and survival of cancer cells. Because the signaling pathway works as a cascade that amplifies the growth signal at each step, small changes in the amount or activity of EGFR may significantly drive the development, or progression, of cancer by promoting cell growth and metastasis (cell migration) and inhibiting apoptosis (programmed cell death). Additionally, several studies have shown that HER signaling, an important regulator of normal cellular and tissue repair, is activated in response to a variety of cancer therapies that damage cells and tissues, including some chemotherapeutic agents and radiation These studies suggest that activation of the HER pathway, including EGFR, may contribute to the development of treatment-resistant cancers.

TARCEVA® is designed to inhibit the tyrosine kinase activity of the HER1 signaling pathway inside the cell. TARCEVA® is an oral dosage tablet. Erlotinib is a quinazolinamine with the chemical name N-(3-ethynylphenyl)-6,7-bis(2-methoxyethoxy)-4-quinazolinamine. TARCEVA® contains erlotinib as the hydrochloride salt. Erlotinib inhibits the intracellular phosphorylation of tyrosine kinase associated with the epidermal growth factor receptor (EGFR). Specificity of inhibition with regard to other tyrosine kinase receptors has not been fully characterized. EGFR is expressed on the cell surface of normal cells and cancer cells. In November 2004, the U.S. Food and Drug Administration (FDA) approved TARCEVA® (150 mg) for the treatment of patients with locally advanced or metastatic non-small cell lung cancer (NSCLC) after failure of at least one prior chemotherapy regimen. Results from two multicenter, placebo-controlled, randomized Phase III trials conducted in first-line patients with locally advanced or metastatic NSCLC showed no clinical benefit with the concurrent administration of TARCEVA® with platinum-based chemotherapy, and its use is not recommended in that setting. In this regard, the increase in sensitization to various chemotherapeutic agents in multiple tumor cell lines by Erlotinib (TARCEVA®) through the method of this invention, i.e. complexing the small molecule with the tumor targeting liganded liposome complex through simple mixing, is highly unexpected. The most common side effects in patients with NSCLC receiving TARCEVA® monotherapy 150 mg were mild-to-moderate rash and diarrhea. Grade 3/4 rash and diarrhea occurred in 9 and 6 percent of TARCEVA®-treated patients, respectively, with each resulting in 1 percent of patients discontinuing the single-agent Phase III trial. There have been infrequent reports of serious Interstitial Lung Disease (ILD)-like events, including fatalities, in patients receiving TARCEVA® for treatment of NSCLC, pancreatic cancer or other advanced solid tumors. In the NSCLC single-agent trial, the incidence of ILD-like events were infrequent (0.8 percent) and were equally distributed between treatment arms.

In November 2005, the FDA approved TARCEVA® (100 mg) in combination with gemcitabine chemotherapy for the treatment of locally advanced, inoperable or metastatic pancreatic cancer in patients who have not received previous chemotherapy. In the Phase III study in pancreatic cancer, the most common adverse events reported were fatigue, rash, nausea, anorexia and diarrhea. Rash was reported in 69 percent of patients who received TARCEVA® plus gemcitabine and in 30 percent of patients who received gemcitabine plus placebo. Diarrhea was reported in 48 percent of patients who received Tarceva plus gemcitabine and in 36 percent of patients who received gemcitabine plus placebo. Rash and diarrhea each resulted in dose reductions in two percent of patients, and resulted in study discontinuation in up to one percent of patients who received TARCEVA® plus gemcitabine. In addition, severe and potential fatal adverse events included interstitial lung disease-like complications, myocardial infarction or ischemia, cerebrovascular accident, and microangiopathic hemolytic anemia with thrombocytopenia of patients who received TARCEVA® plus gemcitabine.

Materials and Methods 1,2-Dioeoyl-3-trimethylammonium propane (DOTAP), dioleolylphosphatidyl ethanolamine (DOPE), and N-maleimido-phenylbutyrate DOPE (MPB-DOPE) were purchased from Avanti Polar Lipids (Alabaster, Ala.).

Cell Lines and Culture

The human prostate cancer cell line DU145 (HTB-81) was obtained from the American Type Culture Collection (ATCC; Manassas, Va.). DU145 was cultured in Eagle minimum essential medium with Earls salts (EMEM) supplemented with 10% heat-inactivated fetal bovine serum (FBS), 2 mM L-glutamine, and 50 µg/mL each of penicillin, streptomycin, and neomycin. The human melanoma cell line MDA-MB-435 and human pancreatic cancer cell line PANC-1 were cultured in improved MEM (IMEM) supplemented with 10% heat-inactivated FBS, 2 mM L-glutamine, and 50 µg/mL each of penicillin, streptomycin, and neomycin. Normal (non-cancerous) skin fibroblast cell line H500 was cultured in EMEM supplemented with 1 mM Sodium pryuvate, 1 mM Non-essential amino acids plus 10% heat inactivated fetal bovine serum, 2 mM L-glutamine and 50 µg/mL each of penicillin, streptomycin, and neomycin. EMEM was purchased from MediaTech (Herndon, Va.) and the other cell culture media and ingredients were obtained from Biofluids (Rockville, Md.).

Preparation of TfRscFv/LipA/Erlotinib (TARCEVA®) Complexes

Cationic liposomal formulation LipA (DOTAP: DOPE or DDAB:DOPE at a 1:1 to 1:2 molar ratio) were prepared using the ethanol injection method as described throughout. TfRscFv/LipA/Erlotinib complexes were prepared as follows: After 10 minutes incubation with rotation or stirring at room temperature of a mixture of LipA and TfRscFv (ratio of TfRscFv to LipA, 1:1 to 1:40 (wt/wt), more suitably 1:10 to 1:30 wt/wt), the Erlotinib at the appropriate concentration was added mixed by inversion or stirring at room temperature and incubated for 10 minutes. For animal injection, dextrose or sucrose was added to each sample to a final concentration of 1% to 20%, more suitably 5-10%. The molar ratio of Erlotinib to Liposome was from 0.2:7 to 14:7, more suitably 2:7 to 8:7, most suitably 7:7. The sizes of the complexes were determined by dynamic light scattering at 25° C. with a ZETASIZER® 3000HS system (Malvern, United Kingdom).

In Vitro Cell Viability with the TfRscFv/LipA/Erlotinib Complex

For in vitro cytotoxicity studies, 2.5 to $3.5 \times 10^3$ cells/well in 100 µL of the appropriate growth medium of each cell line were plated in a 96-well plate. After 24 hours, the cells were washed with serum-free medium, overlaid with 100 µL of TfRscFv/LipA/Erlotinib complex or free Erlotinib in serum-free medium in increasing concentrations, incubated for 4-6 hours, suitably 5 hours, and then supplemented with FBS. The cells were then incubated for an additional 24-72 hours, suitably 48 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3, 4-tetrazolium]-bis(4-methoxy-6- nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

In Vitro Chemosensitization

For the chemosensitization study, 2.5~3.5×10³ cells/well in 100 µL were seeded in a 96-well plate. After 24 hours, the cells were washed with serum-free medium, overlaid with 100 µL of TfRscFv/LipA/Erlotinib complex or free Erlotinib at 3 to 8 µM Erlotinib, incubated for 4-6 hours, suitably 5 hours, and then FBS was added to each well. The cells were incubated for an additional 24-72 hours, suitably 19 hours, followed by the addition of the appropriate supplemented medium with or without chemotherapeutics in increasing concentrations, and incubation continued for approximately 24-72 hours, suitably 48 hours. The chemotherapeutic drugs used were docetaxel (Taxotere; Aventis Pharmaceuticals, Bridgewater, N.J.), mitoxantrone (NOVANTRONE®, Immunex Corp., Seattle Wash.) and gemcitabine (GEMZAR®, Eli Lilly and Co., Indianapolis Ind.). The XTT assays were performed to assess the degree of sensitization to the chemotherapeutics, and $IC_{50}$ values of each cell were calculated. Fold sensitization equals the following: $IC_{50}$ untransfected/$IC_{50}$ each complex.

Results

Comparison of Encapsulated and Free Erlotinib (TARCEVA®)

The effectiveness of TfRscFv/LipA/Erlotinib (TARCEVA®) compared to that of free Erlotinib (TARCEVA®) on cell survival was assessed via XTT assay (as described herein) in a human prostate cancer cell line (DU145) (FIG. 32A), a human pancreatic cancer cell line (PANC-1) (FIG. 32B) and a human melanoma cell line (MDA-MB-435) (FIG. 32C). The molar ratio of Erlotinib (TARCEVA®) to LipA in each complex was 7 to 7. The ratio of single-chain antibody fragment to liposome in each complex was 1:30 (w:w). Erlotinib (TARCEVAO) was dissolved in water. As demonstrated in FIG. 32A, treatment of DU145 cell with liposome complex delivered Erlotinib (TARCEVA®) resulted in a greater than 5 fold increase in cell killing as compared to free when Erlotinib (TARCEVA®).

Similarly, in human pancreatic cancer cells, (FIG. 32B) Erlotinib (TARCEVA®) delivered via the liposome complex had a significantly greater effect on cell kill than when delivered in 'free' form. There was an almost 10 fold improvement with TfRscFv/LipA/Erlotinib (TARCEVA®) over free small molecule.

When the effect of free or TfRScFv/LipA complexed Erlotinib (TARCEVA®) (scL-Tarceva) was compared in human melanoma cells (MDA-MB-435) a >2 fold increase in cell killing with the scL-TARCEVA® over that with free Tarceva was observed (FIG. 32C).

Chemosensitization by TfRscFv/LipA/Erlotinib (scL-TARCEVA®)

The ability of Erlotinib (TARCEVA®), delivered either 'free' or via liposome complex (scL-TARCEVA®), to sensitize tumor cells to first line chemotherapeutic agents was also assessed by XTT assay. Human prostate cell line DU145 was treated with 3.75 µM or 7.5 µM free or complexed Erlotinib (TARCEVA®) followed by addition of increasing doses of Mitoxantrone. The molar ratio of Erlotinib (TARCEVA®) to LipA in each complex was 7 to 7 (equivalent to 1:1). The ratio of single-chain antibody fragment to liposome in each complex was 1:30 (w:w). As shown in FIG. 33A, at a 3.75 uM Erlotinib (TARCEVA®) concentration there is an almost 13 fold increase in response to the chemotherapeutic agent when Erlotinib (TARCEVA®) is delivered by liposome complex (scL-TARCEVA®), as compared to administered as free Erlotinib. At this dose free Erlotinib does not sensitize the cells to Mitoxantrone. Moreover a dose dependent increase in chemosensitization was observed, but only when Erlotinib (TARCEVA®) was delivered via the method of this invention and not as free Erlotinib (TARCEVA®). At 7.5 uM Erlotinib (TARCEVA®), the level of sensitization of DU145 cells to Mitoxantrone after treatment with scL-TARCEVA® was over 34 fold higher than that of free Erlotinib (TARCEVA®) (FIG. 33B). In contrast, even at this higher dose free Erlotinib (TARCEVA®) had no effect on the response to the chemotherapeutic agent.

Similarly in human melanoma cells (MDA-MB-435), Erlotinib (TARCEVA®) delivered by the liposome complex (scL-TARCEVA®) at 3.75 µM enhanced the response of the cells to Taxotere by >4 fold (FIG. 34A) compared to free Erlotinib (TARCEVA®). Here also there was a dose response, but once again only with the scL delivered small molecule. At 7.5 µM the level of sensitization was so strong that an $IC_{50}$ value could not be determined with the TfRscFv/LipA/Erlotinib (TARCEVA®) complex (scL-TARCEVA®) (FIG. 34B), but the fold sensitization as compared to free Erlotinib is estimated to be >140 fold. In contrast there was only minimal effect of free Erlotinib. The molar ratio of Erlotinib (TARCEVA®) to LipA in each complex was 7 to 7. The ratio of single-chain antibody fragment to liposome in each complex was 1:30 (w:w).

The effect of liposome complex delivery of Erlotinib (TARCEVA®) was also assessed in human pancreatic cancer cell line PANC-1. The molar ratio of Imatinib Mesylate to LipA in each complex was 7 to 7. The ratio of single-chain antibody fragment to liposome in each complex was 1:30 (w:w). As was observed in the other tumor cells, there was a dramatic increase in the level of sensitivity to chemotherapeutic agent GEMZAR® (Gemcitabine HCl) when Erlotinib (TARCEVA®) was delivered via the liposome complex of the present invention (scL-TARCEVA®) (FIG. 35). At 7.5 µM, there was an amazing 545 fold increase in the response of PANC-1 to Gemcitabine with liposome complexed Erlotinib (TARCEVA®) over that seen with free Erlotinib. In light of what has been found in clinical trials where free TARCEVA® was found not to enhance the effect of standard chemotherapeutics, such a dramatic effect on response to standard chemotherapeutics is highly unexpected.

Thus, here again as with the other small molecules in the previous examples, we have shown in multiple tumor cell types and with various chemotherapeutic agents that the delivery and efficacy of the small molecule Erlotinib is enhanced when it is encapsulated in the complex of this invention.

The tumor cell specific nature of the ligand/liposome/Erlotinib (TARCEVA®) induced chemosensitization is shown in FIGS. 36 A-C. Normal (non-cancerous) skin fibroblast cells (H500) were transfected as above with LipA only, free Erlotinib (TARCEVA® alone) and TfRscFv/LipA/Erlotinib (TARCEVA®) (scL-TARCEVA®) (at a concentration of 7.5 uM) prior to the addition of chemotherapeutic agents Mitoxantrone (FIG. 36A), taxotere (FIG. 36B) or Gemcitabine (GEMZAR®) (FIG. 36C). The molar ratio of Erlotinib (TARCEVA®) to LipA in each complex was 7 to 7. The ratio of single-chain antibody fragment to liposome in each complex was 1:30 (w:w). In all 3 experiments no significant increase in sensitization to the chemotherapeutic agents were observed. All $IC_{50}$ values were in the same range as that of the controls.

Thus, here again as with the other small molecules in the previous examples, we have shown in multiple tumor cell types and with various chemotherapeutic agents that the delivery and efficacy of the small molecule Erlotinib is enhanced when it is encapsulated in the complex of this invention.

EXAMPLE 14

Preparation and Characterization of Small Molecule Sunitinib Malate (SUTENT®) Comprising-Immunoliposomes by Simple Mixing The majority of cancers, including renal cell carcinoma (RCC) and gastiointestinal stromal tumor (GIST), result from mutations or other abnormalities in multiple signaling pathways, as opposed to a single, well defined mutation or abnormality. These changes ultimately enable the processes critical to cancer growth and include: self-sufficiency in growth signals, insensitivity to growth-inhibitory signals, evasion of programmed cell death (apoptosis), limitless replicative potential, sustained angiogenesis, and tissue invasion and metastasis. Sunitinib malate (SUTENT®) is an oral multi-kinase inhibitor that simultaneously inhibits several receptor kinases involved in RCC and GIST development. Sunitinib malate (SUTENT®) simultaneously inhibits all known PDGF and VEGF receptors, which play a role in both tumor cell proliferation and angiogenesis. SUTENT® is the first multi-kinase GIST therapy to simultaneously inhibit PDGF, VEGF, and KIT receptors. SUTENT® demonstrated antiangiogenic activity by inhibiting PDGF receptors on pericytes and VEGF receptors on endothelial cells in preclinical studies in both RCC and GIST. SUTENT® induced tumor regression and inhibited angiogenesis and metastatic progression in preclinical studies. SUTENT®, therefore inhibits multiple signaling pathways, resulting in a dual-action antiproliferative and antiangiogenic effect.

SUTENT® is indicated for the treatment of gastrointestinal stromal tumor (GIST) after disease progression on or intolerance to imatinib mesylate, and for the treatment of advanced renal cell carcinoma (RCC). Approval for advanced RCC is based on partial response rates and duration of responses. There are no randomized trials of SUTENT® demonstrating clinical benefit such as increased survival or improvement in disease-related symptoms in RCC.

Materials and Methods 1,2-Dioeoyl-3-trimethylammonium propane (DOTAP), dioleolylphosphatidyl ethanolamine (DOPE), and N-maleimido-phenylbutyrate DOPE (MPB-DOPE) were purchased from Avanti Polar Lipids (Alabaster, Ala.)

Cell Lines and Culture

The human prostate cancer cell line DU145 (HTB-81) was obtained from the American Type Culture Collection (ATCC; Manassas, Va.). DU145 was cultured in Eagle minimum essential medium with Earls salts (EMEM) supplemented with 10% heat-inactivated fetal bovine serum (FBS), 2 mM L-glutamine, and 50 µg/mL each of penicillin, streptomycin, and neomycin. The human melanoma cell line MDA-MB-435 and human pancreatic cancer cell line PANC-1 were cultured in improved MEM (IMEM) supplemented with 10% heat-inactivated FBS, 2 mM L-glutamine, and 50 µg/mL each of penicillin, streptomycin, and neomycin. Normal human lung fibroblast IMR-90 cells, a gift from Dr. I. Panyutin (Nuclear Medicine Department, National Institutes of Health, Bethesda, Md.), were cultured in EMEM supplemented with 10% heat-inactivated FBS, 2 mM L-glutamine, 0.1 mM non-essential amino acids, 1 mM sodium pyruvate, and 50 µg/mL each of penicillin, streptomycin, and neomycin. Normal (non-cancerous) skin fibroblast cell line H500 was cultured in EMEM supplemented with 1 mM Sodium pryuvate, 1 mM Non-essential amino acids plus 10% heat inactivated fetal bovine serum, 2 mM L-glutamine and 50 µg/mL each of penicillin, streptomycin, and neomycin. EMEM was purchased from MediaTech (Herndon, Va.) and the other cell culture media and ingredients were obtained from Biofluids (Rockville, Md.).

Preparation of TfRscFv/LipA/Sunitinib malate (SUTENT®) Complexes

Cationic liposomal formulation LipA (DOTAP: DOPE or DDAB:DOPE at a 1:1 to 1:2 molar ratio) were prepared using the ethanol injection method as described throughout. TfR-scFv/LipA/Sunitinib malate (SUTENT®) complexes were prepared as follows: After 10 minutes incubation with rotation or stirring at room temperature of a mixture of LipA and TfRscFv (ratio of TfRscFv to LipA, 1:1 to 1:40 (wt/wt), more suitably 1:10 to 1:30 wt/wt), the Sunitinib malate (SUTENT®) at the appropriate concentration was added mixed by inversion or stirring at room temperature and incubated for 10 minutes. For animal injection, dextrose or sucrose was added to each sample to a final concentration of 1% to 20%, more suitably 5-10%. The molar ratio of Sunitinib malate (SUTENT®) to Liposome was from 0.2:7 to 14:7, more suitably 3:7 to 11:7, most suitably 7:7. The sizes of the complexes were determined by dynamic light scattering at 25° C. with a ZETASIZER® 3000HS system (Malvern, United Kingdom).

In Vitro Cell Viability with the TfRscFv/LipA/Sunitinib malate (SUTENT®) Complex For in vitro cytotoxicity studies, 2.5 to $3.5 \times 10^3$ cells/well in 100 µL of the appropriate growth medium of each cell line were plated in a 96-well plate. After 24 hours, the cells were washed with serum-free medium, overlaid with 100 µL of TfRscFv/LipA/Sunitinib malate (SUTENT®) complex or free Sunitinib malate (SUTENT®) in serum-free medium in increasing concentrations, incubated for 4-6 hours, suitably 5 hours, and then supplemented with FBS. The cells were then incubated for an additional 24-72 hours, suitably 48 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3,4-tetrazolium]-bis(4-methoxy-6-nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

In Vitro Chemosensitization

For the chemosensitization study, $2.5 \sim 3.5 \times 10^3$ cells/well in 100 µL were seeded in a 96-well plate. After 24 hours, the cells were washed with serum-free medium, overlaid with 100 µL of TfRscFv/LipA/Sunitinib malate (SUTENT®) complex or free Sunitinib malate (SUTENT®) at 2 to 6 µM Sunitinib malate (SUTENT®), incubated for 4-6 hours, suitably 5 hours, and then FBS was added to each well. The cells were incubated for an additional 24-72 hours, suitably 19 hours, followed by the addition of the appropriate supplemented medium with or without chemotherapeutics in increasing concentrations, and incubation continued for approximately 24-72 hours, suitably 48 hours. The chemotherapeutic drugs used were docetaxel (Taxotere; Aventis Pharmaceuticals, Bridgewater, N.J.), mitoxantrone (NOVANTRONE®, Immunex Corp., Seattle Wash.) and gemcitabine (GEMZAR®), Eli Lilly and Co., Indianapolis Ind.). The XTT assays were performed to assess the degree of sensitization to the chemotherapeutics, and $IC_{50}$ values of each cell were calculated. Fold sensitization equals the following: $IC_{50}$ untransfected/$IC_{50}$ each complex.

Results

In Vitro Optimization of the Molar Ratio of TfRscFv/LipA/Sunitinib malate (SUTEN®) Complex The TfRscFv/LipA/Sunitinib malate (SUTENT®) complex was prepared and the molar ratio of the small molecule to liposome of the TfRscFv/LipA/Sunitinib malate (SUTENT®) complex was optimized. The cell killing effect of complexed and free Sunitinib malate (SUTENT®) at different ratios of Sunitinib malate (SUTENT®) to LipA on DU1455 human prostate cancer cells was compared. The ratio of TfRscFv to LipA was 1:30 (wt/wt). $3\times10^3$ cells/well were seeded in a 96-well plate and treated after 24 hours with TfRscFv/LipA/Sunitinib malate (SUTENT®) complexes, or free Sunitinib malate (SUTENT®). The XTT assays were performed 72 hours after treatment to assess cytotoxicity, and the $IC_{50}$ values (the drug concentration yielding 50% growth inhibition) were calculated from the concentration-cell viability curve. FIG. 37 shows the $IC_{50}$ values for each ratio. At the range of the molar ratio of Sunitinib malate (SUTENT®) to liposome of 3:7~7:7, a decrease in the $IC_{50}$ values were observed in cells treated with the complexed Sunitinib malate (SUTENT®) in comparison with cells treated with free Sunitinib malate (SUTENT®).

Comparison of Encapsulated and Free Sunitinib malate (SUTENT®)

The effectiveness of TfRscFv/LipA/Sunitinib malate (SUTENT®) compared to that of free Sunitinib malate (SUTENT®) on cell survival was assessed via XTT assay (as described herein) in a human prostate cancer cell line (DU145) (FIG. 38A), and a human pancreatic cancer cell line (PANC-1) (FIG. 38B). The molar ratio of Sunitinib malate (SUTENT®) to LipA in each complex was 7 to 7 (equivalent to 1:1). The ratio of single-chain antibody fragment to liposome in each complex was 1:30 (w:w). As demonstrated in FIG. 38A, treatment of DU145 cell with liposome complex delivered Sunitinib malate (SUTENT®) resulted in a significant increase in cell killing as compared to free Sunitinib malate (SUTENT®).

Similarly, in human pancreatic cancer cells, (FIG. 38B) Sunitinib malate (SUTENT®) delivered via the liposome complex had a significantly greater effect on cell kill than when delivered in 'free' form. There was a 4 fold improvement with TfRscFv/LipA/Sunitinib malate (SUTENT®) over free small molecule.

Chemosensitization by TfRscFv/LipA/Sunitinib malate (scL-SUTENT®)

The ability of Sunitinib malate (SUTENT®), delivered either 'free' or via liposome complex (scL-SUTENT®), to sensitize tumor cells to first line chemotherapeutic agents was also assessed by XTT assay. Human melanoma cell line MDA-MB-435 was treated with 2.5 µM or 5 µM free or complexed Sunitinib malate (SUTENT®) followed by addition of increasing doses of Taxotere. The molar ratio of Sunitinib malate (SUTENT®) to LipA in each complex was 7 to 7 (equivalent to 1:1). The ratio of single-chain antibody fragment to liposome in each complex was 1:30 (w:w). As shown in FIG. 39A, at a 2.5 uM Sunitinib malate (SUTENT®) concentration there is greater than 8 fold increase in response to the chemotherapeutic agent when delivered by Sunitinib malate (SUTENT®) liposome complex (scL-SUTENT®), as compared to administered as free Sunitinib malate (SUTENT®). Moreover a dose dependent increase in chemosensitization was observed when Sunitinib malate (SUTENT®) was delivered via the method of this invention. At 5 uM Sunitinib malate (SUTENT®) the level of sensitization was so high that an $IC_{50}$ value could not be reached however it was estimated that the level of sensitization of MDA-MB-435 cells to Taxotere after treatment with scL-SUTENT® was over 300 fold higher than that of free Sunitinib malate (SUTENT®) (FIG. 39B).

Similarly in human prostate cancer cells (DU145), Sunitinib malate (SUTENT®) delivered by the liposome complex (scL-SUTENT®) at 5 µM enhanced the response of the cells to Mitoxantrone by >400 fold (FIG. 40) compared to free Sunitinib malate (SUTENT®) where there was only minimal effect on sensitization of the prostate cancer cells to the chemotherapeutic agent. The molar ratio of Sunitinib malate (SUTENT®) to LipA in each complex was 7 to 7. The ratio of single-chain antibody fragment to liposome in each complex was 1:30 (w:w).

The effect of liposome complex delivery of Sunitinib malate (SUTENT®) was also assessed in human pancreatic cancer cell line PANC-1. The molar ratio of Sunitinib malate (SUTENT®) to LipA in each complex was 7 to 7. The ratio of single-chain antibody fragment to liposome in each complex was 1:30 (w:w). As was observed in the other tumor cells, there was a dramatic increase in the level of sensitivity to chemotherapeutic agent GEMZAR® (Gemcitabine HCl) when Sunitinib malate (SUTENT®) was delivered via the liposome complex of the present invention (scL-SUTENT®) (FIG. 41). At 2.5 µM, there was an almost 6 fold increase in the response of PANC-1 to Gemcitabine (GEMZAR®) with liposome complexed Sunitinib malate (SUTENT®) over that seen with free Sunitinib malate (SUTENT®).

The tumor cell specific nature of the ligand/liposome/Sunitinib malate (SUTENT®) induced chemosensitization is shown in FIGS. 42 (A-C) and 43 (A-C) Normal (non-cancerous) skin fibroblast cells (H500) were transfected as above with LipA only, free Sunitinib malate (SUTENT®) alone and TfRscFv/LipA/Sunitinib malate (SUTENT®) (scL-SUTENT®) (at a concentration of 2.5 or 5 uM) prior to the addition of chemotherapeutic agents Mitoxantrone (FIG. 42A), taxotere (FIG. 42B) or Gemcitabine (GEMZAR®) (FIG. 42C). The molar ratio of Sunitinib malate (SUTENT®) to LipA in each complex was 7 to 7. The ratio of single-chain antibody fragment to liposome in each complex was 1:30 (w:w). In all 3 experiments no significant increase in sensitization to the chemotherapeutic agents were observed. All $IC_{50}$ values were in the same range as that of the controls.

Similar results were observed when normal human lung fibroblasts (IMR-90) cells were transfected as above with LipA only, free Sunitinib malate (SUTENT®) alone and TfRscFv/LipA/Sunitinib malate (SUTENT®) (scL-SUTENT®) (at a concentration of 2.5 uM) prior to the addition of chemotherapeutic agents Mitoxantrone (FIG. 43A), taxotere (FIG. 43B) or Gemcitabine (GEMZAR®) (FIG. 43C). The molar ratio of Sunitinib malate (SUTENT®) to LipA in each complex was 7 to 7. The ratio of single-chain antibody fragment to liposome in each complex was 1:30 (w:w). In all 3 experiments no significant increase in sensitization to the chemotherapeutic agents were observed. All $IC_{50}$ values were in the same range as that of the controls.

Thus, here again as with the other small molecules in the previous examples, we have shown in multiple tumor cell types and with various chemotherapeutic agents that the delivery and efficacy of the small molecule Sunitinib malate (SUTENT®) is enhanced when it is encapsulated in the complex of this invention. Since the three tumor types shown in this example to be significantly more sensitized to Sunitinib malate (SUTENT®) when complexed as described in this invention, as compared to free Sunitinib malate (SUTENT®) are not tumor types in which the use of this small molecule has been found to be useful, it is an unexpected finding that these tumor cells respond so well to this invention

EXAMPLE 15

Preparation and Characterization of Small Molecule
(Geftinib (IRESSA®))
Comprising-Immunoliposomes by Simple Mixing Geftinib (IRESSA®) was the first in a new class of anticancer drugs, known as epidermal growth factor receptor tyrosine kinase (EGFR-TK) inhibitors, to gain market approval and is currently licensed for the treatment of advanced non-small-cell lung cancer (NSCLC) in 36 countries worldwide. Many cells, including cancer cells, have receptors on their surfaces for epidermal growth factor (EGF), a protein that is normally produced by the body and that promotes the growth and multiplication of cells. When EGF attaches to epidermal growth factor receptors (EGFRs), it causes an enzyme called tyrosine kinase to become active within the cells. Tyrosine kinase triggers chemical processes that cause the cells, including cancer cells, to grow, multiply, and spread. Gefitinib attaches to EGFRs and thereby blocks the attachment of EGF and the activation of tyrosine kinase. This mechanism for stopping cancer cells from growing and multiplying is very different from the mechanisms of chemotherapy and hormonal therapy. Gefitinib was approved by the FDA in May of 2003. Gefitinib is used alone (monotherapy) for the treatment of patients with a certain type of lung cancer, i.e non-small cell lung cancer (NSCLC).

Approvals were based on two phase II trials, IDEAL 1 and 2, which showed IRESSA to be an effective treatment for many patients with previously-treated advanced NSCLC. Approximately 50% of patients in the IDEAL trials achieved tumor shrinkage or stabilization of their tumor and the drug was found to be generally well tolerated with the most commonly reported adverse drug reactions being mild-to-moderate skin rash and diarrhea. However, Interstitial Lung Disease (ILD), which may be acute in onset, has been observed in patients receiving IRESSA, and some cases have been fatal. Patients with concurrent idiopathic pulmonary fibrosis/interstitial pneumonia/pneumoconiosis/radiation pneumonia/drug-induced pneumonia have been observed to have an increased rate of mortality from this condition.

In December 2004, AstraZeneca announced the results of the phase III ISEL (IRESSA® Survival Evaluation in Lung Cancer) study which compared IRESSA® with placebo in patients with advanced NSCLC who had failed one or two prior chemotherapy regimens. ISEL showed some improvement in survival with IRESSA® but this failed to reach statistical significance, compared with placebo, in the overall population or in patients with adenocarcinoma. Pre-planned subgroup analyses showed a statistically significant increase in survival with IRESSA®, compared with placebo, in patients of Asian origin and in patients who had never smoked. In addition, exploratory analyses of biomarker data from ISEL have suggested that high EGFR gene copy number is a strong predictor of benefit with IRESSA® in pre-treated advanced NSCLC.

Following the announcement of the ISEL data, AstraZeneca voluntarily withdrew the European submission for IRESSA® and regulatory authorities in the USA and Canada limited the use of IRESSA® to those patients already experiencing benefit from the drug. In the Asia Pacific region, due to the molecular differences in lung cancer, IRESSA® has become an established therapy for pre-treated advanced NSCLC and use of the drug in the first-line advanced setting is now being studied in a large phase III pan-Asian trial known as the IPASS study.

From the ISEL results, and broad clinical experience, it is clear that IRESSA® is an effective treatment for some advanced NSCLC patients. AstraZeneca is now focused on identifying those NSCLC patients who are most likely to benefit from the drug.

Since IRESSA® targets signaling pathways that appear to play a major role in the growth of many solid tumors it therefore may have a therapeutic potential in a broad range of cancers. Ongoing investigation of this potential includes clinical trials in head and neck cancer and breast cancer.

Materials and Methods 1,2-Dioeoyl-3-trimethylammonium propane (DOTAP), dioleolylphosphatidyl ethanolamine (DOPE), and N-male-imido-phenylbutyrate DOPE (MPB-DOPE) were purchased from Avanti Polar Lipids (Alabaster, Ala.).

Cell Lines and Culture

The human prostate cancer cell line DU145 (HTB-81) was obtained from the American Type Culture Collection (ATCC; Manassas, Va.). DU145 was cultured in Eagle minimum essential medium with Earls salts (EMEM) supplemented with 10% heat-inactivated fetal bovine serum (FBS), 2 mM L-glutamine, and 50 µg/mL each of penicillin, streptomycin, and neomycin. The human melanoma cell line MDA-MB-435 and human breast cancer cell line MDA-MB-231 cell line were cultured in improved MEM (IMEM) supplemented with 10% heat-inactivated FBS, 2 mM L-glutamine, and 50 µg/mL each of penicillin, streptomycin, and neomycin. EMEM was purchased from MediaTech (Herndon, Va.) and the other cell culture media and ingredients were obtained from Biofluids (Rockville, Md.).

Preparation of TfRscFv/LipA/Geftinib (IRESSA®) Complexes

Cationic liposomal formulation LipA (DOTAP: DOPE or DDAB:DOPE at a 1:1 to 1:2 molar ratio) were prepared using the ethanol injection method as described throughout. TfRscFv/LipA/Geftinib (IRESSA®) complexes were prepared as follows. After 10 minutes incubation with rotation or stirring at room temperature of a mixture of LipA and TfRscFv (ratio of TfRscFv to LipA, 1:1 to 1:40 (wt/wt), more suitably 1:10 to 1:30 wt/wt), Geftinib (IRESSA®) at the appropriate concentration, was added mixed by inversion or stirring at room temperature and incubated for 10 minutes. For animal injection, dextrose or sucrose was added to each sample to a final concentration of 1% to 20%, more suitably 5-10%. The molar ratio of Geftinib (IRESSA®) to Liposome was from 0.2:7 to 14:7, more suitably 3.5:7 to 7:7, most suitably 7:7. The sizes of the complexes were determined by dynamic light scattering at 25° C. with a ZETASIZER® 3000HS system (Malvern, United Kingdom).

In Vitro Cell Viability with the TfRscFv/LipA/Geftinib (IRESSA®) Complex

For in vitro cytotoxicity studies, 2.5 to $3.5 \times 10^3$ cells/well in 100 µL of the appropriate growth medium of each cell line were plated in a 96-well plate. After 24 hours, the cells were washed with serum-free medium, overlaid with 100 μL of TfRscFv/LipA/Geftinib (IRESSA®) complex or free Geftinib (IRESSA®) in serum-free medium in increasing concentrations, incubated for 4-6 hours, suitably 5 hours, and then supplemented with FBS. The cells were then incubated for an additional 24-72 hours, suitably 72 hours at 37° C. in a humidified atmosphere containing 5% $CO_2$. Afterward, the wells were washed with IMEM without phenol red and the cell-viability XTT-based assay was performed according to the manufacturer's protocol (Boehringer Mannheim, Indianapolis, Ind.). In the presence of an electron-coupling reagent, XTT, sodium 3'-[1-(phenylamino-carbonyl)-3,4-tetrazolium]-bis(4-methoxy-6-nitro)benzene sulfonate is converted into orange formazan by dehydrogenase in the mitochondria of living cells. The formazan absorbance, which correlates to the number of living cells, was measured at 450 nm using a microplate reader (Molecular Devices, Menlo Park, Calif.). The $IC_{50}$ yielding 50% growth inhibition was interpolated from the graph of the log of drug concentration versus the fraction of surviving cells.

In Vitro Chemosensitization

For the chemosensitization study, $2.5~3.5 \times 10^3$ cells/well in 100 μL were seeded in a 96-well plate. After 24 hours, the cells were washed with serum-free medium, overlaid with 100 μL of TfRscFv/LipA/Geftinib (IRESSA®); complex or free Geftinib (IRESSA®) at 8 to 15 μM Geftinib (IRESSA®), incubated for 4-6 hours, suitably 5 hours, and then FBS was added to each well. The cells were incubated for an additional 24-72 hours, suitably 19 hours, followed by the addition of the appropriate supplemented medium with or without chemotherapeutics in increasing concentrations, and incubation continued for approximately 24-72 hours, suitably 48 hours. The chemotherapeutic drugs used were docetaxel (Taxotere; Aventis Pharmaceuticals, Bridgewater, N.J.), and mitoxantrone (Novantrone®, Immunex Corp., Seattle Wash.). The XTT assays were performed to assess the degree of sensitization to the chemotherapeutics, and $IC_{50}$ values of each cell were calculated. Fold sensitization equals the following: $IC_{50}$ untransfected/$IC_{50}$ each complex.

Results

In Vitro Optimization of the Molar Ratio of TfRscFv/LipA/Geftinib (IRESSA®) Complex The TfRscFv/LipA/Geftinib (IRESSA®) complex was prepared and the molar ratio of the small molecule to liposome of the TfRscFv/LipA/Geftinib (IRESSA®) complex was optimized. The cell killing effect of complexed and free Geftinib (IRESSA®) at different ratios of Geftinib (IRESSA®) to LipA on MDA-MB-231 human breast cancer cells was compared. The ratio of TfRscFv to LipA was 1:30 (wt/wt). $3 \times 10^3$ cells/well were seeded in a 96-well plate and treated after 24 hours with TfRscFv/LipA/Geftinib (IRESSA®) complexes, or free Geftinib (IRESSA®). The XTT assays were performed 72 hours after treatment to assess cytotoxicity, and the $IC_{50}$ values (the drug concentration yielding 50% growth inhibition) were calculated from the concentration-cell viability curve. FIG. 44 shows the $IC_{50}$ values for each ratio. At the range of the molar ratio of Geftinib (IRESSA®) to liposome of 3:5~7:7, a decrease in the $IC_{50}$ values were observed in cells treated with the complexed Geftinib (IRESSA®) in comparison with cells treated with free Geftinib (IRESSA®).

Comparison of Encapsulated and Free Geftinib (IRESSA®)

The effectiveness of TfRscFv/LipA/Geftinib (IRESSA®) compared to that of free Geftinib (IRESSA®) on cell survival was assessed via XTT assay (as described herein) in a human breast cancer cell line (MDA-MB-231) (FIG. 45A), a human melanoma cell line (MDA-MB-435) (FIG. 45B), and a human prostate cancer cell line (DU145) (FIG. 45C). The molar ratio of Geftinib (IRESSA®) to LipA in each complex was 7 to 7 (equivalent to 1:1). The ratio of single-chain antibody fragment to liposome in each complex was 1:30 (w:w). As demonstrated in FIG. 45A, treatment of MDA-MB-231 cells with liposome complex delivered Geftinib (IRESSA®) resulted in a 2 fold increase in cell killing as compared to free Geftinib (IRESSA®).

Moreover, in MDA-MB-435 cells a 1.5 fold increase in response was observed when the Geftinib (IRESSA®) was delivered as part of the complex of this invention (scL-IRESSA®), as compared to free Geftinib (IRESSA®) (FIG. 45B).

Similarly, in human prostate cancer cells, (FIG. 45C) Geftinib (IRESSA®) delivered via the liposome complex had a significantly greater effect on cell kill than when delivered in 'free' form. There was a 1.7 fold improvement with TfRscFv/LipA/Geftinib (IRESSA®) over free small molecule.

Chemosensitization by TfRscFv/LipA/Geftinib (IRESSA®)

The ability of Geftinib (IRESSA®), delivered either 'free' or via liposome complex (scL-IRESSA®), to sensitize tumor cells to first line chemotherapeutic agents was also assessed by XTT assay (FIG. 46A-C). Three different human cancer cell lines were treated with 8-15 uM free or complexed Geftinib (IRESSA®) followed by addition of increasing doses of chemotherapeutic agent. The molar ratio of Geftinib (IRESSA®) to LipA in each complex was 7 to 7 (equivalent to 1:1). The ratio of single-chain antibody fragment to liposome in each complex was 1:30 (w:w). As shown in FIG. 46A, at a 12 uM Geftinib (IRESSA®) concentration there is greater than 2 fold increase in response to the chemotherapeutic agent Taxotere when delivered by the Geftinib (IRESSA®) liposome complex (scL-IRESSA®), as compared to when it is administered as free Geftinib (IRESSA®).

Similarly in human melanoma cells (MDA-MB-435), Geftinib (IRESSA®) delivered by the liposome complex (scL-IRESSA®)) at 15 μM enhanced the response of the cells to Taxotere by 2.2 fold (FIG. 46B) compared to free Geftinib (IRESSA®) which did not sensitize the cells at all to the chemotherapeutic agent. The molar ratio of Geftinib (IRESSA®) to LipA in each complex was 7 to 7. The ratio of single-chain antibody fragment to liposome in each complex was 1:30 (w:w).

The effect of liposome complex delivery of Geftinib (IRESSA®) was also assessed in human prostate cancer cell line DU145. The molar ratio of Geftinib (IRESSA®) to LipA in each complex was 7 to 7. The ratio of single-chain antibody fragment to liposome in each complex was 1:30 (w:w). As was observed in the other tumor cells, there was a significant increase in the level of sensitivity to chemotherapeutic agent Mitoxantrone when Geftinib (IRESSA®) was delivered via the liposome complex of the present invention (scL-IRESSA®) (FIG. 46C). At 8 μM, there was an almost 5 fold increase in the response of DU145 to Mitoxantrone with liposome complexed Geftinib (IRESSA®) over that seen with free Geftinib (IRESSA®).

Thus, here again as with the other small molecules in the previous examples, we have shown in multiple tumor cell types and with various chemotherapeutic agents that the delivery and efficacy of the small molecule Geftinib (IRESSA®) is enhanced when it is encapsulated in the complex of this invention. Since the three tumor types shown in this example to be more sensitized to Geftinib (IRESSA®) when complexed as described in this invention, as compared to free Geftinib (IRESSA®) are not tumor types in which the use of this small molecule has been found to be effective, it is an unexpected finding that these tumor cells respond so well to this invention.

REFERENCES

1. Tseng, S., Pak, G., Washenik, K., Pomeranz, M. K., and Shupack, J. L. Rediscovering thalidomide: a review of its mechanism of action, side effects, and potential uses. (Review). Journal of the American Academy of Dermatology, 35: 969-979, 1996.
2. Vogelsang, G. B., Hess, A. D., Gordon, G., and Santos, G. W. Treatment and prevention of acute graft-versus-host disease with thalidomide in a rat model. Transplantation, 41: 644-647, 1986.
3. McCarthy, D. M., Kanfer, E. J., and Barrett, A. J. Thalidomide for the therapy of graft-versus-host disease following allogeneic bone marrow transplantation. (Review). Biomedicine & Pharmacotherapy, 43: 693-697, 1989.
4. Forsyth, C. J., Cremer, P. D., Torzillo, P., Iland, H. J., and Young, G. A. Thalidomide responsive chronic pulmonary GVHD. Bone Marrow Transplantation, 17: 291-293, 1996.
5. Reyes-Teran, G., Sierra-Madero, J. G., Martinez, d. C., V, Arroyo-Figueroa, H., Pasquetti, A., Calva, J. J., and Ruiz-Palacios, G. M. Effects of thalidomide on HIV-associated wasting syndrome: a randomized, double-blind, placebo-controlled clinical trial. AIDS, 10: 1501-1507, 1996.
6. Jacobson, J. M., Greenspan, J. S., Spritzler, J., Ketter, N., Fahey, J. L., Jackson, J. B., Fox, L., Chernoff, M., Wu, A. W., MacPhail, L. A., Vasquez, G. J., and Wohl, D. A. Thalidomide for the treatment of oral aphthous ulcers in patients with human immunodeficiency virus infection. National Institute of Allergy and Infectious Diseases AIDS Clinical Trials Group. New England Journal of Medicine, 336: 1487-1493, 1997.
7. D'Amato, R. J., Loughnan, M. S., Flynn, E., and Folkman, J. Thalidomide is an inhibitor of angiogenesis. Proceedings of the National Academy of Sciences of the United States of America, 91: 4082-4085, 1994.
8. Bauer, K. S., Dixon, S.C., and Figg, W. D. Inhibition of angiogenesis by thalidomide requires metabolic activation, which is species-dependent. Biochemical Pharmacology, 55: 1827-1834, 1998.
9. Kenyon, B. M., Browne, F., and D'Amato, R. J. Effects of thalidomide and related metabolites in a mouse corneal model of neovascularization. Experimental Eye Research, 64: 971-978, 1997.
10. Ng, S. S., Gutschow, M., Weiss, M., Hauschildt, S., Teubert, U., Hecker, T. K., Luzzio, F. A., Kruger, E. A., Eger, K., and Figg, W. D. Antiangiogenic activity of N-substituted and tetrafluorinated thalidomide analogues. Cancer Research, 63: 3189-3194, 2003.
11. Dredge, K., Marriott, J. B., Macdonald, C. D., Man, H. W., Chen, R., Muller, G. W., Stirling, D., and Dalgleish, A. G. Novel thalidomide analogues display anti-angiogenic activity independently of immunomodulatory effects. British Journal of Cancer, 87: 1166-1172, 2002.
12. Lima, L. M., Castro, P., Machado, A. L., Fraga, C. A., Lugnier, C., de Moraes, V. L., and Barreiro, E. J. Synthesis and anti-inflammatory activity of phthalimide derivatives, designed as new thalidomide analogues. Bioorganic & Medicinal Chemistry, 10: 3067-3073, 2002.
13. Dredge, K., Marriott, J. B., and Dalgleish, A. G. Immunological effects of thalidomide and its chemical and functional analogs. (Review). Critical Reviews in Immunology, 22: 425-437, 2002.
14. Capitosti, S. M., Hansen, T. P., and Brown, M. L. Thalidomide analogues demonstrate dual inhibition of both angiogenesis and prostate cancer. Bioorganic & Medicinal Chemistry, 12: 327-336, 2004.
15. Hamel, E., Lin, C. M., Plowman, J., Wang, H. K., Lee, K. H., and Paull, K. D. Antitumor 2,3-dihydro-2-(aryl)-4 (1H)-quinazolinone derivatives. Interactions with tubulin. Biochemical Pharmacology, 51: 53-59, 1996.
16. Hour, M. J., Huang, L. J., Kuo, S.C., Xia, Y., Bastow, K., Nakanishi, Y., Hamel, E., and Lee, K. H. 6-Alkylamino- and 2,3-dihydro-3'-methoxy-2-phenyl-4-quinazolinones and related compounds: their synthesis, cytotoxicity, and inhibition of tubulin polymerization. Journal of Medicinal Chemistry, 43: 4479-4487, 2000.
17. Rowinsky, E. K. and Donehower, R. C. Paclitaxel (taxol) (erratum appears in N Engl J Med 1995 Jul. 6; 333(1):75). (Review). New England Journal of Medicine, 332: 1004-1014, 1995.
18. Miller, K. D. and Sledge, G. W., Jr. Taxanes in the treatment of breast cancer: a prodigy comes of age. (see comment). (Review). Cancer Investigation, 17: 121-136, 1999.
19. Marinina, J., Shenderova, A., Mallery, S. R., and Schwendeman, S. P. Stabilization of vinca alkaloids encapsulated in poly(lactide-co-glycolide) microspheres. Pharmaceutical Research, 17: 677-683, 2000.
20. Sachdeva, M. S. Drug targeting systems for cancer chemotherapy. Expert Opin Investig Drugs, 7 (11):1849-1864, 1998.
21. Sapra, P., Moase, E. H., Ma, J., and Allen, T. M. Improved therapeutic responses in a xenograft model of human B lymphoma (Namalwa) for liposomal vincristine versus liposomal doxorubicin targeted via anti-CD19 IgG2a or Fab' fragments. Clinical Cancer Research, 10: 1100-1111, 2004.
22. Mastrobattista, E., Koning, G. A., Storm, G. Immunoliposomes for the targeted delivery of antitumor drugs. AdvrDrug Deliv Rev. 40 (1-2):103-127, 1999.
23. Xu, L., Tang, W. H., Huang, C. C., Alexander, W., Xiang, L. M., Pirollo, K. F., Rait, A., and Chang, E. H. Systemic p53 gene therapy of cancer with immunolipoplexes targeted by anti-transferrin receptor scFv. Molecular Medicine, 7: 723-734, 2001.
24. Xu, L., Pirollo, K. F., and Chang, E. H. Tumor-targeted p53-gene therapy enhances the efficacy of conventional chemo/radiotherapy. (Review). Journal of Controlled Release, 74: 115-128, 2001.
25. Xu, L., Huang, C. C., Huang, W., Tang, W. H., Rait, A., Yin, Y. Z., Cruz, I., Xiang, L. M., Pirollo, K. F., and Chang, E. H. Systemic tumor-targeted gene delivery by anti-transferrin receptor scFv-immunoliposomes. Molecular Cancer Therapeutics, 1: 337-346, 2002.
26. Yu, W., Pirollo, K. F., Yu, B., Rait, A., Xiang, L., Huang, W., Zhou, Q., Ertem, G., and Chang, E. H. Enhanced transfection efficiency of a systemically delivered tumor-targeting immunolipoplex by inclusion of a pH-sensitive histidylated oligolysine peptide. Nucleic Acids Research, 32: e48, 2004.
27. Zignani, M., Drummond, D.C., Meyer, O., Hong, K., and Leroux, J. C. In vitro characterization of a novel polymeric-based pH-sensitive liposome system. Biochimica et Biophysica Acta, 1463: 383-394, 2000.
28. Venugopalan, P., Jain, S., Sankar, S., Singh, P., Rawat, A., and Vyas, S. P. pH-sensitive liposomes: mechanism of triggered release to drug and gene delivery prospects. (Review). Pharmazie, 57: 659-671, 2002.
29. Turk, M. J., Reddy, J. A., Chmielewski, J. A., and Low, P. S. Characterization of a novel pH-sensitive peptide that enhances drug release from folate-targeted liposomes at endosomal pHs. Biochimica et Biophysica Acta, 1559: 56-68, 2002.

30. Mattioli, R., Lippe, P., Massacesi, C., Cappelletti, C., Nacciarriti, D., Bisonni, R., Graziano, F., Menichetti, E. T., Imperatori, L., Testa, E., Laici, G., Balletra, A., Silva, R.R. Long-survival in responding patients with metastatic breast cancer treated with doxorubicin-docetaxel combination. A multicentre phase II trial. Anticancer Res. 24 (5B):3257-3261, 2004.

31. Lee, Y.J., Doliny, P., Gomez-Fernandez, C., Powell, J., Reis, I., Hurley, J. Docetaxel and cisplatin as primary chemotherapy for treatment of locally advanced breast cancers. Clin Breast Cancer. 5 (5):371-376, 2004.

32. Nguyen, M., Tran, C., Barsky, S. et al. Thalidomide and chemotherapy combination: preliminary results of preclinical and clinical studies. Int J Oncol, 10: 965-969, 1997.

33. Heere-Ress, E., Boehm, J., Thallinger, C., Hoeller, C., Wacheck, V., Birner, P., Wolff, K., Pehamberger, H., Jansen, B., Thalidomide enhances the anti-tumor activity of standard chemotherapy in a human melanoma xenotransplantation model. J Invest Dermatol, 125 (2): 201-206, 2005.

34. Nicholson, D. W., Ali, A., Thornberry, N. A., Vaillancourt, J. P., Ding, C. K., Gallant, M., Gareau, Y., Griffin, P. R., Labelle, M., and Lazebnik, Y. A. Identification and inhibition of the ICE/CED-3 protease necessary for mammalian apoptosis. Nature, 376: 37-43, 1995.

35. Tewari, M., Quan, L. T., O'Rourke, K., Desnoyers, S., Zeng, Z., Beidler, D. R., Poirier, G. G., Salvesen, G. S., and Dixit, V. M. Yama/CPP32 beta, a mammalian homolog of CED-3, is a CrmA-inhibitable protease that cleaves the death substrate poly(ADP-ribose) polymerase. Cell, 81: 801-809, 1995.

36. Fernandes-Alnemri, T., Litwack, G., and Alnemri, E. S. CPP32, a novel human apoptotic protein with homology to *Caenorhabditis elegans* cell death protein Ced-3 and mammalian interleukin-1 beta-converting enzyme. Journal of Biological Chemistry, 269: 30761-30764, 1994

ADDITIONAL LITERATURE CITED

Felgner, P. L., Tsai Y. J., Sukhu, L., Wheeler, C.J., Manthorpe M., Marshall, J. and Cheng S. H., *Ann NY Acad. Sci.*, 772, 126-139 (1995).

Lewis, J. G., Lin, K. Y., Kothavale, A., Flanagan, W. M., Matteucci, M. D., DePrince, R. B., Mook, R. A., Hendren, R. W., and Wagner, R. W., *Proc. Natl. Acad. Sci. USA*, 93, 3176-3181 (1996).

Aoki, K., Yoshida, T., Sugimura, T. and Terada, *Cancer Res.*, 55, 3810-3816 (1997).

Clark, P. R., Hersh, E. M., *Curr. Opin Mol. Ther,* 1, 158-176 (1999).

Thierry, A. R., Lunardi-Iskandar, Y., Bryant, J. L., Rabinovich, P., Gallo, R. C. and Mahan, L.C., *Proc Natl. Acad Sci,* 92, 9742-9746 (1997).

The Journal of Gene Medicine Clinical Trials Database, September, (2001).

Cristiano, R. J. and Curiel, D. T., *Cancer Gene Ther,* 3(1), 49-57 (1996).

Cheng, P. W., *Hum Gene Ther,* 7, 275-282 (1996).

Keer, H. N., Kozlowski, J. M. and Tsai, M. C., *J. Urol* 143, 381-385 (1990).

Chackal-Roy, M., Niemeyer, C and Moore, M., *J. Clin. Invest.,* 84, 43-50 (1989).

Rossi, M. C. and Zetter, B. R., *PNAS,* 89, 6197-6201 (1992).

Grayhack, J. T., Wendel, E. F. and Oliver, L., *J. Urol.* 121, 295-299 (1979).

Elliott, R. L., Elliott, M. C., Wang, F. and Head, J. F., *Ann NY Acad Sci,* 698, 159-166 (1993).

Miyamoto, T., Tanaka, N., Eishi, Y. and Amagasa, T., *Int. J. Oral Maxillofac Surg* 23, 430-433 (1994).

Thorstensen, K. and Romslo, I., *Scad J. Clin Lab Invest. Suppl.,* 215, 113-120 (1993).

Xu, L., Pirollo, K. F. and Chang, E. H., *Hum Gen Ther,* 8, 467-475 (1997)

Xu, L., Pirollo, K. F., Tang, W-H., Rait, A., and Chang, E.H., *Human Gene Therapy,* 10, 2941-2952 (1999).

Xu, L., Frederik, P., Pirollo, K.F., Tang, W-H, Rait, A., Xiang, L-M, Huang, W., Cruz, I., Yin, Y. and Chang, E. H., *Human Gene Therapy,* 13, 1-13 (2002).

Allen, T. M., Hansen, C. B. & Zalipsky, S., *Stealth Liposomes,* 233-44 (1995).

Allen, T. M., *Biochim Biophys Acta,* 1237, 99-108 (1995).

Lasic, D. D., Vallner, J. J. and Working, P. K., *Current Opinions in Molecular Therapeutics,* 1, 177-185 (1999).

Park, J. W., Hong, K., Carter, P., Asgari, H., Guo, L. Y., Keller, G. A., Wirth, C., Shalaby, R., Kotts, C., Wood, W. I., Papahadjopoulos, D and Benz, C. C., *Proc. Natl. Acad. Sci. USA,* 92, 1327-1331 (1995).

Park, J. W., Kirpotin, D. B., Hong, K., Shalaby, R., Shao, Y., Nielson, U. B., Marks, J. D., Papahadjopoulos, D., Benz, C. C., *J. Control Release,* 74 (1-3), 95-113 (2001).

Koning, G. A., Gorter, A., Scherphof, G. L. and Kamps, J. A., *British Journal of Cancer,* 80, 1718-1725 (1999).

Koning, G. A., Morselt, H. W., Velinova, M. J., Donga, J., Gorter, A., Allen, T. M., Zalipsky, S., Kamps, J. A. and Scherphof, G. L., *Biochemica et Biophysica Acta,* 1420, 153-167 (1999).

Nam, S. M., Kim, H. S., Ahn, W. S., and Park, Y. S., *Oncology Research* 11, 9-16 (1999).

Pagnan, G., Montaldo, P. G., Pastorino, F., Raffaghello, L., Kirchmeier, M., Allen, T. M. and Ponzoni, M., *International Journal of Cancer,* 81, 268-274 (1999).

Ng, K., Zhao, L., Liu, Y and Mahapatro, M., *International Journal of Pharmaceutics,* 193, 157-166 (2000).

Pirollo, K. F., Xu, L., Chang, E. H., Immunoliposomes: a targeted delivery tool for cancer treatment. In: *Vector Targeting for Therapeutic Gene Delivery,* D. Curiel (Ed.); Wiley Press (2002) In Press Poon, R.Y., in *Biotechnology International: International Developments in the Biotechnology Industry* (eds. Fox F and Connor, T. H.) 113-128 (Universal Medical Press, Inc., San Francisco, Calif., 1997).

Weinberg, E.D., *Biol. Trace Elements Res.,* 34, 123-140 (1992).

Reviews: p. 53. In: *Oncogene Reviews.* Jenkins, J. R., Banks L. M. (Eds), Stockton Press, London (1999): 18, 7617-777.

Sidransky, D., Hollstein, M., *Annual Review of Medicine,* 1996, 47, 285-301.

Ruley, H. E., In: *Important Advances in Oncology* 1996. Edited by DeVita, V.T., Hellman, S and S.A. Rosenberg, Philadelphia: Lippincott-Raven Publishers; 1996: 37-56.

Bristow, R.G., Benchimol, S., Hill, R. P.: *Radiotherapy & Oncology,* 40, 1996, 197-223.

Chiarugi, V., Magnelli, L., Gallo, O., *Int. J. Mol. Med.,* 2, 715-719, 1998.

Volpert, O. V., Dameron, K. M., Bouck, N., *Oncogene,* 1997, 14, 1495-1502.

Kerr, J. F., Winterford, C. M. and Harmon, B. V., *Cancer,* 73, 1994, pp. 2013-2026.

Lowe, S. W., *Curr. Opin Oncol.,* 7, 547-553 (1995).

Johnson, P., Gray, D., Mowat, M. and Benchimol, J. S., *Mol. Cell. Biol.*, 11, 1-11 (1991).

Yang, C., Cirielli, C., Capogrossi, M. C. and Passaniti, A., *Cancer Res.*, 55, 4210-4213 (1995).

Srivastava, S., Katayose, D., Tong, Y. A., Craig, C. R., McLeod, D. G., Moul, J. W., Cowan, K. H. and Seth, P., *Urology*, 46, 843-848 (1995).

Pirollo, K. F., Zhengmei, H., Rait, A., Jang, Y. J., Fee, W. E., Ray, P., Chiang, Y. and Chang, E. H., *Oncogene*, 14, 1735-1746 (1997).

Liu, T. J., Zhang, W. W., Taylor, D. L., Roth, J. A., Goepfert, H. and Clayman, G. L., *Cancer Res.*, 54, 3662-3667 (1994).

Miyashita, T., Krajewski, S., Krajewska, M., Wang, H. G., Lin, H. K., Liebermann, D. A., Hoffman, B. & Reed, J.C., *Oncogene*, 9(6), 1799-1805 (1994).

Hamada, K., Alemany, R., Zhang, W. W., Hittelman, W. N., Lotan, R., Roth, J. A. and Mitchell, M. F., *Cancer Res.*, 56 (3), 3047-3054 (1996).

Fujiwara, T., Grimm, E. A., Mukhopadhyay, T., Zhang, W. W., Owen-Schaub, L. B. and Roth, J. A., *Cancer Res*, 54, 2287-2291 (1994).

Fujiwara, T., Grimm, E. A., Mukhopadhyay, T., Cai, D. W., Owen-Schaub, L. B. and Roth, J. A., *Cancer Res*, 53, 4129-4133 (1993).

Xu, L., Pirollo, K. F., Rait, A., Murray, A. L. and Chang, D. H., *Tumor Targeting*, 4, 92-104 (1999).

Xu, L., Pirollo, K. F., Tang, W., Rait, A. and Chang, E. H., *Human Gene Therapy*, 10, 2941-2952 (1999), Rait, A., Pirollo, K., Rait, V., Krkygier, J., Xiang, L. and Chang, E. H., *Cancer Gene Therapy* 8, 728-739 (2001).

Yazdi, P. T., Wenning, L. A. and Murphy, R. M., *Cancer Res.*, 55, 3763-3771 (1995).

Dube'D, Francis, M., Leroux J-C and Winnik, F. M., *Bioconjugate Chemistry* 10, On line article, 2002.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of preparing an antibody- or antibody fragment-targeted cationic immunoliposome complex comprising:
   (a) preparing an antibody or antibody fragment;
   (b) mixing said antibody or antibody fragment with a cationic liposome to form a cationic immunoliposome, wherein said antibody or antibody fragment is complexed with said cationic liposome, but is not chemically conjugated to said cationic liposome, and wherein said antibody or antibody fragment does not comprise a lipid tag; and
   (c) mixing said cationic immunoliposome with a small molecule inhibitor to form said antibody- or antibody fragment-targeted-cationic immunoliposome complex, wherein said antibody- or antibody fragment-targeted-cationic immunoliposome is about 50-500 nm in size.

2. The method of claim 1, wherein an antibody is mixed with said cationic liposome.

3. The method of claim 1, wherein an antibody fragment is mixed with said cationic liposome.

4. The method of claim 3, wherein said antibody fragment is a single chain Fv fragment.

5. The method of claim 4, wherein said antibody fragment is an anti-transferrin receptor single chain Fv (TfRscFv).

6. The method of claim 1, wherein said antibody or antibody fragment is an anti-HER-2 antibody or antibody fragment.

7. The method of claim 1, wherein said antibody fragment comprises a cysteine moiety at a carboxy terminus prior to being mixed with said cationic liposome.

8. The method of claim 1, wherein said cationic liposome comprises a mixture of one or more cationic lipids and one or more neutral or helper lipids.

9. The method of claim 1, wherein said antibody or antibody fragment is mixed with said cationic liposome at a ratio in the range of about 1:20 to about 1:40 (w:v).

10. The method of claim 1, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleolphosphatidylethanolamine and cholesterol, a mixture of dimethyldioctadecylammonium bromide with dioleoylphosphatidylethanolamine, a mixture of dimethyldioctadecylammonium bromide with cholesterol, a mixture of dioleiyltrimethylammonium phosphate with dioleoylphosphatidylethanolamine.

11. The method of claim 1, wherein said cationic immunoliposome is mixed with said small molecule inhibitor at a molar ratio in the range of about 0.2:7 to about 14:7 (small molecule inhibitor:immunoliposome).

12. The method of claim 1, wherein said cationic immunoliposome is mixed with said small molecule inhibitor at a molar ratio of about 7:7 (small molecule inhibitor:immunoliposome).

13. The method of claim 1, wherein said small molecule inhibitor has a molecular weight of less than about 5000 Daltons.

14. The method of claim 13, wherein said small molecule inhibitor has a molecular weight of less than about 1000 Daltons.

15. The method of claim 14, wherein said small molecule inhibitor has a molecular weight of about 300 to about 700 Daltons.

16. The method of claim 1, wherein said small molecule inhibitor has at least one pKa in the range of about 2 to about 9.

17. The method of claim 1, wherein said small molecule inhibitor is an anticancer small molecule inhibitor.

18. The method of claim 1, wherein said small molecule inhibitor is selected from the group consisting of GMC-5-193, YK-3-250, imatinib mesylate, erlotinib hydrochloride, sunitinib malate, gefitinib, and analogs and derivatives thereof.

19. A cationic immunoliposome complex prepared by the method of claim 1.

20. An antibody- or antibody fragment-targeted cationic immunoliposome complex comprising a cationic liposome, an antibody or antibody fragment, and a small molecule inhibitor, wherein said antibody or antibody fragment is complexed with said cationic liposome, but is not chemically conjugated to said cationic liposome, wherein said antibody or antibody fragment does not comprise a lipid tag, and wherein said antibody- or antibody fragment-targeted cationic immunoliposome is about 50-500 nm in size.

21. The cationic immunoliposome complex of claim 20, wherein said small molecule inhibitor is encapsulated within said cationic liposome.

22. The cationic immunoliposome complex of claim 20, wherein said small molecule inhibitor is contained within a hydrocarbon chain region of said cationic liposome.

23. The cationic immunoliposome complex of claim 20, wherein said small molecule inhibitor is associated with an inner or outer monolayer of said cationic liposome.

24. The cationic immunoliposome complex of claim 20, wherein said antibody fragment is a single chain Fv fragment.

25. The cationic immunoliposome complex of claim 20, wherein said antibody fragment is an anti-transferrin receptor single chain Fv (TfRscFv).

26. The cationic immunoliposome complex of claim 20, wherein said antibody or antibody fragment is an anti-HER-2 antibody or antibody fragment.

27. The cationic immunoliposome complex of claim 20, wherein said cationic liposome comprises a mixture of one or more cationic lipids and one or more neutral or helper lipids.

28. The cationic immunoliposome complex of claim 20, wherein said antibody or antibody fragment and said cationic liposome are present at a ratio in the range of about 1:20 to about 1:40 (w:w).

29. The cationic immunoliposome complex of claim 20, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

30. The cationic immunoliposome complex of claim 20, wherein said small molecule inhibitor and said cationic immunoliposome are present at a molar ratio in the range of about 0.2:7 to about 14:7 (small molecule inhibitor:immunoliposome).

31. The cationic immunoliposome complex of claim 20, wherein small molecule inhibitor and said cationic immunoliposome are present at a molar ratio of about 7:7 (small molecule inhibitor:immunoliposome).

32. The cationic immunoliposome complex of claim 20, wherein said small molecule inhibitor has a molecular weight of less than about 5000 Daltons.

33. The cationic immunoliposome complex of claim 32, wherein said small molecule inhibitor has a molecular weight of less than about 1000 Daltons.

34. The cationic immunoliposome complex of claim 33, wherein said small molecule inhibitor has a molecular weight of about 300 to about 700 Daltons.

35. The cationic immunoliposome complex of claim 20, wherein said small molecule inhibitor has al least one pKa the range of about 2 to about 9.

36. The cationic immunoliposome complex of claim 20, wherein said small molecule inhibitor is an anticancer small molecule inhibitor.

37. The cationic immunoliposome complex of claim 20, wherein said small molecule inhibitor is selected from the group consisting of GMC-5-193, YK-3-250, imatinib mesylate, erlotinib hydrochloride, sunitinib malate, gefitinib, and analogs and derivatives thereof.

38. The cationic immunoliposome complex of claim 20, wherein said small molecule inhibitor and said cationic immunoliposome are present at a molar ratio in the range of about 2:7 to about 14:7 (small molecule inhibitor:immunoliposome).

39. The cationic immunoliposome complex of claim 20, wherein said small molecule inhibitor and said cationic immunoliposome are present at a molar ratio in the range of about 4:7 to about 10:7 (small molecule inhibitor:immunoliposome).

40. The cationic immunoliposome complex of claim 20, wherein said small molecule inhibitor and said cationic immunoliposome are present at a molar ratio in the range of about 5:7 to about 8:7 (small molecule inhibitor:immunoliposome).

41. The cationic immunoliposome complex of claim 20, wherein said small molecule inhibitor and said cationic immunoliposome are present at a molar ratio in the range of about 2.8:7 (small molecule inhibitor:immunoliposome).

42. The cationic immunoliposome complex of claim 30, wherein said small molecule inhibitor is selected from the group consisting of GMC-5-193, YK-3-250, imatinib mesylate, erlotinib hydochloride, sunitinib malate, gefitinib, and analogs and derivatives thereof.

43. The cationic immunoliposome complex of claim 31, wherein said small molecule inhibitor is selected from the group consisting of GMC-5-193, YK-3-250, imatinib mesylate, erlotinib hydochloride, sunitinib malate, gefitinib, and analogs and derivatives thereof.

44. The cationic immunoliposome complex of claim 38, wherein said small molecule inhibitor is selected from the group consisting of GMC-5-193, YK-3-250, imatinib mesylate, erlotinib hydochloride, sunitinib malate, gefitinib, and analogs and derivatives thereof.

45. The cationic immunoliposome complex of claim 39, wherein said small molecule inhibitor is selected from the group consisting of GMC-5-193, YK-3-250, imatinib mesylate, erlotinib hydochloride, sunitinib malate, gefitinib, and analogs and derivatives thereof.

46. The cationic immunoliposome complex of claim 40, wherein said small molecule inhibitor is selected from the group consisting of GMC-5-193, YK-3-250, imatinib mesylate, erlotinib hydochloride, sunitinib malate, gefitinib, and analogs and derivatives thereof.

47. The cationic immunoliposome complex of claim 41, wherein said small molecule inhibitor is selected from the group consisting of GMC-5-193, YK-3-250, imatinib mesylate, erlotinib hydochloride, sunitinib malate, gefitinib, and analogs and derivatives thereof.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic HER-2 antisense oligonucleotide

<400> SEQUENCE: 1
tccatggtgc tcact                                                    15

<210> SEQ ID NO 2
<211> LENGTH: 31
<212> TYPE: PRT
<213> ORGANISM: Artificial Sequence
<220> FEATURE:
<223> OTHER INFORMATION: Synthetic HoKC peptide chemically synthesized

<400> SEQUENCE: 2

Lys Lys His Lys Lys Lys Lys His Lys Lys Lys Lys His Lys Lys Lys
1               5                   10                  15

Lys His Lys Lys Lys Lys His Lys Lys Lys Lys His Lys Lys Cys
            20                  25                  30
```